United States Patent
Wang et al.

(10) Patent No.: US 11,396,503 B2
(45) Date of Patent: Jul. 26, 2022

(54) SULFONYL SUBSTITUTED BICYCLIC COMPOUND WHICH ACTS AS ROR INHIBITOR

(71) Applicants: CHIA TAI TIANQING PHARMACEUTICAL GROUP CO., LTD, Jiangsu (CN); NANJING GEAR PHARMA & TECH CO., LTD., Jiansu (CN)

(72) Inventors: Xiaolong Wang, Jiangsu (CN); Anle Yang, Jiangsu (CN); Hongjian Jiang, Jiangsu (CN); Jian Zhou, Jiangsu (CN); Lei Chen, Jiangsu (CN); Xiaolong Jiang, Jiangsu (CN); Ling Yang, Jiangsu (CN); Hongjiang Xu, Jiangsu (CN); Xiaohan Geng, Jiangsu (CN)

(73) Assignees: Chia Tai Tianqing Pharmaceutical Group Co., Ltd., Jiangsu (CN); Nanjing Gear Pharma & Tech Co., Ltd., Jiangsu (CN)

( * ) Notice: Subject to any disclaimer, the term of this patent is extended or adjusted under 35 U.S.C. 154(b) by 0 days.

(21) Appl. No.: 16/652,277

(22) PCT Filed: Sep. 30, 2018

(86) PCT No.: PCT/CN2018/109110
§ 371 (c)(1),
(2) Date: Mar. 30, 2020

(87) PCT Pub. No.: WO2019/063015
PCT Pub. Date: Apr. 4, 2019

(65) Prior Publication Data
US 2020/0239454 A1     Jul. 30, 2020

(30) Foreign Application Priority Data

Sep. 30, 2017  (CN) .......................... 201710913429.3

(51) Int. Cl.
| | | |
|---|---|---|
| *C07D 405/12* | (2006.01) | |
| *C07D 405/14* | (2006.01) | |
| *C07D 498/04* | (2006.01) | |
| *C07D 487/04* | (2006.01) | |
| *C07D 471/04* | (2006.01) | |
| *C07D 215/58* | (2006.01) | |
| *C07D 409/12* | (2006.01) | |
| *C07D 413/12* | (2006.01) | |

(52) U.S. Cl.
CPC ......... *C07D 405/12* (2013.01); *C07D 215/58* (2013.01); *C07D 405/14* (2013.01); *C07D 409/12* (2013.01); *C07D 413/12* (2013.01); *C07D 471/04* (2013.01); *C07D 487/04* (2013.01); *C07D 498/04* (2013.01)

(58) Field of Classification Search
CPC .. C07D 405/12; C07D 405/14; C07D 498/04; C07D 487/04; C07D 471/04; C07D 215/58; C07D 409/12; C07D 413/12
See application file for complete search history.

(56) References Cited

U.S. PATENT DOCUMENTS

| | | | |
|---|---|---|---|
| 5,814,631 A | * | 9/1998 | Fukami ................ C07D 239/96 514/234.5 |
| 9,266,827 B2 | | 2/2016 | Aicher et al. |

FOREIGN PATENT DOCUMENTS

| | | |
|---|---|---|
| CA | 2 949 229 A1 | 11/2015 |
| CN | 104284657 A | 1/2015 |
| CN | 106458991 A | 2/2017 |
| EP | 0 795 548 A1 | 9/1997 |
| WO | WO 2013/045431 A1 | 4/2013 |
| WO | WO 2013/160418 A1 | 10/2013 |
| WO | WO 2013/160419 A1 | 10/2013 |
| WO | WO2014/179564 A1 | 11/2014 |
| WO | WO 2015/116904 A1 | 8/2015 |
| WO | WO 2015/171610 A2 | 11/2015 |
| WO | WO 2016/061160 A1 | 4/2016 |

OTHER PUBLICATIONS

Chemical Abstracts Registry No. 915882-42-7, indexed in the Registry file on STN CAS Online Dec. 19, 2006. (Year: 2006).*
Chemical Abstracts Registry No. 915891-87-1, indexed in the Registry file on STN CAS Online Dec. 19, 2006. (Year: 2006).*
STN "RN 2217321-08-7," STN Registry, p. 1 (2021).
ACS, "RN 915882-42-7, 915888-36-7, 915891-87-1, 943095-59-8, 943198-61-6, 948816-15-7," STN Registry, pp. 1-3 (Sep. 30, 2007).

* cited by examiner

*Primary Examiner* — Laura L Stockton
(74) *Attorney, Agent, or Firm* — Muncy, Geissler, Olds & Lowe, P.C.

(57) ABSTRACT

Provided is a sulfonyl-substituted bicyclic compound (A) which acts as a RORγ inhibitor, said compound has good RORγ inhibitory activity and is expected to be used for treating diseases mediated by a RORγ receptor in mammals.

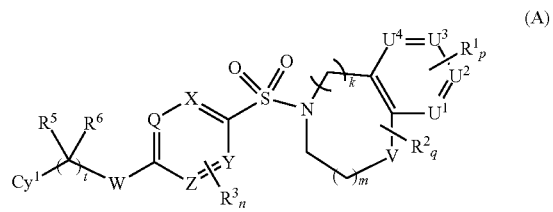

18 Claims, No Drawings

SULFONYL SUBSTITUTED BICYCLIC COMPOUND WHICH ACTS AS ROR INHIBITOR

This nonprovisional application is a National Stage of International Application No. PCT/CN2018/109110, which was filed on Sep. 30, 2018, and which claims priority to Chinese Patent Application No. 201710913429.3, which was filed in China on Sep. 30, 2017.

TECHNICAL FIELD

The present disclosure relates to a sulfonyl-substituted bicyclic compound acting as a RORγ inhibitor, and belongs to the field of medicinal chemistry.

BACKGROUND

Retinoic acid-related orphan nuclear receptor (ROR) is a member of the nuclear receptor family, and is capable of regulating a variety of physiological and biochemical processes. The ROR family includes three types, i.e., RORα, RORβ, and RORγ. These three different RORs may be expressed in different tissues and regulate different physiological processes. RORα is mainly distributed in liver, skeletal muscle, skin, lung, adipose tissue, kidney, thymus and brain; RORβ mainly acts on the central nervous system; and RORγ may be expressed in many tissues, including liver, animal fat, and skeletal muscle.

RORγ has two subtypes: RORγ1 and RORγt (RORy2). RORγ1 is expressed in many tissues such as thymus, muscle, kidney, and liver, while RORγt is only expressed in immune cells. RORγt is considered to be capable of regulating the differentiation of T cells, such as T helper 17 (Th17) cells. Th17 is a class of T helper cells, and this kind of cells may produce interleukin 17 (IL-17) and other cytokines. Th17 cells are associated with the pathology of numerous autoimmune and inflammatory diseases, said diseases include, but are not limited to, psoriasis, multiple sclerosis, rheumatoid arthritis, Crohn's disease, asthma, chronic obstructive pulmonary disease, Behcet's disease, irritable bowel syndrome, and the like.

In the prior art, the patent applications of Vitae Pharmaceuticals Inc., such as WO2014179564, WO2015116904 and WO2016061160, and the patent applications of GlaxoSmithKline, such as WO2013045431, WO2013160418 and WO2013160419, all disclose a series of compounds that may be used as RORγ inhibitors. In view of the great potential value of RORγ inhibitors, it is quite necessary to further seek for compounds with inhibitory function on RORγ.

SUMMARY

The present disclosure relates to a compound of formula (A) or a pharmaceutically acceptable salt thereof,

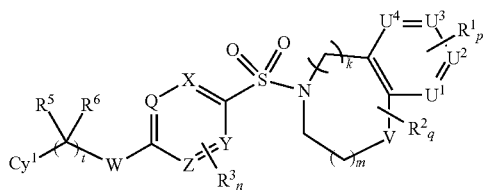

Formula (A)

wherein $U^1$, $U^2$, $U^3$, and $U^4$ are each independently selected from CH or N;

X, Y, Z, and Q are each independently selected from CH or N;

V is selected from $CH_2$, NH, O, or S;

W is selected from $CR^7R^8$, O, S,

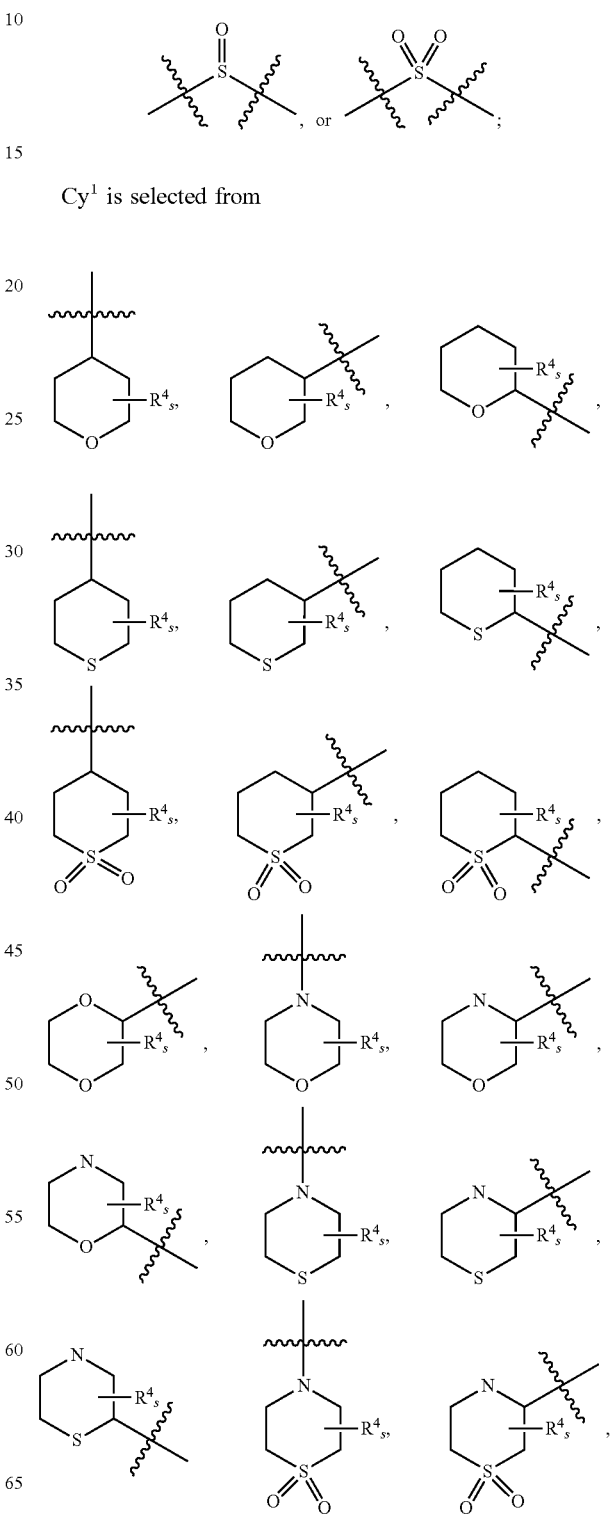

$Cy^1$ is selected from

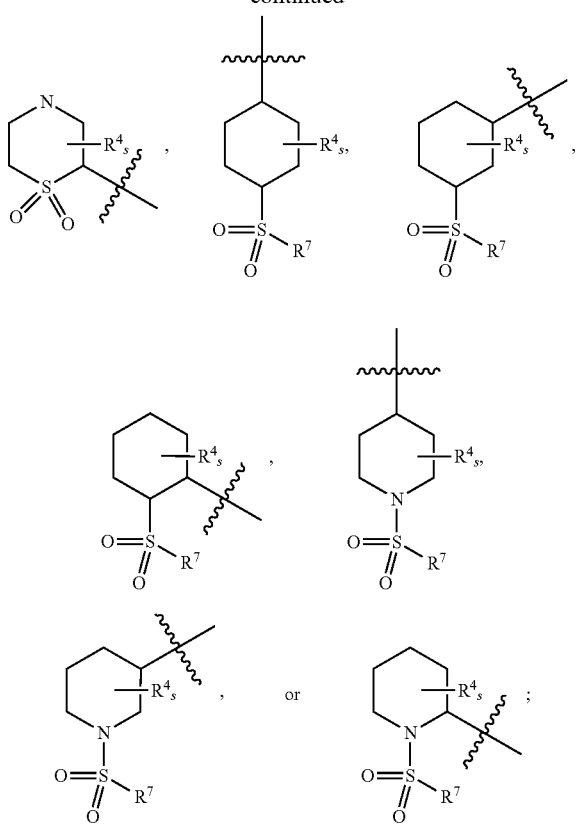

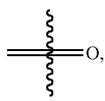

halogen, hydroxy, cyano, amino, or nitro, wherein said $C_1$-$C_6$ alkyl or $C_1$-$C_6$ alkoxy is optionally substituted with one, two or three substituents selected from halogen, hydroxy, cyano, amino or nitro;

$R^5$ and $R^6$ are independently selected from hydrogen, $C_1$-$C_6$ alkyl, $C_1$-$C_6$ alkoxy, halogen, hydroxy, cyano, amino, or nitro, wherein said $C_1$-$C_6$ alkyl or $C_1$-$C_6$ alkoxy is optionally substituted with one, two or three substituents selected from halogen, hydroxy, cyano, amino or nitro; or $R^5$ and $R^6$ together constitute

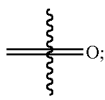

$R^7$ and $R^8$ are independently selected from hydrogen, $C_1$-$C_6$ alkyl, $C_1$-$C_6$ alkoxy, halogen, hydroxy, cyano, amino, or nitro, wherein said $C_1$-$C_6$ alkyl or $C_1$-$C_6$ alkoxy is optionally substituted with one, two or three substituents selected from halogen, hydroxy, cyano, amino, or nitro; or $R^7$ and $R^8$ together constitute

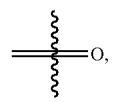

$R^1$ is independently selected from $C_1$-$C_6$ alkyl, $C_2$-$C_6$ alkenyl, $C_2$-$C_6$ alkynyl, $C_1$-$C_6$ alkoxy, 3- to 6-membered cycloalkyl, halogen, hydroxy, cyano, amino, or nitro, wherein said $C_1$-$C_6$ alkyl, $C_2$-$C_6$ alkenyl, $C_2$-$C_6$ alkynyl, $C_1$-$C_6$ alkoxy or 3- to 6-membered cycloalkyl is optionally substituted with one, two or three substituents selected from halogen, hydroxy, cyano, amino or nitro;

$R^2$ is independently selected from $C_1$-$C_6$ alkyl, $C_1$-$C_6$ alkoxy, 3- to 8-membered cycloalkyl, 3- to 8-membered heterocycloalkyl,

halogen, hydroxy, cyano, amino, or nitro, wherein said $C_1$-$C_6$ alkyl, $C_1$-$C_6$ alkoxy, 3- to 8-membered cycloalkyl, or 3- to 8-membered heterocycloalkyl is optionally substituted with one, two or three substituents selected from halogen, hydroxy, cyano, amino or nitro;

$R^3$ is independently selected from carboxy, halogen, hydroxy, cyano, amino, nitro, aminosulfonyl, $C_1$-$C_6$ alkyl, $C_1$-$C_6$ alkoxy, $C_1$-$C_6$ alkylsulfonyl, or 3- to 6-membered cycloalkyl, said $C_1$-$C_6$ alkyl, $C_1$-$C_6$ alkoxy, $C_1$-$C_6$ alkylsulfonyl or 3- to 6-membered cycloalkyl is optionally substituted with one, two or three substituents selected from deuterium, halogen, hydroxy, cyano, amino or nitro;

$R^4$ is independently selected from $C_1$-$C_6$ alkyl, $C_1$-$C_6$ alkoxy, m is selected from 0 or 1; k is selected from 0 or 1; and m+k is 0 or 1;

n is selected from 0, 1, 2, 3, or 4;
p is selected from 0, 1, 2, 3, or 4;
q is selected from 0, 1, 2, 3, 4, 5 or 6;
s is selected from 0, 1, 2, 3, 4, 5, 6, 7, 8 or 9;
t is selected from 0, 1 or 2; and
when t=0, X, Y, Z and Q are each independently selected from CH, $R^3$ is hydroxymethyl, and n=1.

In some embodiments, at least one of $U^1$, $U^2$, $U^3$ and $U^4$ is CH.

In some embodiments, at most one of $U^1$, $U^2$, $U^3$ and $U^4$ is N.

In some typical embodiments, $U^1$ is selected from N, and $U^2$, $U^3$, and $U^4$ are all CH.

In some typical embodiments, $U^3$ is selected from N, and $U^1$, $U^2$, and $U^4$ are all CH.

In some typical embodiments, $U^4$ is selected from N, and $U^1$, $U^2$, and $U^3$ are all CH.

In some typical embodiments, $U^1$, $U^2$, $U^3$, and $U^4$ are all CH.

In some embodiments, at least one of X, Y, Z and Q is CH.
In some embodiments, at most one of X, Y, Z and Q is N.
In some embodiments, Q and Z are both CH.
In some typical embodiments, X, Y, Z and Q are all CH.
In some typical embodiments, X is N, and Y, Z, and Q are all CH.
In some typical embodiments, Y is N, and X, Z, and Q are all CH.

In some more typical embodiments, $U^1$, $U^2$, $U^3$, $U^4$, X, Y, Z, and Q are all CH.

In some embodiments, V is selected from $CH_2$ or O.

In some typical embodiments, V is selected from $CH_2$.

In some typical embodiments, W is selected from $CR^7R^8$ or O.

In some more typical embodiments, W is O.

In some embodiments, $R^7$ and $R^8$ are independently selected from hydrogen, $C_1$-$C_3$ alkyl, $C_1$-$C_3$ alkoxy, fluorine, chlorine, bromine, iodine, hydroxyl, cyano, amino, or nitro, wherein said $C_1$-$C_3$ alkyl or $C_1$-$C_3$ alkoxy is optionally substituted with one, two or three substituents selected from fluorine, chlorine, bromine, iodine, hydroxyl, cyano, amino or nitro.

In some embodiments, $R^7$ and $R^8$ are independently selected from hydrogen, $C_1$-$C_3$ alkyl, or hydroxyl, wherein said $C_1$-$C_3$ alkyl is optionally substituted with one, two or three hydroxyl groups.

In some embodiments, $R^7$ and $R^8$ are independently selected from hydrogen, hydroxy, or hydroxymethyl.

In some typical embodiments, $R^7$ is hydrogen, and $R^8$ is selected from hydrogen, hydroxy, or hydroxymethyl.

In some embodiments, $Cy^1$ is selected from

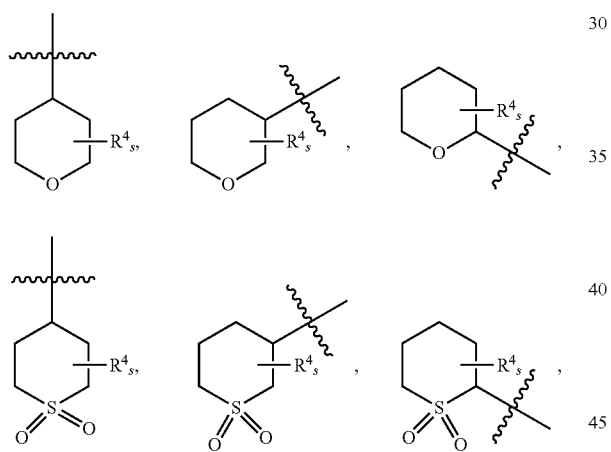

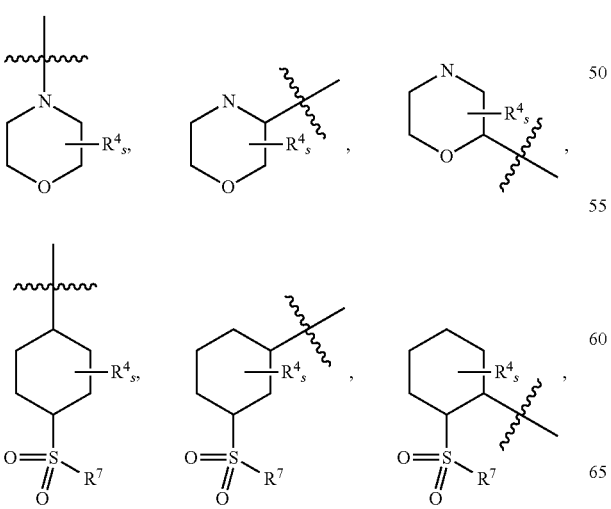

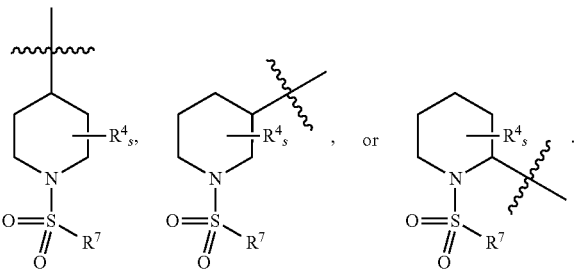

In some typical embodiments, $Cy^1$ is selected from

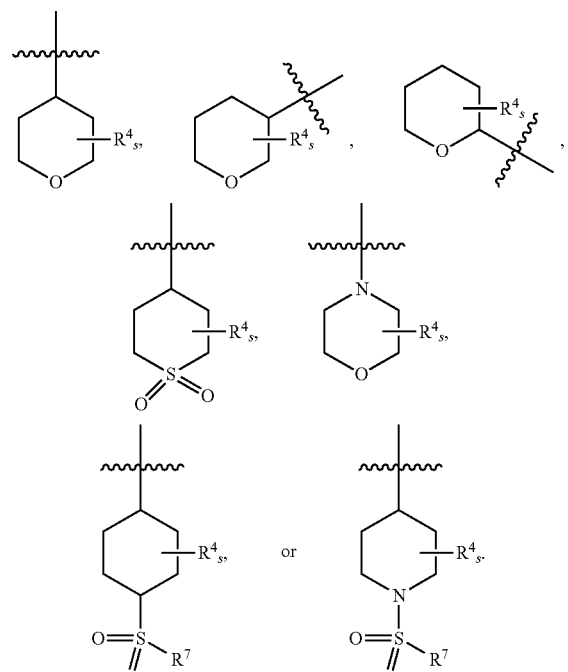

In some more typical embodiments, $Cy^1$ is selected from

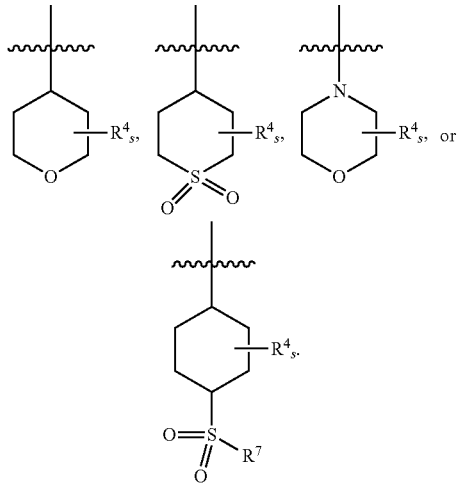

In some of the most typical embodiments, $Cy^1$ is

[structure: tetrahydropyran ring with $R^4_s$ substituent]

In some embodiments, $R^1$ is independently selected from $C_1$-$C_4$ alkyl, $C_2$-$C_4$ alkenyl, $C_2$-$C_4$ alkynyl, $C_1$-$C_4$ alkoxy, 3- to 6-membered cycloalkyl, fluorine, chlorine, bromine, iodine, hydroxyl, cyano, amino, or nitro, wherein said $C_1$-$C_4$ alkyl, $C_2$-$C_4$ alkenyl, $C_2$-$C_4$ alkynyl, $C_1$-$C_4$ alkoxy, or 3- to 6-membered cycloalkyl is optionally substituted with one, two or three substituents selected from fluorine, chlorine, bromine, iodine, hydroxyl, cyano, amino or nitro.

In some embodiments, 1e is independently selected from methyl, ethyl, n-propyl, isopropyl, n-butyl, isobutyl, tert-butyl, vinyl, propenyl, cyclopropyl, cyclobutyl, cyclopentyl, cyclohexyl, fluorine, chlorine or cyano, wherein said methyl, ethyl, n-propyl, isopropyl, n-butyl, isobutyl, tert-butyl, vinyl, propenyl, cyclopropyl, cyclobutyl, cyclopentyl or cyclohexyl is optionally substituted with one, two or three substituents selected from fluorine or hydroxyl.

In some of the most typical embodiments, 1e is independently selected from methyl, ethyl, n-propyl, isopropyl, tert-butyl, 2-hydroxyprop-2-yl, vinyl, propen-2-yl, trifluoromethyl, 2,2,2-trifluoroethyl (—$CH_2CF_3$), 1,1-difluoroethyl (—$CF_2CH_3$), cyclopropyl, cyclobutyl, fluorine, chlorine or cyano.

In some of the most typical embodiments, 1e is independently selected fromethyl, isopropyl, trifluoromethyl, or 1,1-difluoroethyl (—$CF_2CH_3$).

In some embodiments, p is selected from 0, 1 or 2.
In some typical embodiments, p is selected from 1 or 2.
In some more typical embodiments, p is 1.
In some embodiments, $R^2$ is independently selected from $C_1$-$C_4$ alkyl, $C_1$-$C_4$ alkoxy, 3- to 6-membered cycloalkyl, 3- to 6-membered heterocycloalkyl,

[structure: =O]

fluorine, chlorine, bromine, iodine, hydroxy, cyano, amino, or nitro, wherein said $C_1$-$C_4$ alkyl, $C_1$-$C_4$ alkoxy, 3- to 6-membered cycloalkyl, or 3- to 6-membered heterocycloalkyl is optionally substituted with one, two or three substituents selected from fluorine, chlorine, bromine, iodine, hydroxyl, cyano, amino or nitro.

In some typical embodiments, $R^2$ is independently selected from methyl, ethyl, n-propyl, isopropyl, n-butyl, isobutyl, tert-butyl, cyclopropyl, cyclobutyl, cyclopentyl, cyclohexyl, oxiranyl, pyrrolidinyl, piperidinyl, piperazinyl, fluorine, chlorine, bromine, iodine, hydroxyl, cyano, amino, or nitro; said methyl, ethyl, n-propyl, isopropyl, n-butyl, isobutyl, tert-butyl, cyclopropyl, cyclobutyl, cyclopentyl, cyclohexyl, oxiranyl, pyrrolidinyl, piperidinyl, or piperazinyl is optionally substituted with one, two or three substituents selected from fluorine or hydroxyl.

In some more typical embodiments, $R^2$ is independently selected from methyl, ethyl, isopropyl, isobutyl, cyclopropyl, cyclobutyl, trifluoromethyl, 2,2,2-trifluoroethyl, or hydroxyl.

In some of the most typical embodiments, $R^2$ is ethyl.
In some embodiments, q is selected from 0, 1, or 2.
In some typical embodiments, q is 1.
In some of the most typical embodiments, $R^2$ is ethyl, and q is 1.

In some embodiments, $R^3$ is independently selected from carboxy, fluorine, chlorine, bromine, iodine, hydroxyl, cyano, amino, nitro, aminosulfonyl, $C_1$-$C_4$ alkyl, $C_1$-$C_4$ alkoxy, $C_1$-$C_4$ alkylsulfonyl or 3- to 6-membered cycloalkyl; said $C_1$-$C_4$ alkyl, $C_1$-$C_4$ alkoxy, $C_1$-$C_4$ alkylsulfonyl or 3- to 6-membered cycloalkyl is optionally substituted with one, two or three substituents selected from deuterium, fluorine, chlorine, bromine, iodine, hydroxyl, cyano, amino, or nitro.

In some typical embodiments, $R^3$ is independently selected from cyano, nitro, aminosulfonyl, $C_1$-$C_3$ alkyl, $C_1$-$C_3$ alkylsulfonyl, or 3- to 5-membered cycloalkyl; said $C_1$-$C_3$ alkyl, $C_1$-$C_3$ alkylsulfonyl or 3- to 5-membered cycloalkyl is optionally substituted with one, two or three substituents selected from deuterium, fluorine, or hydroxyl.

In some typical embodiments, $R^3$ is independently selected from cyano, nitro, aminosulfonyl, methyl, ethyl, n-propyl, isopropyl, methylsulfonyl, ethylsulfonyl, or cyclopropyl; said methyl, ethyl, n-propyl, isopropyl, methylsulfonyl, ethylsulfonyl or cyclopropyl is optionally substituted with one, two or three substituents selected from deuterium, fluorine, or hydroxyl.

In some typical embodiments, $R^3$ is independently selected from cyano, nitro, aminosulfonyl, methylsulfonyl,

[structure: cyclopropyl with OH]

trifluoromethyl, hydroxymethyl, and dideuterated hydroxymethyl.

In some more typical embodiments, $R^3$ is independently selected from methyl or ethyl, which is optionally substituted with one, two or three hydroxyl.

In some of the most typical embodiments, $R^3$ is hydroxymethyl.

In some embodiments, n is 0, 1, or 2.
In some typical embodiments, n is 0 or 1.
In some more typical embodiments, n is 1.
In some of the most typical embodiments, $R^3$ is hydroxymethyl and n is 1.

In some embodiments, $R^4$ is independently selected from $C_1$-$C_3$ alkyl, $C_1$-$C_3$ alkoxy,

[structure: =O]

fluorine, chlorine, bromine, iodine, hydroxyl, cyano, amino, or nitro, wherein said $C_1$-$C_3$ alkyl or $C_1$-$C_3$ alkoxy is optionally substituted with one, two or three substituents selected from fluorine, chlorine, bromine, iodine, hydroxyl, cyano, amino, or nitro.

In some typical embodiments, $R^4$ is independently selected from $C_1$-$C_3$ alkyl optionally substituted with one, two or three substituents selected from fluorine or hydroxyl.

In some more typical embodiments, $R^4$ is independently selected from methyl, ethyl, n-propyl, or isopropyl.

In some embodiments, s is selected from 0, 1, or 2.

In some typical embodiments, s is 0.

In some embodiments, $R^5$ and $R^6$ are independently selected from hydrogen, $C_1$-$C_3$ alkyl, $C_1$-$C_3$ alkoxy, fluorine, chlorine, bromine, iodine, hydroxyl, cyano, amino, or nitro, wherein said $C_1$-$C_3$ alkyl or $C_1$-$C_3$ alkoxy is optionally substituted with one, two or three substituents selected from fluorine, chlorine, bromine, iodine, hydroxyl, cyano, amino, or nitro.

In some embodiments, $R^5$ and $R^6$ are independently selected from hydrogen or $C_1$-$C_3$ alkyl, wherein said $C_1$-$C_3$ alkyl is optionally substituted with one, two or three substituents selected from fluorine, chlorine, bromine, iodine, hydroxyl, cyano, amino, or nitro.

In some typical embodiments, $R^5$ and $R^6$ are independently selected from hydrogen or $C_1$-$C_3$ alkyl, wherein said $C_1$-$C_3$ alkyl is optionally substituted with one, two or three substituents selected from fluorine or hydroxyl.

In some more typical embodiments, $R^5$ and $R^6$ are independently selected from hydrogen or hydroxylmethyl.

In some of the most typical embodiments, $R^5$ and $R^6$ are independently selected from hydrogen.

In some embodiments, t is 0.

In some embodiments, t is selected from 1 or 2.

In some typical embodiments, t is 1.

In another aspect, the disclosure relates to a compound of formula (I) or a pharmaceutically acceptable salt thereof, Formula (I)

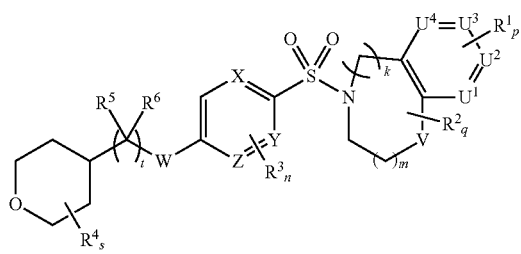

wherein $U^1$, $U^2$, $U^3$, $U^4$, X, Y, and Z are independently selected from CH or N;

V is selected from $CH_2$, NH, O, or S;

W is selected from $CR^7R^8$, $NR^7$, O, S,

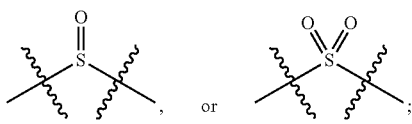

$R^1$ is selected from $C_1$-$C_6$ alkyl, $C_1$-$C_6$ alkoxy, 3- to 6-membered cycloalkyl, halogen, hydroxy, cyano, amino, or nitro, wherein said $C_1$-$C_6$ alkyl, $C_1$-$C_6$ alkoxy or 3- to 6-membered cycloalkyl is optionally substituted with one or more halogen, hydroxy, cyano, amino, or nitro;

$R^2$ and $R^4$ are independently selected from $C_1$-$C_6$ alkyl, $C_1$-$C_6$ alkoxy,

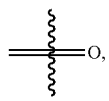

halogen, hydroxy, cyano, amino, or nitro, wherein said $C_1$-$C_6$ alkyl or $C_1$-$C_6$ alkoxy is optionally substituted with one or more halogen, hydroxy, cyano, amino, or nitro;

$R^3$ is selected from carboxy, halogen, hydroxy, cyano, amino, nitro, $C_1$-$C_6$ alkyl, $C_1$-$C_6$ alkoxy, or $C_1$-$C_6$ alkylsulfonyl, wherein said $C_1$-$C_6$ alkyl, $C_1$-$C_6$ alkoxy or $C_1$-$C_6$ alkylsulfonyl is optionally substituted with one or more halogen, hydroxy, cyano, amino, or nitro;

$R^5$ and $R^6$ are independently selected from hydrogen, $C_1$-$C_6$ alkyl, $C_1$-$C_6$ alkoxy, halogen, hydroxy, cyano, amino, or nitro, wherein said $C_1$-$C_6$ alkyl or $C_1$-$C_6$ alkoxy is optionally substituted with one or more halogen, hydroxy, cyano, amino, or nitro; or $R^5$ and $R^6$ together constitute

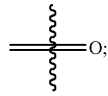 [SMILES: *=O]

$R^7$ and $R^8$ are independently selected from hydrogen, $C_1$-$C_6$ alkyl, $C_1$-$C_6$ alkoxy, halogen, hydroxy, cyano, amino, or nitro, wherein said $C_1$-$C_6$ alkyl or $C_1$-$C_6$ alkoxy is optionally substituted with one or more halogen, hydroxy, cyano, amino, or nitro; or $R^7$ and $R^8$ together constitute

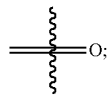 [SMILES: *=O]

m is selected from 0 or 1; k is selected from 0 or 1; and m+k 1;

n is selected from 0, 1, 2, 3, or 4;

p is selected from 0, 1, 2, 3, or 4;

q is selected from 0, 1, 2, 3, 4, 5, or 6;

s is selected from 0, 1, 2, 3, 4, 5, 6, 7, or 8; and t is selected from 1 or 2.

In some embodiments, $U^1$, $U^2$, $U^3$ and $U^4$ are selected from CH or N.

In some typical embodiments, at most one of $U^1$, $U^2$, $U^3$ and $U^4$ is N.

In some more typical embodiments, $U^1$ is selected from C or N, and $U^2$, $U^3$ and $U^4$ are all CH.

In some embodiments, X, Y and Z are all CH.

In some typical embodiments, $U^1$ is selected from C or N, and $U^2$, $U^3$, $U^4$, X, Y and Z are all CH.

In some more typical embodiments, $U^1$, $U^2$, $U^3$, $U^4$, X, Y and Z are all CH.

In some embodiments, V is selected from $CH_2$ or O.

In some typical embodiments, V is selected from $CH_2$.

In some embodiments, W is selected from NR', O, or S.

In some typical embodiments, W is selected from NH, O, or S.

In some more typical embodiments, W is O.

In some embodiments, le is selected from $C_1$-$C_3$ alkyl, $C_1$-$C_3$ alkoxy, 3- to 6-membered cycloalkyl, fluorine, chlorine, bromine, iodine, hydroxyl, cyano, amino, or nitro, wherein said $C_1$-$C_3$ alkyl, $C_1$-$C_3$ alkoxy, or 3- to 6-membered cycloalkyl is optionally substituted with one or more fluorine, chlorine, bromine, iodine, hydroxyl, cyano, amino, or nitro.

In some typical embodiments, le is selected from $C_1$-$C_3$ alkyl, cyclopropyl, cyclobutyl, cyclopentyl, cyclohexyl, fluorine, chlorine, bromine, iodine, hydroxyl, cyano, amino, or nitro, wherein said $C_1$-$C_3$ alkyl, cyclopropyl, cyclobutyl, cyclopentyl or cyclohexyl is optionally substituted with one or more fluorine, chlorine, bromine, iodine, hydroxyl, cyano, amino, or nitro.

In some more typical embodiments, le is selected from $C_1$-$C_3$ alkyl, cyclopropyl, chlorine, or cyano, wherein said $C_1$-$C_3$ alkyl or cyclopropyl is optionally substituted with one or more fluorine.

In some of the most typical embodiments, le is selected from methyl, n-propyl, isopropyl, trifluoromethyl, 2,2,2-trifluoroethyl (—$CH_2CF_3$), 1,1-difluoroethyl (—$CF_2CH_3$), chlorine, cyano, or cyclopropyl.

In some embodiments, p is selected from 0, 1, or 2.
In some typical embodiments, p is selected from 1 or 2.
In some more typical embodiments, p is 1.
In some embodiments, $R^2$ is selected from $C_1$-$C_3$ alkyl, $C_1$-$C_3$ alkoxy,

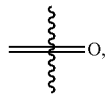 [SMILES: *=O]

fluorine, chlorine, bromine, iodine, hydroxy, cyano, amino, or nitro, wherein said $C_1$-$C_3$ alkyl or $C_1$-$C_3$ alkoxy is optionally substituted with one or more fluorine, chlorine, bromine, iodine, hydroxyl, cyano, amino, or nitro.

In some embodiments, $R^2$ is selected from $C_1$-$C_3$ alkyl optionally substituted with one or more fluorine, chlorine, bromine, iodine, hydroxyl, cyano, amino, or nitro.

In some typical embodiments, $R^2$ is selected from methyl, ethyl, or 2,2,2-trifluoroethyl.

In some embodiments, q is selected from 0, 1, or 2.

In some embodiments, $R^3$ is selected from carboxy, fluorine, chlorine, bromine, iodine, hydroxyl, cyano, amino, nitro, $C_1$-$C_3$ alkyl, $C_1$-$C_3$ alkoxy, or $C_1$-$C_3$ alkylsulfonyl, wherein said $C_1$-$C_3$ alkyl, $C_1$-$C_3$ alkoxy or $C_1$-$C_3$ alkylsulfonyl is optionally substituted with one or more fluorine, chlorine, bromine, iodine, hydroxyl, cyano, amino, or nitro.

In some typical embodiments, $R^3$ is selected from $C_1$-$C_3$ alkyl optionally substituted with one or more fluorine, chlorine, bromine, iodine, hydroxyl, cyano, amino, or nitro.

In some more typical embodiments, $R^3$ is selected from $C_1$-$C_3$ alkyl optionally substituted with one or more hydroxyl.

In some of the most typical embodiments, $R^3$ is hydroxymethyl.

In some embodiments, n is 0 or 1.

In some embodiments, $R^4$ is selected from $C_1$-$C_3$ alkyl, $C_1$-$C_3$ alkoxy,

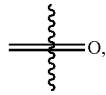 [SMILES: *=O]

fluorine, chlorine, bromine, iodine, hydroxyl, cyano, amino, or nitro, wherein said $C_1$-$C_3$ alkyl or $C_1$-$C_3$ alkoxy is optionally substituted with fluorine, chlorine, bromine, iodine, hydroxyl, cyano, amino, or nitro.

In some typical embodiments, $R^4$ is selected from $C_1$-$C_3$ alkyl.

In some embodiments, s is 0.

In some embodiments, $R^5$ and $R^6$ are independently selected from hydrogen, $C_1$-$C_3$ alkyl, $C_1$-$C_3$ alkoxy, fluorine, chlorine, bromine, iodine, hydroxyl, cyano, amino, or nitro, wherein said $C_1$-$C_3$ alkyl or $C_1$-$C_3$ alkoxy is optionally substituted with one or more fluorine, chlorine, bromine, iodine, hydroxyl, cyano, amino, or nitro; or $R^5$ and $R^6$ together constitute

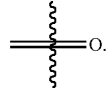 [SMILES: *=O]

In some embodiments, $R^5$ and $R^6$ are independently selected from hydrogen or $C_1$-$C_3$ alkyl, wherein said $C_1$-$C_3$ alkyl is optionally substituted with one or more fluorine, chlorine, bromine, iodine, hydroxyl, cyano, amino, or nitro.

In some typical embodiments, $R^5$ and $R^6$ are independently selected from hydrogen or $C_1$-$C_3$ alkyl, wherein said $C_1$-$C_3$ alkyl is optionally substituted with one or more hydroxyl.

In some more typical embodiments, $R^5$ and $R^6$ are independently selected from hydrogen or hydroxylmethyl.

In some embodiments, t is 1.

In some embodiments, $R^7$ and $R^8$ are independently selected from hydrogen, $C_1$-$C_3$ alkyl, $C_1$-$C_3$ alkoxy, fluorine, chlorine, bromine, iodine, hydroxyl, cyano, amino, or nitro, wherein said $C_1$-$C_3$ alkyl or $C_1$-$C_3$ alkoxy is optionally substituted with one or more fluorine, chlorine, bromine, iodine, hydroxyl, cyano, amino, or nitro; or $R^7$ and $R^8$ together constitute

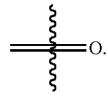

In some typical embodiments, $R^7$ and $R^8$ are independently selected from hydrogen.

In some embodiments, m is 0, and k is 0.
In some embodiments, m is 0, and k is 1.
In some embodiments, m is 1, and k is 0.

In some embodiments, the aforesaid "one or more" refers to one, two or three.

In some embodiments, the aforesaid compound of formula (A) has a structure represented by formula (a), Formula (a)

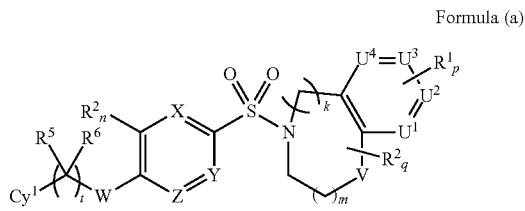

wherein $U^1$, $U^2$, $U^3$, $U^4$, V, X, Y, Z, W, $Cy^1$, $R^1$, $R^2$, $R^3$, $R^4$, $R^5$, $R^6$, m, k, n, p, q, s, and t are defined as those of the aforesaid compound of formula (A).

In some embodiments, the aforesaid compound of formula (A) has a structure represented by formula (I), Formula (I)

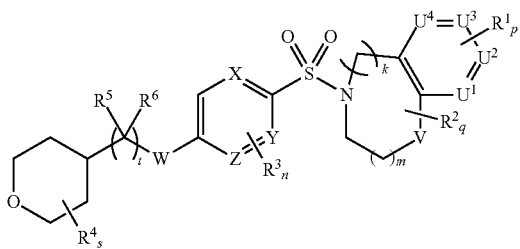

wherein $U^1$, $U^2$, $U^3$, $U^4$, V, X, Y, Z, W, $R^1$, $R^2$, $R^3$, $R^4$, $R^5$, $R^6$, m, k, n, p, q, s, and t are defined as those of the aforesaid compound of formula (A).

In some embodiments, the aforesaid compound of formula (A) has a structure represented by formula (II), Formula (II)

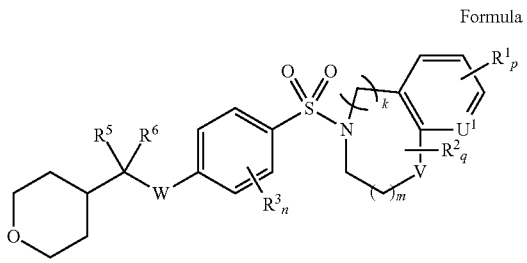

wherein $U^1$, V, W, $R^1$, $R^2$, $R^3$, $R^5$, $R^6$, m, k, n, p, and q are defined as those of the aforesaid compound of formula (A).

In some embodiments, the aforesaid compound of formula (I) has a structure represented by formula (II), Formula (II)

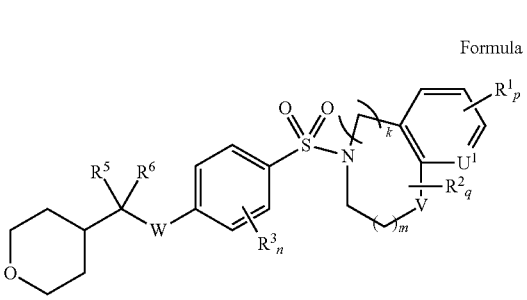

wherein IP, V, W, $R^1$, $R^2$, $R^3$, $R^5$, $R^6$, m, k, n, p, and q are defined as those of the aforesaid compound of formula (I).

In some embodiments, the aforesaid compound of formula (A) has a structure represented by formula (III), Formula (III)

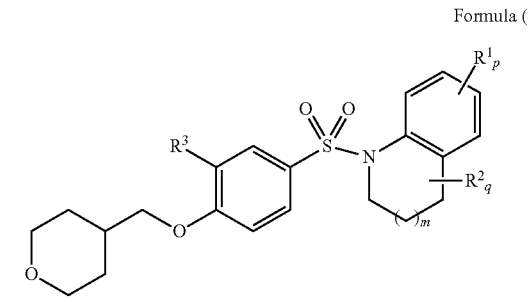

wherein $R^1$, $R^2$, $R^3$, m, p, and q are defined as those of the aforesaid compound of formula (A).

In some embodiments, the aforesaid compound of formula (I) has a structure represented by formula (III), Formula (III)

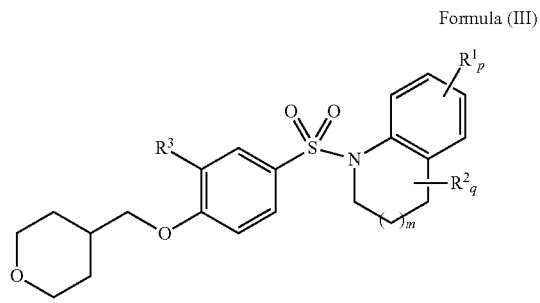

wherein $R^1$, $R^2$, $R^3$, m, p, and q are defined as those of the aforesaid compound of formula (I).

In some embodiments, the aforesaid compound of formula (A) has a structure represented by formula (IV), Formula (IV)

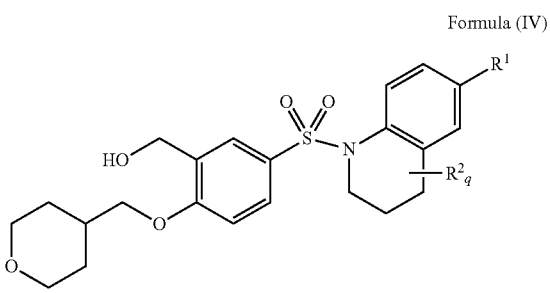

wherein $R^1$, $R^2$, and q are defined as those of the aforesaid compound of formula (A).

In some embodiments, the aforesaid compound of formula (I) has a structure represented by formula (IV), Formula (IV)

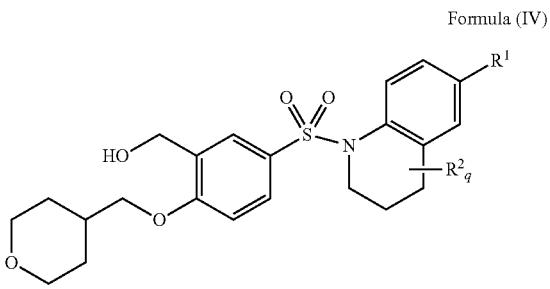

wherein $R^1$, $R^2$, and q are defined as those of the aforesaid compound of formula (I).

In some embodiments, the aforesaid compound of formula (A) has a structure represented by formula (V), Formula (V)

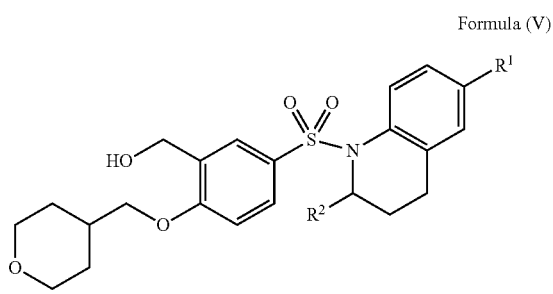

wherein R¹ and R² are defined as those of the aforesaid compound of formula (A).

In some embodiments, the aforesaid compound of formula (I) has a structure represented by formula (V), Formula (V)

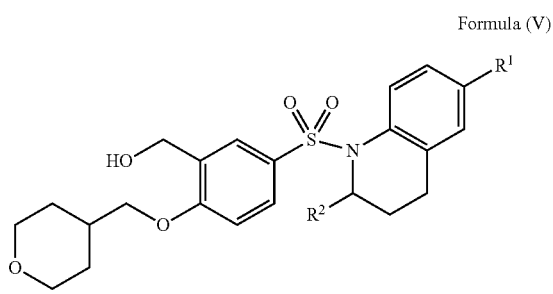

wherein R¹ and R² are defined as those of the aforesaid compound of formula (I).

In some embodiments, the compound related in the present disclosure is selected from the following compounds or the pharmaceutically acceptable salts thereof:

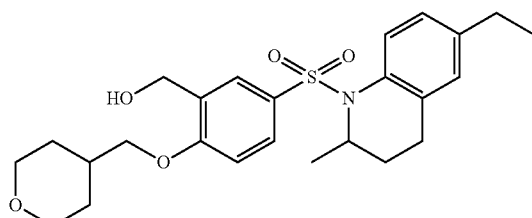

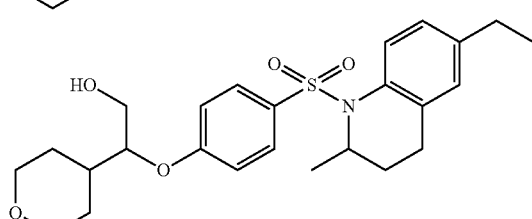

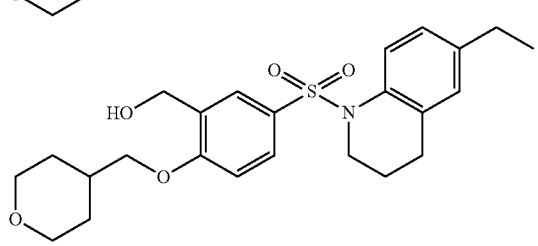

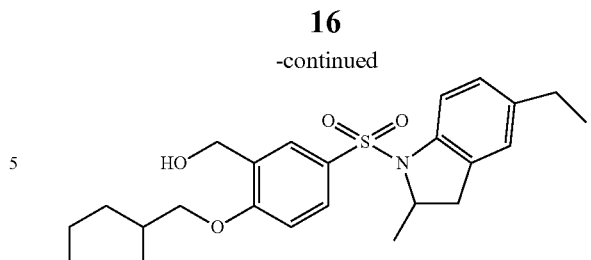

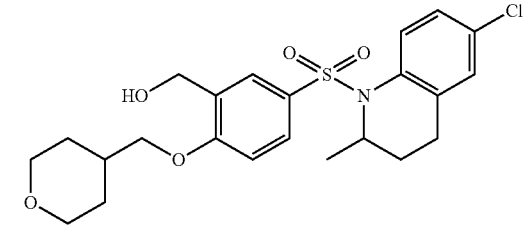

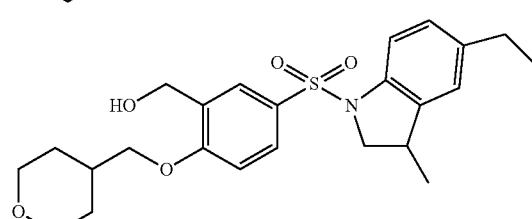

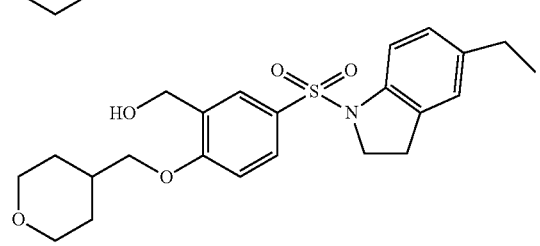

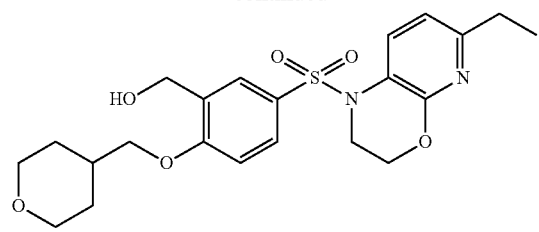
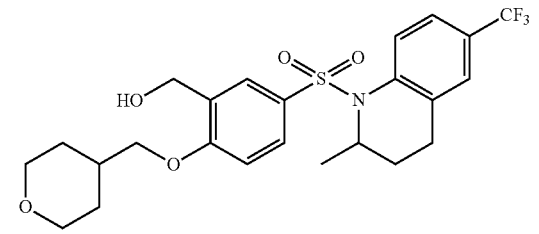
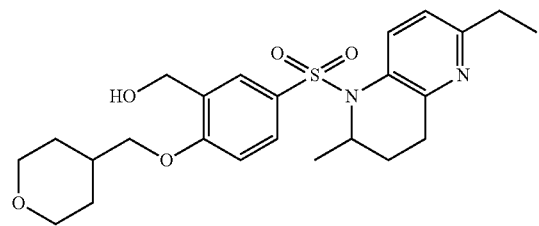
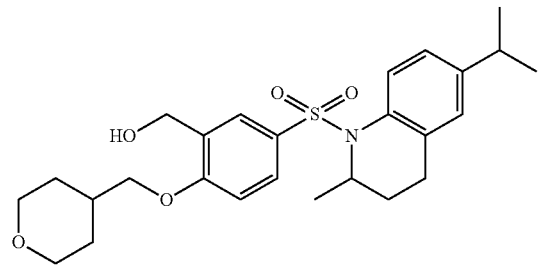
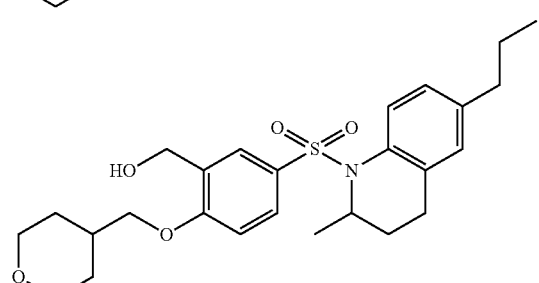
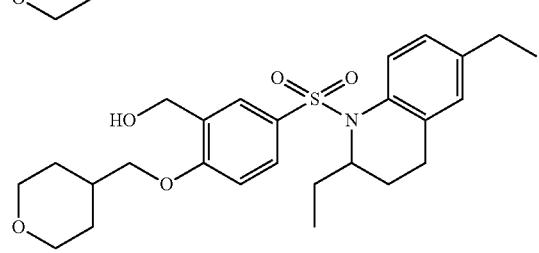
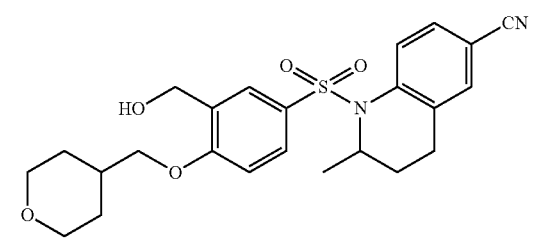
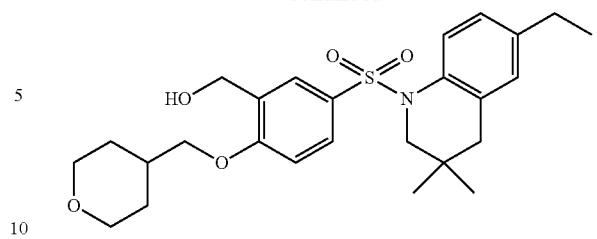
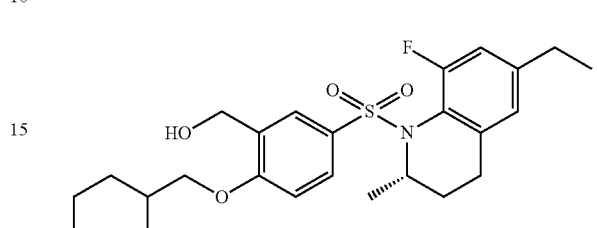
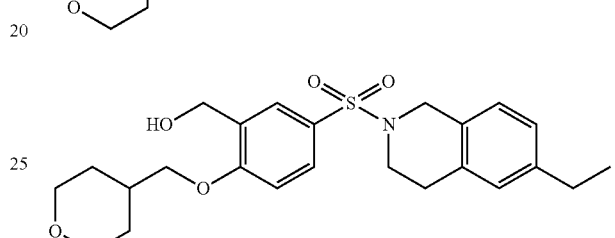
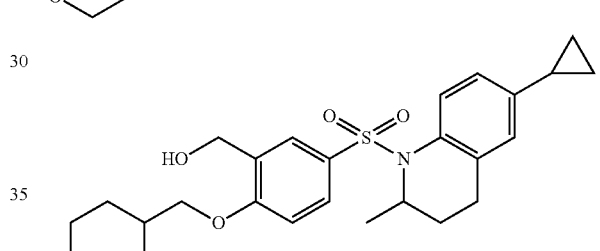
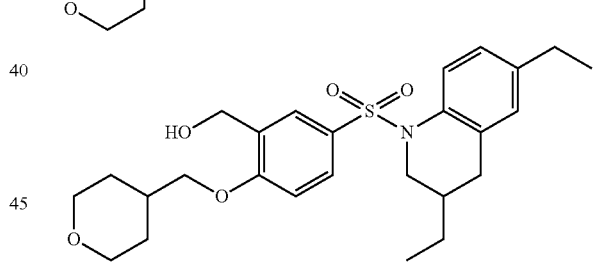
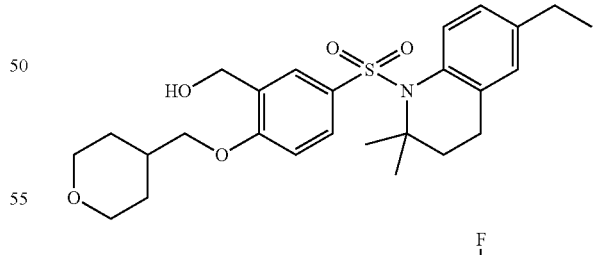
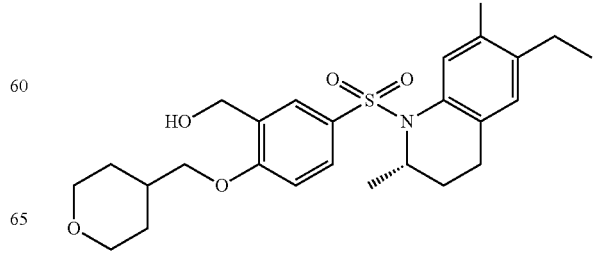

-continued
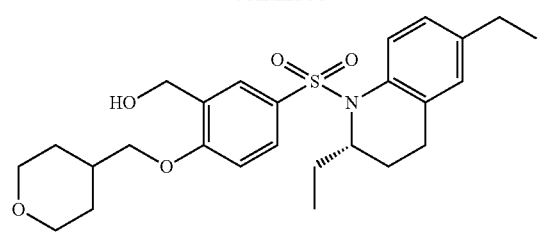
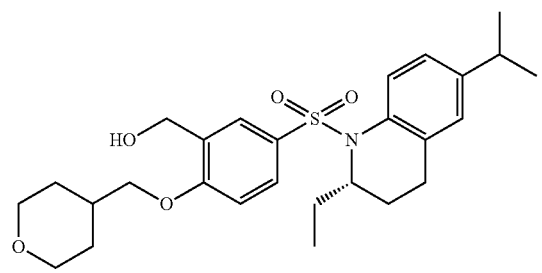
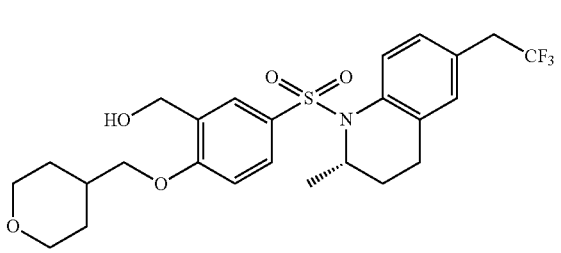
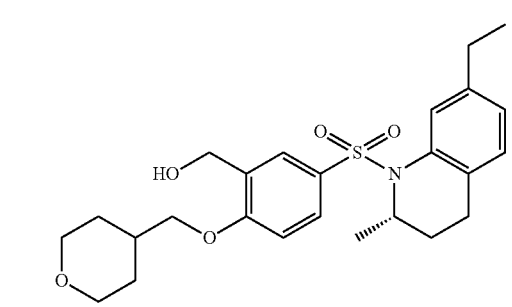
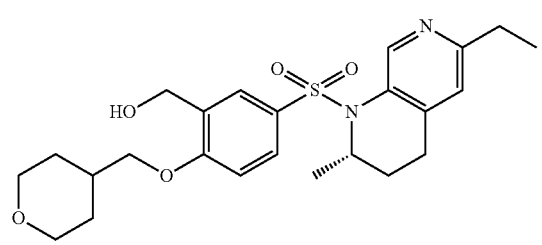
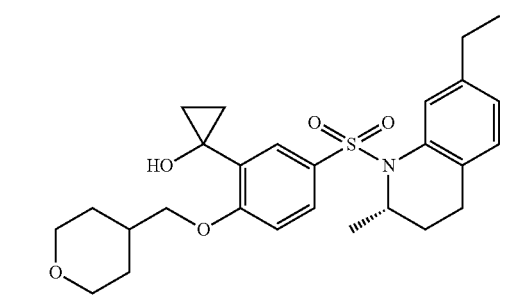
-continued
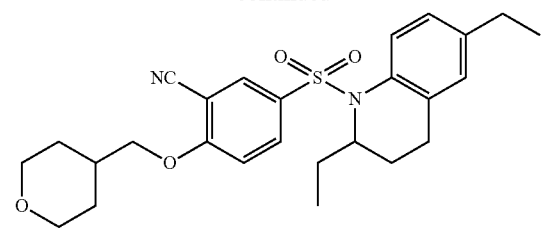
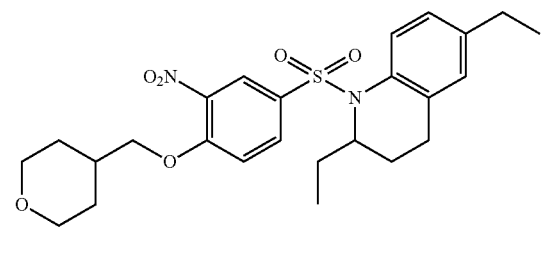
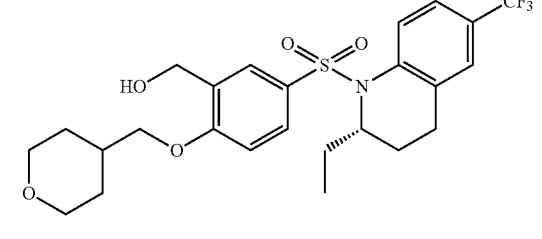
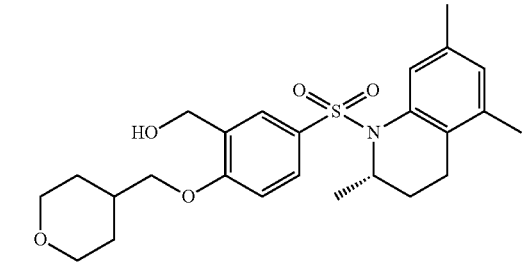
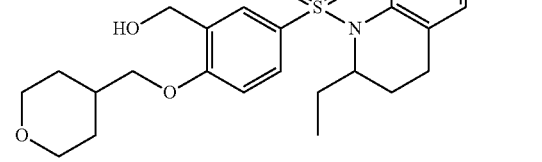
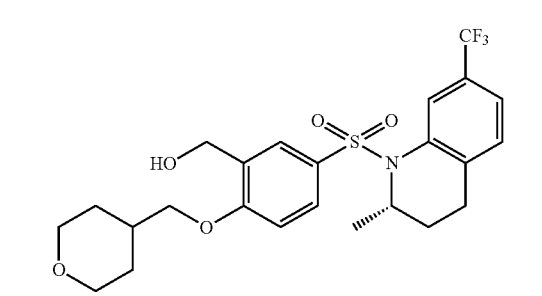

21
-continued
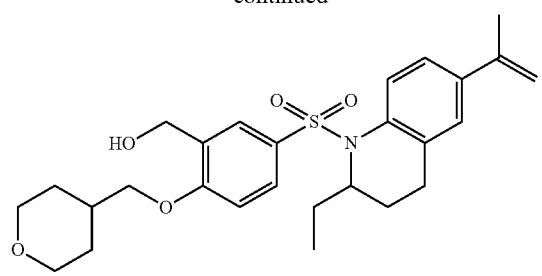
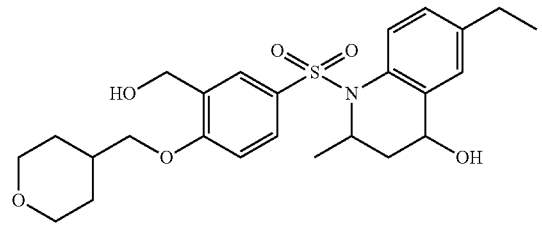
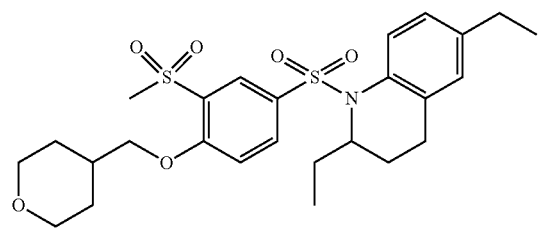
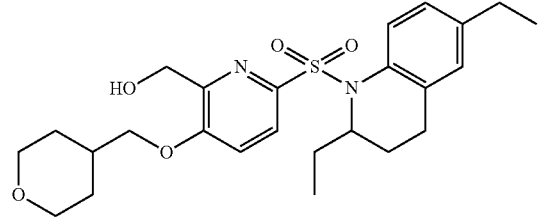
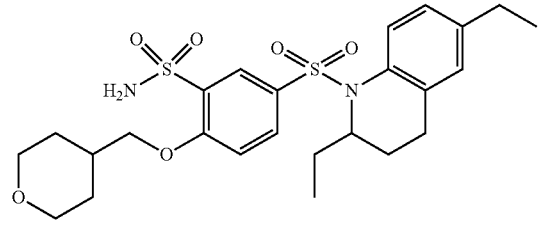
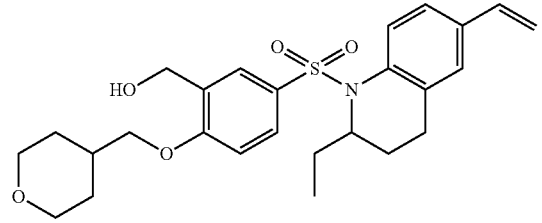
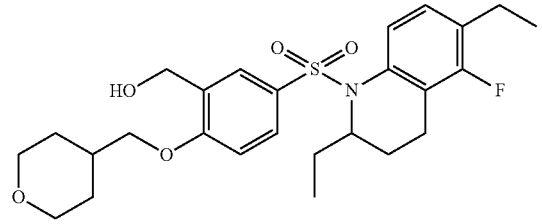
22
-continued
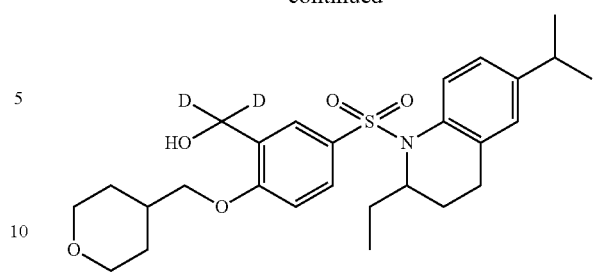
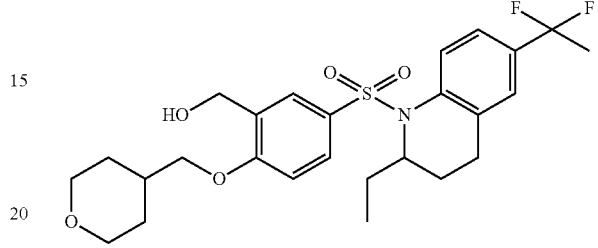
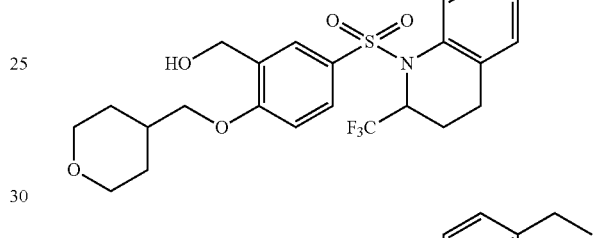
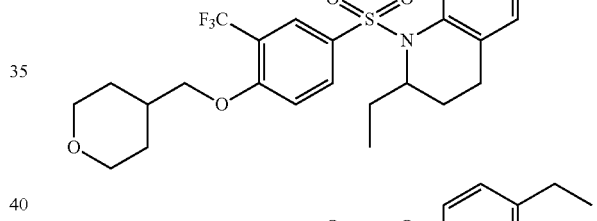
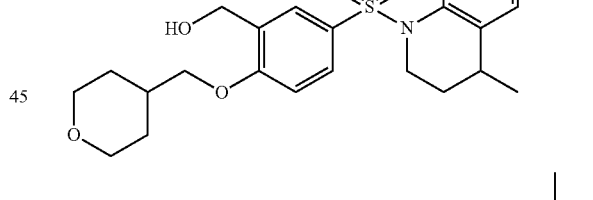
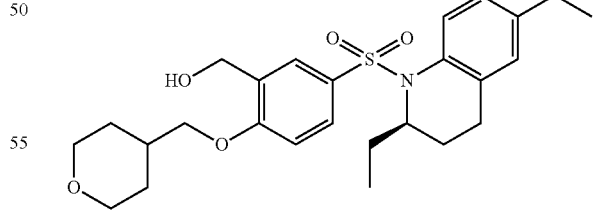
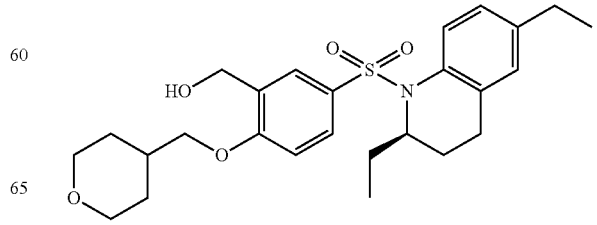

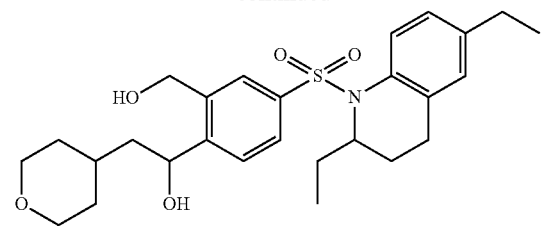
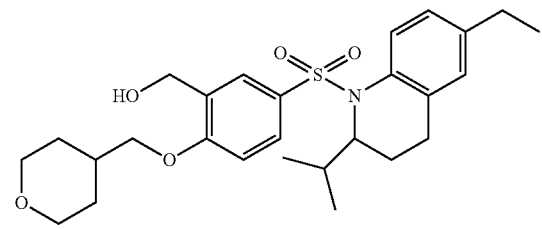
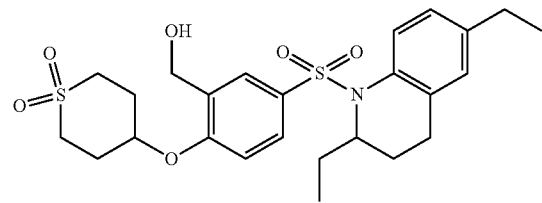
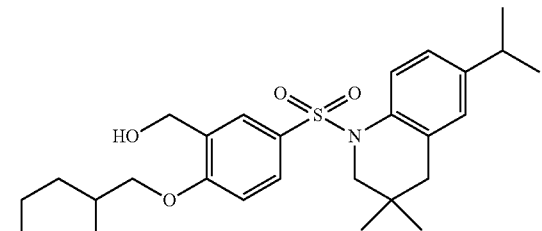
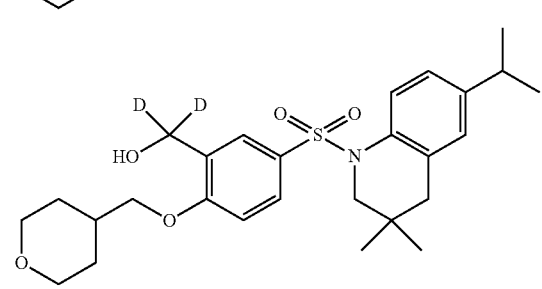
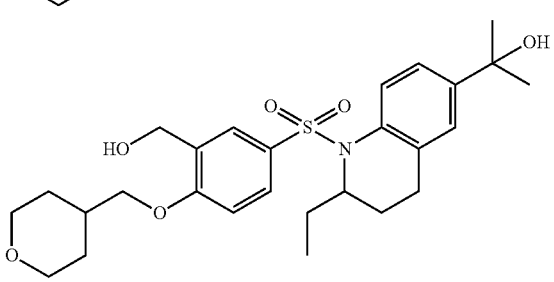
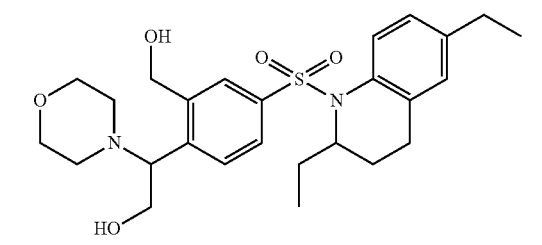
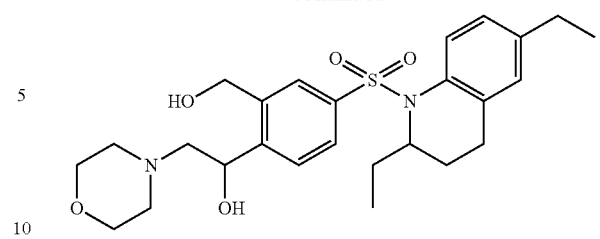
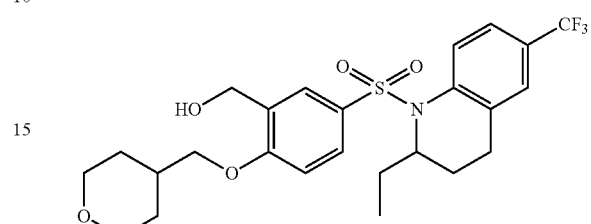
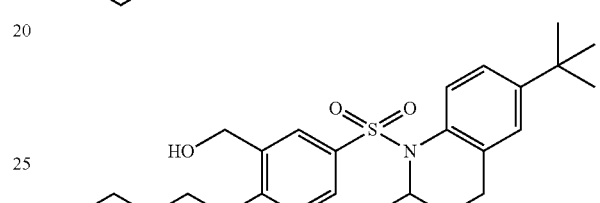
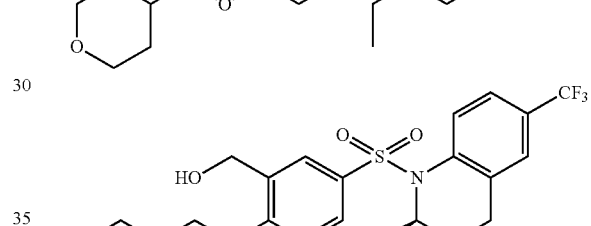
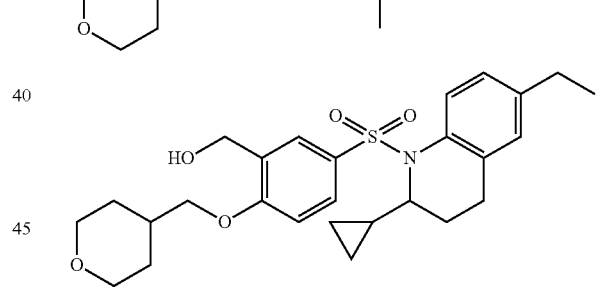
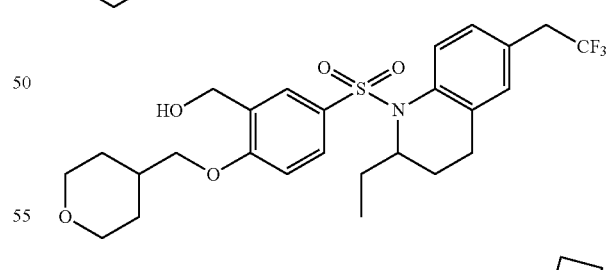
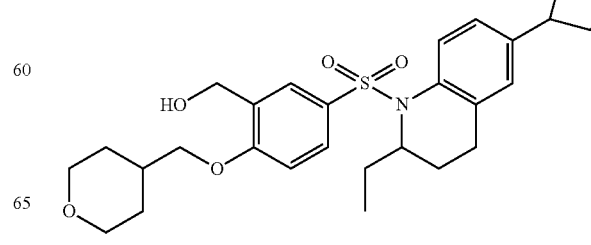

25
-continued
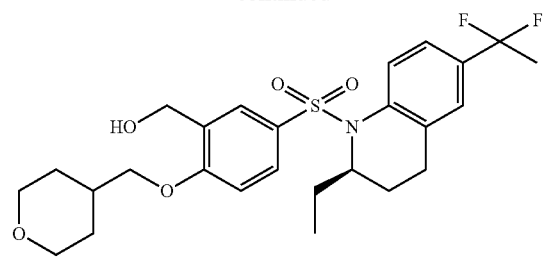
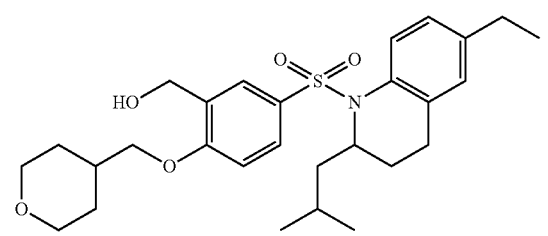
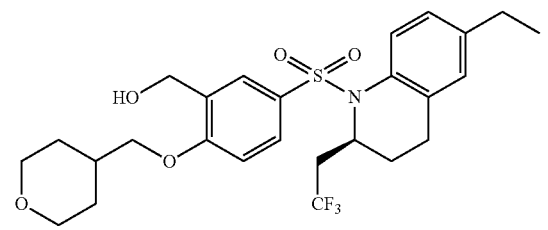
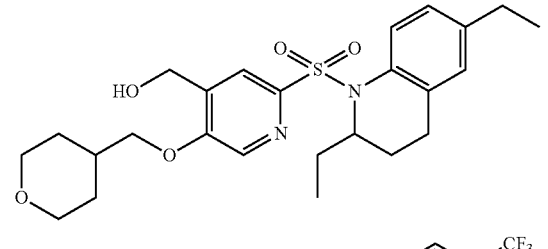
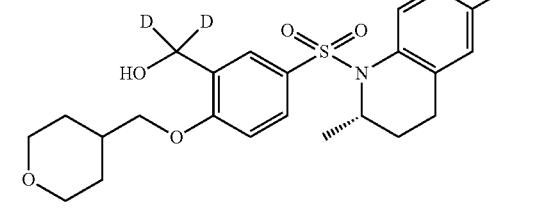
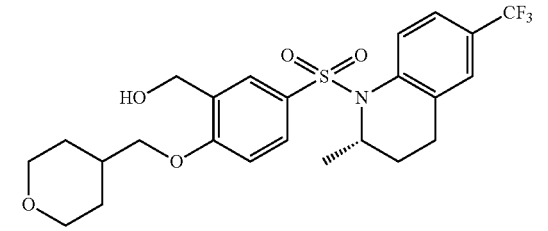
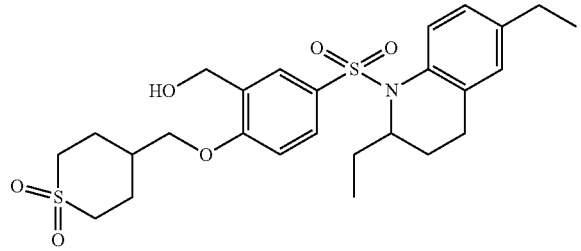
26
-continued
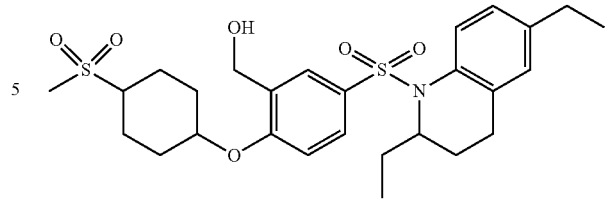
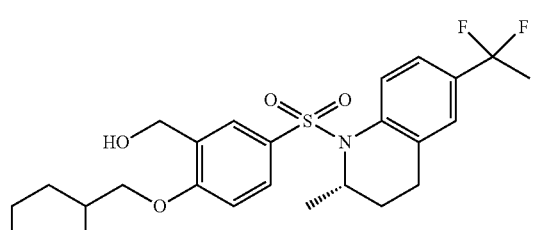
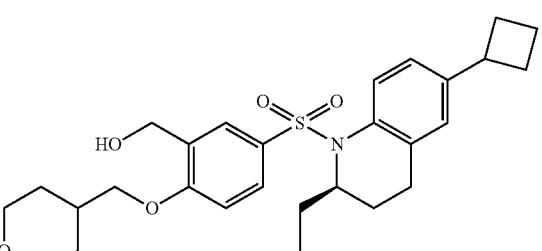
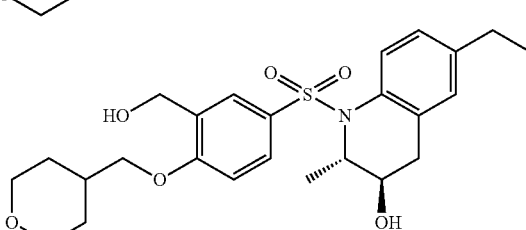
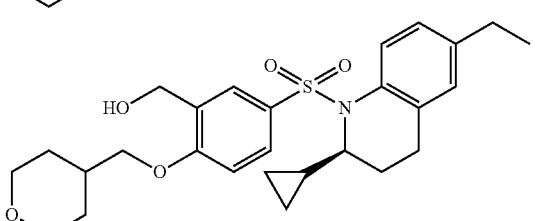
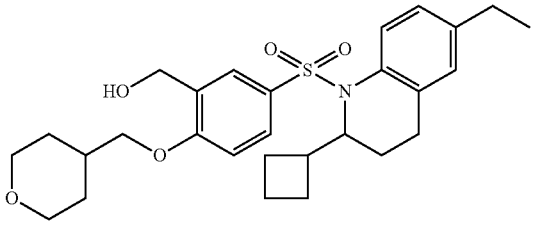
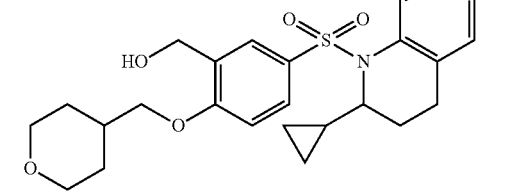

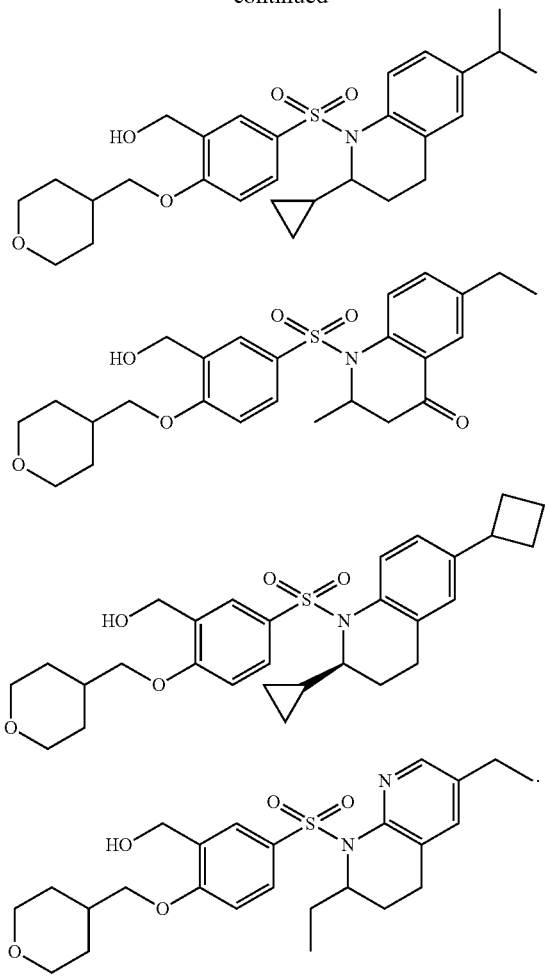

In another aspect, the present disclosure relates to a pharmaceutical composition comprising the compound of formula (A), the compound of formula (a), the compound of formula (I), the compound of formula (II), the compound of formula (III), the compound of formula (IV) or the compound of formula (V) of the present disclosure, or a pharmaceutically acceptable salt thereof.

In some embodiments, the pharmaceutical composition comprises a therapeutically effective amount of the following substances: the compound of formula (A), the compound of formula (a), the compound of formula (I), the compound of formula (II), the compound of formula (III), the compound of formula (IV) or the compound of formula (V) of the present disclosure, or a pharmaceutically acceptable salt thereof.

In some other embodiments, the pharmaceutical composition of the present disclosure further comprises a pharmaceutically acceptable excipient.

The pharmaceutical composition of the present disclosure may be prepared by combining the compound of the present disclosure with an appropriate pharmaceutically acceptable excipient. For example, the pharmaceutical composition may be formulated into a solid, semi-solid, liquid or gaseous preparation, such as a tablet, a pill, a capsule, a powder, a granule, an ointment, an emulsion, a suspension, a suppository, an injection, an inhalant, a gel, a microsphere, and an aerosol.

Typical routes of administering the compound of the present disclosure, or a pharmaceutically acceptable salt thereof, or a pharmaceutical composition thereof include, but are not limited to, oral, rectal, topical, inhalation, parenteral, sublingual, intravaginal, intranasal, intraocular, intraperitoneal, intramuscular, subcutaneous, and intravenous administration.

The pharmaceutical composition of the present disclosure may be manufactured by the methods generally known in the art, e.g., a conventional mixing method, a dissolution method, a granulating method, a dragee-making method, a pulverization method, an emulsification method, a freeze-drying method, etc.

In some embodiments, the pharmaceutical composition is in an oral dosage form. As for oral administration, the pharmaceutical composition may be formulated by mixing an active compound with a pharmaceutically acceptable excipient well known in the art. These excipients enable the compounds of the present disclosure to be formulated into a tablet, a pill, a lozenge, a dragee, a capsule, a liquid, a gel, a syrup, a suspension, and the like, which are used for oral administration to a patient.

A solid composition for oral administration may be prepared by a conventional mixing method, a filling method or a tabletting method. For example, the solid composition for oral administration may be obtained by the method as described below. In said method, the active compound is mixed with a solid excipient, the resulting mixture is grinded optionally, other suitable excipients are added if necessary, and then this mixture is processed into granules to obtain tablets or the cores of dragees. Suitable excipients include, but are not limited to, a binder, a diluent, a disintegrant, a lubricant, a glidant, a sweetener, a flavoring agent, or the like.

The pharmaceutical composition is also applicable to parenteral administration, for example, in a suitable unit dosage form of a sterile solution, a suspension or a lyophilized product.

In another aspect, the present disclosure relates to a method for treating a RORγ receptor-mediated disease in a mammal, comprising administering the compound of formula (A), the compound of formula (a), the compound of formula (I), the compound of formula (II), the compound of formula (III), the compound of formula (IV) or the compound of formula (V), or a pharmaceutically acceptable salt thereof, or a pharmaceutical composition thereof in a therapeutically effective amount to a mammal, preferably human, in need thereof. In some embodiments, said RORγ receptor is RORγt receptor.

In all of the methods for administering the compound of formula (A), the compound of formula (a), the compound of formula (I), the compound of formula (II), the compound of formula (III), the compound of formula (IV) or the compound of formula (V) described herein, the daily dose is from 0.01 to 100 mg/kg body weight, preferably from 0.05 to 50 mg/kg body weight, and more preferably from 0.1 to 5 mg/kg body weight, in the form of a single dose or divided doses.

In another aspect, the present disclosure relates to use of the compound of formula (A), the compound of formula (a), the compound of formula (I), the compound of formula (II), the compound of formula (III), the compound of formula (IV) or the compound of formula (V), or a pharmaceutically acceptable salt thereof, or a pharmaceutical composition thereof in the preparation of a medicament for preventing or treating a RORγ receptor-mediated disease. In some embodiments, said RORγ receptor is RORγt receptor.

In another aspect, the present disclosure relates to a compound of formula (A), a compound of formula (a), a compound of formula (I), a compound of formula (II), a compound of formula (III), a compound of formula (IV) or a compound of formula (V), or a pharmaceutically acceptable salt thereof for preventing or treating a RORγ receptor-mediated disease. In some embodiments, said RORγ receptor is RORγt receptor.

Said RORγ receptor-mediated disease includes immune-related diseases such as tumors and arthritis.

The compounds of the present disclosure may be prepared by a variety of synthesis methods well known to a person skilled in the art, including the specific embodiments listed below, the embodiments formed by combining said specific embodiments with other chemical synthesis methods, and the equivalent alternatives well known to a person skilled in the art. Preferred embodiments include, but are not limited to, the Examples of the present disclosure.

The chemical reactions of the specific embodiments of the present disclosure are accomplished in a suitable solvent, which must be suitable for the chemical change(s) of the present disclosure as well as the reagents and materials required for the same. In order to obtain the compounds of the present disclosure, a person skilled in the art sometimes needs to modify or select synthesis steps or reaction schemes based on the existing embodiments.

An important consideration in the planning of a synthetic route in this field is selecting a suitable protecting group for the reactive functional group (such as the amino group in the present disclosure). For example, refer to "Greene's Protective Groups in Organic Synthesis (4$^{th}$ Ed)", Hoboken, N.J.: John Wiley & Sons, Inc. All references cited in the present disclosure are incorporated herein in their entirety.

In some embodiments of the present disclosure, when R$^3$ is hydroxymethyl, the compound represented by formula (III) may be prepared and obtained via the synthetic route as shown below:

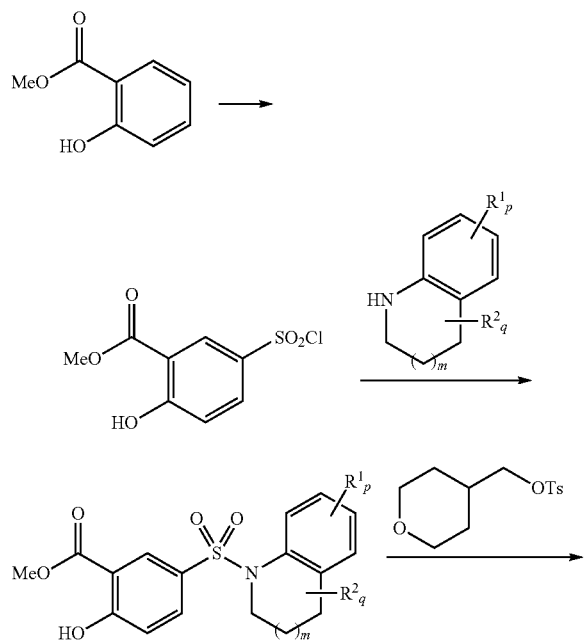

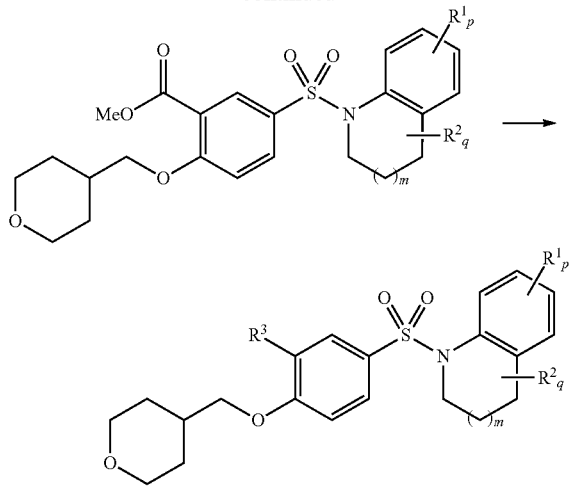

wherein R$^1$, R$^2$, m, p and q are defined as those of the aforesaid compound of formula (III).

Definitions

Unless otherwise specified, the following terms used in the present disclosure have the following meanings. A specific term, if not particularly defined, should not be considered as uncertain or ambiguous, but should be understood as its ordinary meaning in the art. When a trade name appears herein, it is intended to refer to the corresponding commodity thereof or an active ingredient thereof.

The term "substituted" means that any one or more of the hydrogen atom(s) on a specific atom is substituted with a substituent, as long as the valence of the specific atom is normal and the substituted compound is stable. When a substituent is oxo (i.e., =O), it means that two hydrogen atoms are substituted, and oxo does not occur on an aromatic group.

The term "optional" or "optionally" means that the event or situation described later may or may not occur, and the description includes the case where the event or situation occurs and the case where the event or situation does not occur. For example, the case where an ethyl is "optionally" substituted with halogen indicates that the ethyl may be unsubstituted (CH$_2$CH$_3$), mono-substituted (e.g. CH$_2$CH$_2$F), poly-substituted (e.g. CHFCH$_2$F, CH$_2$CHF$_2$, etc.), or fully substituted (CF$_2$CF$_3$). It is understandable to a person skilled in the art that, for any group containing one or more substituents, no substitution or substitution pattern that is sterically impossible and/or cannot be synthesized is incorporated.

C$_m$-C$_n$ herein means that the number of the carbon atom(s) in this moiety is an integer in the given range. For example, "C$_1$-C$_6$" means that this group may have one carbon atom, two carbon atoms, three carbon atoms, four carbon atoms, five carbon atoms, or six carbon atoms.

When any variable (such as R) appears more than once in the composition or structure of a compound, its definition in each case is independent. Therefore, for example, if a group is substituted with two Rs, each R has an independent option; as another example, when t in the structural unit

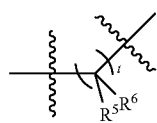

is larger than or equal to 2, le and $R^2$ in each repeating unit have an independent option; and as another example, when n in the structural unit

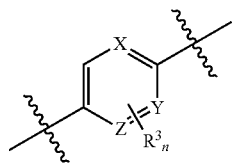

is larger than or equal to 2, each $R^3$ has an independent option.

$R^1$ group herein is a group attached to an aromatic ring; and $R^2$ group is a group attached to an aliphatic ring.

The term "halo" or "halogen" refers to fluorine, chlorine, bromine, and iodine.

The term "hydroxyl" refers to the —OH group.
The term "cyano" refers to the —CN group.
The term "amino" refers to the —NH$_2$ group.
The term "nitro" refers to the —NO$_2$ group.
The term "2-hydroxyprop-2-yl" refers to

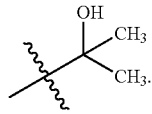 [SMILES: *C(C)(C)O]

The term "propen-2-yl" refers to

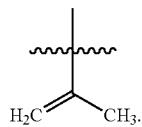

The term "CH(OH)" refers to

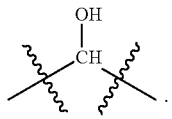 [SMILES: *C(*)O]

The term "hydroxymethyl" refers to —CH$_2$OH.

The term "alkyl" refers to a hydrocarbon group represented by the general formula $C_nH_{2n+1}$. The alkyl may be linear or branched. For example, the term "$C_1$-$C_6$ alkyl" refers to an alkyl group containing 1 to 6 carbon atoms (e.g., methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). Similarly, the alkyl moieties (i.e., alkyl) of alkoxy, alkylamino, dialkylamino, alkylsulfonyl, and alkylsulphanyl have the same meaning as described above.

The term "alkenyl" refers to a linear or branched unsaturated aliphatic hydrocarbon group consisting of carbon atom(s) and hydrogen atoms, which has at least one double bond. Non-limiting examples of alkenyl include, but are not limited to, vinyl, 1-propenyl, 2-propenyl, 1-butenyl, isobutenyl, 1,3-butadienyl, and the like.

The term "alkynyl" refers to a linear or branched unsaturated aliphatic hydrocarbon group consisting of carbon atom(s) and hydrogen atom(s), which has at least one triple bond. Non-limiting examples of alkynyl include, but are not limited to, ethynyl (—C≡CH), 1-propynyl (—C≡C—CH$_3$), 2-propynyl (—CH$_2$—C≡CH), 1,3-butadiynyl (—C≡CC≡CH), and the like.

The term "alkoxy" refers to —O-alkyl.

The term "cycloalkane" refers to a carbocyclic ring that is fully saturated and may exist as a monocyclic ring, a bridged ring or a spiro ring. Unless otherwise indicated, the carbocyclic ring is generally a 3- to 10-membered ring, a 3- to 6-membered ring, a 3- to 5-membered ring, or a 3- to 4-membered ring. Non-limiting examples of cycloalkyl include, but are not limited to, cyclopropyl, cyclobutyl, cyclopentyl, cyclohexyl, bicyclo[2.2.2]octyl, adamantyl, and the like.

The term "heterocycloalkyl" refers to a cyclic group that is fully saturated and may exist as a monocyclic ring, a bridged ring or a spiro ring. Unless otherwise indicated, the heterocyclic ring is generally a 3- to 7-membered ring containing 1 to 3 heteroatoms (preferably 1 or 2 heteroatoms) independently selected from sulfur, oxygen, and/or nitrogen. Examples of 3-membered heterocycloalkyl include, but are not limited to, oxiranyl, thiiranyl, and aziranyl; non-limiting examples of 4-membered heterocycloalkyl include, but are not limited to, azetidinyl, oxetanyl, and thietanyl; examples of 5-membered heterocycloalkyl include, but are not limited to, tetrahydrofuryl, tetrahydrothienyl, pyrrolidinyl, isoxazolidinyl, oxazolidinyl, isothiazolidinyl, thiazolidinyl, imidazolidinyl, and tetrahydropyrazolyl; examples of 6-membered heterocycloalkyl include, but are not limited to, piperidinyl, tetrahydropyranyl, tetrahydrothiapyranyl, morpholinyl, piperazinyl, 1,4-thioxanyl, 1,4-dioxanyl, thiomorpholinyl, 1,3-dithianyl, and 1,4-dithianyl; and examples of 7-membered heterocycloalkyl include, but are not limited to, azepanyl, oxepanyl, and thiepanyl. A monocyclic heterocycloalkyl group having 5 or 6 ring atoms is preferred.

The term "treating" means administering a compound or a drug formulation described in the present disclosure to prevent, ameliorate or eliminate a disease or one or more symptoms associated with the disease, and includes:

(i) preventing a disease or a disease state from occurring in a mammal, especially when such mammal is susceptible to the disease state but has not yet been diagnosed as having the disease state;

(ii) inhibiting a disease or a disease state, i.e., restraining its development; and (iii) alleviating a disease or a disease state, i.e., causing the regression of the disease or the disease state.

The term "therapeutically effective amount" means the using amount of the compound of the present disclosure for use in: (i) treating or preventing a specific disease, condition or disorder, (ii) alleviating, ameliorating or eliminating one or more symptoms of a specific disease, condition or disorder, or (iii) preventing or delaying the onset of one or more symptoms of a specific disease, condition or disorder described herein. The amount of the compound of the present disclosure that constitutes a "therapeutically effective amount" varies depending on the compound, the disease state and its severity, the mode of administration, and the age of the mammal to be treated, but may be routinely determined by those skilled in the art according to their knowledge and the contents of the present disclosure.

The term "pharmaceutically acceptable" is intended to refer to those compounds, materials, compositions and/or dosage forms which, within the scope of reliable medical judgment, are suitable for use in contact with the tissues of human beings and animals without excessive toxicity, irritation, allergic response, or other problems or complications, and commensurate with a reasonable benefit/risk ratio.

As a pharmaceutically acceptable salt, for example, metal salts, ammonium salts, salts formed with organic bases, salts formed with inorganic acids, salts formed with organic acids, salts formed with basic or acidic amino acids, and the like may be mentioned.

The term "pharmaceutical composition" refers to a mixture of one or more compounds of the present disclosure or a salt thereof and a pharmaceutically acceptable excipient. The purpose of a pharmaceutical composition is to be beneficial for the administration of a compound of the present disclosure to an organism.

The term "pharmaceutically acceptable excipient" refers to those excipients that have no significant irritating effect on an organism and do not impair the bioactivity and properties of the active compound. Suitable excipients are those well known to one skilled in the art, such as a carbohydrate, a wax, a water-soluble and/or water-swellable polymer, a hydrophilic or hydrophobic material, a gelatin, an oil, a solvent, water, and the like.

The wording "comprise" and the variants thereof, such as "comprises" or "comprising", should be understood as an open and non-exclusive meaning, namely, "including but not limited to".

In the present disclosure, unless specifically defined, the solvent ratio of the eluent of column chromatography is a volume ratio.

In the present disclosure, unless specifically defined, the meanings of the abbreviations used herein are as shown below.

min refers to minute;
h refers to hour;
d refers to day;
° C. means Celsius;
V:V refers to a volume ratio;
DCM refers to dichloromethane;
KI refers to potassium iodide; EA or EtOAc refers to ethyl acetate;
PE refers to petroleum ether;
MeOH refers to methanol;
THF refers to tetrahydrofuran;
$SOCl_2$ refers to thionyl chloride;
DMF refers to N,N-dimethylformamide;
DMSO refers to dimethyl sulfoxide;
TEA refers to triethylamine;
DIAD refers to diisopropyl azodicarboxylate;
$PPh_3$ refers to triphenylphosphine;
$Pd(PPh_3)_4$ refers to tetrakis(triphenylphosphine)palladium;
$Pd(OAc)_2$ refers to palladium acetate;
CuI refers to cuprous iodide;
TFA refers to trifluoroacetic acid;
$NaBH_4$ refers to sodium borohydride;
LiHMDS refers to sodium hexamethyldisilazide;
NBS refers to N-bromosuccinimide;
NCS refers to N-chlorosuccinimide;
NIS refers to N-iodosuccinimide;

LCMS refers to liquid chromatography-tandem mass spectrometry;
$Cs_2CO_3$ refers to cesium carbonate;
NaH refers to sodium hydride;
TLC refers to thin layer chromatography;
M refers to a molar concentration unit, i.e., mol/L, for example, 2 M refers to 2 mol/L;
mM refers to a molar concentration unit, i.e., mmol/L, for example, 2 mM refers to 2 mmol/L;
N refers to the equivalent concentration, for example, 1 N HCl refers to hydrochloric acid with a concentration of 1 mol/L; 2 N NaOH refers to sodium hydroxide with a concentration of 2 mol/L;
Ts refers to p-toluenesulfonyl;
TsCl refers to p-toluenesulfonyl chloride;
Et refers to ethyl;
Me refers to methyl;
Ac refers to acetyl;
DIPEA refers to N,N-diisopropylethylamine;
LAH or $LiAlH_4$ refers to lithium aluminum hydride;
PCC refers to pyridinium chlorochromate;
TMSCN refers to trimethylsilyl cyanide;
MTBE refers to methyl tert-butyl ether;
DIBAL-H refers to diisobutylaluminum hydride;
TBAI refers to tetrabutylammonium iodide;
$NaBH_3CN$ or $Na(CN)BH_3$ refers to sodium cyanoborohydride;
TFAA refers to trifluoroacetic anhydride;
AIBN refers to azobisisobutyronitrile;
SPhos refers to 2-dicyclohexylphosphino-2',6'-dimethoxybiphenyl;
DMA refers to N,N-dimethylacetamide;
$K_3PO_4$ refers to tripotassium phosphate;
$LiOH.H_2O$ refers to lithium hydroxide monohydrate;
$Et_2NH.HCl$ refers to diethylamine hydrochloride.

The intermediate(s) and the compound(s) of the present disclosure may also exist in different tautomeric forms, and all of such forms are included within the scope of the present disclosure. The term "tautomer" or "tautomeric form" refers to structural isomers with different energies, which are interconvertible via a low energy barrier. For example, a proton tautomer (also referred to as prototropic tautomer) includes interconversion via the migration of a proton, such as keto-enol isomerization and imine-enamine isomerization. A specific example of a proton tautomer is an imidazole moiety, wherein a proton may migrate between two cyclic nitrogen atoms. A valence tautomer includes interconversion via the recombination of some of the bonding electrons. Non-limiting examples of the tautomer include, but are not limited to and -continued

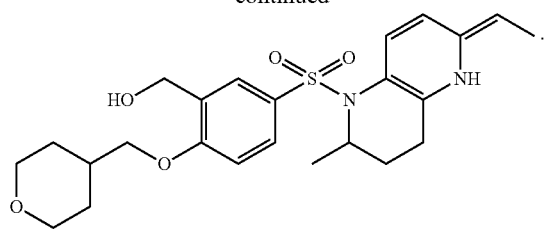

The present disclosure further comprises the isotopically labeled compounds of the present disclosure, wherein the compounds are as same as those described herein, but one or more atoms thereof are replaced with atom(s) having an atomic weight or mass number different from that normally found in nature. Examples of the isotopes that may be incorporated into the compounds of the present disclosure include the isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$ $^{32}P$, $^{35}S$, $^{18}F$, $^{123}I$, $^{125}I$, and $^{36}Cl$.

Certain isotopically labeled compounds of the present disclosure (such as those labeled with $^{3}H$ and $^{14}C$) may be used in the tissue distribution analysis of a compound and/or a substrate. Tritiated isotope (i.e., $^{3}H$) and carbon-14 (i.e., $^{14}C$) isotope are particularly preferred due to their ease of preparation and detectability. Positron-emitting isotopes, such as $^{15}O$, $^{13}N$, $^{11}C$, and $^{18}F$, may be used in positron emission tomography (PET) studies to determine the occupancy of a substrate. Isotopically labeled compounds of the present disclosure are generally prepared by replacing a reagent unlabeled by an isotope with an isotopically labeled reagent via the following procedures similar to those disclosed in the embodiments and/or Examples below.

In addition, substitution with a heavier isotope such as deuterium (i.e., $^{2}H$) may provide certain therapeutic advantages (e.g., a prolonged half-life in vivo or a reduced demand of dose) resulting from higher metabolic stability, and thus being possibly preferred in certain cases, wherein the deuterium substitution may be partial or complete, and a partial deuterium substitution means that at least one hydrogen is substituted with at least one deuterium. Non-limiting examples of deuterated compounds include, but are not limited to

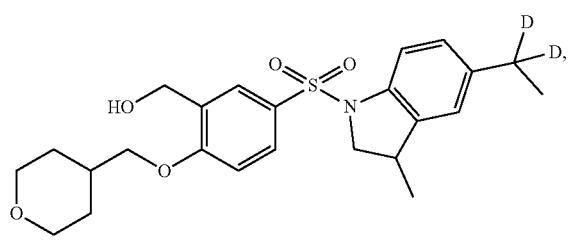

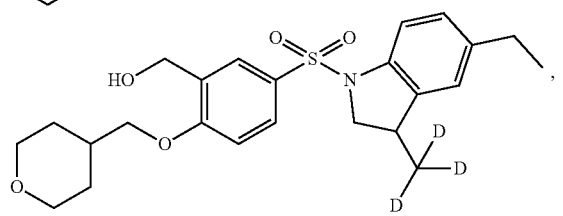

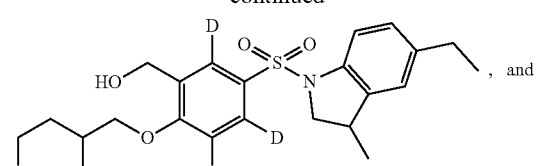

, and

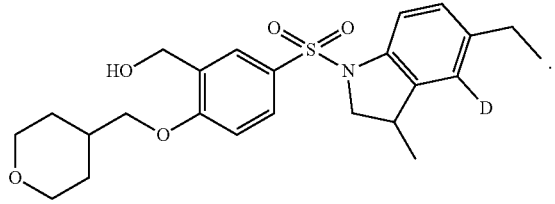

.

The compounds of the present disclosure may be asymmetric, for example, having one or more stereoisomers. Unless otherwise specified, all stereoisomers, e.g., enantiomers and diastereoisomers, are included. The compound(s) containing asymmetric carbon atom(s) of the present disclosure may be isolated in an optically active pure form or in a racemic form. The optically active pure form may be resolved from a racemic mixture or be synthesized using a chiral starting material or a chiral reagent. Non-limiting examples of the stereoisomer include, but are not limited to:

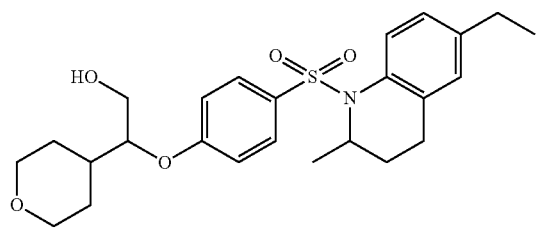

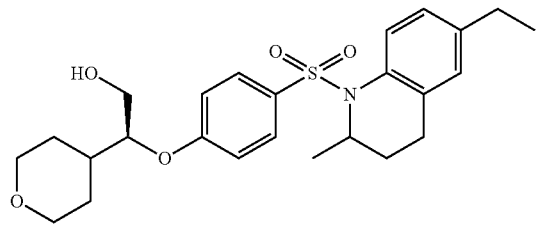

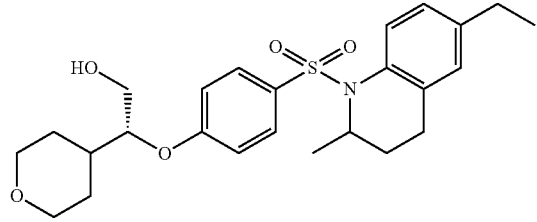

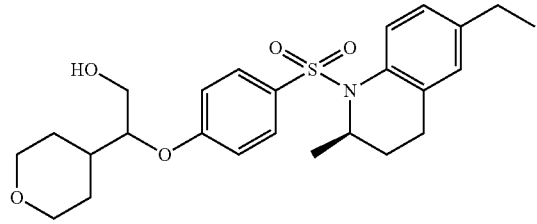

37
-continued

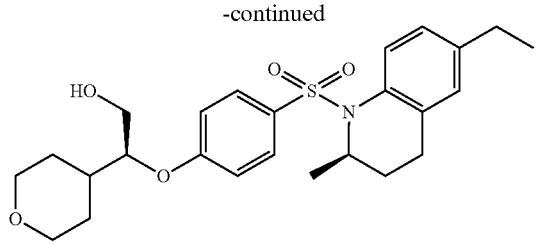

DETAILED DESCRIPTION

The present disclosure is described in detail below by Examples, but it does not imply any disadvantageous limitation on the present disclosure. The present disclosure has been described in detail herein, and its specific embodiments are also disclosed therein. Various changes and improvements made to the specific embodiments of the present disclosure will be apparent to a person skilled in the art without departing from the spirit and scope of the present disclosure.

38

Example 1

Synthesis of (5-((6-ethyl-2-methyl-3,4-dihydroquinolin-1(2H)-yl)sulfonyl)-2-((tetrahydro-2H-pyran-4-yl)methoxy)phenyl)methanol

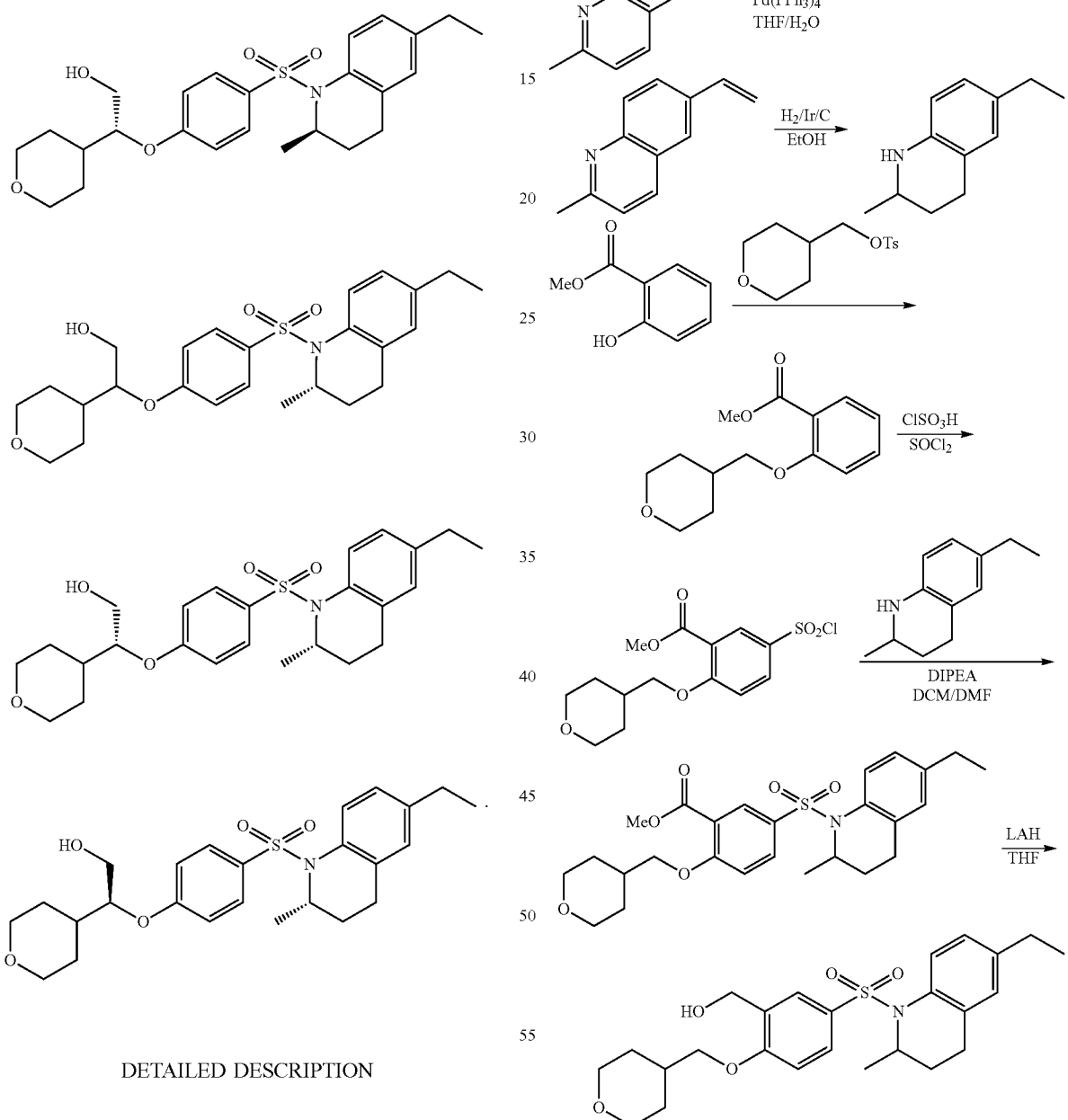

1.1 Synthesis of 6-vinyl-2-methylquinoline

A 100 mL single-necked flask was charged with 6-bromo-2-methylquinoline (2.0 g), 20 mL of THF was added to dissolve the former, followed by addition of potassium vinyltrifluoroborate (1.8 g), 200 mg of Pd(PPh$_3$)$_4$ and 5 mL of water. Under N$_2$ protection, the mixture was heated to 78° C. by an external bath and was stirred under reflux. After 10 h, TLC detection showed that the reaction of the raw materials was complete. The resulting mixture was filtered, 50 mL of water was added thereto, and the mixture was extracted three times with EA (20 mL×3). The organic phases were combined and washed with 50 mL of a saturated aqueous sodium chloride solution, dried over anhydrous sodium sulfate and filtered, and the filtrate was concentrated under reduced pressure to give 1.2 g of the title compound.

1.2 Synthesis of 6-ethyl-2-methyl-1,2,3,4-tetrahydroquinoline

A 100 mL hydrogenation autoclave was charged with 6-vinyl-2-methylquinoline (1.0 g), 15 mL of 95% ethanol was added to dissolve the former, and 89 mg of iridium on carbon was added. The mixture was purged with hydrogen gas three times. The system was pressurized to 0.8 MPa with hydrogen gas and heated to 70° C. by an external bath, and the mixture therein was stirred for 3 days. The reaction was complete as detected by TLC. The mixture was filtered, and the filtrate was concentrated under reduced pressure to give 1.05 g of the title compound.

1.3 Synthesis of methyl 2-((tetrahydro-2H-pyran-4-yl)methoxy)benzoate

A 100 mL single-necked flask was charged with methyl salicylate (2.0 g) and p-toluenesulfonate-4-methyl pyran (5.3 g), and 20 mL of DMF was added to dissolve the formers, followed by addition of potassium carbonate (3.6 g) and 10 mg of KI. The mixture was heated and stirred at 60° C. overnight. The reaction was complete as detected by TLC. 150 mL of water was added, and the mixture was extracted three times with EA (30 mL×3). The combined organic phases were washed with saturated aqueous sodium chloride solution, dried over anhydrous sodium sulfate and filtered, and the filtrate was concentrated under reduced pressure to give 2.5 g of the title compound.

1.4 Synthesis of methyl 5-chlorosulfonyl-2-((tetrahydro-2H-pyran-4-yl)methoxy)benzoate A 50 mL single-necked flask was charged with methyl 2-((tetrahydro-2H-pyran-4-yl) methoxy)benzoate (1.24 g), and 12 mL of SOCl$_2$ was added to dissolve the former, followed by addition of chlorosulfonic acid (1.2 g). The mixture was stirred at room temperature. The reaction was complete as monitored by TLC. The reaction solution was poured into 70 mL of ice water added with 20 mL of DCM and stirred. The resulting mixture was subjected to liquid-liquid separation. The aqueous phase was washed with DCM (20 mL×2). The combined organic phases were washed with saturated aqueous sodium chloride solution, dried over anhydrous sodium sulfate and filtered, and the filtrate was concentrated under reduced pressure to give 1.04 g of the title compound (HPLC purity: 61.2%).

1.5 Synthesis of methyl (5-(((6-ethyl-2-methyl-3,4-dihydroquinolin-1(2H)-yl)sulfonyl)-2-((tetrahydro-2H-pyran-4-yl)methoxy)phenyl)formate A 50 mL single-necked flask was charged with methyl 5-chlorosulfonyl-2-((tetrahydro-2H-pyran-4-yl)methoxy) benzoate (1.04 g) and 6-ethyl-2-methyl-1,2,3,4-tetrahydroquinoline (780 mg) prepared above, and 15 mL of DCM was added to dissolve the formers, followed by addition of DIPEA (775 mg) and 2 drops of DMF. The mixture was heated to 40° C. by an external bath and stirred overnight. The reaction was complete as detected by LC-MS. 20 mL of water was added, and the mixture was subjected to liquid-liquid separation. The aqueous phase was extracted with 20 mL of DCM. The combined organic phases were washed with saturated aqueous sodium chloride solution, dried over anhydrous sodium sulfate and filtered, and the filtrate was concentrated under reduced pressure to give 1.5 g of oil. The resulting product was purified by a column to give 490 mg of the title compound.

1.6 Synthesis of (5-(((6-ethyl-2-methyl-3,4-dihydroquinolin-1(2H)-yl)sulfonyl)-2-((tetrahydro-2H-pyran-4-yl)methoxy)phenyl)methanol A 25 mL single-necked flask was charged with methyl (5-(((6-ethyl-2-methyl-3,4-dihydroquinolin-1(2H)-yl)sulfonyl)-2-((tetrahydro-2H-pyran-4-yl)methoxy)phenyl)formate (240 mg) prepared above, and 6 mL of THF was added to dissolve the former, followed by addition of LiAlH$_4$ (130 mg). Under the protection of N$_2$, the mixture was stirred at room temperature for 2 days, and the reaction was complete as detected by LC-MS. 1 mL of 4 N NaOH aqueous solution was added to quench the reaction, and 15 mL of water and 10 mL of EA were added. The mixture was stirred and filtered by suction, and the filtrate was subjected to liquid-liquid separation. The aqueous phase was extracted with 10 mL of EA, the organic phases were combined, washed with saturated aqueous sodium chloride solution, dried over anhydrous sodium sulfate and filtered, and the filtrate was concentrated under reduced pressure to give 190 mg of oil. 14 mg of the title compound was prepared by HPLC (HPLC purity: 99.65%).

MS (ESI) m/z 460.2 [M+1]+.

$^1$H NMR (400 MHz, DMSO) δ 7.60 (d, J=1.9 Hz, 1H), 7.46 (d, J=8.3 Hz, 1H), 7.25 (dd, J=8.6, 2.2 Hz, 1H), 7.03 (dd, J=13.4, 8.6 Hz, 2H), 6.90 (s, 1H), 4.46 (q, J=15.3 Hz, 2H), 4.29 (dd, J=12.6, 6.3 Hz, 1H), 3.87 (dd, J=10.5, 4.6 Hz, 4H), 3.31 (d, J=11.3 Hz, 2H), 2.58-2.52 (m, 2H), 2.46-2.35 (m, 1H), 1.99 (s, 1H), 1.88-1.71 (m, 2H), 1.64 (d, J=12.5 Hz, 2H), 1.51-1.20 (m, 4H), 1.16 (dd, J=10.3, 4.6 Hz, 6H).

Example 2

Synthesis of 2-(4-((6-ethyl-2-methyl-3,4-dihydroquinolin-1(2H)-yl)sulfonyl)phenoxy)-2-(tetrahydro-2H-pyran-4-yl)ethanol

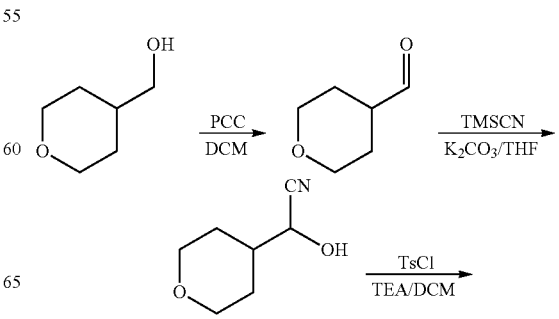

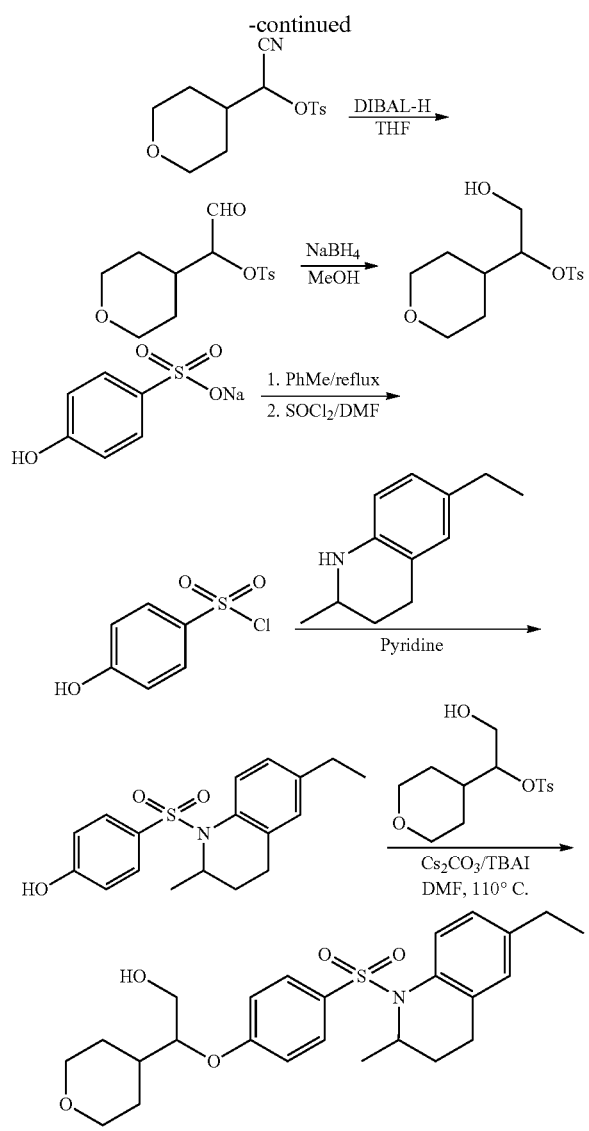

2.1 Synthesis of tetrahydro-2H-pyran-4-carbaldehyde

A 250 mL single-necked flask was charged with 4-hydroxymethyl-tetrahydropyran (4.0 g) and 100 mL of DCM. After the dissolution, 15.0 g of silica gel was charged, the mixture was cooled in an ice bath, and PCC (11.1 g) was added in portions at 0° C. After that, the ice bath was removed, and the reaction proceeded under stirring at a room temperature of 15° C. for 16 h. A sample was taken, and the reaction of the raw materials was complete as detected by TLC. 60 mL of PE was added, and the mixture was stirred uniformly and was then directly subjected to column chromatography (PE:DCM=1:1 (V:V)), so as to obtain 2.0 g of the title compound.

2.2 Synthesis of 2-hydroxy-2-(tetrahydro-2H-pyran-4-yl)acetonitrile

A 50 mL single-necked flask was charged with tetrahydro-2H-pyran-4-carbaldehyde (1.00 g), 10 mL of THF and $K_2CO_3$ (0.24 g). The mixture was cooled in an ice bath, and 0.95 g of TMSCN was added. The mixture was reacted at a room temperature of 12° C. for 16 h, a sample was taken, and the spots of the raw materials disappeared as detected by TLC. 20 mL of water and 50 mL of MTBE were added, and the mixture was subjected to liquid-liquid separation. The aqueous layer was extracted with MTBE (20 mL×2), the organic phases were combined, to which 10 mL of 2 N HCl was added, and the mixture was reacted at a room temperature of 12° C. for 2 h. The mixture was subjected to liquid-liquid separation, washed with 20 mL of saturated saline, and subjected to liquid-liquid separation. The organic phase was dried over 10 g of anhydrous sodium sulfate for 30 min. The mixture was filtered, and the filtrate was concentrated to give 0.9 g of the title compound.

2.3 Synthesis of cyano(tetrahydro-2H-pyran-4-yl)methyl 4-methylbenzenesulfonate A 50 mL single-necked flask was charged with 2-hydroxy-2-(tetrahydro-2H-pyran-4-yl) acetonitrile (0.9 g), 20 mL of DCM, and TsCl (1.28 g), which were cooled in an ice bath, and then 0.97 g of TEA was added thereto. The resulting mixture was reacted at a room temperature of 12° C. for 16 h. A sample was taken, and the spots of the raw materials disappeared as detected by TLC. 50 mL of water was added to the reaction solution, 50 mL of DCM was then added to carry out extraction, and the mixture was subjected to liquid-liquid separation. The aqueous layer was extracted with DCM (20 mL×2). The organic phases were combined, washed with 50 mL of saturated saline and subjected to liquid-liquid separation, and the organic phase was dried over 10 g of anhydrous sodium sulfate. The resulting mixture was filtered, and the filtrate was concentrated and subjected to column chromatography (PE:EA=5:1 (V:V)), so as to give 1.2 g of the title compound.

2.4 Synthesis of 2-oxo-1-(tetrahydro-2H-pyran-4-yl)ethyl 4-methylbenzenesulfonate A 25 mL single-necked flask was charged with cyano(tetrahydro-2H-pyran-4-yl)methyl 4-methylbenzenesulfonate (140 mg) prepared above, and 5 mL of anhydrous THF was added. The mixture was purged with nitrogen gas three times. The mixture was cooled to −78° C. in a dry ice-ethanol bath. DIBAL-H (1.5 M, 1.5 mL) was added dropwise. After the dropwise addition, the dry ice bath was removed, and the mixture was reacted for 1 h at 0° C. in an ice bath. A sample was taken, and the spots of the raw materials disappeared as detected by TLC. After the reaction mixture was cooled with an ice bath, 2 mL of a saturated $NH_4C_1$ aqueous solution was added to quench the reaction, and then 6 mL of 1 M/L $H_2SO_4$ was added. The mixture was stirred at a room temperature of 14° C. for 16 h, and 50 mL of MTBE was added to carry out extraction. The aqueous phase was extracted with MTBE (10 mL×3). Liquid-liquid separation was performed, and the organic phase was washed with 30 mL of saturated saline and subjected to liquid-liquid separation. The organic phase was dried over 10 g of anhydrous sodium sulfate and filtered, and the filtrate was concentrated, so as to give 120 mg of the title compound.

2.5 Synthesis of 2-hydroxy-1-(tetrahydro-2H-pyran-4-yl)ethyl 4-methylbenzenesulfonate A 25 mL single-necked flask was charged with 2-oxo-1-(tetrahydro-2H-pyran-4-yl)ethyl 4-methylbenzenesulfonate (120 mg) prepared above and 5 mL of MeOH. The mixture was cooled to 0° C. with an ice bath. 17 mg of NaBH$_4$ was added in portions. After the addition, the ice bath was removed, and the mixture was reacted for 1 h. A sample was taken, and the spots of the raw materials disappeared as detected by TLC. After the reaction mixture was cooled with an ice bath to 0° C., 2 mL of a saturated NH$_4$C$_1$ aqueous solution was added to quench the reaction. The resulting mixture was stirred for 15 min and concentrated to remove MeOH, followed by extraction with 20 mL of EA, and the aqueous phase was extracted with EA (10 mL×3). Liquid-liquid separation was performed. The organic phase was washed with 10 mL of saturated saline and subjected to liquid-liquid separation. The organic phase was dried over 5 g of anhydrous sodium sulfate and filtered, the filtrate was concentrated, 500 mg of silica gel was added thereto, and the mixture was stirred and subjected to column chromatography (PE:EA=2:1), so as to obtain 80 mg of the title compound.

2.6 Synthesis of 4-hydroxybenzenesulfonyl chloride

A 100 mL single-necked flask was charged with sodium 4-hydroxybenzenesulfonate (5 g) and 50 mL of toluene, which were subjected to reflux at 130° C. in an oil bath for 5 h. Water was separated by a water separator. After water was separated, the resulting mixture was concentrated to remove toluene. 6 mL of SOCl$_2$ was added to the flask, 0.2 mL of DMF was added dropwise, and the mixture was stirred for 4 h in an oil bath at 60° C. The oil bath was removed, and the resulting mixture was concentrated to remove SOCl$_2$. The residue in the flask was added dropwise into 100 mL of ice water, the mixture was stirred for 15 min, and then 100 mL of DCM was added to perform extraction, followed by liquid-liquid separation. The aqueous phase was extracted with DCM (20 mL×2). The organic phases were combined, washed with 30 mL of a saturated NaCl aqueous solution, and subjected to liquid-liquid separation. The organic phase was dried over 20 g of anhydrous sodium sulfate and filtered, and the filtrate was concentrated, so as to obtain 4.4 g of 4-hydroxybenzenesulfonyl chloride.

2.7 Synthesis of 4-((6-ethyl-2-methyl-3,4-dihydroquinolin-1(2H)-yl)sulfonyl)phenol A 250 mL single-necked flask was charged with 4-hydroxybenzenesulfonyl chloride (200 mg) and 5 mL of pyridine. After the dissolution, the mixture was cooled by an ice bath, and 6-ethyl-2-methyl-1,2,3,4-tetrahydroquinoline (200 mg) was added in portions at 0° C. After the addition, the ice bath was removed, and the reaction proceeded under stirring for 16 h at a room temperature of 15° C. A sample was taken, and the reaction of the raw materials was complete as detected by TLC. The resulting mixture was concentrated to remove pyridine, and 20 mL of water was added to the flask, followed by addition of 20 mL of EA to perform extraction. The resulting mixture was subjected to liquid-liquid separation, and the aqueous layer was extracted with EA (10 mL×3). The organic phases were combined, washed with 20 mL of saturated saline, and subjected to liquid-liquid separation. The organic phase was dried over 5 g of anhydrous sodium sulfate. The resulting mixture was filtered, and the filtrate was concentrated and subjected to column chromatography (PE:EA=3:1), so as to obtain 170 mg of the title compound.

2.8 Synthesis of 2-(4-((6-ethyl-2-methyl-3,4-dihydroquinolin-1(2H)-yl)sulfonyl) phenoxy)-2-(tetrahydro-2H-pyran-4-yl)ethanol A 10 mL single-necked flask was charged with 4-((6-ethyl-2-methyl-3,4-dihydroquinolin-1(2H)-yl)sulfonyl)phenol (170 mg) prepared above, 2-hydroxy-1-(tetrahydro-2H-pyran-4-yl)ethyl 4-methylbenzenesulfonate (170 mg) prepared above, and 3 mL of DMF, followed by addition of 500 mg of cesium carbonate and 38 mg of TBAI. The mixture was reacted for 6 h under stirring at 110° C. in an oil bath. A sample was taken, and the spots of the raw materials disappeared as detected by TLC. The oil bath was removed, and the resulting mixture was concentrated to remove DMF. 5 mL of water was added, and then 20 mL of EA was added to carry out extraction. The resulting mixture was subjected to liquid-liquid separation, and the aqueous layer was extracted with EA (10 mL×3). The organic phases were combined, washed with 10 mL of saturated saline and subjected to liquid-liquid separation. The organic phase was dried over 5 g of anhydrous sodium sulfate. The filtrate was concentrated, 1 g of silica gel was added thereto, and the mixture was stirred and subjected to column chromatography (DCM:EA=4:1). The resulting product was concentrated to obtain 100 mg of the title compound (HPLC purity: 95%).

MS (ESI) m/z 460.3 [M+1]+.

$^1$H NMR (400 MHz, CDCl3) δ 7.63 (d, J=8.3 Hz, 1H), 7.42 (d, J=8.9 Hz, 2H), 7.06 (dd, J=8.3, 1.7 Hz, 1H), 6.84 (d, J=8.9 Hz, 2H), 6.80 (s, 1H), 4.31 (dd, J=13.0, 6.5 Hz, 1H), 4.12-3.88 (m, 4H), 3.80-3.72 (m, 1H), 3.39 (dd, J=19.2, 7.7 Hz, 2H), 2.60 (q, J=7.6 Hz, 2H), 2.40-2.31 (m, 1H), 2.21 (d, J=4.5 Hz, 1H), 1.88-1.69 (m, 4H), 1.57 (s, 2H), 1.28-1.18 (m, 8H).

Example 3

Synthesis of 5-((6-ethyl-3,4-dihydroquinolin-1(2H)-yl)sulfonyl)-2-((tetrahydro-2H-pyran-4-yl)methoxy) benzyl Alcohol

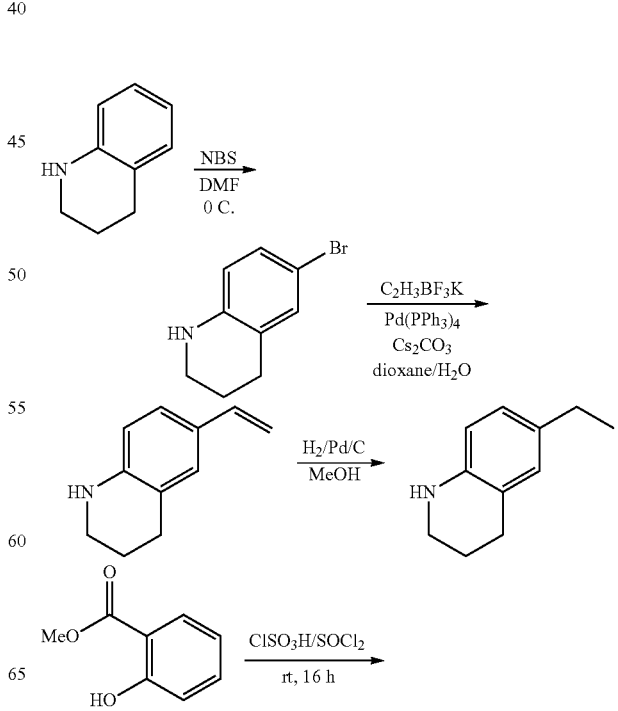

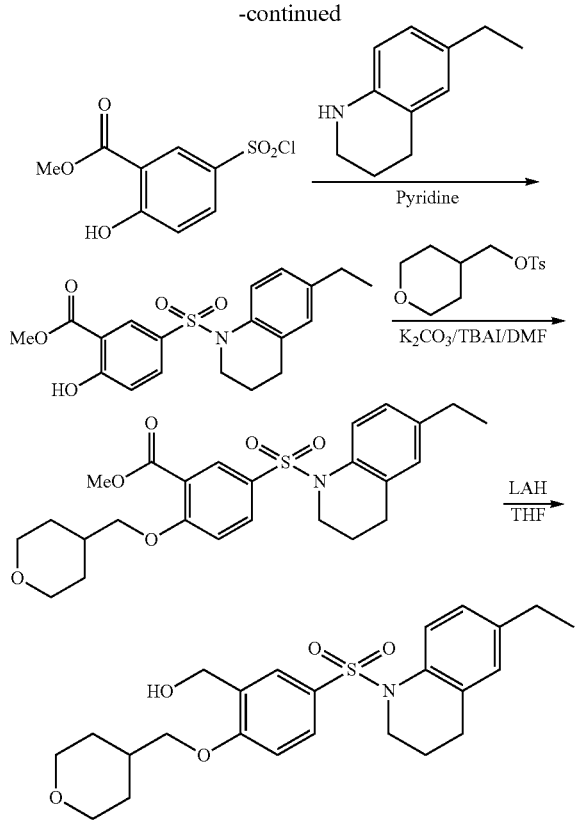

3.1 Synthesis of 6-bromotetrahydroquinoline

Tetrahydroquinoline (1.0 g) was taken and placed in a 100 mL single-necked flask, and 20 mL of DMF was added to dissolve the former. The mixture was cooled with an ice bath. A solution of NBS (1.4 g) in 10 mL of DMF was added dropwise. After the completion of the dropwise addition, the mixture was stirred in an ice bath for 1 h. The reaction was complete as detected by TLC. 100 mL of water was added, and the mixture was extracted with 20 mL of EA three times. The combined organic phases were washed with 20 mL of a saturated aqueous sodium chloride solution, dried over anhydrous sodium sulfate and filtered, and the filtrate was concentrated under reduced pressure to obtain 1.8 g of 6-bromotetrahydroquinoline.

3.2 Synthesis of 6-vinyl-tetrahydroquinoline

A 250 mL single-necked flask was charged with 6-bromotetrahydroquinoline (1.8 g), and 80 mL of 1,4-dioxane was added to dissolve the former. Potassium vinyltrifluoroborate (1.25 g), 20 mL of water and cesium carbonate (8.3 g) were added. The mixture was purged with nitrogen gas three times. 100 mg of tetrakis(triphenylphosphine)palladium was added. Then, the mixture was purged with nitrogen gas three times again. The mixture was heated to 90° C. with an external bath and stirred for 16 h. The reaction was complete as detected by LC-MS. 80 mL of water was added, and the mixture was extracted three times with EA (40 mL×3). The combined organic phases were washed with saturated aqueous sodium chloride solution, and dried over anhydrous sodium sulfate. The resulting mixture was filtered, and the filtrate was concentrated under reduced pressure to obtain 578 mg of 6-vinyl-tetrahydroquinoline.

3.3 Synthesis of 6-ethyl-tetrahydroquinoline

A 50 mL single-necked flask was charged with 6-vinyl-tetrahydroquinoline (578 mg), and 10 mL of MeOH was added to dissolve the former. 100 mg of Pd/C was added, and the mixture was purged with hydrogen gas three times under stirring at room temperature. The reaction was complete as monitored by TLC. The resulting mixture was filtered, and the filtrate was concentrated under reduced pressure, filtered and purified to obtain 280 mg of 6-ethyl-tetrahydroquinoline, of which the HPLC purity was 48.4%.

3.4 Synthesis of methyl 5-chlorosulfonyl-2-hydroxybenzoate

A reaction flask was charged with 2 mL of thionyl chloride and 6 mL of chlorosulfonic acid, which were freezed to 0° C. to 5° C. with an ice-water bath. 2 g of methyl salicylate was weighed and slowly added dropwise into the reaction flask. After the dropwise addition was complete, the reaction further proceeded at room temperature under stirring for 16 h. The reaction solution was slowly added dropwise into ice water to precipitate a white solid. After the ice was completely melted, the product was obtained by suction filtration and naturally dried in air to obtain 3.0 g of methyl 5-chlorosulfonyl-2-hydroxybenzoate.

3.5 Synthesis of methyl 5-((6-ethyl-3,4-dihydroquinolin-1(2H)-yl)sulfonyl)-2-hydroxybenzoate A 50 mL single-necked flask was charged with 6-ethyl-tetrahydroquinoline (280 mg), and 8 mL of pyridine was added to dissolve the former. The mixture was cooled in an ice bath, methyl 5-chlorosulfonyl-2-hydroxybenzoate (653 mg) prepared above was added thereto, and the resulting mixture was stirred at room temperature overnight. The reaction was complete as detected by TLC. 15 mL of DCM and 20 mL of 1 N HCl were added and the mixture was subjected to liquid-liquid separation. The aqueous phase was extracted with 20 mL of DCM. The combined organic phases were washed with saturated aqueous sodium chloride solution, dried over anhydrous sodium sulfate and filtered, and the filtrate was concentrated under reduced pressure to obtain 120 mg of the title compound.

3.6 Synthesis of methyl 5-((6-ethyl-3,4-dihydroquinolin-1(2H)-yl)sulfonyl)-2-((tetrahydro-2H-pyran-4-yl)methoxy)benzoate A 25 mL single-necked flask was charged with methyl 5-((6-ethyl-3,4-dihydroquinolin-1(2H)-yl)sulfonyl)-2-hydroxybenzoate (120 mg) prepared above and p-toluenesulfonate-4-methyl pyran (173 mg), and 3 mL of DMF was added to dissolve the formers. $K_2CO_3$ (100 mg, 0.72 mmol) and a small amount of tetrabutylammonium iodide were added. The mixture was heated to 70° C. in an external bath and stirred for 4 h. The reaction was complete as detected by TLC. 30 mL of water was added, and the mixture was extracted with 10 mL of EA three times. The organic phases were combined, washed with saturated aqueous sodium chloride solution and dried over anhydrous sodium sulfate. The resulting mixture was filtered, and the filtrate was concentrated under reduced pressure to obtain 250 mg of the title compound.

3.7 Synthesis of 5-((6-ethyl-3,4-dihydroquinolin-1 (2H)-yl)sulfonyl)-2-((tetrahydro-2H-pyran-4-yl) methoxy)benzyl Alcohol A 25 mL single-necked flask was charged with methyl 5-((6-ethyl-3,4-dihydroquinolin-1(2H)-yl)sulfonyl)-2-((tetrahydro-2H-pyran-4-yl)methoxy)benzoate (250 mg), and 6 mL of THF was added to dissolve the former. The mixture was cooled in an ice bath, 100 mg of LiAlH$_4$ was added in portions, and the mixture was stirred for 5 h at room temperature. The reaction was complete as detected by TLC. 0.5 mL of 15% NaOH aqueous solution was added dropwise to quench the reaction. The resulting mixture was filtered, and the filtrate was concentrated under reduced pressure to give 180 mg of oil, which was allowed to pass a preparative HPLC column, so as to obtain 20 mg of the title compound (HPLC purity: 96.67%).

MS (ESI) m/z 446.2 [M+1]+.

$^1$H NMR (400 MHz, DMSO) δ 7.68 (d, J=1.8 Hz, 1H), 7.50 (d, J=8.4 Hz, 1H), 7.39 (dd, J=8.6, 2.2 Hz, 1H), 7.03 (dd, J=8.7 Hz, 1H), 6.99 (dd, J=8.4 Hz, 1H), 6.89 (s, 1H), 5.26 (s, 1H), 4.46 (d, J=4.9 Hz, 2H), 3.87 (dd, J=14.9, 4.8 Hz, 4H), 3.73-3.66 (m, 2H), 3.30 (d, J=11.3 Hz, 2H), 2.56-2.51 (m, 2H), 2.43 (q, J=7.0 Hz, 2H), 2.00 (d, J=6.3 Hz, 1H), 1.59 (dt, J=12.5, 10.8 Hz, 4H), 1.33 (ddd, J=16.4, 12.5, 4.4 Hz, 2H), 1.14 (t, J=7.6 Hz, 3H).

Example 4

Synthesis of (5-((5-ethyl-2-methyldihydroindol-1-yl)sulfonyl)-2-((tetrahydro-2H-pyran-4-yl)methoxy) benzyl alcohol

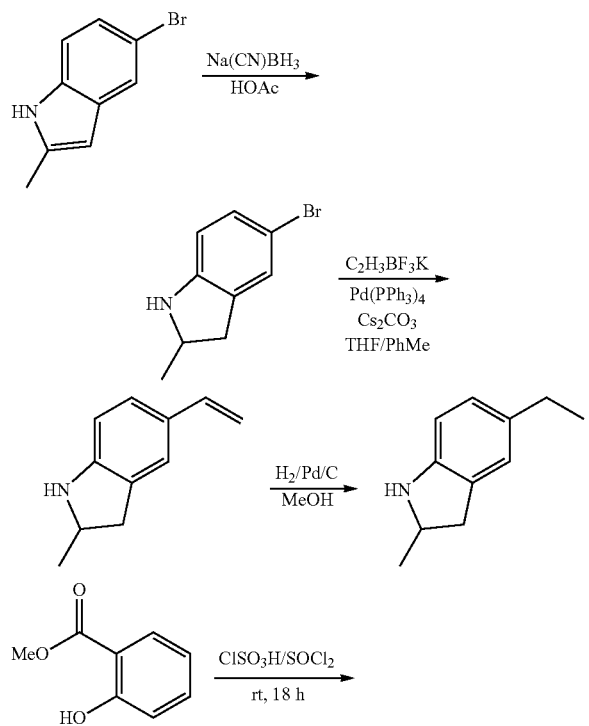

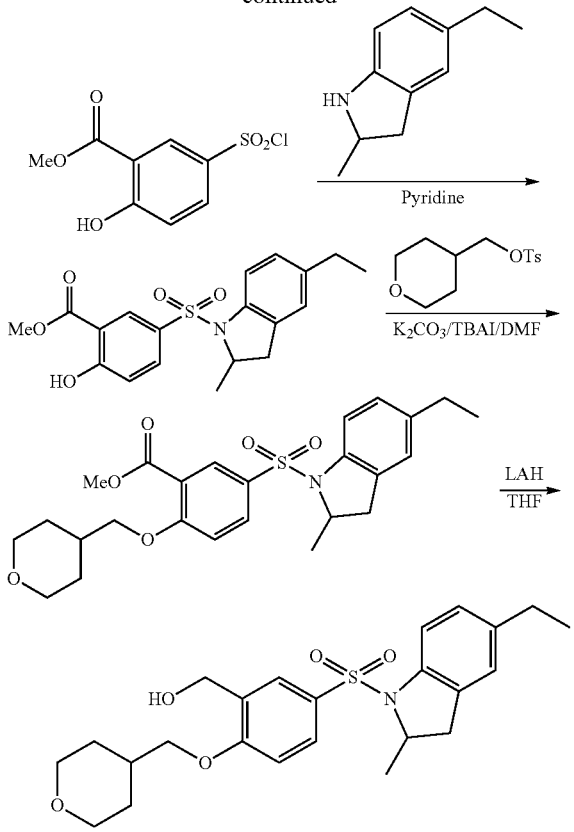

4.1 Synthesis of 5-bromo-2-methyldihydroindole

5-Bromo-2-methylindole (1.0 g) was added to acetic acid (10 mL), to which NaBH$_3$CN (0.98 g) was added in portions. After the completion of the addition, the mixture was stirred at room temperature for 5 h. The reaction solution was poured into water, to which NaHCO$_3$ was added to adjust the pH to 8, and then ethyl acetate was added to conduct extraction, followed by drying by rotary evaporation. The resultant was uniformly stirred and then directly subjected to column chromatography (PE:DCM=1:1), so as to obtain 0.85 g of 5-bromo-2-methyldihydroindole, which was directly added in the next step.

4.2 Synthesis of 5-vinyl-2-methyldihydroindole

5-Bromo-2-methyldihydroindole (0.85 g), potassium vinyltrifluoroborate (1.8 g), tetrakis(triphenylphosphine)palladium (100 mg) and cesium carbonate (2.5 g) were added to THF/toluene (10 mL/10 mL). After the completion of the addition, the mixture was reacted overnight at 80° C. under the protection of nitrogen gas. The reaction solution was poured into water, added with EA and then extracted with EA, dried over anhydrous sodium sulfate, and then dried by rotary evaporation. The resulting mixture was allowed to pass through a column to obtain 5-vinyl-2-methyldihydroindole (150 mg).

4.3 Synthesis of 5-ethyl-2-methyldihydroindole

A 50 mL single-necked flask was charged with 5-vinyl-2-methyldihydroindole (0.15 g), 10 mL of MeOH, and Pd/C (0.05 g). The mixture was purged with hydrogen gas and reacted at room temperature for 5 h. The resulting mixture was filtered by suction and dried by rotary evaporation, so as to obtain 5-ethyl-2-methyldihydroindole (152 mg), which was directly used in the next step.

4.4 Synthesis of (5-((5-ethyl-2-methyldihydroindol-1-yl)sulfonyl)-2-((tetrahydro-2H-pyran-4-yl)methoxy)benzyl Alcohol The rest synthesis steps proceeded with reference to the method described in Example 3, so as to prepare and obtain 100 mg of the title compound (HPLC purity: 98.13%).
MS (ESI) m/z 446.2 [M+1]+.
$^1$H NMR (400 MHz, CDCl$_3$) δ 7.66 (d, J=1.7 Hz, 1H), 7.55 (dd, J=11.8, 5.2 Hz, 2H), 7.02 (d, J=8.2 Hz, 1H), 6.87 (s, 1H), 6.77 (d, J=8.7 Hz, 1H), 4.61 (d, J=5.8 Hz, 2H), 4.38-4.27 (m, 1H), 4.01 (dd, J=11.4, 3.8 Hz, 2H), 3.84 (d, J=6.3 Hz, 2H), 3.43 (t, J=11.3 Hz, 2H), 2.87 (dd, J=16.0, 9.3 Hz, 1H), 2.57 (q, J=7.6 Hz, 2H), 2.40 (dd, J=16.0, 2.5 Hz, 1H), 2.07 (s, 1H), 2.02-1.98 (m, 1H), 1.70 (d, J=12.5 Hz, 2H), 1.52-1.39 (m, 5H), 1.18 (t, J=7.6 Hz, 3H).

Example 5

Synthesis of (R)-(5-((6-ethyl-2-methyl-3,4-dihydroquinolin-1 (2H)-yl)sulfonyl)-2-((tetrahydro-2H-pyran-4-yl)methoxy)benzyl Alcohol

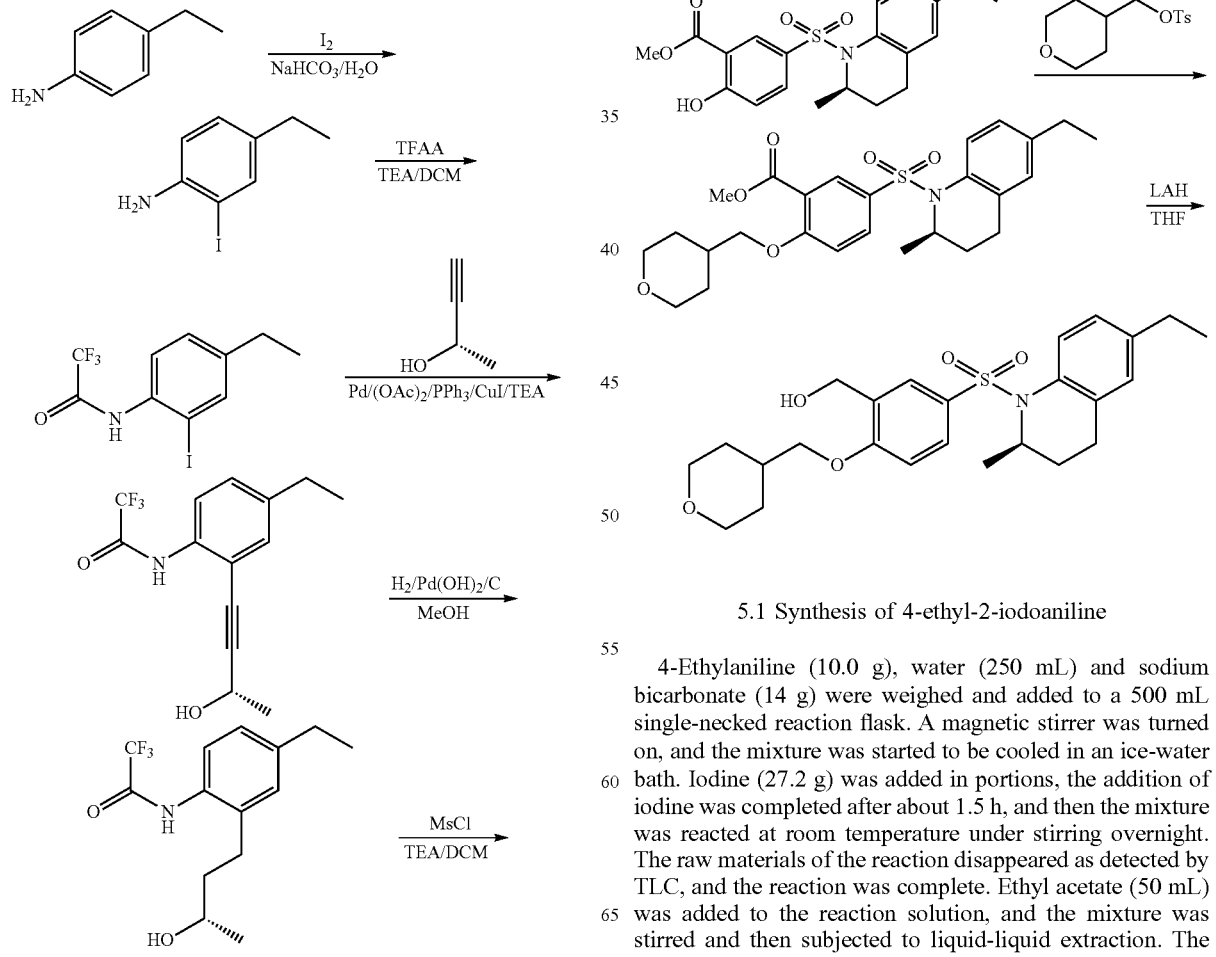

5.1 Synthesis of 4-ethyl-2-iodoaniline

4-Ethylaniline (10.0 g), water (250 mL) and sodium bicarbonate (14 g) were weighed and added to a 500 mL single-necked reaction flask. A magnetic stirrer was turned on, and the mixture was started to be cooled in an ice-water bath. Iodine (27.2 g) was added in portions, the addition of iodine was completed after about 1.5 h, and then the mixture was reacted at room temperature under stirring overnight. The raw materials of the reaction disappeared as detected by TLC, and the reaction was complete. Ethyl acetate (50 mL) was added to the reaction solution, and the mixture was stirred and then subjected to liquid-liquid extraction. The combined organic phases were washed with 20 mL of a saturated aqueous sodium chloride solution, dried over anhydrous sodium sulfate, filtered and concentrated under reduced pressure to obtain a red oil, which was separated by passing through a column (EA:PE=5:95) to obtain 8.4 g of 4-ethyl-2-iodoaniline.

5.2 Synthesis of N-(4-ethyl-2-iodophenyl)-2,2,2-trifluoroacetamide

A 500 mL single-necked flask was charged with 4-ethyl-2-iodoaniline (19.00 g) and TEA (15.5 g), DCM (250 mL) was added to dissolve the formers. The mixture was magnetically stirred and cooled in an ice-water bath. Trifluoroacetic anhydride (13 mL) was added dropwise, the dropwise addition was complete after about 0.5 h, and the reaction was complete as detected by TLC. 150 mL of water was added, followed by extraction with DCM for three times (30 mL×3). The combined organic phases were washed with saturated aqueous sodium chloride solution, dried over anhydrous sodium sulfate, filtered and concentrated under reduced pressure to obtain a red oil, which was separated by passing through a column to obtain 18 g of the title compound.

5.3 Synthesis of (S)—N-(4-ethyl-2-(3-hydroxybutyn-1-yl)phenyl)-2,2,2-trifluoroacetamide A 250 mL single-necked flask was charged with N-(4-ethyl-2-iodophenyl)-2,2,2-trifluoroacetamide (2.4 g), (S)-(−)-3-butyn-2-ol (500 mg) and TEA (24 mL), which were stirred at room temperature. The flask was evacuated, and the mixture was purged with nitrogen gas three times, followed by the addition of palladium acetate (80 mg), cuprous iodide (67 mg) and triphenylphosphine (190 mg) as catalysts. After the completion of the addition, the flask was evacuated again, and the mixture was purged once with nitrogen gas and then stirred and reacted at room temperature. The reaction was complete as monitored by TLC. A saturated aqueous ammonium chloride solution (50 mL) and EA (50 mL) were added to the reaction solution, and the mixture was stirred for 0.5 hours. The resulting mixture was subjected to liquid-liquid extraction. The organic phases were combined, dried over anhydrous sodium sulfate and filtered, and the filtrate was concentrated under reduced pressure to obtain an oil (2 g), which was separated by passing through a column (EA:PE=10:90) to obtain 1.5 g of the title compound. LCMS: 286.1 (M+1).

5.4 Synthesis of (S)—N-(4-ethyl-2-(3-hydroxybutyl)phenyl)-2,2,2-trifluoroacetamide A 100 mL single-necked flask was charged with (S)—N-(4-ethyl-2-(3-hydroxybutyn-1-yl) phenyl)-2,2,2-trifluoroacetamide (1.5 g) prepared above, MeOH (30 mL) and 15% palladium hydroxide on carbon (300 mg). The flask was evacuated, and the mixture was purged with hydrogen gas and then stirred and reacted at room temperature for 10 h. After that, the reaction of the raw materials was complete as detected by LCMS. The resulting mixture was filtered, and the filtrate was concentrated under reduced pressure to obtain 1.52 g of the title compound.

5.5 Synthesis of (S)-4-(5-ethyl-2-(2,2,2-trifluoroacetamido)phenyl)butane-2-yl mesylate A 100 mL single-necked reaction flask was charged with (S)—N-(4-ethyl-2-(3-hydroxybutyl)phenyl)-2,2,2-trifluoroacetamide (1.52 g) prepared above, DCM (15 mL) and TEA (1.1 g). Under a condition where a magnetic stirrer was turned on and the mixture was cooled in an ice-water bath, MSCl (0.5 mL) was added dropwise. After the dropwise addition, the mixture was stirred and reacted at room temperature, and the reaction was complete as detected by TLC. Water (30 mL) was added to the reaction solution. The mixture was subjected to liquid-liquid extraction for three times. The organic phases were combined, extracted and washed once with 1N HCl, extracted and washed with saturated sodium carbonate solution, extracted and washed with saturated saline, dried over anhydrous sodium sulfate, filtered, and concentrated under reduced pressure to obtain 2.1 g of the title compound, which was directly used in the next step of the reaction without purification.

5.6 Synthesis of (R)-6-ethyl-2-methyl-1,2,3,4-tetrahydroquinoline

A 50 mL single-necked flask was charged with (S)-4-(5-ethyl-2-(2,2,2-trifluoroacetamido) phenyl)butane-2-yl mesylate (2.1 g) prepared above, MeOH (20 mL) and lithium hydroxide (660 mg), which were then stirred and reacted at room temperature. The raw materials of the reaction disappeared as detected by TLC. The reaction solution was subjected to rotary evaporation to remove the organic solvent. Then, water (10 mL) was added and the mixture was extracted with DCM (30 mL) three times. The organic phases were combined, washed with saturated saline, dried over anhydrous sodium sulfate, dried by rotary evaporation, and purified by passing through a column, so as to obtain 520 mg of (R)-6-ethyl-2-methyl-1,2,3,4-tetrahydroquinoline. LCMS: 176.1 (M+1), ee 97%.

5.7 Synthesis of (R)-(5-((6-ethyl-2-methyl-3,4-dihydroquinolin-1(2H)-yl)sulfonyl)-2-((tetrahydro-2H-pyran-4-yl)methoxy)benzyl alcohol The rest synthesis steps proceeded with reference to the method described in Example 3, so as to prepare and obtain 70 mg of the title compound (HPLC purity: 98%).

MS (ESI) m/z 460.0 [M+1]+.

$^1$H NMR (400 MHz, DMSO) δ 7.61 (s, 1H), 7.46 (d, J=8.3 Hz, 1H), 7.26 (d, J=8.8 Hz, 1H), 7.11-6.98 (m, 2H), 6.90 (s, 1H), 4.46 (qd, J=15.2, 5.6 Hz, 2H), 4.30 (dd, J=12.8, 6.4 Hz, 1H), 3.88 (t, J=8.5 Hz, 4H), 2.59-2.52 (m, 2H), 2.40 (t, J=24.4, 13.2 Hz, 1H), 2.00 (d, J=7.2 Hz, 1H), 1.81 (ddd, J=20.2, 14.4, 7.3 Hz, 2H), 1.64 (d, J=12.5 Hz, 2H), 1.40-1.22 (m, 5H), 1.17 (t, J=7.2 Hz, 6H).

Example 6

Synthesis of (S)-(5-((6-ethyl-2-methyl-3,4-dihydroquinolin-1(2H)-yl)sulfonyl)-2-((tetrahydro-2H-pyran-4-yl)methoxy)benzyl Alcohol

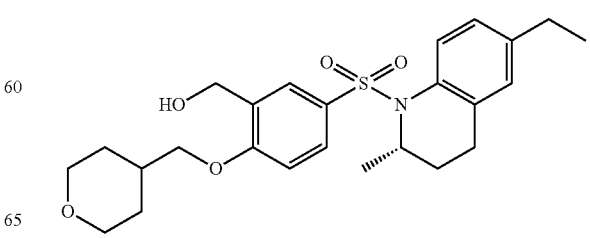

170 mg of the title compound (HPLC purity: 98%) was prepared and obtained with reference to the synthesis method in Example 5.

MS (ESI) m/z 460.0 [M+1]+.

$^1$H NMR (400 MHz, DMSO) δ 7.61 (s, 1H), 7.46 (d, J=8.3 Hz, 1H), 7.26 (d, J=8.6 Hz, 1H), 7.03 (dd, J=12.3, 8.8 Hz, 2H), 6.89 (s, 1H), 4.46 (qd, J=15.2, 5.3 Hz, 2H), 4.30 (dd, J=12.7, 6.4 Hz, 1H), 3.88 (dd, J=12.2, 4.2 Hz, 4H), 2.62-2.52 (m, 2H), 2.47-2.37 (m, 1H), 2.00 (d, J=7.7 Hz, 1H), 1.90-1.71 (m, 2H), 1.64 (d, J=12.3 Hz, 2H), 1.37-1.23 (m, 5H), 1.17 (t, J=7.2 Hz, 6H).

Example 7

Synthesis of (5-(((6-ethyl-3-methyl-3,4-dihydroquinolin-1(2H)-yl)sulfonyl)-2-((tetrahydro-2H-pyran-4-yl)methoxy)benzyl Alcohol

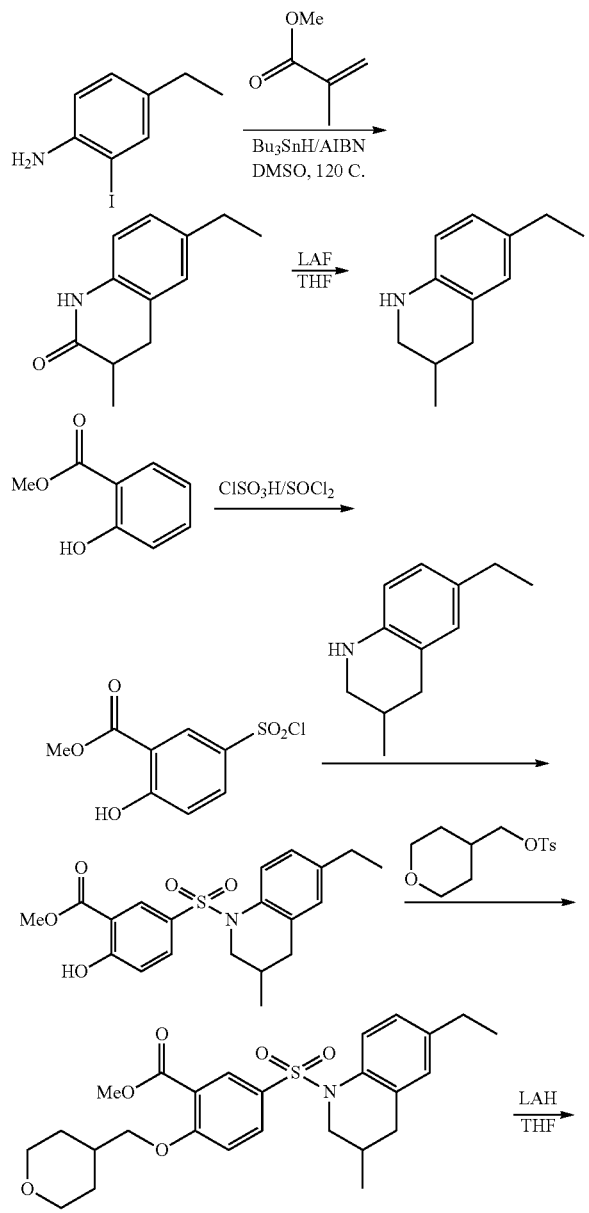

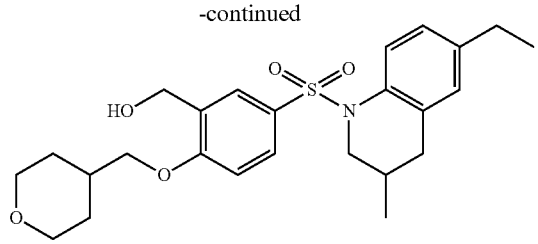

7.1 Synthesis of 6-ethyl-3-methyl-3,4-dihydroquinolin-2(1H)-one

A reaction flask was charged with 1.977 g of 4-ethyl-2-iodoaniline, 3.20 g of methyl methacrylate, 3.49 g of tributyltin hydride, 526 mg of AIBN, and 30 mL of DMSO. The mixture was heated to 120° C., and stirred and reacted for 16 h. LCMS detection showed the formation of the target product. The reaction system was naturally cooled to room temperature, 150 mL of water was added to dilute the reaction solution, and the mixture was extracted with ethyl acetate (250 mL×2). The organic phases were combined, dried over anhydrous sodium sulfate, filtered, and concentrated to give a crude product. The crude product was subjected to silica gel column chromatography, so as to obtain 400 mg of the title compound.

7.2 Synthesis of 6-ethyl-3-methyl-1,2,3,4-tetrahydroquinoline 500 mg of 6-ethyl-3-methyl-3,4-dihydroquinolin-2(1H)-one was dissolved in 30 mL of tetrahydrofuran, and the mixture was added to a reaction flask. 201 mg of lithium aluminum hydride was weighed and slowly added to the reaction flask in portions. 235 mg of anhydrous aluminum trichloride was weighed and slowly added to the reaction flask in portions. After the completion of the addition, the mixture was stirred and reacted at room temperature for 4 h. LCMS detection showed the formation of the target product. 5 mL of a saturated aqueous ammonium chloride solution was slowly added to quench the reaction, 150 mL of ethyl acetate was added to dilute the reaction solution, and the salt was removed by filtration. The organic phase was dried over anhydrous sodium sulfate, filtered, and concentrated to obtain a crude product. The crude product was subjected to silica gel column chromatography, so as to obtain 350 mg of 6-ethyl-3-methyl-1,2,3,4-tetrahydroquinoline.

7.3 Synthesis of (5-(((6-ethyl-3-methyl-3,4-dihydroquinolin-1(2H)-yl)sulfonyl)-2-((tetrahydro-2H-pyran-4-yl)methoxy)benzyl Alcohol The rest synthesis steps proceeded with reference to the method described in Example 3, so as to prepare and obtain 53.9 mg of the title compound (HPLC purity: 99.3%).

MS (ESI) m/z 460.0 [M+1]+.

$^1$H NMR (400 MHz, CDCl$_3$) δ 7.66 (d, J=8.4 Hz, 1H), 7.58 (s, 1H), 7.57-7.52 (m, 1H), 6.99 (d, J=8.4 Hz, 1H), 6.85-6.78 (m, 2H), 4.63 (d, J=5.5 Hz, 2H), 4.11 (dd, J=13.1, 4.0 Hz, 1H), 4.02 (dd, J=11.4, 4.0 Hz, 2H), 3.87 (d, J=6.3 Hz, 2H), 3.44 (t, J=11.4 Hz, 2H), 3.07-2.96 (m, 1H), 2.56 (dd, J=15.1, 7.4 Hz, 3H), 2.14-2.03 (m, 2H), 1.96 (t, J=6.1 Hz, 1H), 1.72 (d, J=13.0 Hz, 3H), 1.47 (qd, J=12.3, 4.4 Hz, 2H), 1.19 (t, J=7.6 Hz, 3H), 0.94 (d, J=6.6 Hz, 3H).

Example 8

Synthesis of (5-((6-chloro-2-methyl-3,4-dihydroquinolin-1(2H)-yl)sulfonyl)-2-((tetrahydro-2H-pyran-4-yl)methoxy)benzyl Alcohol

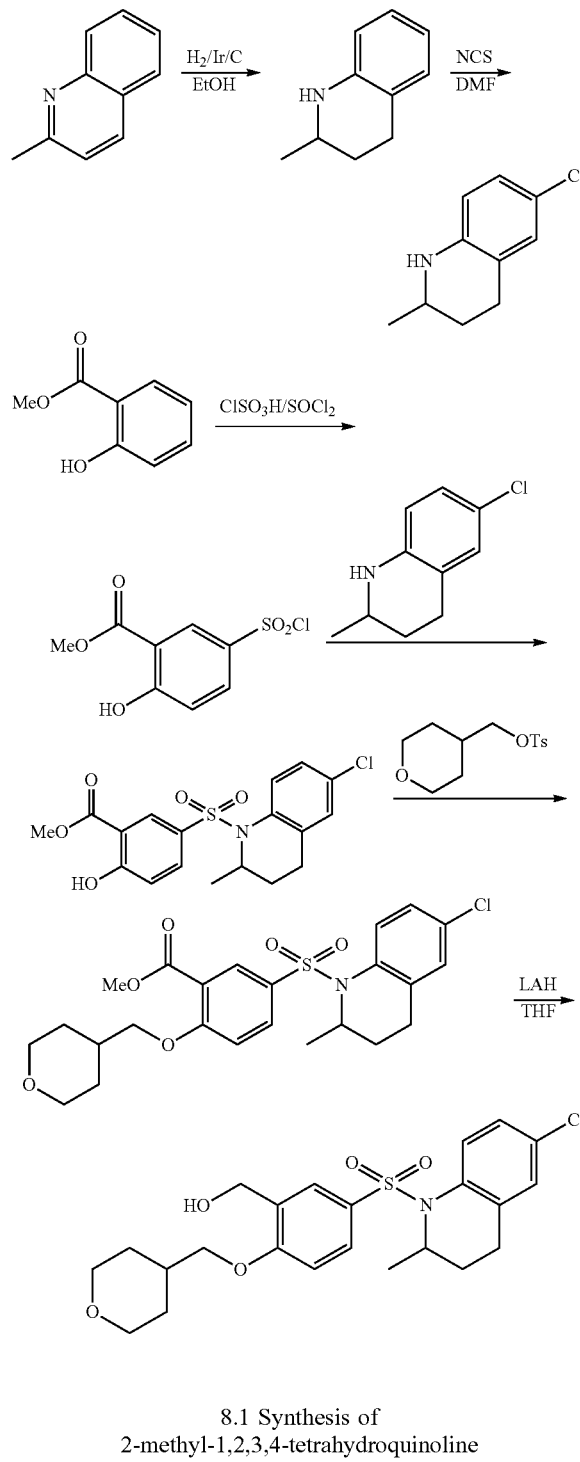

8.1 Synthesis of 2-methyl-1,2,3,4-tetrahydroquinoline

A 100 mL hydrogenation autoclave was charged with 2-methyl-quinoline (5.05 g), 25 mL of 95% ethanol was added to dissolve the former, and 750 mg of iridium on carbon was added. The mixture was purged with hydrogen gas three times. The system was pressurized to 0.5 MPa and heated to 79° C. by an external bath, and the mixture therein was stirred for 3 d. The reaction was complete as detected by TLC. The resulting mixture was filtered, and the filtrate was concentrated under reduced pressure to a constant weight, so as to obtain 4.7 g of 2-methyl-1,2,3,4-tetrahydroquinoline.

8.2 Synthesis of 6-chloro-2-methyl-1,2,3,4-tetrahydroquinoline

A 25 mL single-necked flask was charged with 2-methyl-1,2,3,4-tetrahydroquinoline (416 mg), and 10 mL of DMF was added to dissolve the former. The mixture was cooled with an ice bath, and NCS (396 mg) was added in portions. After the addition was complete, the mixture was stirred for 3 h in an ice bath, and the reaction was complete as detected by TLC. 100 mL of water was added, and the mixture was extracted with 20 mL of ethyl acetate three times. The combined organic phases were washed with 20 mL of a saturated aqueous sodium chloride solution, dried over anhydrous sodium sulfate, filtered and concentrated under reduced pressure to obtain 390 mg of 6-chloro-2-methyl-1,2,3,4-tetrahydroquinoline.

8.3 Synthesis of (5-((6-chloro-2-methyl-3,4-dihydroquinolin-1(2H)-yl)sulfonyl)-2-((tetrahydro-2H-pyran-4-yl)methoxy)benzyl alcohol The rest synthesis steps proceeded with reference to the method described in Example 3, so as to prepare and obtain 30 mg of the title compound (HPLC purity: 94.08%).

MS (ESI) m/z 466.0 [M+1]+.

$^1$H NMR (400 MHz, CDCl3) δ 7.71 (d, J=8.7 Hz, 1H), 7.59 (s, 1H), 7.38 (d, J=8.6 Hz, 1H), 7.21 (d, J=8.7 Hz, 1H), 7.00 (s, 1H), 6.81 (d, J=8.7 Hz, 1H), 4.67 (d, J=4.3 Hz, 2H), 4.40 (dd, J=12.8, 6.4 Hz, 1H), 4.05 (dd, J=11.3, 3.9 Hz, 2H), 3.89 (d, J=6.3 Hz, 2H), 3.47 (t, J=11.6 Hz, 2H), 2.48-2.39 (m, 1H), 2.18-2.08 (m, 1H), 2.02 (d, J=4.8 Hz, 1H), 1.90 (dd, J=15.7, 7.2 Hz, 1H), 1.82 (dd, J=13.1, 7.1 Hz, 1H), 1.74 (d, J=12.4 Hz, 2H), 1.51 (tt, J=12.2, 6.2 Hz, 2H), 1.38 (dd, J=13.3, 6.6 Hz, 1H), 1.28 (d, J=6.4 Hz, 3H).

Example 9

Synthesis of (5-((5-ethyl-3-methyldihydroindol-1-yl)sulfonyl)-2-((tetrahydro-2H-pyran-4-yl)methoxy) benzyl Alcohol

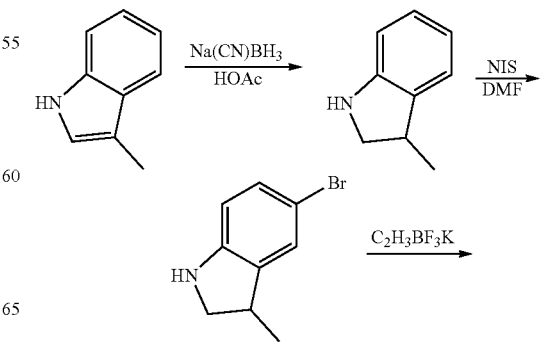

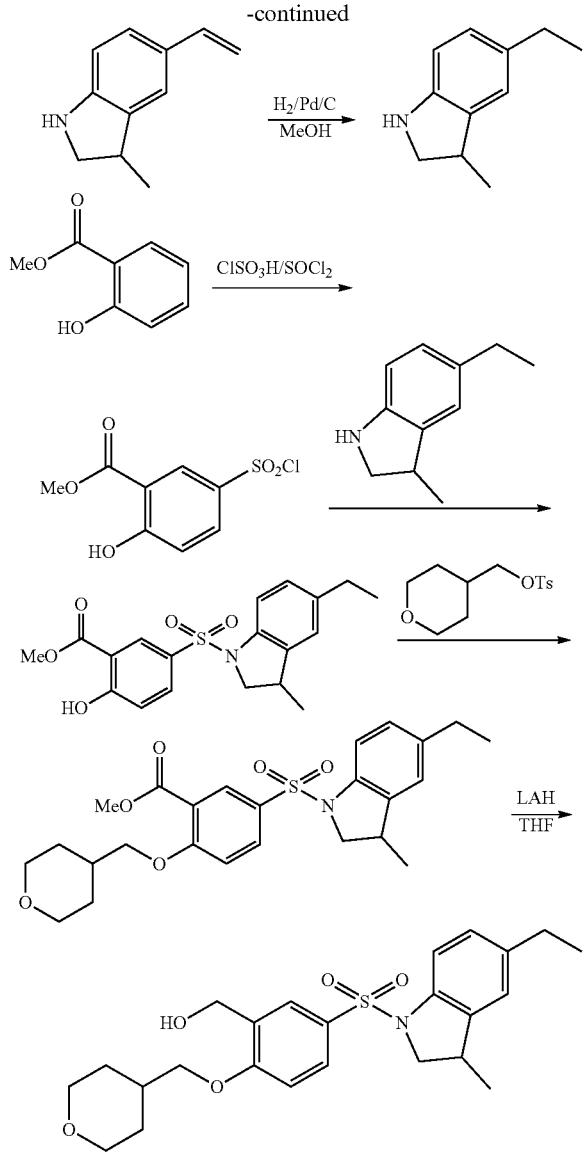

9.1 Synthesis of 3-methyldihydroindole

A 100 mL eggplant-shaped flask was charged with 3-methylindole (5 g), 40 mL of acetic acid was added to dissolve the former, 4 g of Na(CN)BH₃ was added, and the mixture was stirred at room temperature for 5 h. The reaction was complete as detected by TLC. Sodium carbonate was added to adjust the pH until the mixture became alkaline, followed by extraction with EA. The organic layer was washed three times with water, and the organic layer was concentrated to obtain 6.1 g of 3-methyldihydroindole.

9.2 Synthesis of 5-bromo-3-methyldihydroindole

A 25 mL single-necked flask was charged with 3-methyldihydroindole (3 g), 10 mL of DMF was added to dissolve the former. The mixture was cooled to −10° C., to which 1.92 g of NBS was added in portions. After the completion of the addition, the mixture was placed in an ice bath while being stirred for 1 h. The reaction was complete as detected by TLC. 100 mL of water was added, and the mixture was extracted with 20 mL of EA three times. The combined organic phases were washed with 20 mL of a saturated aqueous sodium chloride solution, dried over anhydrous sodium sulfate, filtered and concentrated under reduced pressure to obtain 5-bromo-3-methyldihydroindole (1.46 g).

9.3 Synthesis of 5-vinyl-3-methyldihydroindole

A 100 mL eggplant-shaped flask was charged with 5-bromo-3-methyldihydroindole (1.4 g), 1 g of potassium vinyltrifluoroborate, and 6.5 g of cesium carbonate, which were dissolved with a solution of 1,4-dioxane/water (4:1 (V:V)), and 420 mg of tetrakis(triphenylphosphine) was added. The mixture was purged with nitrogen gas and protected thereby. The mixture was stirred at 90° C. overnight. The reaction was complete as detected by TLC. The mixture in the system was extracted with EA, and the organic layer was subjected to column chromatography to obtain 600 mg of 5-vinyl-3-methyldihydroindole.

9.4 Synthesis of 5-ethyl-3-methyldihydroindole

A 50 mL eggplant-shaped flask was charged with 5-vinyl-3-methyldihydroindole (600 mg), which was dissolved with methanol, and an appropriate amount of palladium on carbon was added. The mixture was purged with hydrogen gas and protected thereby, and was stirred at room temperature overnight. The reaction was complete as detected by TLC. The resulting mixture was filtered, and the filtrate was dried by rotary evaporation, so as to obtain 480 mg of 5-ethyl-3-methyldihydroindole.

9.5 Synthesis of (5-((5-ethyl-3-methyldihydroindol-1-yl)sulfonyl)-2-((tetrahydro-2H-pyran-4-yl)methoxy)benzyl Alcohol The rest synthesis steps proceeded with reference to the method described in Example 3, so as to prepare and obtain 100 mg of the title compound (HPLC purity: 99.8%).

MS (ESI) m/z 446.0 [M+1]+.

¹H NMR (400 MHz, CDCl₃) δ 7.78 (s, 1H), 7.70 (d, J=8.2 Hz, 1H), 7.51 (d, J=8.2 Hz, 1H), 7.01 (d, J=8.0 Hz, 1H), 6.94-6.77 (m, 2H), 4.65 (s, 2H), 4.14-3.97 (m, 3H), 3.86 (d, J=6.0 Hz, 2H), 3.41 (dd, J=20.8, 10.0 Hz, 3H), 3.23-3.10 (m, 1H), 2.57 (dd, J=14.8, 7.3 Hz, 2H), 2.05 (s, 2H), 1.70 (d, J=12.7 Hz, 2H), 1.53-1.40 (m, 2H), 1.16 (ddd, J=12.3, 8.7, 5.5 Hz, 6H).

Example 10

Synthesis of (5-((5-ethyl-dihydroindol-1-yl)sulfonyl)-2-((tetrahydro-2H-pyran-4-yl) methoxy)benzyl Alcohol

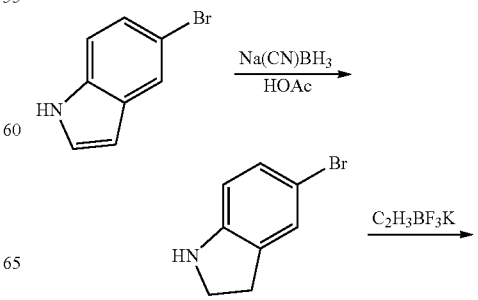

-continued
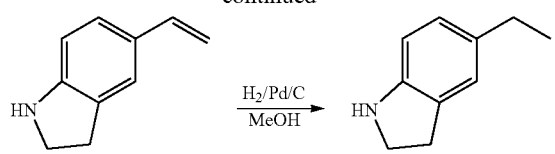
Example 11
Synthesis of 54(6-ethyl-2,3-dihydro-1H-pyrido[2,3-b][1,4]oxazin-1-yl)sulfonyl)-2-((tetrahydro-2H-pyran-4-yl)methoxy)benzyl Alcohol
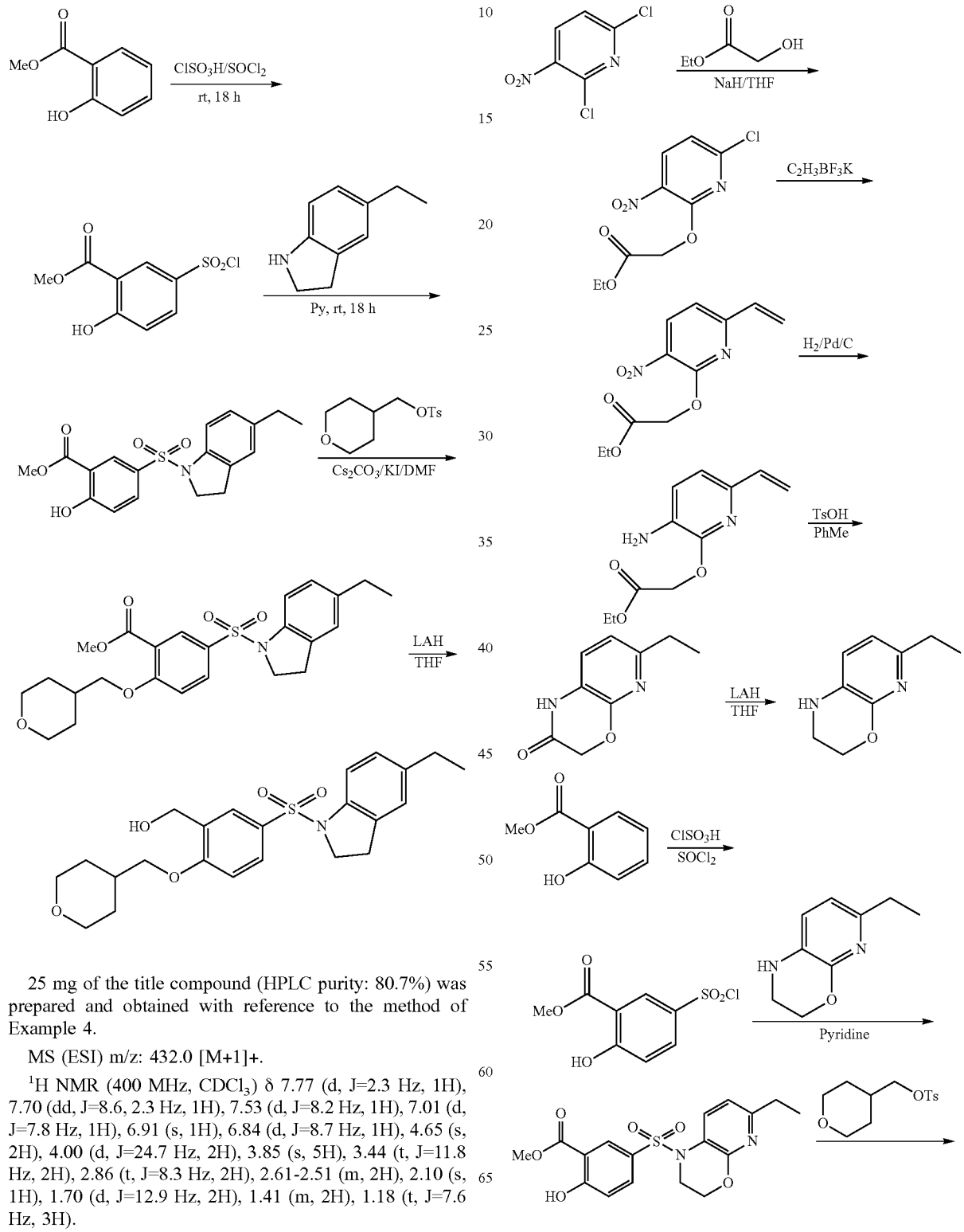
25 mg of the title compound (HPLC purity: 80.7%) was prepared and obtained with reference to the method of Example 4.
MS (ESI) m/z: 432.0 [M+1]+.
$^1$H NMR (400 MHz, CDCl$_3$) δ 7.77 (d, J=2.3 Hz, 1H), 7.70 (dd, J=8.6, 2.3 Hz, 1H), 7.53 (d, J=8.2 Hz, 1H), 7.01 (d, J=7.8 Hz, 1H), 6.91 (s, 1H), 6.84 (d, J=8.7 Hz, 1H), 4.65 (s, 2H), 4.00 (d, J=24.7 Hz, 2H), 3.85 (s, 5H), 3.44 (t, J=11.8 Hz, 2H), 2.86 (t, J=8.3 Hz, 2H), 2.61-2.51 (m, 2H), 2.10 (s, 1H), 1.70 (d, J=12.9 Hz, 2H), 1.41 (m, 2H), 1.18 (t, J=7.6 Hz, 3H).

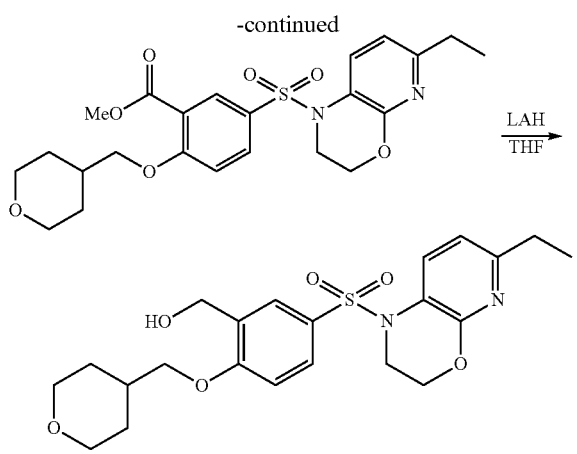

11.1 Synthesis of ethyl 2-((6-chloro-3-nitro-2-pyridyl)oxy)acetate

A 100 mL eggplant-shaped flask was charged with 5 g of 2,6-dichloro-3-nitropyridine, 2.96 g of ethyl glycolate, and 20 mL of THF. The mixture was cooled to 0° C., and 1.04 g of NaH was added in portions. The flask was transferred to an environment under room temperature and the mixture therein was stirred overnight. The reaction was complete as detected by TLC. The mixture in the system was directly concentrated, and sand was prepared and subjected to column chromatography, so as to obtain 6.9 g of ethyl 2-((6-chloro-3-nitro-2-pyridyl)oxy)acetate.

11.2 Synthesis of ethyl 2-((3-nitro-6-vinyl-2-pyridyl)oxy)acetate

A 100 mL eggplant-shaped flask was charged with 3 g of ethyl 2-((6-chloro-3-nitro-2-pyridyl)oxy)acetate, 2 g of potassium vinyltrifluoroborate, and 12 g of cesium carbonate, which were dissolved with a solution of 1,4-dioxane/water (4:1 (V:V)), and 700 mg of tetrakis(triphenylphosphine) was added. The mixture was purged with nitrogen gas and protected thereby, and was stirred at 90° C. overnight. The reaction was complete as detected by TLC. The mixture in the system was extracted with EA, and the organic layer was subjected to column chromatography to obtain 1 g of ethyl 2-((3-nitro-6-vinyl-2-pyridyl)oxy)acetate.

11.3 Synthesis of ethyl 2-((3-amino-6-ethyl-2-pyridyl)oxy)acetate

A 50 mL eggplant-shaped flask was charged with 900 mg of ethyl 2-((3-nitro-6-vinyl-2-pyridyl)oxy)acetate, which was dissolved with methanol, and 50 mg of palladium on carbon was added. The mixture was purged with hydrogen gas and protected thereby, and was stirred at room temperature overnight. The reaction was complete as detected by TLC. The resulting mixture was filtered, and the filtrate was dried by rotary evaporation, so as to obtain 750 mg of ethyl 2-((3-amino-6-ethyl-2-pyridyl)oxy)acetate.

11.4 Synthesis of 6-ethyl-1H-pyrido[2,3-b][1,4]oxazin-2(3H)-one

A 50 mL eggplant-shaped flask was charged with 700 mg of ethyl 2-((3-amino-6-ethyl-2-pyridyl)oxy)acetate and 60 mg of p-toluenesulfonic acid, which were dissolved with toluene. The mixture was stirred at 80° C. overnight. The reaction was complete as detected by TLC. 450 mg of the title compound was obtained by column chromatography.

11.5 Synthesis of 6-ethyl-2,3-dihydro-1H-pyrido[2,3-b][1,4]oxazine

A 25 mL single-necked flask was charged with 450 mg of 6-ethyl-1H-pyrido[2,3-b][1,4]oxazin-2(3H)-one, and 5 mL of THF was added to dissolve the former. The mixture was cooled in an ice bath, and 400 mg of LiAlH$_4$ was added in portions. The mixture was stirred at room temperature overnight. The reaction was complete as detected by TLC. 2 mL of 15% NaOH aqueous solution was added dropwise to quench the reaction. The resulting mixture was filtered, and the filtrate was concentrated under reduced pressure to give 422 mg of the title compound.

11.6 Synthesis of 54(6-ethyl-2,3-dihydro-1H-pyrido[2,3-b][1,4]oxazin-1-yl)sulfonyl)-2-((tetrahydro-2H-pyran-4-yl)methoxy)benzyl Alcohol The rest synthesis steps proceeded with reference to the method described in Example 3, so as to prepare and obtain 100 mg of the title compound (HPLC purity: 99.8%).

MS (ESI) m/z 449.0 [M+1]+.

$^1$H NMR (400 MHz, CDCl$_3$) δ 8.12 (d, J=8.2 Hz, 1H), 7.68 (d, J=2.3 Hz, 1H), 7.48 (s, 1H), 6.84 (dd, J=8.4, 4.5 Hz, 2H), 5.30 (s, 1H), 4.67 (s, 2H), 4.03 (dd, J=11.3, 3.7 Hz, 2H), 3.88 (d, J=6.2 Hz, 4H), 3.86-3.81 (m, 2H), 3.45 (td, J=11.9, 1.7 Hz, 2H), 2.69 (q, J=7.6 Hz, 2H), 2.14-2.07 (m, 1H), 1.72 (d, J=12.9 Hz, 2H), 1.48 (ddd, J=25.2, 12.3, 4.5 Hz, 2H), 1.26 (t, J=7.6 Hz, 3H).

Example 12

Synthesis of (5-((2-methyl-6-trifluoromethyl-3,4-dihydroquinolin-1(2H)-yl)sulfonyl)-2-((tetrahydro-2H-pyran-4-yl)methoxy)phenyl)methanol

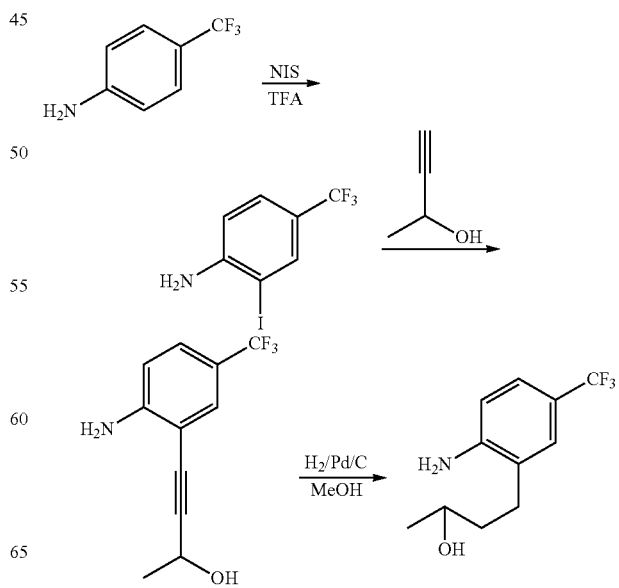

-continued

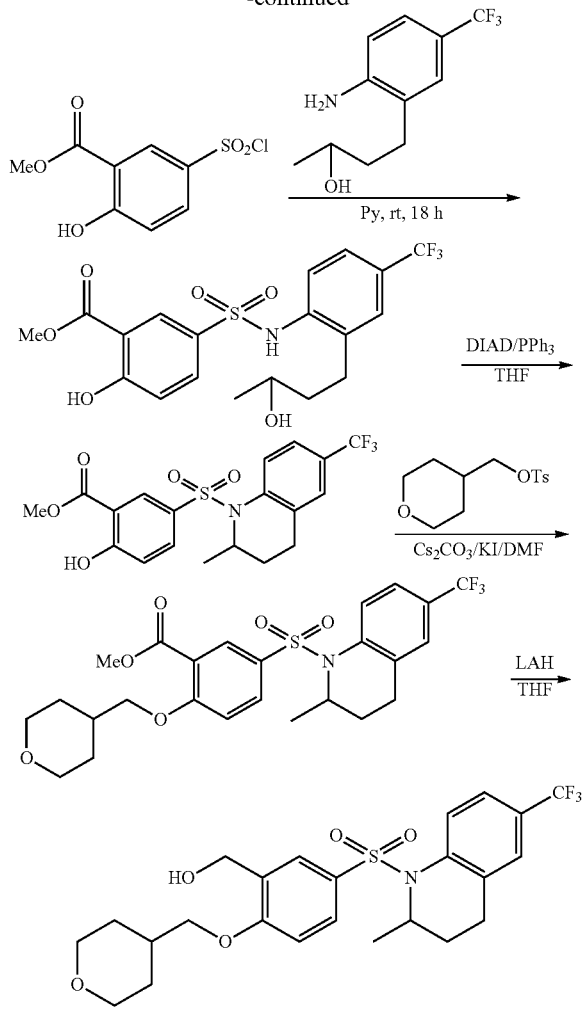

12.1 Synthesis of 2-iodo-4-trifluoromethylaniline

A single-necked flask was charged with 4-trifluoromethylaniline (374 mg), and TFA (5 mL) was added to dissolve the former. The mixture was cooled in an ice bath, and N-iodosuccinimide (522 mg) was added in portions. The mixture was stirred at room temperature overnight. A small amount of the raw materials remained as detected by TLC, and the target product was detected by LCMS. Post-treatment: 2N aqueous sodium hydroxide solution was added, and the mixture was extracted with ethyl acetate (20 ml) three times. The organic phases were combined, washed with saturated aqueous sodium chloride solution, dried over anhydrous sodium sulfate, filtered, and concentrated under reduced pressure. The resulting mixture was allowed to pass through a column, so as to obtain 574 mg of 2-iodo-4-trifluoromethylaniline. LC-MS 287.8 (M+1).

12.2 Synthesis of 4-(2-amino-5-trifluoromethylphenyl)-3-butyn-2-ol

A 100 mL three-necked flask was charged with 574 mg of 2-iodo-4-trifluoromethylaniline, 3 mL of THF and 3 mL of TEA were added, followed by addition of 190 mg of 3-butyn-2-ol, 26 mg of triphenylphosphine and 9.5 mg of CuI under stirring. The flask was evacuated, the mixture was purged with nitrogen gas three times, and 0.05 g of Pd(OAc)$_2$ was added. After the completion of the addition, the flask was evacuated, and the mixture was purged with nitrogen gas three times and stirred at room temperature overnight. The reaction was complete as monitored by TLC. The reaction solution was poured into 100 mL of ice water, and EA (50 mL×2) was added to carry out extraction twice. The organic phases were combined, washed with 15 mL of a saturated aqueous sodium carbonate solution, washed with 15 mL of a saturated NaCl aqueous solution, dried over anhydrous sodium sulfate, filtered, concentrated under reduced pressure, and subjected to column purification (PE: EA=3:1), so as to obtain 0.45 g of 4-(2-amino-5-trifluoromethylphenyl)-3-butyn-2-ol

12.3 Synthesis of 4-(2-amino-5-trifluoromethylphenyl)-2-butanol

A 100 mL single-necked flask was charged with 2.0 g of 4-(2-amino-5-trifluoromethylphenyl)-3-butyn-2-ol, and 10 mL of MeOH was added to dissolve the former under stirring. The flask was evacuated, the mixture was purged with hydrogen gas three times, and 0.2 g of Pd/C was added. The flask was evacuated, and the mixture was purged with hydrogen gas three times. The mixture was heated to 25° C. to 30° C. and stirred overnight. The reaction was complete as monitored by TLC. The mixture was cooled to room temperature, filtered and concentrated under reduced pressure, so as to obtain 2.0 g of 4-(2-amino-5-trifluoromethylphenyl)-2-butanol.

12.4 Synthesis of methyl 2-hydroxy-5-(N-(2-(3-hydroxybutyl)-4-trifluoromethylphenyl) aminosulfonyl)benzoate A 100 mL single-necked flask was charged with 110 mg of 4-(2-amino-5-trifluoromethylphenyl)-2-butanol, and 5 mL of pyridine was added to dissolve the former. The mixture was cooled in an ice bath, and 125 mg of methyl 5-chlorosulfonylsalicylate was added in a small amount repeatedly. The addition was complete over 2 min. The resulting mixture was naturally warmed to room temperature, and the reaction was allowed to proceed overnight. The reaction was complete as monitored by TLC. The mixture was dried by rotary evaporation at 50° C., to which 10 mL of 1N HCl aqueous solution was added, followed by extraction with DCM (100 mL×2). The organic phases were combined, washed with 15 mL of a saturated NaCl aqueous solution, dried over anhydrous sodium sulfate, filtered and concentrated under reduced pressure, so as to obtain 120 mg of the title compound.

12.5 Synthesis of methyl 2-hydroxy-(5-((2-methyl-6-trifluoromethyl-3,4-dihydroquinolin-1(2H)-yl) sulfonyl)benzoate A 50 mL single-necked flask was charged with 120.0 mg of methyl 2-hydroxy-5-(N-(2-(3-hydroxybutyl)-4-trifluoromethylphenyl)aminosulfonyl)benzoate, 1 mL of THF was added to dissolve the former under stirring, and then 140 mg of triphenylphosphine was added. The mixture was stirred and cooled to 0° C. to 5° C., and 82.6 mg of DIAD was added dropwise. After the addition was complete, the mixture was stirred overnight at room temperature. The reaction was complete as monitored by TLC. The resulting mixture was filtered by suction and concentrated, so as to obtain 120 mg of the title compound.

12.6 Synthesis of methyl 5-((2-methyl-6-trifluoromethyl-3,4-dihydroquinolin-1(2H)-yl) sulfonyl)-2-((tetrahydro-2H-pyran-4-yl)methoxy)benzoate A 50 mL single-necked flask was charged with 120.0 mg of methyl 2-hydroxy-(5-((2-methyl-6-trifluoromethyl-3,4-dihydroquinolin-1(2H)-yl)sulfonyl)benzoate, 2 mL of DMF was added to dissolve the former under stirring, and then 75.3 mg (0.279 mmol) of p-toluenesulfonate-4-methyl pyran, 10 mg of KI and 578 mg (0.419 mmol) of cesium carbonate were added. The mixture was heated to 65° C. to 70° C., and was stirred overnight while the temperature of the mixture was kept still. The reaction was complete as monitored by TLC. The reaction solution was poured into 10 mL of ice water, and was extracted twice with DCM (50 mL×2). The organic phases were combined, washed with 10 mL of 1N HCl aqueous solution, washed with 15 mL of a saturated NaCl aqueous solution, dried over anhydrous sodium sulfate, filtered and concentrated under reduced pressure, so as to obtain 0.2 g of the title compound (yield: 136%, crude product).

12.7 Synthesis of 5-((2-methyl-6-trifluoromethyl-3,4-dihydroquinolin-1(2H)-yl)sulfonyl)-2-((tetrahydro-2H-pyran-4-yl)methoxy)benzyl alcohol A 50 mL single-necked flask was charged with 200 mg of methyl 2-hydroxy-(5-((2-methyl-6-trifluoromethyl-3,4-dihydroquinolin-1(2H)-yl)sulfonyl)benzoate, and 2 mL of THF was added to dissolve the former under stirring. The mixture was cooled to 0° C. to 5° C., to which 57.8 mg of LAH was added in a small amount repeatedly. After the completion of the addition, the mixture was stirred at room temperature overnight. The reaction solution was poured into 10 mL of ice water, and 20 mL of DCM was added. The mixture was dried over anhydrous sodium sulfate, filtered, concentrated under reduced pressure, and subjected to separation by passing through a column, so as to obtain 4.0 mg of the title compound.

MS (ESI) m/z 500.0 [M+1]+.

$^1$H NMR (400 MHz, CDCl3) δ 7.88 (d, J=8.6 Hz, 1H), 7.60 (d, J=2.3 Hz, 1H), 7.48-7.38 (m, 2H), 7.26 (s, 1H), 6.80 (d, J=8.7 Hz, 1H), 4.65 (s, 2H), 4.46 (dd, J=12.5, 6.3 Hz, 1H), 4.02 (dd, J=11.2, 3.6 Hz, 2H), 3.87 (d, J=6.3 Hz, 2H), 3.44 (td, J=11.9, 1.8 Hz, 2H), 2.61-2.50 (m, 1H), 2.10 (dt, J=13.5, 6.1 Hz, 2H), 1.99 (d, J=17.3 Hz, 1H), 1.87-1.75 (m, 1H), 1.72 (d, J=12.6 Hz, 2H), 1.52-1.47 (m, 2H), 1.28 (s, 3H).

Example 13

Synthesis of 5-((6-ethyl-2-methyl-3,4-dihydro-1,5-naphthyridin-1(2H)-yl)sulfonyl)-2-((tetrahydro-2H-pyran-4-yl)methoxy)benzyl Alcohol

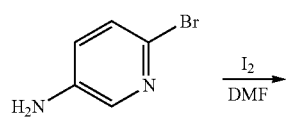

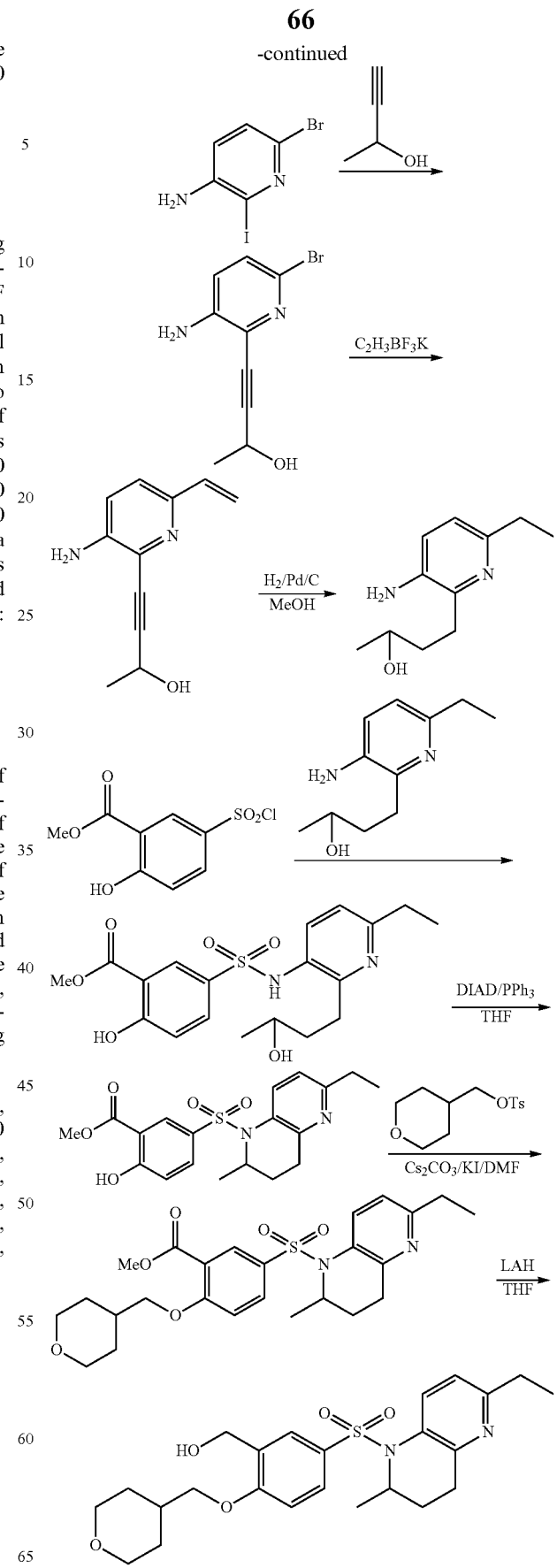

13.1 Synthesis of 5-amino-2-bromo-6-iodopyridine

A 250 mL single-necked flask was charged with 8.65 g of 5-amino-2-bromopyridine, 86 mL of DMF was added to dissolve the former under stirring, followed by addition of 14.0 g of iodine. After the completion of the addition, the mixture was heated to 100° C. and stirred for 4 h while the temperature of the mixture was kept still. The reaction was complete as monitored by TLC. The reaction solution was poured into 100 mL of water, and EA (50 mL×2) was added to carry out extraction twice. The organic phases were combined, washed with 15 mL of a saturated NaCl aqueous solution, dried over anhydrous sodium sulfate, filtered, concentrated under reduced pressure, and purified by passing through a column (PE:EA=5:1), so as to obtain 12.5 g of 5-amino-2-bromo-6-iodopyridine.

13.2 Synthesis of 4-(3-amino-6-bromo-2-pyridyl)-3-butyn-2-ol

A 100 mL three-necked flask was charged with 2.4 g of 5-amino-2-bromo-6-iodopyridine, 3 mL of THF and 3 mL of TEA were added, and 0.76 g of 3-butyn-2-ol, 0.3 g of triphenylphosphine, and 0.1 g of CuI were added under stirring. The flask was evacuated, and the mixture was purged with nitrogen gas three times. 0.1 g of palladium acetate was added. After the completion of the addition, the flask was evacuated, and the mixture was purged with nitrogen gas three times. The mixture was stirred at room temperature overnight, and the reaction was complete as monitored by TLC. The reaction solution was poured into 100 mL of ice water, and EA (50 mL×2) was added to carry out extraction twice. The organic phases were combined, washed with 15 mL of a saturated aqueous sodium carbonate solution, washed with 15 mL of a saturated NaCl aqueous solution, dried over anhydrous sodium sulfate, filtered, concentrated under reduced pressure, and purified by passing through a column (PE:EA=3:1), so as to obtain 2.2 g of the title compound.

13.3 Synthesis of 4-(3-amino-6-vinyl-2-pyridyl)-3-butyn-2-ol

A 100 mL single-necked flask was charged with 1.4 g of 4-(3-amino-6-bromo-2-pyridyl)-3-butyn-2-ol, and 20 mL of 1,4-dioxane and 8 mL of $H_2O$ were added to dissolve the former under stirring. Then, 0.94 g of potassium vinyltrifluoroborate and 6.1 g of cesium carbonate were added. The flask was evacuated, and the mixture was purged with nitrogen gas three times. 0.1 g of Pd(PPh$_3$)$_4$ was added, the flask was evacuated, and the mixture was purged with nitrogen gas three times. The mixture was heated to 90° C. to 95° C. and stirred overnight. The reaction was complete as monitored by TLC. After being cooled to room temperature, the reaction solution was poured into 100 mL of ice water, and EA (50 mL×2) was added to carry out extraction twice. The organic phases were combined, washed with 15 mL of a saturated NaCl aqueous solution, dried over anhydrous sodium sulfate, filtered, concentrated under reduced pressure, and purified by passing through a column (PE:EA=1:1), so as to obtain 1.2 g of the title compound.

13.4 Synthesis of 4-(3-amino-5-ethyl-2-pyridyl)-2-butanol

A 100 mL single-necked flask was charged with 1.0 g of 4-(3-amino-6-vinyl-2-pyridyl)-3-butyn-2-ol, and 10 mL of MeOH was added to dissolve the former under stirring. The flask was evacuated, and the mixture was purged with hydrogen gas three times. 0.2 g of Pd/C was added, the flask was evacuated, and the mixture was purged with hydrogen gas three times. The mixture was heated to 45° C. to 50° C. and stirred for 9 h. The reaction was complete as monitored by TLC. After being cooled to room temperature, the resulting mixture was filtered, concentrated under reduced pressure, and purified by passing through a column (PE/EA 1/1), so as to obtain 1.0 g of 4-(3-amino-5-ethyl-2-pyridyl)-2-butanol.

13.5 Synthesis of methyl 2-hydroxy-5-(N-(6-ethyl-2-(3-hydroxybutyl)-3-pyridyl) aminosulfonyl)benzoate A 100 mL single-necked flask was charged with 4-(3-amino-5-ethyl-2-pyridyl)-2-butanol (1.5 g), and 10 mL of pyridine was added to dissolve the former. The mixture was cooled in an ice bath. Methyl 5-chlorosulfonylsalicylate (2.9 g) was added in a small amount repeatedly, and the mixture was stirred at room temperature overnight. The reaction was complete as detected by TLC. 100 mL of DCM and 20 mL of 1N HCl were added, and the resulting mixture was subjected to liquid-liquid separation. The aqueous phase was extracted with 20 mL of DCM. The combined organic phases were washed with saturated aqueous sodium chloride solution, dried over anhydrous sodium sulfate, filtered and concentrated under reduced pressure, so as to obtain 3.5 g of the title compound.

13.6 Synthesis of methyl 2-hydroxy-5-((6-ethyl-2-methyl-3,4-dihydro-1,5-naphthyridin-1(2H)-yl)sulfonyl)benzoate A 50 mL single-necked flask was charged with 120.0 mg of methyl 2-hydroxy-5-(N-(6-ethyl-2-(3-hydroxybutyl)-3-pyridyl)aminosulfonyl)benzoate, 1 mL of THF was added to dissolve the former under stirring, 154.0 mg of triphenylphosphine was added, and the mixture was stirred and cooled to 0° C. to 5° C. 90.6 mg of DIAD was added dropwise. After the completion of the addition, the mixture was stirred at room temperature overnight. The reaction was complete as monitored by TLC. The resulting mixture was filtered by suction, concentrated, and purified by passing through a column, so as to obtain 118.0 mg of the title compound.

13.7 Synthesis of methyl 5-((6-ethyl-2-methyl-3,4-dihydro-1,5-naphthyridin-1(2H)-yl) sulfonyl)-2-((tetrahydro-2H-pyran-4-yl)methoxy)benzoate A 50 mL single-necked flask was charged with 100.0 mg of methyl 2-hydroxy-5-((6-ethyl-2-methyl-3,4-dihydro-1,5-naphthyridin-1(2H)-yl)sulfonyl)benzoate, and 2 mL of DMF was added to dissolve the former under stirring. 103.8 mg of p-toluenesulfonate-4-methyl pyran, 10 mg of KI and 166.4 mg of cesium carbonate were added. The mixture was heated to 65° C. to 70° C., and was stirred overnight while the temperature of the mixture was kept still. The reaction was complete as monitored by TLC. The reaction solution was poured into 10 mL of ice water, and the mixture was extracted twice with DCM (50 mL×2). The organic phases were combined, washed with 10 mL of 1N HCl aqueous solution, washed with 15 mL of a saturated NaCl aqueous solution, dried over anhydrous sodium sulfate, filtered and concentrated under reduced pressure, so as to obtain 0.2 g of the title compound.

13.8 Synthesis of 5-((6-ethyl-2-methyl-3,4-dihydro-1,5-naphthyridin-1(2H)-yl)sulfonyl)-2-((tetrahydro-2H-pyran-4-yl)methoxy)benzyl Alcohol A 50 mL single-necked flask was charged with 200 mg of methyl 5-((6-ethyl-2-methyl-3,4-dihydro-1,5-naphthyridin-1(2H)-yl)sulfonyl)-2-((tetrahydro-2H-pyran-4-yl)methoxy) benzoate, and 2 mL of THF was added to dissolve the former under stirring. The mixture was cooled to 0° C. to 5° C., and 76.0 mg of LAH was added in a small amount repeatedly. After the completion of the addition, the mixture was stirred at room temperature overnight. The reaction solution was poured into 10 mL of ice water, and 20 mL of DCM was added. The mixture was dried over anhydrous sodium sulfate, filtered, concentrated under reduced pressure, and purified by passing through a column, so as to obtain 4.0 mg of the title compound.

MS (ESI) m/z 461.0 [M+1]+.

$^1$H NMR (400 MHz, CDCl$_3$) δ 8.00 (d, J=8.4 Hz, 1H), 7.49 (d, J=2.3 Hz, 1H), 7.38 (dd, J=8.6, 2.4 Hz, 1H), 7.06 (d, J=8.4 Hz, 1H), 6.80 (d, J=8.7 Hz, 1H), 5.30 (s, 1H), 4.63 (s, 2H), 4.35 (dd, J=12.3, 5.9 Hz, 1H), 4.02 (dd, J=11.1, 3.6 Hz, 2H), 3.86 (d, J=6.3 Hz, 2H), 3.44 (td, J=11.8, 1.9 Hz, 2H), 2.77 (q, J=7.6 Hz, 2H), 2.69-2.56 (m, 1H), 2.15 (ddd, J=24.6, 15.2, 4.9 Hz, 2H), 1.77-1.66 (m, 3H), 1.52-1.41 (m, 3H), 1.30 (d, J=7.6 Hz, 3H), 1.27 (d, J=2.8 Hz, 3H).

Example 14

Synthesis of 5-((6-isopropyl-2-methyl-3,4-dihydroquinolin-1(2H)-yl)sulfonyl)-2-((tetrahydro-2H-pyran-4-yl)methoxy)benzyl Alcohol and 5-((6-propyl-2-methyl-3,4-dihydroquinolin-1(2H)-yl)sulfonyl)-2-((tetrahydro-2H-pyran-4-yl)methoxy)benzyl Alcohol

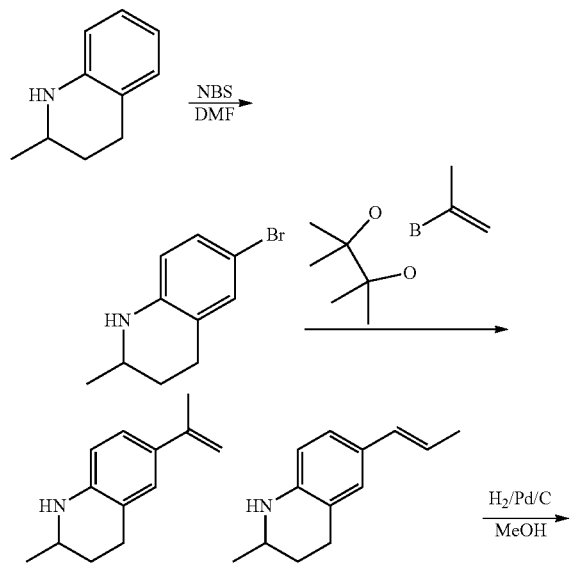

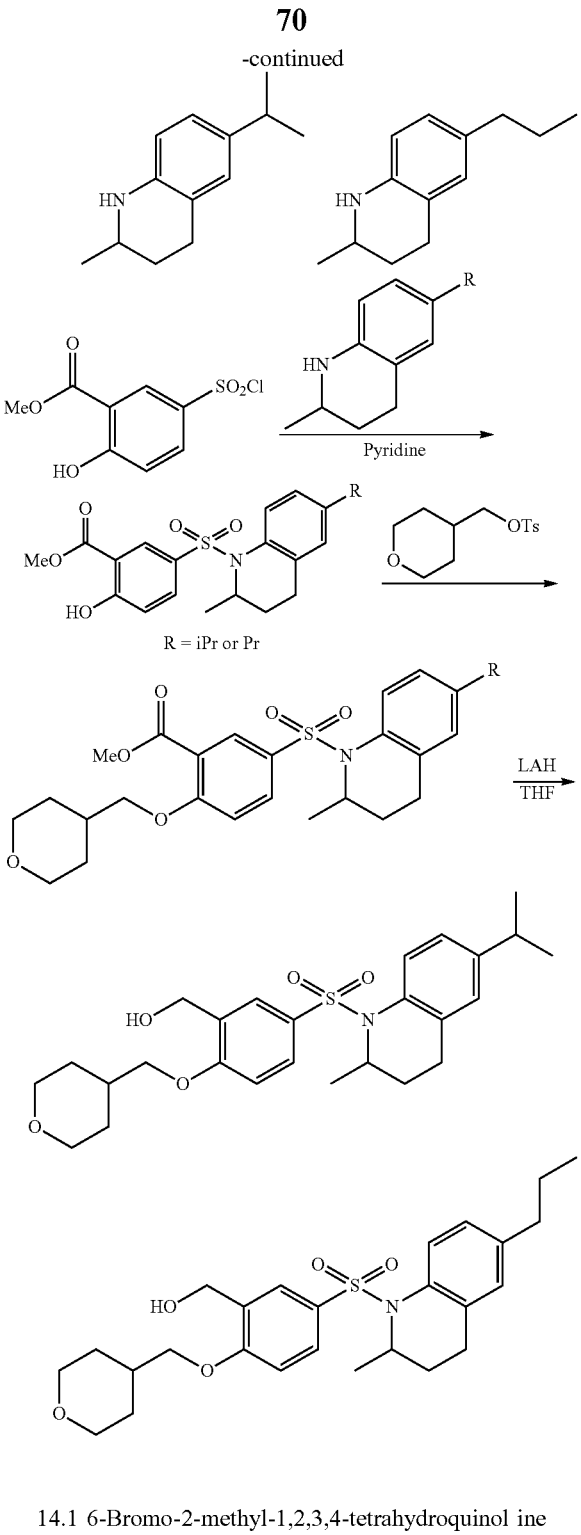

14.1 6-Bromo-2-methyl-1,2,3,4-tetrahydroquinoline

A 25 mL single-necked flask was charged with 2-methyl-1,2,3,4-tetrahydroquinoline (416 mg), and 10 mL of DMF was added to dissolve the former. The mixture was cooled in an ice bath, and NBS (396 mg) was added in portions. After the completion of the addition, the mixture was placed in an ice bath and stirred for 3 h. The reaction was complete as detected by TLC. 100 mL of water was added, and the mixture was extracted with 20 mL of EA three times. The combined organic phases were washed with 20 mL of a saturated aqueous sodium chloride solution, dried over anhydrous sodium sulfate, filtered and concentrated under reduced pressure, so as to obtain 390 mg of 6-bromo-2-methyl-1,2,3,4-tetrahydroquinoline.

14.2 Synthesis of a mixture of 2-methyl-6-isopropenyl-1,2,3,4-tetrahydroquinoline and 2-methyl-6-propenyl-1,2,3,4-tetrahydroquinoline A 50 mL single-necked flask was charged with 805 mg of 6-bromo-2-methyl-1,2,3,4-tetrahydroquinoline and 718 mg of isopropenylboronic acid pinacol ester, and 10 mL of 1,4-dioxane was added to dissolve the formers, followed by addition of 1.4 g of $K_2CO_3$, 4 mL of water and 32 mg of SPhos. The mixture was purged with nitrogen gas three times, 18 mg of $Pd(OAc)_2$ was added, and the resultant was purged with nitrogen gas three times again. The mixture was heated to 90° C. with an external bath and stirred overnight. The reaction was complete as detected by TLC. Post-treatment: 20 mL of water was added, and the mixture was extracted with 30 mL of EA three times. The combined organic phases were washed with saturated aqueous sodium chloride solution, dried over anhydrous sodium sulfate, filtered and concentrated under reduced pressure to obtain an oil, which was purified by passing through a column, so as to obtain 630 mg of the title mixture.

14.3 A mixture of 2-methyl-6-isopropyl-1,2,3,4-tetrahydroquinoline and 2-methyl-6-propyl-1,2,3,4-tetrahydroquinoline A 250 mL single-necked flask was charged with 0.6 g of the mixture of 2-methyl-6-isopropenyl-1,2,3,4-tetrahydroquinoline and 2-methyl-6-propenyl-1,2,3,4-tetrahydroquinoline prepared in the last step and 10 mL of MeOH. After the dissolution, 0.12 g of Pd/C was added. The mixture was purged with hydrogen gas three times, and was stirred and reacted at a room temperature of 18° C. for 16 h. A sample was taken, and TLC detection showed that the reaction of the raw materials was complete. The resulting mixture was filtered through celite and concentrated, so as to obtain 0.3 g of the title mixture.

14.4 5-((6-isopropyl-2-methyl-3,4-dihydro quinolin-1(2H)-yl)sulfonyl)-2-((tetrahydro-2H-pyran-4-yl)methoxy)benzyl Alcohol and 5-((6-propyl-2-methyl-3,4-dihydroquinolin-1(2H)-yl)sulfonyl)-2-((tetrahydro-2H-pyran-4-yl)methoxy)benzyl Alcohol The rest synthesis steps proceeded with reference to the method described in Example 3, and mg of 5-((6-isopropyl-2-methyl-3,4-dihydroquinolin-1(2H)-yl)sulfonyl)-2-((tetrahydro-2H-pyran-4-yl)methoxy)benzyl alcohol and 15 mg of 5-((6-propyl-2-methyl-3,4-dihydroquinolin-1(2H)-yl)sulfonyl)-2-((tetrahydro-2H-pyran-4-yl)methoxy)benzyl alcohol were obtained by separation.

5-((6-Isopropyl-2-methyl-3,4-dihydroquinolin-1(2H)-yl)sulfonyl)-2-((tetrahydro-2H-pyran-4-yl)methoxy)benzyl alcohol: MS (ESI) m/z 474.0 [M+1]+. $^1$H NMR (400 MHz, CDCl3) δ 7.65 (d, J=8.3 Hz, 1H), 7.43 (t, J=2.5 Hz, 1H), 7.41 (dd, J=8.5, 2.3 Hz, 1H), 7.11 (dd, J=8.4, 2.0 Hz, 1H), 6.84 (d, J=1.6 Hz, 1H), 6.79 (d, J=8.5 Hz, 1H), 4.61 (s, 2H), 4.38-4.26 (m, 1H), 4.04 (dd, J=11.3, 3.7 Hz, 2H), 3.88 (d, J=6.4 Hz, 2H), 3.46 (td, J=11.9, 1.8 Hz, 2H), 2.92-2.82 (m, 1H), 2.41 (s, 1H), 2.11 (s, 1H), 2.03 (s, 1H), 1.83 (dd, J=9.6, 5.7 Hz, 2H), 1.74 (dd, J=12.9, 1.8 Hz, 2H), 1.49 (dd, J=12.7, 4.3 Hz, 2H), 1.36 (dd, J=7.1, 5.4 Hz, 1H), 1.29 (d, J=6.5 Hz, 3H), 1.25 (d, J=6.9 Hz, 6H).

5-((6-Propyl-2-methyl-3,4-dihydroquinolin-1(2H)-yl)sulfonyl)-2-((tetrahydro-2H-pyran-4-yl) methoxy)benzyl alcohol: MS (ESI) m/z 474.0 [M+1]+. $^1$H NMR (400 MHz, CDCl3) δ 7.64 (d, J=8.3 Hz, 1H), 7.47 (d, J=2.3 Hz, 1H), 7.37 (dd, J=8.6, 2.3 Hz, 1H), 7.05 (dd, J=8.3, 1.9 Hz, 1H), 6.81-6.75 (m, 2H), 4.61 (s, 2H), 4.34 (dd, J=12.9, 6.5 Hz, 1H), 4.03 (dd, J=11.3, 3.6 Hz, 2H), 3.88 (d, J=6.4 Hz, 2H), 3.46 (td, J=11.9, 1.8 Hz, 2H), 2.59-2.48 (m, 2H), 2.43-2.31 (m, 1H), 2.17-2.04 (m, 2H), 1.88-1.78 (m, 2H), 1.78-1.70 (m, 3H), 1.64 (dd, J=15.1, 7.5 Hz, 2H), 1.50 (td, J=12.4, 4.4 Hz, 2H), 1.34 (ddd, J=9.9, 6.6, 2.9 Hz, 1H), 1.28 (d, J=6.5 Hz, 3H), 0.95 (t, J=7.3 Hz, 3H).

Example 15

Synthesis of 5-((2,6-diethyl-3,4-dihydroquinolin-1(2H)-yl)sulfonyl)-2-((tetrahydro-2H-pyran-4-yl)methoxy)benzyl Alcohol

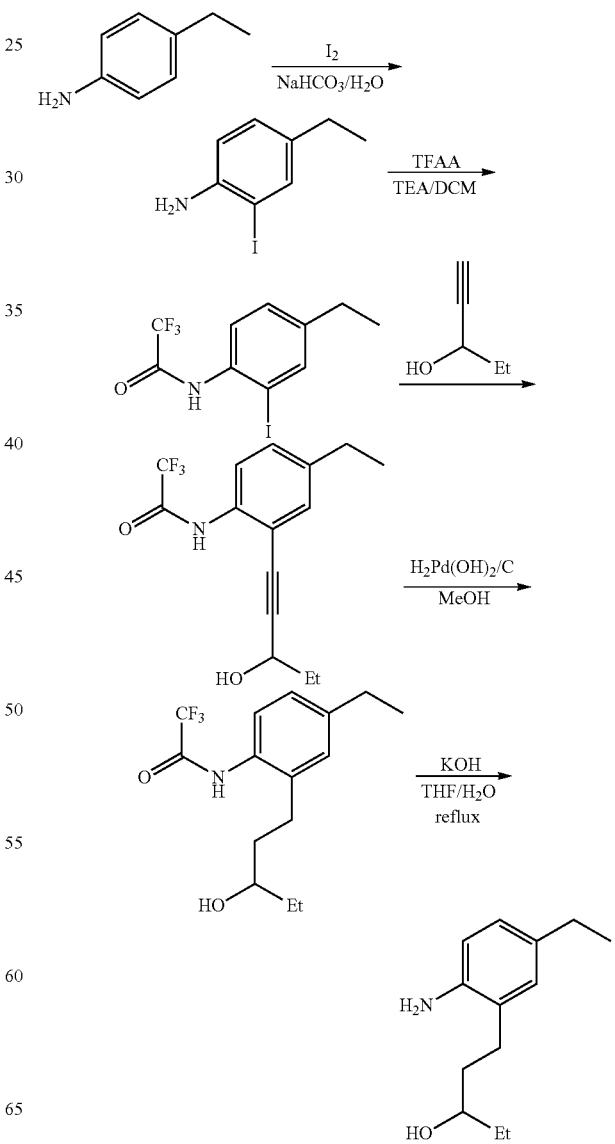

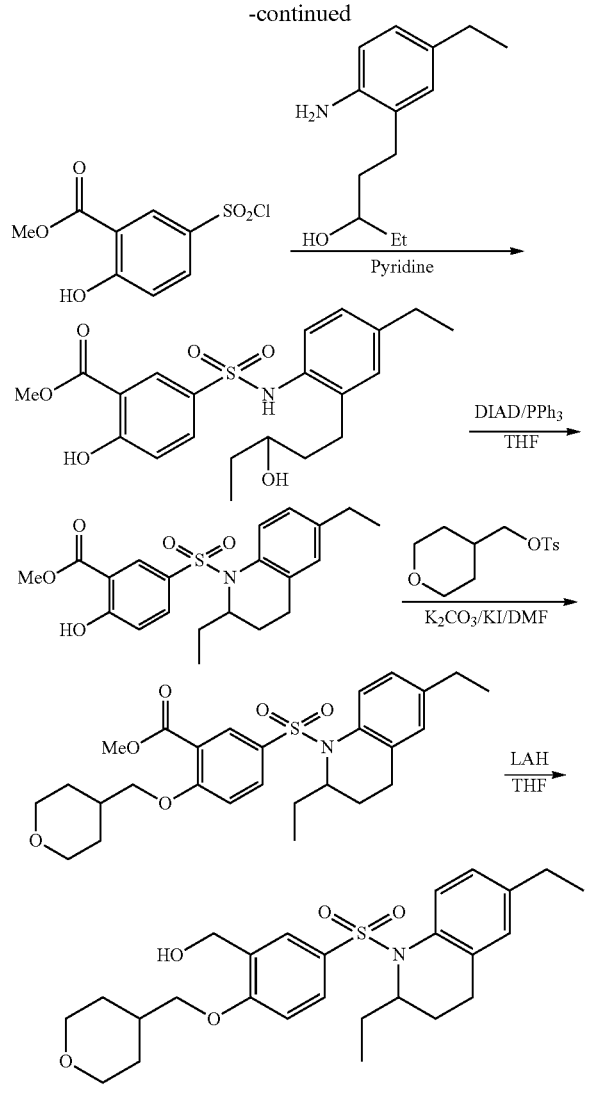

15.1 Synthesis of N-(4-ethyl-2-(3-hydroxypentyl)phenyl)-2,2,2-trifluoroacetamide 1.95 g of the title compound was prepared and obtained with reference to the synthesis methods in steps 5.1 to 5.4 of Example 5.

15.2 Synthesis of 1-(2-amino-5-ethylphenyl)-3-pentanol 700 mg of N-(4-ethyl-2-(3-hydroxypentyl)phenyl)-2,2,2-trifluoroacetamide was dissolved in 20 mL of tetrahydrofuran, and 646 mg of potassium hydroxide was weighed and dissolved in 10 mL of water. The freshly prepared solution of N-(4-ethyl-2-(3-hydroxypentyl)phenyl)-2,2,2-trifluoroacetamide in tetrahydrofuran and the aqueous potassium hydroxide solution were charged into a reaction flask. The mixture was heated to 80° C., and was stirred and reacted for 16 h while the temperature of the mixture was kept still. The completion of the reaction of the raw materials was monitored by LCMS. Tetrahydrofuran was removed by rotary evaporation under reduced pressure, and the resulting aqueous solution was extracted with ethyl acetate (50 mL×2). The organic phases were combined, dried over anhydrous sodium sulfate, filtered, and concentrated to obtain a crude product. The crude product was subjected to silica gel column chromatography (PE:EA=4:1), so as to obtain 410 mg of the title compound.

15.3 Synthesis of 5-((2,6-diethyl-3,4-dihydroquinolin-1(2H)-yl)sulfonyl)-2-((tetrahydro-2H-pyran-4-yl)methoxy)benzyl Alcohol The rest synthesis steps proceeded with reference to the synthesis method in Example 12, so as to prepare and obtain 200 mg of the title compound (HPLC purity: 96.8%).

MS (ESI) m/z 474.0 [M+1]+.

$^1$H NMR (400 MHz, CDCl$_3$) δ 7.63 (d, J=8.3 Hz, 1H), 7.46 (d, J=2.3 Hz, 1H), 7.37 (dd, J=8.6, 2.3 Hz, 1H), 7.04 (dd, J=8.3, 1.8 Hz, 1H), 6.82-6.73 (m, 2H), 4.59 (d, J=6.3 Hz, 2H), 4.20-4.09 (m, 1H), 4.01 (dd, J=11.3, 3.7 Hz, 2H), 3.85 (d, J=6.4 Hz, 2H), 3.43 (td, J=11.9, 1.8 Hz, 2H), 2.58 (q, J=7.6 Hz, 2H), 2.44-2.32 (m, 1H), 2.10 (dddd, J=15.5, 11.7, 8.0, 3.9 Hz, 1H), 1.86 (dt, J=16.1, 6.4 Hz, 1H), 1.74-1.68 (m, 3H), 1.64-1.54 (m, 1H), 1.52-1.35 (m, 4H), 1.21 (t, J=7.6 Hz, 3H), 0.93 (t, J=7.4 Hz, 3H).

Example 16

Synthesis of 1-((3-(hydroxymethyl)-4-((tetrahydro-2H-pyran-4-yl)methoxy)phenyl) sulfonyl)-2-methyl-1,2,3,4-tetrahydroquinoline-6-carbonitrile

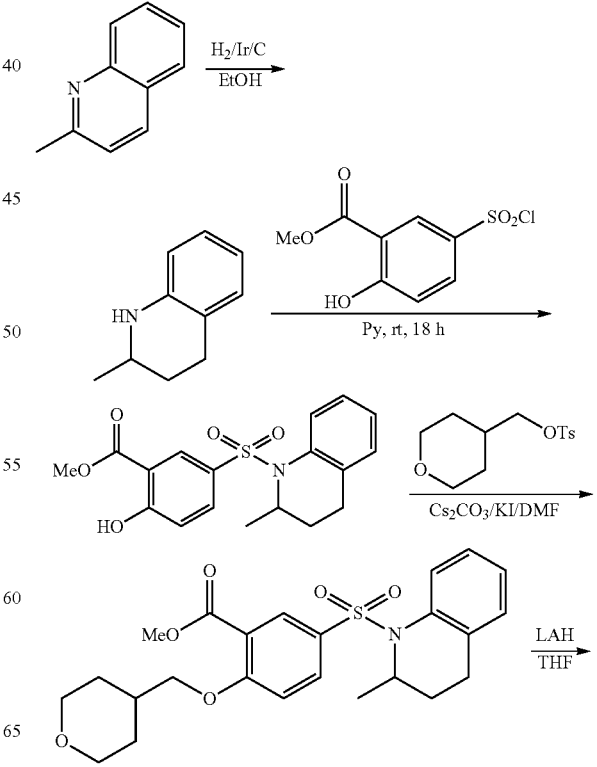

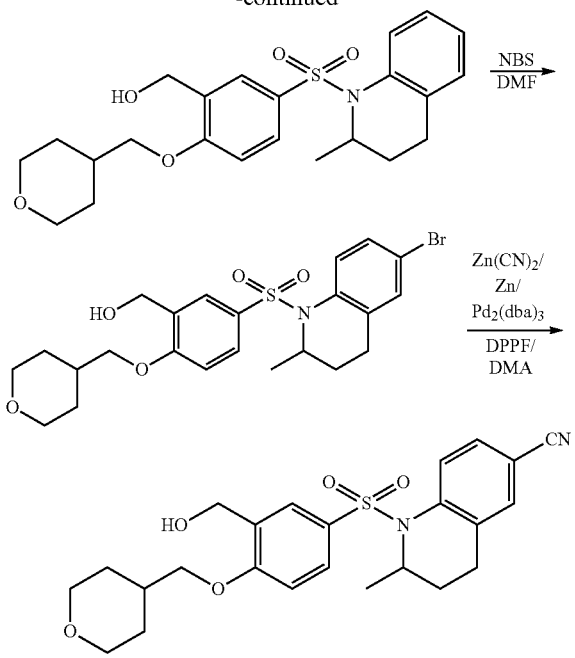

16.1 5-((2-methyl-3,4-dihydroquinolin-1(2H)-yl) sulfonyl)-2-((tetrahydro-2H-pyran-4-yl) methoxy) benzyl Alcohol 420 mg of the title compound was prepared and obtained with reference to the synthesis method in Example 8.

16.2 5-((6-bromo-2-methyl-3,4-dihydroquinolin-1 (2H)-yl) sulfonyl)-2-((tetrahydro-2H-pyran-4-yl) methoxy)benzyl Alcohol A 25 mL single-necked flask was charged with 370 mg of 5-((2-methyl-3,4-dihydroquinolin-1(2H)-yl) sulfonyl)-2-((tetrahydro-2H-pyran-4-yl)methoxy)benzyl alcohol prepared in the last step, and 4 mL of DMF was added to dissolve the former. The mixture was cooled to −10° C., and 164 mg of NBS was added in portions. After the completion of the addition, the mixture was stirred for 1 h in an ice bath. The reaction was complete as detected by TLC. 100 mL of water was added, and the mixture was extracted with 20 mL of EA three times. The combined organic phases were washed with 20 mL of a saturated aqueous sodium chloride solution, dried over anhydrous sodium sulfate, filtered, concentrated under reduced pressure, and purified by passing through a column, so as to obtain 440 mg of the title compound.

16.3 1-((3-(hydroxy methyl)-4-((tetrahydro-2H-pyran-4-yl)methoxy)phenyl)sulfonyl)-2-methyl-1,2,3,4-tetrahydroquinoline-6-carbonitrile A 25 mL single-necked flask was charged with 400 mg of 5-((6-bromo-2-methyl-3,4-dihydroquinolin-1(2H)-yl) sulfonyl)-2-((tetrahydro-2H-pyran-4-yl)methoxy)benzyl alcohol, 480 mg of zinc cyanide, 10 mg of zinc powder, 80 mg of tris(dibenzylideneindeneacetone) dipalladium, 25 mg of 1,1'-bis(diphenylphosphino)ferrocene, and 6 mL of DMA, which were purged and protected with nitrogen gas, and stirred at 120° C. for 4 h. The reaction was complete as detected by TLC. After the resulting mixture was filtered, 100 mL of water was added, and the mixture was extracted with 20 mL of EA three times. The combined organic phases were washed with 20 mL of a saturated aqueous sodium chloride solution, dried over anhydrous sodium sulfate, and purified by passing through a column, so as to obtain 110 mg of a yellow oil, which was subjected to HPLC to prepare and obtain 24 mg of the title compound (HPLC purity: 94%).

MS (ESI) m/z 457.0 [M+1]+.

$^1$H NMR (400 MHz, CDCl$_3$) δ 7.88 (d, J=8.6 Hz, 1H), 7.63 (d, J=2.4 Hz, 1H), 7.47 (dd, J=8.6, 1.9 Hz, 1H), 7.41 (dd, J=8.7, 2.4 Hz, 1H), 7.31 (s, 1H), 6.80 (d, J=8.7 Hz, 1H), 4.66 (s, 2H), 4.49 (dd, J=12.4, 6.0 Hz, 1H), 4.02 (dd, J=11.4, 3.5 Hz, 2H), 3.87 (d, J=6.3 Hz, 2H), 3.44 (td, J=11.9, 1.9 Hz, 2H), 2.62-2.52 (m, 1H), 2.21-2.04 (m, 2H), 1.85-1.75 (m, 1H), 1.75-1.66 (m, 2H), 1.57-1.41 (m, 4H), 1.26 (d, J=6.6 Hz, 3H).

Example 17

Synthesis of 5-((6-ethyl-3,3-di methyl-3,4-dihydroquinolin-1(2H)-yl)sulfonyl)-2-((tetrahydro-2H-pyran-4-yl)methoxy)benzyl Alcohol

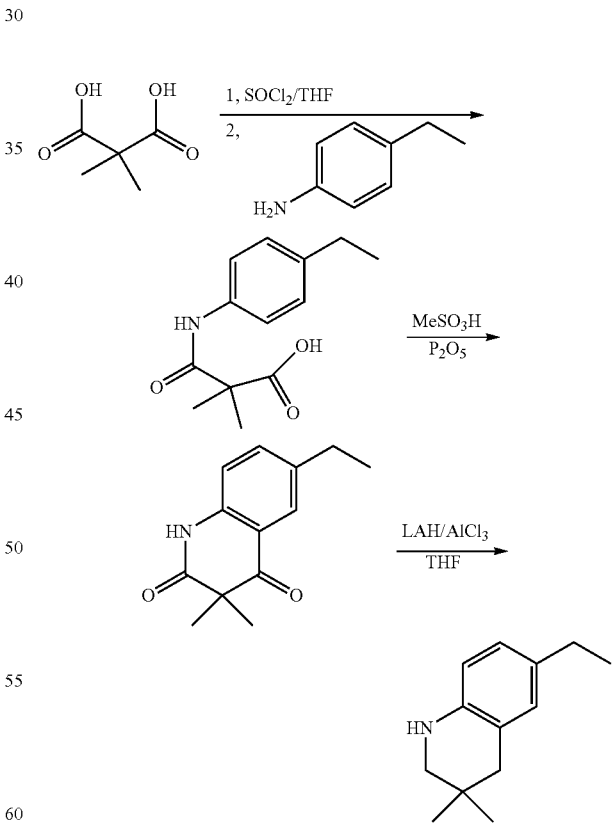

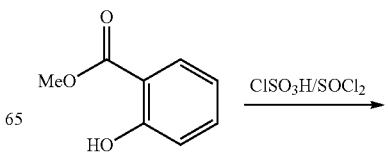

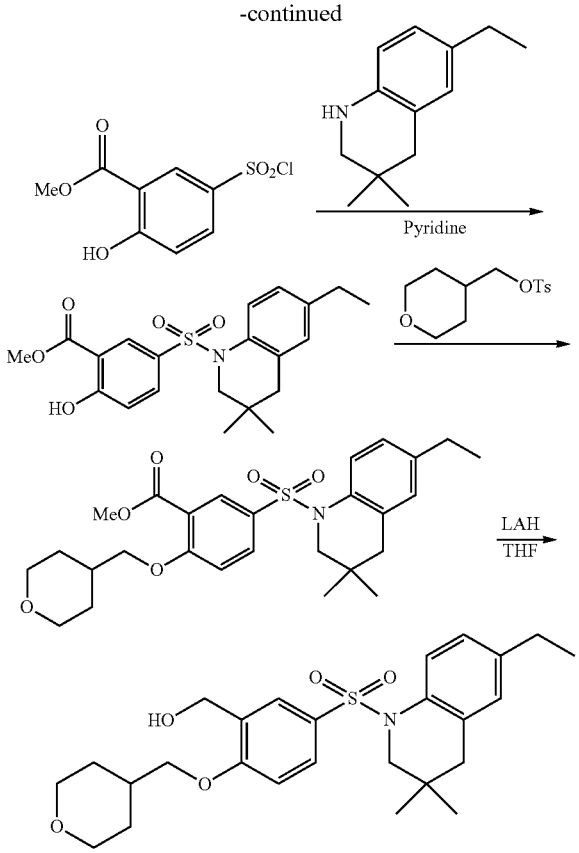

17.1
3-(4-ethylphenylamino)-2,2-dimethyl-3-oxopropionic Acid

A 250 mL single-necked flask was charged with 10.0 g of dimethylmalonic acid and 100 mL of THF, 7 mL of SOCl₂ was added dropwise at a room temperature of 18° C., followed by reflux in an oil bath to react for 2 h. The heating was stopped, the mixture was naturally cooled to room temperature, and p-ethylaniline was slowly added dropwise under stirring. After the completion of the addition, the reaction proceeded at a room temperature of 18° C. under stirring for 16 h. A sample was taken, and the raw materials disappeared as monitored by TLC. The reaction solution was poured into 5 N HCl (150 mL) and extracted three times with EA (80 mL×3). The organic phases were combined, washed three times with saturated NaHCO₃ solution (80 mL×3). The NaHCO₃ phases were combined and adjusted to pH 2 by 5 N HCl, and then extracted three times with EA (100 mL×3). The organic phases were combined, washed twice with saturated NaCl solution (100 mL×2), dried over anhydrous Na₂SO₄ and concentrated, so as to obtain 12.0 g of 3-(4-ethylphenylamino)-2,2-dimethyl-3-oxopropionic acid.

17.2 6-ethyl-3,3-dimethylquinolin-2,4(1H,3H)-dione

A 100 mL single-necked flask was charged with 5.00 g of 3-(4-ethylphenylamino)-2,2-dimethyl-3-oxopropionic acid, 60 mL of methanesulfonic acid, and 4.8 g of phosphorus pentoxide. The mixture was reacted in an oil bath at 70° C. for 16 h. A sample was taken, and the spots of the raw materials disappeared and the reaction was complete as monitored by TLC. The reaction mixture was naturally cooled to room temperature, and was slowly poured into ice water (150 mL), and a large amount of solid was precipitated. EA (100 mL×3) was used to perform extraction three times. The organic phases were combined, washed twice with water (150 mL×2), washed twice with saturated NaCl solution (100 mL×2), dried over anhydrous Na₂SO₄ and concentrated, so as to obtain 3.9 g of 6-ethyl-3,3-dimethylquinolin-2,4(1H,3H)-dione.

17.3
6-ethyl-3,3-dimethyl-1,2,3,4-tetrahydroquinoline

A 50 mL single-necked flask was charged with 2.45 g of AlCl₃ and 1.4 g of LiAlH₄, 20 mL of THF was then slowly added dropwise into the reaction flask, and a large amount of white smoke was generated during the dropwise addition. After the completion of the addition, the mixture was stirred at a room temperature of 18° C. for 0.5 h. A solution of 2.0 g of 6-ethyl-3,3-dimethylquinolin-2,4(1H,3H)-dione in 20 mL of THF was added to the reaction system, which was then stirred for 2 h at a room temperature of 18° C. A sample was taken, TLC detection showed that the spots of the raw materials disappeared and the reaction was complete. The reaction solution was poured into 60 mL of ice water and extracted four times with EA (30 mL×4). The organic phases were combined, washed twice with saturated saline (60 mL×2), dried over anhydrous sodium sulfate, concentrated, and subjected to column chromatography (PE:EA=15:1), so as to obtain 980 mg of 6-ethyl-3,3-dimethyl-1,2,3,4-tetrahydroquinoline.

17.4 5-((6-ethyl-3,3-di methyl-3,4-dihydro quinolin-1 (2H)-yl)sulfonyl)-2-((tetrahydro-2H-pyran-4-yl)methoxy)benzyl Alcohol The rest reaction steps proceeded with reference to the synthesis method in Example 3, so as to prepare and obtain 27 mg of the title compound, of which HPLC purity was 95.4%.

MS (ESI) m/z 474.0 [M+1]+.

¹H NMR (400 MHz, CDCl₃) δ 7.79 (d, J=2.2 Hz, 1H), 7.73 (dd, J=8.6, 2.3 Hz, 1H), 7.47 (d, J=8.5 Hz, 1H), 6.91 (dd, J=8.6, 1.6 Hz, 1H), 6.87 (d, J=8.7 Hz, 1H), 6.82 (s, 1H), 4.67 (s, 2H), 4.01 (dd, J=11.3, 3.7 Hz, 2H), 3.88 (d, J=6.3 Hz, 2H), 3.57 (s, 2H), 3.48-3.40 (m, 2H), 2.52 (q, J=7.6 Hz, 2H), 2.41 (s, 2H), 2.13-2.05 (m, 1H), 1.75-1.67 (m, 2H), 1.52-1.41 (m, 2H), 1.17 (t, J=7.6 Hz, 3H), 1.03 (s, 6H).

Example 18

Synthesis of (S)-(5-((6-ethyl-8-fluoro-2-methyl-3,4-dihydroquinolin-1 (2H)-yl)sulfonyl)-2-((tetrahydro-2H-pyran-4-yl)methoxy)benzyl Alcohol

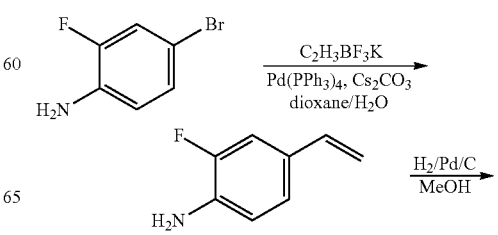

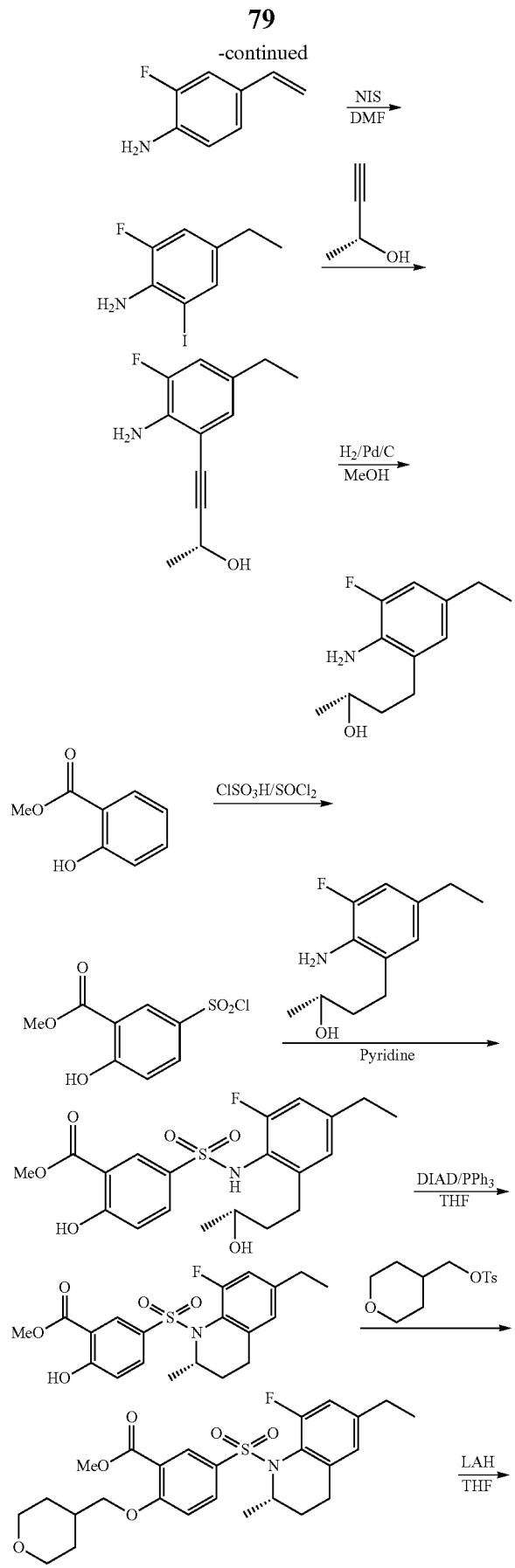
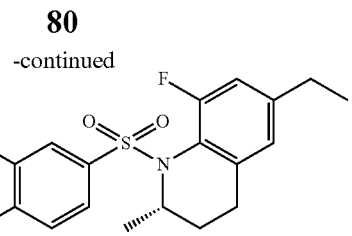

18.1 4-Vinyl-2-fluoroaniline

A 500 mL single-necked flask was charged with 5.0 g of 4-bromo-2-fluoroaniline, and 120 mL of 1,4-dioxane and 30 mL of water were added to dissolve the former under stirring. 0.94 g of potassium vinyltrifluoroborate and 27.5 g of cesium carbonate were added. The flask was evacuated, and the mixture was purged with nitrogen gas three times. 0.2 g of Pd(PPh$_3$)$_4$ was added. The flask was evacuated, and the mixture was purged with nitrogen gas three times. The mixture was heated to 90° C. to 95° C. and stirred overnight. The reaction was complete as monitored by TLC. After being cooled to room temperature, the reaction solution was poured into 100 mL of ice water, to which EA (50 mL×2) was added to perform extraction twice. The organic phases were combined, washed with 15 mL of a saturated NaCl aqueous solution, dried over anhydrous sodium sulfate, filtered, concentrated under reduced pressure, and purified by passing through a column (PE/EA 1/1), so as to obtain 2.8 g of 4-vinyl-2-fluoroaniline.

18.2 4-Ethyl-2-fluoroaniline

A 100 mL single-necked flask was charged with 2.8 g (20.4 mmol) of 4-vinyl-2-fluoroaniline, and 10 mL of MeOH was added to dissolve the former under stirring. The flask was evacuated, and the mixture was purged with hydrogen gas three times. 0.2 g of Pd/C was added. The flask was evacuated, and the mixture was purged with hydrogen gas three times. The mixture was heated to 25° C. to 30° C. and stirred for 17 h. The reaction was complete as monitored by TLC. After being cooled to room temperature, the reaction mixture was filtered, concentrated under reduced pressure, and purified by passing through a column (PE:EA=10:1), so as to obtain 1.3 g of 4-ethyl-2-fluoroaniline.

18.3 4-Ethyl-2-fluoro-6-iodoaniline

A 100 mL single-necked flask was charged with 1.3 g (9.35 mmol) of 4-ethyl-2-fluoroaniline, and 13 mL of DMF was added to dissolve the former under stirring. The mixture was cooled to 0° C. to 5° C., and 2.4 g (10.75 mmol) of NIS was added in a small amount repeatedly over 20 min. The ice-water bath was removed, the mixture was naturally warmed to room temperature, and the mixture was stirred while the temperature was kept still. The reaction was complete as monitored by TLC. The reaction solution was poured into 100 mL of water, and EA (50 mL×2) was added to perform extraction twice. The organic phases were combined, washed with 15 mL of a saturated NaCl aqueous solution, dried over anhydrous sodium sulfate, filtered, and concentrated under reduced pressure, so as to obtain 2.5 g of 4-ethyl-2-fluoro-6-iodoaniline.

18.4 (R)-4-(2-amino-5-ethyl-3-fluorophenyl)-3-butyn-2-ol

A 100 mL three-necked flask was charged with 2.65 g (10 mmol) of 4-ethyl-2-fluoro-6-iodoaniline as a solid, and 5 mL of THF and 5 mL of TEA were added. 0.9 g (13 mmol) of (R)-2-hydroxybutyne, 0.26 g (1 mmol) of triphenylphosphine and 0.1 g (0.5 mmol) of CuI were added under stirring. The flask was evacuated, and the mixture was purged with nitrogen gas three times. 0.1 g of Pd(OAc)$_2$ was added. After the completion of the addition, the flask was evacuated, and the mixture was purged with nitrogen gas three times. The mixture was stirred at room temperature overnight. The reaction was complete as monitored by TLC. The reaction solution was poured into 100 mL of ice water, and EA (50 mL×2) was added to perform extraction twice. The organic phases were combined, washed with 15 mL of a saturated NaHCO$_3$ aqueous solution, washed with 15 mL of a saturated NaCl aqueous solution, dried over anhydrous sodium sulfate, filtered, concentrated under reduced pressure, and purified by passing through a column (PE:EA=3:1), so as to obtain 0.7 g of the title compound.

18.5 (R)-4-(2-amino-5-ethyl-3-fluorophenyl)-2-butanol

A 100 mL single-necked flask was charged with 0.7 g of (R)-4-(2-amino-5-ethyl-3-fluorophenyl)-3-butyn-2-ol, and 10 mL of MeOH was added to dissolve the former under stirring. The flask was evacuated, and the mixture was purged with hydrogen gas three times. 0.2 g of Pd/C was added. The flask was evacuated, and the mixture was purged with hydrogen gas three times. The mixture was heated to 25° C. to 30° C. and stirred overnight. The reaction was complete as monitored by TLC. After being cooled to room temperature, the reaction mixture was filtered and concentrated under reduced pressure, so as to obtain 0.55 g of the title compound.

18.6 (S)-5-((6-ethyl-8-fluoro-2-methyl-3,4-dihydroquinolin-1(2H)-yl)sulfonyl)-2-((tetrahydro-2H-pyran-4-yl)methoxy)benzyl Alcohol The rest reaction steps proceeded with reference to the synthesis method in Example 13, so as to prepare and obtain 8.0 mg of the title compound.

MS (ESI) m/z 478.0 [M+1]+.

$^1$H NMR (400 MHz, CDCl$_3$) δ 7.77 (d, J=2.1 Hz, 1H), 7.67 (dd, J=8.6, 2.2 Hz, 1H), 6.91-6.83 (m, 2H), 6.68 (s, 1H), 4.69 (s, 2H), 4.17 (dd, J=13.7, 6.9 Hz, 1H), 4.03 (dd, J=11.4, 3.9 Hz, 2H), 3.91 (d, J=6.4 Hz, 2H), 3.46 (t, J=11.0 Hz, 2H), 2.60 (q, J=7.6 Hz, 2H), 2.34 (dt, J=15.3, 5.1 Hz, 1H), 2.24 (dt, J=12.3, 5.2 Hz, 1H), 2.11 (dd, J=10.8, 4.4 Hz, 2H), 1.96 (ddd, J=20.0, 10.1, 5.0 Hz, 1H), 1.74 (d, J=12.3 Hz, 2H), 1.56-1.46 (m, 2H), 1.23 (t, J=7.6 Hz, 3H), 1.13 (d, J=6.6 Hz, 3H).

Example 19: Synthesis of 54(6-ethyl-3,4-dihydroisoquinolin-2(1H)-yl)sulfonyl)-2-((tetrahydro-2H-pyran-4-yl)methoxy)benzyl Alcohol

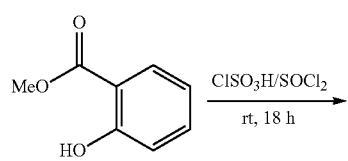

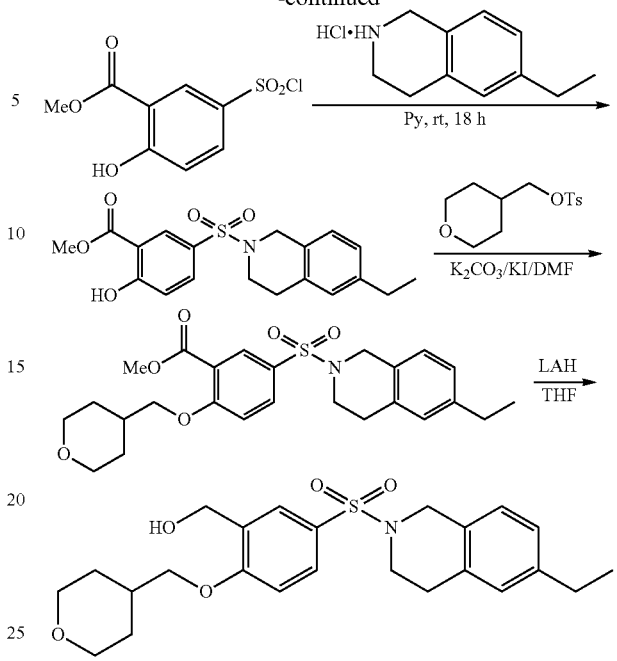

47 mg of the title compound (HPLC purity: 99.03%) was prepared and obtained with reference to the synthesis method of Example 3.

MS (ESI) m/z 446.0 [M+1]+.

$^1$H NMR (400 MHz, CDCl$_3$) δ 7.82 (d, J=2.3 Hz, 1H), 7.75 (dd, J=8.6, 2.3 Hz, 1H), 6.95 (td, J=15.5, 7.4 Hz, 4H), 4.72 (s, 2H), 4.22 (s, 2H), 4.03 (dd, J=11.3, 3.5 Hz, 2H), 3.91 (d, J=6.3 Hz, 2H), 3.45 (td, J=11.9, 1.9 Hz, 2H), 3.35 (t, J=5.9 Hz, 2H), 2.88 (t, J=5.8 Hz, 2H), 2.57 (q, J=7.6 Hz, 2H), 2.11 (d, J=3.9 Hz, 1H), 1.73 (dd, J=12.9, 1.8 Hz, 2H), 1.49 (dd, J=13.0, 4.5 Hz, 2H), 1.18 (t, J=7.6 Hz, 3H).

Example 20

Synthesis of 5-((6-cyclopropyl-2-methyl-3,4-dihydroquinolin-1(2H)-yl)sulfonyl)-2-((tetrahydro-2H-pyran-4-yl)methoxy)benzyl Alcohol

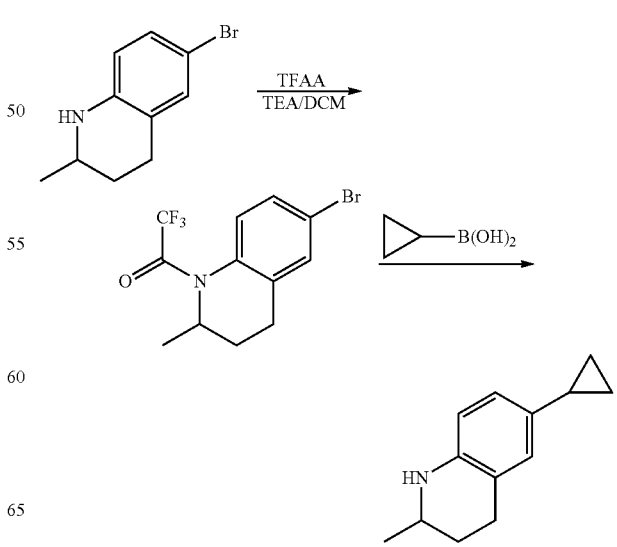

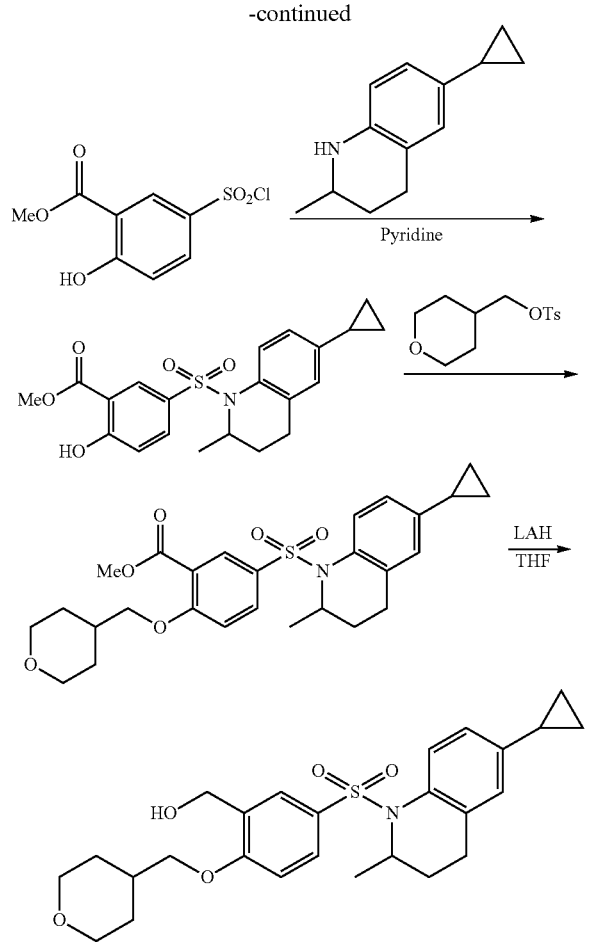

20.1 1-(6-bromo-2-methyl-3,4-dihydroquinolin-1(2H)-yl)-2,2,2-trifluoroethanone A 100 mL single-necked flask was charged with 520 mg of 6-bromo-2-methyl-1,2,3,4-tetrahydroquinoline, 15 mL of DCM was added to dissolve the former, and 930 mg of TEA was added. The mixture was cooled in an ice bath, and 1.4 g of TFAA was added dropwise. After the completion of the dropwise addition, the temperature of the mixture was raised to room temperature and the mixture was stirred overnight. TLC detection showed that the reaction of the raw materials was complete. 30 mL of water was added to perform liquid-liquid separation. The aqueous phase was extracted with 10 mL of DCM twice. The combined organic phases were washed with saturated NaCl aqueous solution, dried over anhydrous sodium sulfate, filtered and concentrated under reduced pressure, so as to obtain 1.1 g of 1-(6-bromo-2-methyl-3,4-dihydroquinolin-1(2H)-yl)-2,2,2-trifluoroethanone.

20.2 6-Cyclopropyl-2-methyl-1,2,3,4-tetrahydroquinoline

A 100 mL single-necked flask was charged with 820 mg of 1-(6-bromo-2-methyl-3,4-dihydroquinolin-1(2H)-yl)-2,2,2-trifluoroethanone and 656 mg of cyclopropylboronic acid, and 15 mL of 1,4-dioxane was added to dissolve the formers. 4 mL of water was added, and 3.0 g of $K_3PO_4$ was added and dissolved, followed by addition of 420 mg of tricyclohexylphosphine. The mixture was purged with nitrogen gas three times. 168 mg of palladium acetate was added, and then the mixture was purged with nitrogen gas three times and stirred in an external bath at 100° C. overnight. TLC detection and LCMS detection showed that the reaction of the raw materials was complete. 40 mL of water was added, and the resulting mixture was extracted three times with EA (10 mL×3). The organic phases were combined, washed with saturated aqueous sodium chloride solution, dried over anhydrous sodium sulfate, filtered and concentrated under reduced pressure to obtain an oil, which was purified by column chromatography. The product was collected and concentrated under reduced pressure, so as to obtain 130 mg of 6-cyclopropyl-2-methyl-1,2,3,4-tetrahydro quinoline.

20.3 5-((6-cyclopropyl-2-methyl-3,4-dihydro quinolin-1(2H)-yl) sulfonyl)-2-((tetrahydro-2H-pyran-4-yl)methoxy)benzyl Alcohol The rest reaction steps proceeded with reference to the synthesis method in Example 3, so as to prepare and obtain 40 mg of the title compound (HPLC purity: 99.28%).
MS (ESI) m/z 472.0 [M+1]+.
$^1$H NMR (400 MHz, CDCl$_3$) δ 7.60 (d, J=8.4 Hz, 1H), 7.46 (d, J=2.3 Hz, 1H), 7.37 (dd, J=8.6, 2.4 Hz, 1H), 6.91 (dd, J=8.4, 2.1 Hz, 1H), 6.77 (d, J=8.7 Hz, 1H), 6.69 (d, J=2.0 Hz, 1H), 4.61 (s, 2H), 4.32 (dd, J=12.9, 6.5 Hz, 1H), 4.02 (dd, J=11.3, 3.5 Hz, 2H), 3.87 (d, J=6.4 Hz, 2H), 3.44 (td, J=11.9, 2.0 Hz, 2H), 2.39-2.30 (m, 1H), 2.09 (d, J=3.8 Hz, 1H), 1.84-1.79 (m, 2H), 1.72 (dd, J=13.5, 2.6 Hz, 3H), 1.48 (dd, J=12.6, 4.3 Hz, 2H), 1.31 (d, J=7.0 Hz, 1H), 1.26 (d, J=6.5 Hz, 3H), 0.98-0.91 (m, 2H), 0.69-0.63 (m, 2H).

Example 21

Synthesis of 5-((3,6-diethyl-3,4-dihydroquinolin-1(2H)-yl) sulfonyl)-2-((tetrahydro-2H-pyran-4-yl)methoxy)benzyl Alcohol

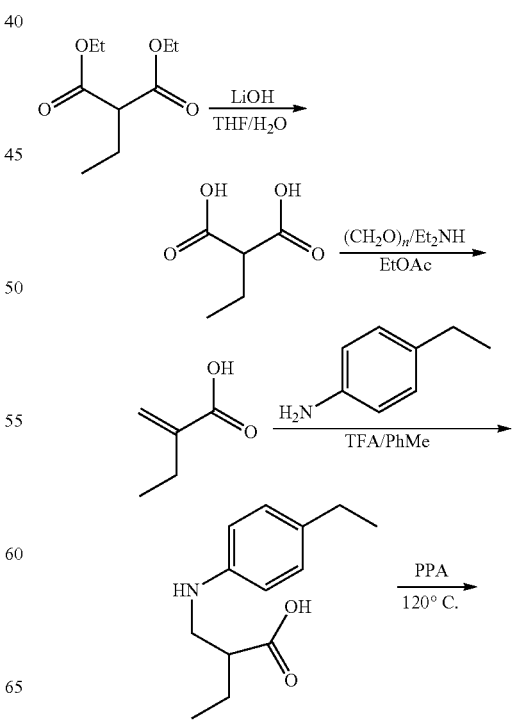

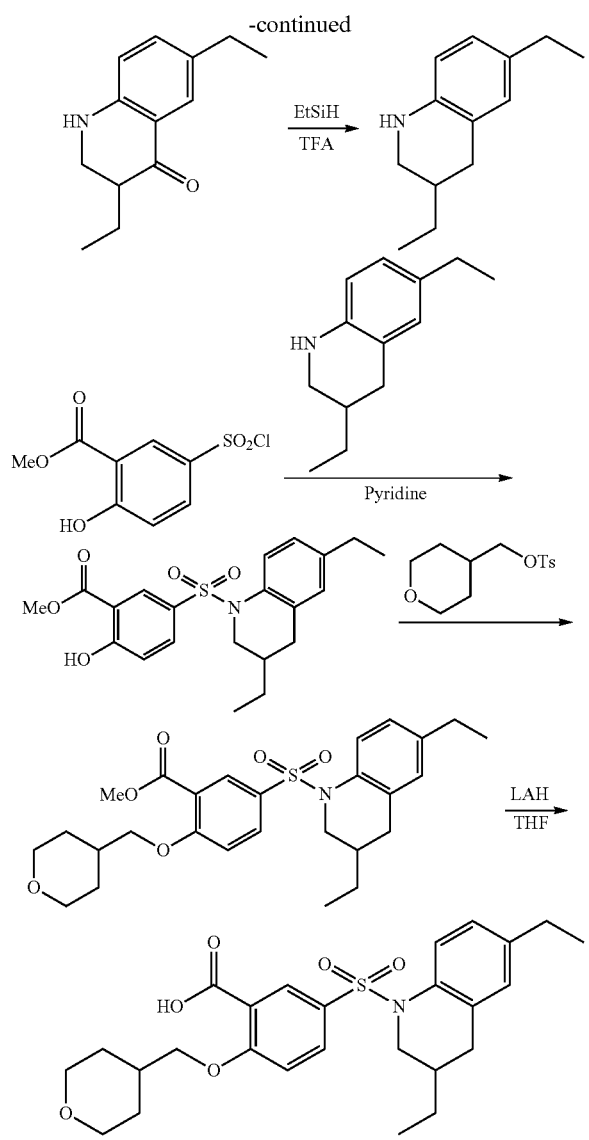

21.1 2-Ethylmalonic Acid

A 100 mL single-necked flask was charged with 5.0 g of diethyl 2-ethylmalonate and 60 mL of THF/H$_2$O (V/V=1/1), and 8.7 g of LiOH.H$_2$O was added in portions under stirring at room temperature. After the completion of the addition, the mixture was reacted at a room temperature of 28° C. under stirring for 16 h. A sample was taken, and the raw materials disappeared as monitored by TLC. The reaction solution was concentrated to remove excess reaction solvent THF, and water (50 mL) was added. When the pH was adjusted to 1.0 with 5 N HCl, the mixture was extracted twice with EA (60 mL×2). The organic phases were combined, washed twice with saturated NaCl aqueous solution (50 mL×2), dried over anhydrous sodium sulfate and concentrated, so as to obtain 3.5 g of 2-ethylmalonic acid.

21.2 2-Ethyl Acrylic Acid

A 100 mL single-necked flask was charged with 1.50 g of 2-ethylmalonic acid and 20 mL of EtOAc, and 1.87 g of Et$_2$NH.HCl was added in portions while the mixture was stirred in an ice bath. After the completion of the addition, 0.682 g of paraformaldehyde was added, and the mixture was further stirred for 10 min in the ice bath and then reacted for 4.5 h under reflux in an oil bath at 80° C. A sample was taken, the spots of the raw materials disappeared as monitored by TLC, and the reaction was ended. The reaction mixture was naturally cooled to room temperature and was slowly poured into 50 mL of ice water, 1 N HCl was added to adjust the pH value to 10 to 11, and the resulting mixture was extracted twice with EA (40 mL×2). The organic phases were combined, washed once with saturated sodium bicarbonate solution (40 mL×1). The alkaline solutions were combined, adjusted by 2 N HCl to have a pH of about 1.0, and then extracted three times with EA (50 mL×3). The organic phases were combined, washed once with saturated NaCl aqueous solution (60 mL×1), dried over anhydrous Na$_2$SO$_4$ and concentrated, so as to obtain 420 mg of 2-ethyl acrylic acid.

21.3 2-(4-ethylphenylaminomethyl)butanoic Acid

A 50 mL single-necked flask was charged with 0.33 g of 2-ethyl acrylic acid and 10 mL of toluene. 0.80 g of p-ethylaniline was added under stirring, and the color of the reaction system darkened during the dropwise addition. After the completion of the addition, TFA (0.3 mL) was added. The mixture was reacted while being heated at 95° C. for 16 h. A sample was taken, TLC detection showed that the spots of the raw materials disappeared, and the reaction was ended. 100 mL of EA was added to dilute the reaction system, which was then washed twice with water (50 mL×2) and washed three times with saturated sodium bicarbonate solution (40 mL×3). The organic phases were discarded. The alkaline solutions were combined, adjusted with 5 N HCl to have a pH of about 1.0, and then extracted three times with EA (40 mL×3). The organic phases were combined, washed twice with saturated saline (50 mL×2), dried over anhydrous sodium sulfate and concentrated, so as to obtain 280 mg of 2-(4-ethylphenylaminomethyl)butanoic acid.

21.4 3,6-diethyl-2,3-dihydroquinolin-4(1H)-one

A 10 mL single-necked flask was charged with 0.28 g of 2-(4-ethylphenylamino methyl)butanoic acid and 1.04 g of polyphosphoric acid, which were reacted while being heated at 120° C. for 4 h. A sample was taken, TLC detection showed that the spots of the raw materials disappeared, and the reaction was ended. The reaction solution was poured into 30 g of ice water and stirred, and the resulting mixture was extracted three times with EA (20 mL×3). The organic phases were combined, washed once with water (30 mL×1), washed twice with saturated saline (30 mL×2), dried over anhydrous sodium sulfate and concentrated, so as to obtain 320 mg of 3,6-diethyl-2,3-dihydroquinolin-4(1H)-one (crude product).

21.5 3,6-diethyl-1,2,3,4-tetrahydroquinoline

A 50 mL single-necked flask was charged with 0.32 g of 3,6-diethyl-2,3-dihydroquinolin-4(1H)-one, to which TFA (5 mL) was added while the flask was kept in an ice bath. After the mixture was stirred for 10 min, 2.6 mL of triethylsilane was added dropwise. After the completion of the addition, the mixture was further stirred for 0.5 h in an ice bath. Then, the ice bath was removed, and the reaction proceeded at room temperature for 40 h. A sample was taken, TLC detection showed that the spots of the raw materials disappeared, and the reaction was ended. The reaction solution was diluted with 50 mL of EA, washed three times with water (30 mL×3), washed three times with saturated sodium bicarbonate solution (20 mL×3), washed once with saturated saline (30 mL×1), dried over anhydrous sodium sulfate and concentrated, so as to obtain 380 mg of 3,6-diethyl-1,2,3,4-tetrahydroquinoline, which was a crude product and was directly used in the reaction of the next step.

21.6 5-((3,6-diethyl-3,4-dihydroquinolin-1(2H)-yl)sulfonyl)-2-((tetrahydro-2H-pyran-4-yl)methoxy)benzyl Alcohol The rest reaction steps proceeded with reference to the synthesis method in Example 3, so as to prepare and obtain 22 mg of the title compound (HPLC purity: 97.6%).

MS (ESI) m/z 474.0 [M+1]+.

$^1$H NMR (400 MHz, CDCl3) δ 7.67 (d, J=8.4 Hz, 1H), 7.59 (d, J=2.3 Hz, 1H), 7.52 (dd, J=8.6, 2.3 Hz, 1H), 6.99 (dd, J=8.4, 1.8 Hz, 1H), 6.81 (d, J=8.9 Hz, 2H), 4.63 (s, 2H), 4.20-4.12 (m, 1H), 4.02 (dd, J=11.3, 3.8 Hz, 2H), 3.87 (d, J=6.4 Hz, 2H), 3.44 (td, J=11.9, 1.9 Hz, 2H), 3.03 (dd, J=13.2, 11.0 Hz, 1H), 2.57 (dd, J=15.1, 7.5 Hz, 3H), 2.07 (dd, J=16.4, 10.8 Hz, 2H), 1.72 (dd, J=12.8, 1.8 Hz, 2H), 1.49 (td, J=12.1, 4.4 Hz, 3H), 1.29-1.24 (m, 2H), 1.20 (dd, J=10.2, 5.0 Hz, 3H), 0.91 (t, J=7.4 Hz, 3H).

Example 22

Synthesis of 5-(((6-ethyl-2,2-dimethyl-3,4-dihydroquinolin-1(2H)-yl)sulfonyl)-2-((tetrahydro-2H-pyran-4-yl)methoxy)benzyl Alcohol

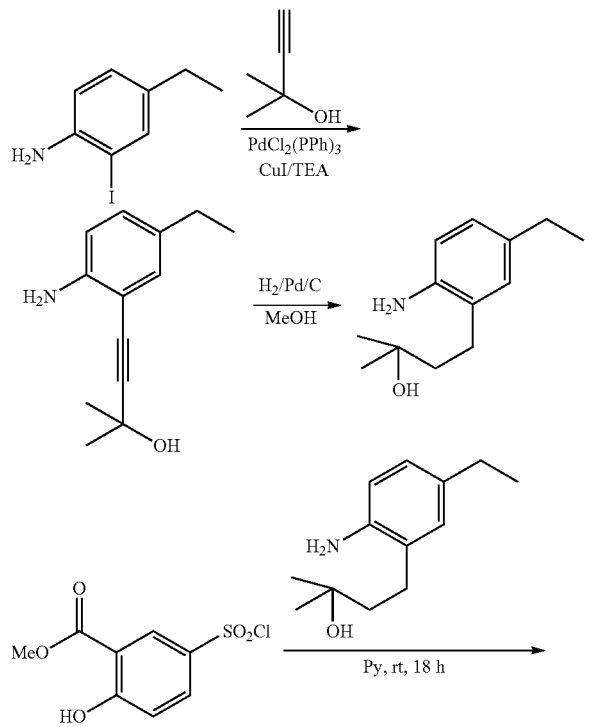

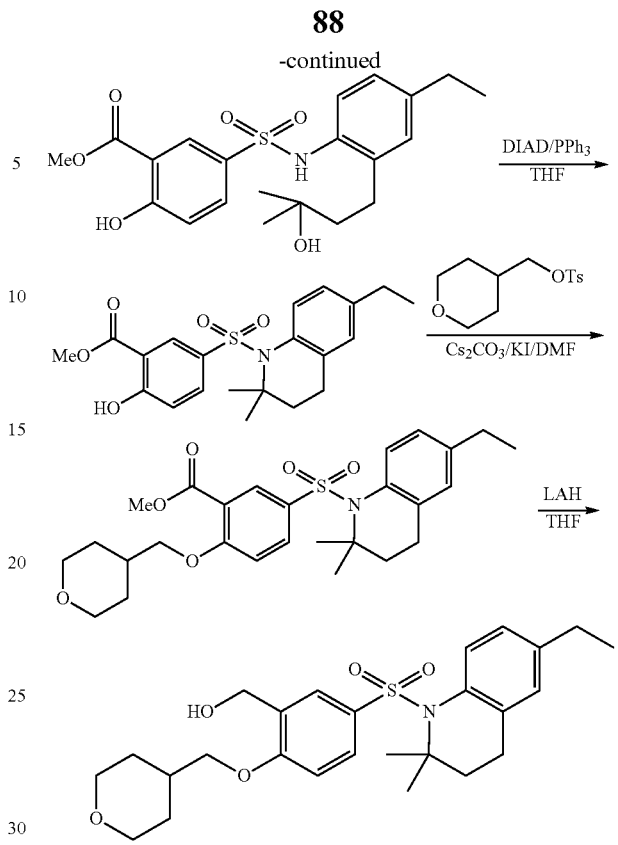

100 mg of the title compound (HPLC purity: 99.1%) was prepared and obtained with reference to the method in Example 12.

MS (ESI) m/z: 474.0 [M+1]+.

$^1$H NMR (400 MHz, CDCl3): δ 7.51 (dt, J=8.6, 2.5 Hz, 3H), 7.02 (dd, J=8.3, 1.7 Hz, 1H), 6.87 (s, 1H), 6.82 (d, J=8.6 Hz, 1H), 4.63 (s, 2H), 4.02 (dd, J=11.3, 3.7 Hz, 2H), 3.89 (d, J=6.4 Hz, 2H), 3.44 (td, J=11.9, 1.8 Hz, 2H), 2.61 (q, J=7.6 Hz, 2H), 2.52 (t, J=7.0 Hz, 2H), 2.10 (ddd, J=11.4, 8.4, 4.5 Hz, 1H), 1.73 (dd, J=12.9, 1.7 Hz, 2H), 1.60 (t, J=7.1 Hz, 2H), 1.51 (dd, J=12.2, 4.5 Hz, 1H), 1.47 (d, J=4.3 Hz, 1H), 1.39 (s, 6H), 1.23 (t, J=7.6 Hz, 3H)).

Example 23

Synthesis of (S)-5-(((6-ethyl-7-fluoro-2-methyl-3,4-dihydroquinolin-1(2H)-yl)sulfonyl)-2-((tetrahydro-2H-pyran-4-yl)methoxy)benzyl Alcohol

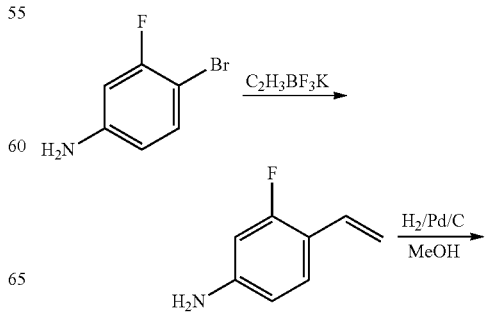

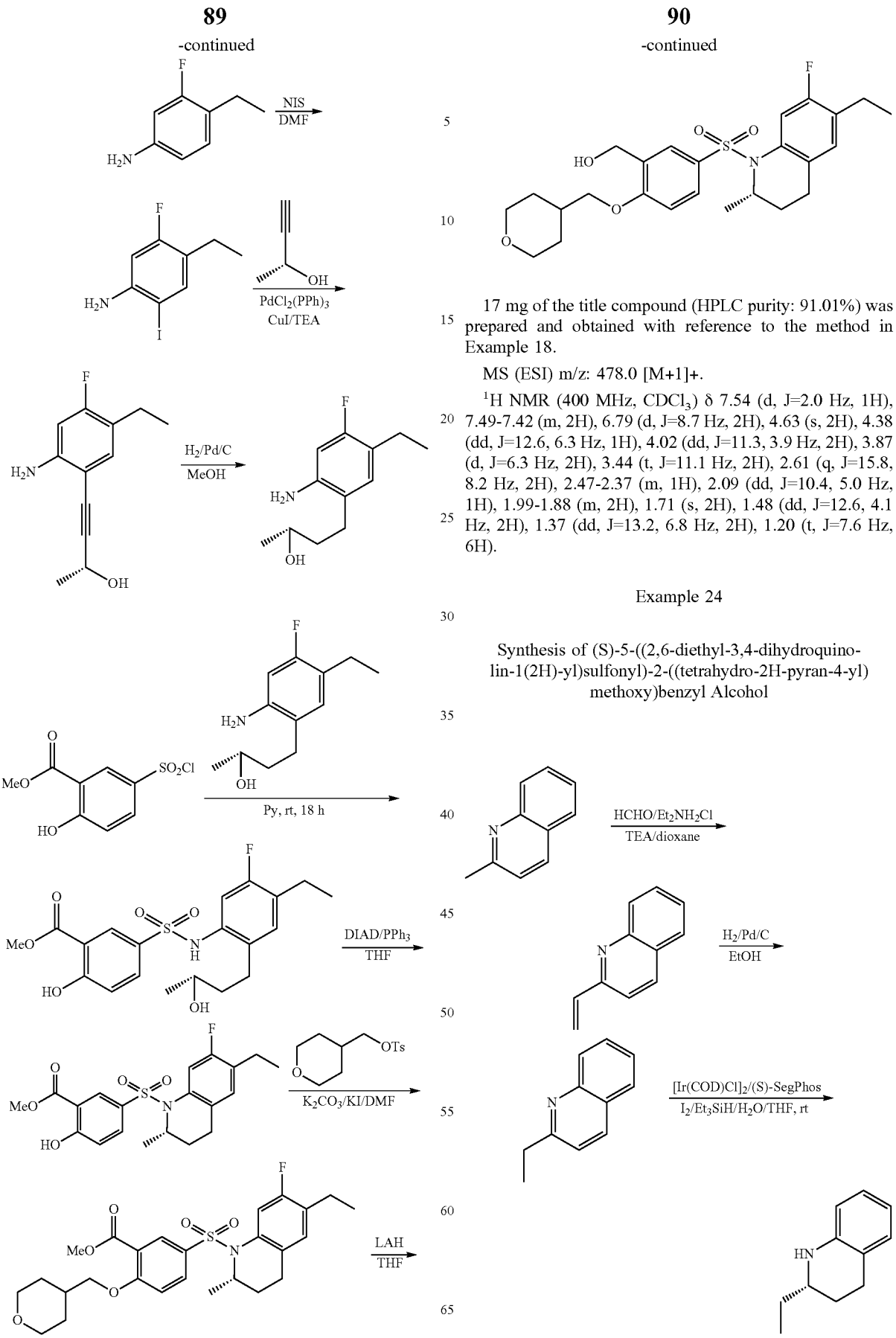
17 mg of the title compound (HPLC purity: 91.01%) was prepared and obtained with reference to the method in Example 18.
MS (ESI) m/z: 478.0 [M+1]+.
$^1$H NMR (400 MHz, CDCl$_3$) δ 7.54 (d, J=2.0 Hz, 1H), 7.49-7.42 (m, 2H), 6.79 (d, J=8.7 Hz, 2H), 4.63 (s, 2H), 4.38 (dd, J=12.6, 6.3 Hz, 1H), 4.02 (dd, J=11.3, 3.9 Hz, 2H), 3.87 (d, J=6.3 Hz, 2H), 3.44 (t, J=11.1 Hz, 2H), 2.61 (q, J=15.8, 8.2 Hz, 2H), 2.47-2.37 (m, 1H), 2.09 (dd, J=10.4, 5.0 Hz, 1H), 1.99-1.88 (m, 2H), 1.71 (s, 2H), 1.48 (dd, J=12.6, 4.1 Hz, 2H), 1.37 (dd, J=13.2, 6.8 Hz, 2H), 1.20 (t, J=7.6 Hz, 6H).
Example 24
Synthesis of (S)-5-((2,6-diethyl-3,4-dihydroquinolin-1(2H)-yl)sulfonyl)-2-((tetrahydro-2H-pyran-4-yl)methoxy)benzyl Alcohol

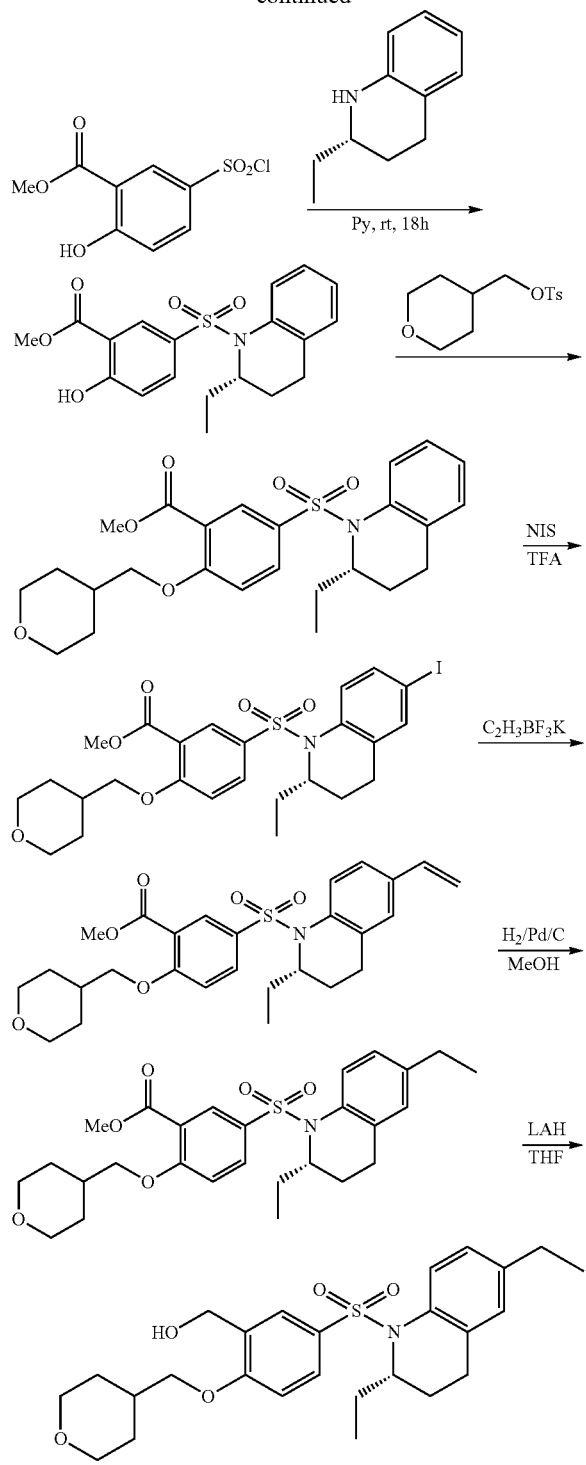

24.1 2-Vinylquinoline

A 500 mL single-necked flask was charged with 10 g of 2-methylquinoline, 10 g of diethylamine hydrochloride, 2.73 g of 37% formaldehyde aqueous solution, triethylamine (1.5 mL) and 1,4-dioxane (30 mL), which were stirred at 100° C. for 3 h. The reaction was complete as detected by TLC. 30 mL of water was added, and the resulting mixture was extracted three times with ethyl acetate (50 mL×3). The organic phases were combined, washed with saturated aqueous sodium chloride solution, dried over anhydrous sodium sulfate, filtered and concentrated under reduced pressure, so as to obtain an oil, which was purified by passing through a column to obtain 2.6 g of 2-vinylquinoline.

24.2 2-Ethylquinoline

A 100 mL single-necked flask was charged with 2.6 g of 2-vinylquinoline and 50 mL of ethanol, and then 150 mg of 5 mol % palladium on carbon was added. The mixture was purged with hydrogen gas and protected thereby, and was stirred at room temperature overnight. The reaction was complete as detected by TLC. The system was filtered and concentrated under reduced pressure to obtain 2.5 g of 2-ethylquinoline.

24.3 (S)-2-ethyl-1,2,3,4-tetrahydroquinoline

A 100 mL three-necked flask was charged with 1,5-cyclooctadiene-iridium chloride dimer (78 mg) and (S)-(−)-5,5'-bis(diphenylphosphino)-4,4'-di-1,3-benzodioxole (200 mg), which were dissolved in 10 mL of tetrahydrofuran. The mixture was purged with nitrogen gas and protected thereby, and was stirred at room temperature for 15 min. Iodine (410 mg) was added under nitrogen protection and the mixture was stirred at room temperature for 15 min. 2-Ethylquinoline (2.5 g) and triethylsilane (16 mL) were added under the protection of nitrogen gas, and the mixture was stirred at room temperature for 10 min. Water (578 mg) was added and the mixture was stirred at room temperature overnight. The reaction was complete as detected by TLC, and a peak of the product (162.0[M+1]+) was detected by LC-MS. The system was concentrated, dissolved by adding 50 mL of ethyl acetate, and extracted with dilute hydrochloric acid (25 mL×3). The combined aqueous phases were basified with sodium carbonate, and ethyl acetate (50 mL×2) was added to carry out extraction. The organic layer was washed three times with saturated saline, dried over anhydrous sodium sulfate, filtered and concentrated under reduced pressure, so as to obtain 2.5 g of (S)-2-ethyl-1,2,3,4-tetrahydroquinoline.

24.4 Methyl (S)-5-((2-ethyl-3,4-dihydroquinolin-1 (2H)-yl)sulfonyl)-2-hydroxybenzoate A 50 mL single-necked flask was charged with 2.5 g of (S)-2-ethyl-1,2,3,4-tetrahydroquinoline, and 10 mL of pyridine was added to dissolve the former, followed by addition of 5 g of methyl 5-chlorosulfonyl-2-hydroxybenzoate. The mixture was stirred at room temperature overnight. The solvent was removed by rotary evaporation under reduced pressure, the residue was diluted by adding 50 mL of ethyl acetate, and the resulting mixture was washed with 1N hydrochloric acid and saturated saline, respectively. The organic phase was dried over anhydrous sodium sulfate, filtered and concentrated under reduced pressure to give an oil, which was purified by passing through a column to give 1.74 g of the title compound.

24.5 Methyl (S)-5-((2-ethyl-3,4-dihydroquinolin-1 (2H)-yl)sulfonyl)-2-((tetrahydro-2H-pyran-4-yl) methoxy)benzoate A 25 mL single-necked flask was charged with 1.74 g of methyl (S)-5-((2-ethyl-3,4-dihydroquinolin-1(2H)-yl)sulfonyl)-2-hydroxybenzoate and 1.5 g of p-toluenesulfonate-4-methyl pyran, and 5 mL of N,N-dimethylformamide was added to dissolve the formers, followed by addition of 1.92 g of potassium carbonate and 170 mg of tetrabutylammonium iodide. The mixture was heated in an external bath at 70° C. overnight while being stirred. The reaction was complete as detected by TLC. 30 mL of water was added, and the resulting mixture was extracted with 20 mL of ethyl acetate three times. The organic phases were combined, washed with saturated aqueous sodium chloride solution, dried over anhydrous sodium sulfate, filtered, concentrated under reduced pressure, and purified by passing through a column, so as to obtain 1.72 g of the title compound.

24.6 Methyl (S)-5-((6-iodo-2-ethyl-3,4-dihydroquinolin-1(2H)-yl)sulfonyl)-2-((tetra hydro-2H-pyran-4-yl)methoxy)benzoate A 50 mL single-necked flask was charged with 1.74 g of methyl (S)-5-((2-ethyl-3,4-dihydroquinolin-1(2H)-yl)sulfonyl)-2-((tetrahydro-2H-pyran-4-yl)methoxy)benzoate, and 10 mL of trifluoroacetic acid was added to dissolve the former. The mixture was cooled to −0° C., and 1 g of N-iodosuccinimide was added in portions. After the completion of the addition, the mixture was stirred in an ice bath for 1 h and then was transferred to an environment under room temperature and stirred overnight. The reaction was complete as detected by LC-MS. 50 mL of water was added, and the resulting mixture was extracted with 20 mL of ethyl acetate three times. The combined organic phases were washed with 20 mL of a saturated aqueous sodium chloride solution, dried over anhydrous sodium sulfate, filtered, concentrated under reduced pressure, and purified by passing through a column, so as to obtain 1.4 g of the title compound.

24.7 Methyl (S)-5-((6-vinyl-2-ethyl-3,4-dihydroquinolin-1(2H)-yl)sulfonyl)-2-((tetrahydro-2H-pyran-4-yl)methoxy)benzoate A 100 mL eggplant-shaped flask was charged with 300 mg of raw material, 136 mg of potassium vinyltrifluoroborate, and 500 mg of cesium carbonate, which were dissolved with a solution of 1,4-dioxane/water (4:1). 25 mg of tetrakis (triphenylphosphine)palladium was added. The mixture was purged with nitrogen gas and protected thereby, and was stirred at 90° C. overnight. The reaction was complete as detected by LC-MS. The system was extracted with ethyl acetate, and the organic layer was subjected to column chromatography to obtain 240 mg of the title compound.

24.8 Methyl (S)-5-((2,6-diethyl-3,4-dihydroquinolin-1(2H)-yl)sulfonyl)-2-((tetrahydro-2H-pyran-4-yl)methoxy)benzoate A 50 mL eggplant-shaped flask was charged with 240 mg of methyl (S)-5-((6-vinyl-2-ethyl-3,4-dihydroquinolin-1 (2H)-yl)sulfonyl)-2-((tetrahydro-2H-pyran-4-yl)methoxy) benzoate, which was dissolved with methanol. 25 mg of 20% palladium hydroxide on carbon was added. The mixture was purged with hydrogen gas and protected thereby, and was stirred at 45° C. for 3 h. The reaction was complete as detected by LC-MS. The resulting mixture was filtered, and the filtrate was dried by rotary evaporation to obtain 88 mg of the title compound.

24.9 (S)-5-((2,6-diethyl-3,4-dihydroquinolin-1(2H)-yl)sulfonyl)-2-((tetrahydro-2H-pyran-4-yl)methoxy) benzyl Alcohol A 25 mL single-necked flask was charged with 88 mg of methyl (S)-5-((2,6-diethyl-3,4-dihydroquinolin-1(2H)-yl) sulfonyl)-2-((tetrahydro-2H-pyran-4-yl)methoxy)benzoate, and 5 mL of tetrahydrofuran was added to dissolve the former. The mixture was cooled in an ice bath, 20 mg of lithium aluminum hydride was added in portions, and the mixture was stirred in an ice bath for 1 h. The reaction was complete as detected by TLC. 15% aqueous sodium hydroxide solution (5 mL) was added dropwise to quench the reaction. The resulting mixture was filtered, concentrated under reduced pressure and purified, so as to obtain 22 mg of the title compound (HPLC purity: 99.0%).

MS (ESI) m/z: 474.0 [M+1]+.

$^1$H NMR: (400 MHz, CDCl$_3$) δ 7.64 (d, J=8.3 Hz, 1H), 7.45 (s, 1H), 7.40 (d, J=8.6 Hz, 1H), 7.05 (d, J=8.3 Hz, 1H), 6.82-6.74 (m, 2H), 4.60 (d, J=6.3 Hz, 2H), 4.22-4.11 (m, 1H), 4.02 (dd, J=11.3, 3.6 Hz, 2H), 3.87 (d, J=6.3 Hz, 2H), 3.44 (t, J=11.6 Hz, 2H), 2.59 (q, J=7.6 Hz, 2H), 2.45-2.34 (m, 1H), 2.09 (m, 1H), 1.86 (dd, J=12.3, 6.4 Hz, 2H), 1.73 (dd, J=13.5 Hz, 2H), 1.58 (m, 2H), 1.52-1.36 (m, 4H), 1.22 (t, J=7.6 Hz, 3H), 0.94 (t, J=7.4 Hz, 3H).

Example 25

Synthesis of (S)-5-((6-isopropyl-2-ethyl-3,4-dihydroquinolin-1(2H)-yl)sulfonyl)-2-((tetrahydro-2H-pyran-4-yl)methoxy)benzyl Alcohol

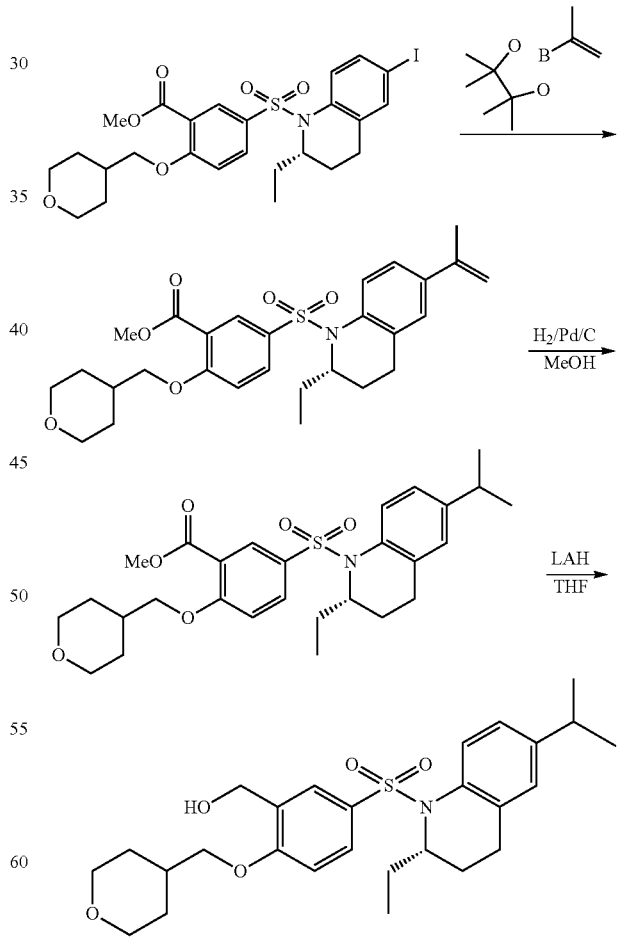

25 mg of the title compound (HPLC purity: 99.1%) was prepared and obtained with reference to the method in Example 24.

MS (ESI) m/z: 488.0 [M+1]+.

¹H NMR: (400 MHz, CDCl₃) δ 7.65 (d, J=8.3 Hz, 1H), 7.41 (d, J=6.7 Hz, 2H), 7.08 (d, J=6.9 Hz, 1H), 6.81-6.77 (m, 2H), 4.59 (d, J=6.4 Hz, 2H), 4.15 (m, 1H), 4.02 (dd, J=11.2, 3.7 Hz, 2H), 3.87 (d, J=6.4 Hz, 2H), 3.44 (t, J=11.1 Hz, 2H), 2.92-2.75 (m, 1H), 2.39 (dd, J=15.9, 7.4 Hz, 1H), 2.09 (m, 1H), 1.93-1.80 (m, 2H), 1.75-1.69 (m, 2H), 1.59 (m, 2H), 1.47 (m, 4H), 1.23 (d, J=6.9 Hz, 6H), 0.94 (t, J=7.4 Hz, 3H).

Example 26

Synthesis of (S)-5-((2-methyl-6-(2,2,2-trifluoroethyl)-3,4-dihydroquinolin-1(2H)-yl) sulfonyl)-2-((tetrahydro-2H-pyran-4-yl)methoxy)benzyl Alcohol

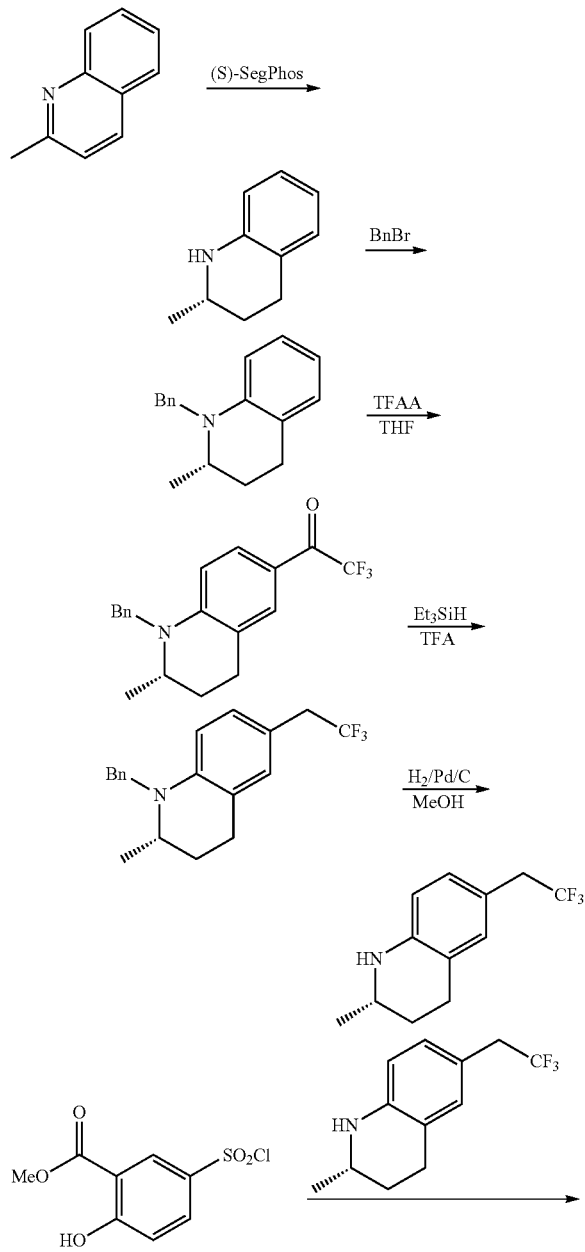

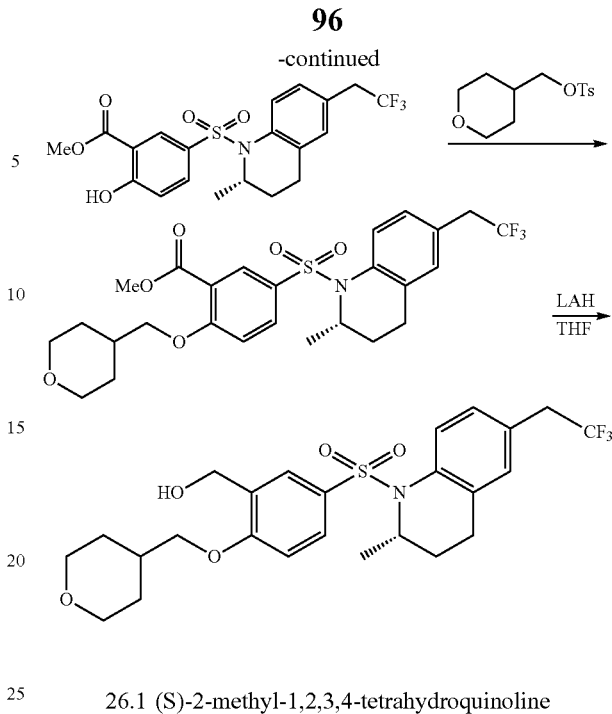

26.1 (S)-2-methyl-1,2,3,4-tetrahydroquinoline 700 mg of (S)-2-methyl-1,2,3,4-tetrahydroquinoline was prepared and obtained with reference to the method in Example 24.3.

26.2 (S)-1-benzyl-2-methyl-1,2,3,4-tetrahydroquinoline

A 50 mL round-bottom flask was charged with (S)-2-methyl-1,2,3,4-tetrahydroquinoline (500 mg), benzyl bromide (575 mg), potassium carbonate (937.5 mg), potassium iodide (56.5 mg) and N, N-dimethylformamide (12 mL). The mixed solution was stirred at 50° C. for 2 h. A sample was taken, and TLC detection showed that the spots of the raw materials disappeared. The reaction solution was cooled to room temperature and diluted with 100 mL of ethyl acetate. The organic phase was washed with saturated saline (30 mL×3), dried over anhydrous sodium sulfate, and filtered. The solvent was removed by rotary evaporation under reduced pressure, and the resulting mixture was subjected to silica gel column chromatography, so as to obtain 700 mg of the title compound. MS(ESI) m/z 238.0[M+1]⁺).

26.3 (S)-1-(1-benzyl-2-methyl-1,2,3,4-tetrahydroquinolin-6-yl)-2,2,2-trifluoroethanone A 50 mL round-bottom flask was charged with (S)-1-benzyl-2-methyl-1,2,3,4-tetrahydroquinoline (550 mg), trifluoroacetic anhydride (1.22 g), and tetrahydrofuran (10 mL). The mixture was stirred at 35° C. for 3.5 h. A sample was taken, and TLC detection showed that the spots of the raw materials disappeared. The reaction solution was concentrated under reduced pressure to give a pale blue oil, which was subjected to silica gel column chromatography (PE: EA=10:1), so as to obtain 600 mg of the title compound (LCMS purity: 98.63%, MS(ESI) m/z 334.0 [M+1]⁺).

26.4 (S)-1-benzyl-2-methyl-6-(2,2,2-trifluoroethyl)-1,2,3,4-tetrahydroquinoline

A 50 mL round-bottom flask was charged with (S)-1-(1-benzyl-2-methyl-1,2,3,4-tetrahydroquinolin-6-yl)-2,2,2-trifluoroethanone (650 mg) and trifluoroacetic acid (7.8 mL). The reaction system was stirred at 0° C. under nitrogen protection. Triethylsilane (2.27 g) was added to the reaction mixture, and the reaction solution was stirred at room temperature for 16 h and then further stirred at 46° C. for 20 h. A sample was taken, and TLC detection showed that the spots of the raw materials disappeared. The reaction solution was concentrated under reduced pressure, diluted with ethyl acetate (150 mL), washed with saturated sodium bicarbonate solution (50 mL×2), washed with saturated saline (50 mL), dried over anhydrous sodium sulfate, and filtered. The solvent was removed by rotary evaporation under reduced pressure, and the resulting mixture was subjected to silica gel column chromatography, so as to obtain 620 mg of the title compound (LCMS purity: 94.14%, MS(ESI) m/z 320.0 [M+1]$^+$).

26.5 (S)-2-methyl-6-(2,2,2-trifluoroethyl)-1,2,3,4-tetrahydroquinoline (S)-1-benzyl-2-methyl-6-(2,2,2-trifluoroethyl)-1,2,3,4-tetrahydroquinoline (400 mg) was charged into a hydrogenation autoclave and dissolved with ethanol (5 mL), and palladium hydroxide on carbon (100 mg) was added. The system was pressurized to 0.5 MPa with hydrogen gas, and the mixture was stirred at room temperature for 21 h. A sample was taken, and TLC detection showed that the spots of the raw materials disappeared. The sample was subjected to LC-MS detection, and a peak of the product (230.1[M+1]$^+$) was detected. The reaction solution was filtered through celite and concentrated to obtain 280 mg of the title compound.

26.6 (S)-5-((2-methyl-6-(2,2,2-trifluoroethyl)-3,4-dihydroquinolin-1(2H)-yl)sulfonyl)-2-((tetrahydro-2H-pyran-4-yl)methoxy)benzyl Alcohol The rest reaction steps proceeded with reference to the synthesis method in Example 3, so as to prepare and obtain 45 mg of the title compound (HPLC purity: 98.4%).
MS (ESI) m/z 514.0 [M+1]+.
$^1$H NMR (400 MHz, CDCl$_3$) δ 7.73 (d, J=8.4 Hz, 1H), 7.48 (s, 1H), 7.38 (d, J=8.4 Hz, 1H), 7.15 (d, J=8.0 Hz, 1H), 6.91 (s, 1H), 6.77 (d, J=8.6 Hz, 1H), 4.60 (d, J=5.8 Hz, 2H), 4.37 (dd, J=12.6, 6.4 Hz, 1H), 4.10-3.96 (m, 2H), 3.86 (d, J=6.0 Hz, 2H), 3.44 (t, J=11.6 Hz, 2H), 3.31 (q, J=10.6 Hz, 2H), 2.50-2.36 (m, 1H), 2.16-2.07 (m, 1H), 2.06-1.97 (m, 1H), 1.94-1.77 (m, 2H), 1.76-1.68 (m, 2H), 1.54-1.33 (m, 3H), 1.28 (d, J=6.4 Hz, 3H).

Example 27

Synthesis of (S)-5-((7-ethyl-2-methyl-3,4-dihydroquinolin-1(2H)-yl)sulfonyl)-2-((tetrahydro-2H-pyran-4-yl)methoxy)benzyl Alcohol

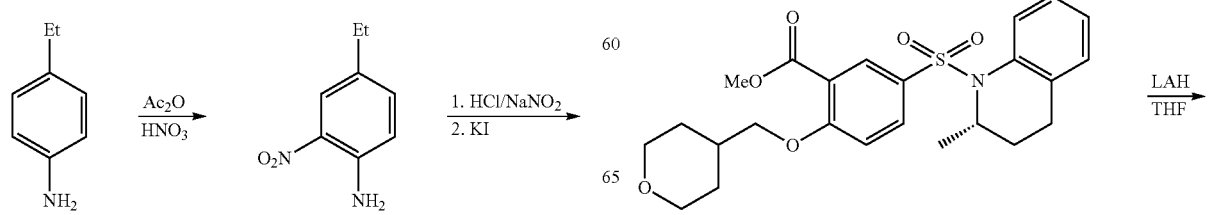

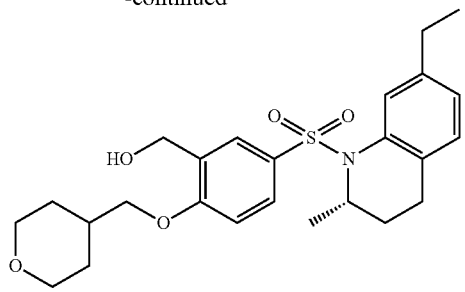

27.1 4-Ethyl-2-nitroaniline

A 100 mL round-bottom flask was charged with acetic anhydride (3.39 g) and 1,2-dichloroethane (30 mL), p-ethylaniline (3.5 g) was then added, and the mixture was stirred at 80° C. for 1 h. The reaction solution was cooled to 50° C., fuming nitric acid (4.37 g) was slowly added dropwise thereto, and the resulting mixture was stirred at 45° C. for 1 h. Sodium hydroxide (3.76 g) was dissolved in a minimum amount of water and added to the reaction solution within 10 minutes. The temperature was raised to 80° C. or higher, and 1,2-dichloroethane was distilled out of the reaction system. When the reaction temperature rose to between 95° C. and 97° C., stirring was continued for 16 h. A sample was taken and subjected to LC-MS detection, and a peak of the product (167.0[M+1]$^+$) was detected. The reaction solution was cooled to room temperature, diluted with 50 mL of water, and extracted with ethyl acetate (50 mL×4). The organic phases were washed with saturated saline (30 mL), dried over anhydrous sodium sulfate and filtered, and the solvent was distilled off under reduced pressure, so as to obtain 3.3 g of 4-ethyl-2-nitroaniline. MS(ESI) m/z 167.0[M+1]$^+$.

27.2 4-Ethyl-1-iodo-2-nitrobenzene

4-Ethyl-2-nitroaniline (1.6 g) was dissolved in concentrated hydrochloric acid (3.2 mL) and the mixture was stirred at 100° C. for 10 min. The reaction solution was cooled to 0° C., and a solution of sodium nitrite (0.798 g) in water (3.2 mL) was added thereto. The reaction solution was stirred at 0° C. for 30 min. The reaction mixture was slowly added to a solution of potassium iodide (2.4 g) in water (2.5 mL) at 0° C. The resulting mixture was stirred at 70° C. for 2 h. A sample was taken, and TLC detection showed that the spots of the raw materials disappeared. The reaction solution was diluted with 80 mL of water and extracted with ethyl acetate (80 mL×3). The organic layer was washed with saturated sodium sulfite solution (50 mL) and saturated saline (50 mL). The obtained organic layer was dried over anhydrous sodium sulfate and filtered. The solvent was distilled off under reduced pressure, and the resulting mixture was subjected to silica gel column chromatography, so as to obtain 2.2 g of 4-ethyl-1-iodo-2-nitrobenzene.

27.3 5-Ethyl-2-iodoaniline

A 10 mL round-bottom flask was charged with 4-ethyl-1-iodo-2-nitrobenzene (2.0 g), reduced iron powder (2.02 g), ammonium chloride (3.8 g), and ethanol/water (10:1/v/v). The mixture was stirred at 80° C. for 4 h. A sample was taken, and TLC detection showed that the spots of the raw materials disappeared. The reaction solution was filtered through celite, and the filtrate was concentrated under reduced pressure and subjected to column chromatography (PE:EA=10:0 to 4:1), so as to obtain 5-ethyl-2-iodoaniline (MS(ESI) m/z 247.9[M+1]$^+$).

27.4 (R)-4-(2-amino-4-ethylphenyl)-3-butyn-2-ol

A 50 mL single-necked flask was charged with 5-ethyl-2-iodoaniline (600 mg) and (R)-(-)-3-butyn-2-ol (170 mg), which were dissolved with 8 mL of triethylamine and 8 mL of tetrahydrofuran, and the mixture was purged with nitrogen gas three times. Then, bis(triphenylphosphine)palladium chloride (255.2 mg) and cuprous iodide (23.1 mg) were added. The mixture was purged with nitrogen gas three times. The reaction solution was stirred at room temperature overnight (23 h). A sample was taken, and TLC detection showed that the spots of the raw materials disappeared. The sample was subjected to LC-MS detection, and a peak of the product (190.0[M+1]$^+$) was detected. The reaction solution was filtered through celite, concentrated and subjected to column chromatography (eluent: PE:EA=10:0 to 2:1), so as to obtain 470 mg of (R)-4-(2-amino-4-ethylphenyl)-3-butyn-2-ol.

27.5 (R)-4-(2-amino-4-ethylphenyl)-2-butanol

A 50 mL single-necked flask was charged with 6 (900 mg), and palladium on carbon (225 mg) and 20 mL of methanol were added. A hydrogen balloon was provided and the mixture was purged with hydrogen gas three times. Reaction proceeded at room temperature for 15 h. A sample was taken, and TLC detection showed that the spots of the raw materials disappeared. The sample was subjected to LC-MS detection, and a peak of the product (194.1[M+1]$^+$) was detected. The reaction mixture was filtered through celite and concentrated, so as to obtain 750 mg of a brown oil (yield: 81.6%).

27.6 (S)-5-((7-ethyl-2-methyl-3,4-dihydro quinolin-1(2H)-yl)sulfonyl)-2-((tetrahydro-2H-pyran-4-yl)methoxy)benzyl Alcohol The rest synthesis steps proceeded with reference to the corresponding synthesis method in Example 12, so as to prepare and obtain 250 mg of the title compound (HPLC purity: 99.7%). (ESI) m/z 460.0 [M+1]+.
$^1$H NMR (400 MHz, CDCl$_3$): δ 7.61 (s, 1H), 7.48 (s, 1H), 7.40 (d, J=7.8 Hz, 1H), 6.99-6.87 (m, 2H), 6.79 (d, J=8.6 Hz, 1H), 4.62 (d, J=6.4 Hz, 2H), 4.39 (dd, J=11.6, 5.4 Hz, 1H), 4.04 (d, J=10.8 Hz, 2H), 3.88 (d, J=6.2 Hz, 2H), 3.46 (t, J=11.4 Hz, 2H), 2.68 (dd, J=14.9, 7.5 Hz, 2H), 2.46-2.33 (m, 1H), 2.11 (m, 1H), 1.92 (d, J=4.2 Hz, 1H), 1.85 (dd, J=11.0, 6.0 Hz, 1H), 1.74 (d, J=12.4 Hz, 2H), 1.55-1.42 (m, 2H), 1.39-1.25 (m, 8H).

Example 28

Synthesis of (S)-5-((6-ethyl-2-methyl-3,4-dihydro-1,7-naphthyridin-1(2H)-yl)sulfonyl)-2-((tetrahydro-2H-pyran-4-yl)methoxy)benzyl Alcohol

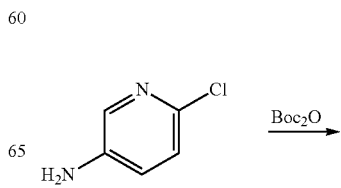

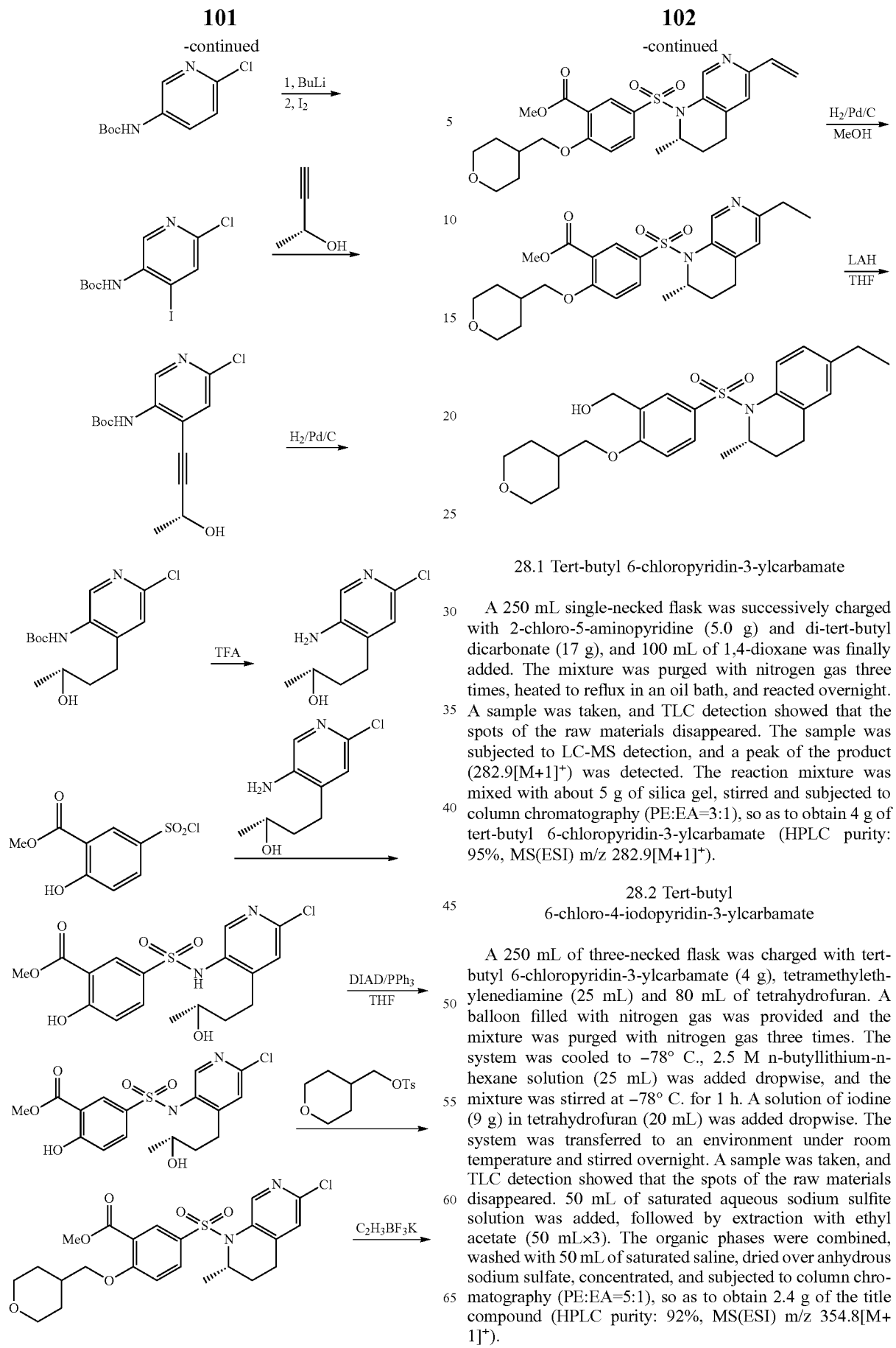

28.1 Tert-butyl 6-chloropyridin-3-ylcarbamate

A 250 mL single-necked flask was successively charged with 2-chloro-5-aminopyridine (5.0 g) and di-tert-butyl dicarbonate (17 g), and 100 mL of 1,4-dioxane was finally added. The mixture was purged with nitrogen gas three times, heated to reflux in an oil bath, and reacted overnight. A sample was taken, and TLC detection showed that the spots of the raw materials disappeared. The sample was subjected to LC-MS detection, and a peak of the product (282.9[M+1]$^+$) was detected. The reaction mixture was mixed with about 5 g of silica gel, stirred and subjected to column chromatography (PE:EA=3:1), so as to obtain 4 g of tert-butyl 6-chloropyridin-3-ylcarbamate (HPLC purity: 95%, MS(ESI) m/z 282.9[M+1]$^+$).

28.2 Tert-butyl 6-chloro-4-iodopyridin-3-ylcarbamate

A 250 mL of three-necked flask was charged with tert-butyl 6-chloropyridin-3-ylcarbamate (4 g), tetramethylethylenediamine (25 mL) and 80 mL of tetrahydrofuran. A balloon filled with nitrogen gas was provided and the mixture was purged with nitrogen gas three times. The system was cooled to −78° C., 2.5 M n-butyllithium-n-hexane solution (25 mL) was added dropwise, and the mixture was stirred at −78° C. for 1 h. A solution of iodine (9 g) in tetrahydrofuran (20 mL) was added dropwise. The system was transferred to an environment under room temperature and stirred overnight. A sample was taken, and TLC detection showed that the spots of the raw materials disappeared. 50 mL of saturated aqueous sodium sulfite solution was added, followed by extraction with ethyl acetate (50 mL×3). The organic phases were combined, washed with 50 mL of saturated saline, dried over anhydrous sodium sulfate, concentrated, and subjected to column chromatography (PE:EA=5:1), so as to obtain 2.4 g of the title compound (HPLC purity: 92%, MS(ESI) m/z 354.8[M+1]$^+$).

28.3 Tert-butyl (R)-6-chloro-4-(3-hydroxy-1-butyn-1-yl)pyridin-3-ylcarbamate A 100 mL single-necked flask was charged with tert-butyl 6-chloro-4-iodopyridin-3-ylcarbamate (2.3 g), (R)-(−)-3-butyn-2-ol (0.69 g), bis(triphenylphosphine)palladium chloride (450 mg), cuprous iodide (70 mg) and 30 mL of triethylamine. The mixture was purged with nitrogen gas three times, and reacted for 16 h at room temperature. A sample was taken, and TLC detection showed that the spots of the raw materials disappeared. The sample was subjected to LC-MS detection, and a peak of the product (297.0[M+1]$^+$) was detected. The reaction mixture was cooled to room temperature, filtered through celite, concentrated, and subjected to column chromatography (PE:EA=5:1), so as to obtain 1.67 g of the title compound (MS(ESI) m/z 297.0 [M+1]$^+$).

28.4 Tert-butyl (R)-6-chloro-4-(3-hydroxybutyl)pyridin-3-ylcarbamate

A 50 mL single-necked flask was charged with tert-butyl (R)-6-chloro-4-(3-hydroxy-1-butyn-1-yl)pyridin-3-ylcarbamate (1 g), palladium on carbon (0.071 g) and 20 mL of ethyl acetate. A hydrogen balloon was provided, and the mixture was purged with hydrogen gas three times and reacted at room temperature for 16 h. A sample was taken, and TLC detection showed that the spots of the raw materials disappeared. The resulting mixture was filtered through celite and the solvent was removed by rotary evaporation under reduced pressure, so as to obtain 1.05 g of the title compound (MS(ESI) m/z 301.0[M+1]$^+$).

28.5 (R)-4-(5-amino-2-chloropyridin-4-yl)-2-butanol

A 50 mL single-necked flask was charged with tert-butyl (R)-6-chloro-4-(3-hydroxybutyl) pyridin-3-ylcarbamate (1.05 g), trifluoroacetic acid (2 mL), and 20 mL of dichloromethane. The mixture was reacted for 3 h at room temperature, a sample was taken, and TLC detection showed that the spots of the raw materials disappeared. 2N diluted hydrochloric acid (10 mL×3) was added to the system for extraction. The aqueous phase was adjusted to alkaline pH with sodium carbonate, and then extracted with ethyl acetate (20 mL×3). The organic phases were combined, washed with 50 mL of saturated saline and dried over anhydrous sodium sulfate, and the solvent was removed by rotary evaporation under reduced pressure, so as to obtain 500 mg of the title compound (MS(ESI) m/z 201.0[M+1]$^+$).

28.6 Methyl (S)-5-((6-chloro-2-methyl-3,4-dihydro-1,7-naphthyridin-1(2H)-yl)sulfonyl)-2-((tetrahydro-2H-pyran-4-yl)methoxy)benzoate The synthesis steps of the experiment proceeded with reference to the corresponding synthesis method in Example 12, so as to prepare and obtain 540 mg of the title compound (MS(ESI) m/z 494.9[M+1]$^+$).

28.7 Methyl (S)-5-((6-vinyl-2-methyl-3,4-dihydro-1,7-naphthyridin-1(2H)-yl)sulfonyl)-2-((tetrahydro-2H-pyran-4-yl)methoxy)benzoate A 50 mL single-necked flask was successively charged with methyl (S)-5-((6-chloro-2-methyl-3,4-dihydro-1,7-naphthyridin-1(2H)-yl)sulfonyl)-2-((tetrahydro-2H-pyran-4-yl)methoxy)benzoate (540 mg), potassium vinyltrifluoroborate (270 mg), tetrakis(triphenylphosphine)palladium (54 mg) and cesium carbonate (1.4 g), and 20 mL of 1,4-dioxane and 2 mL of water were finally added. The mixture was purged with nitrogen gas three times, heated to reflux in an oil bath, and reacted overnight. A sample was taken, and TLC detection showed that the spots of the raw materials disappeared. The sample was subjected to LC-MS detection, and a peak of the product (486.9[M+1]$^+$) was detected. The resulting mixture was filtered through celite and subjected to liquid-liquid separation. The aqueous phase was extracted with ethyl acetate (20 mL×3). The organic phases were combined, washed with 50 mL of saturated saline and dried over anhydrous sodium sulfate, and the solvent was removed by rotary evaporation under reduced pressure, so as to obtain 250 mg of the title compound (MS(ESI) m/z 486.9[M+1]$^+$).

28.8 Methyl (S)-5-((6-ethyl-2-methyl-3,4-dihydro-1,7-naphthyridin-1(2H)-yl)sulfonyl)-2-((tetrahydro-2H-pyran-4-yl)methoxy)benzoate A 50 mL single-necked flask was charged with methyl (S)-5-((6-vinyl-2-methyl-3,4-dihydro-1,7-naphthyridin-1(2H)-yl)sulfonyl)-2-((tetrahydro-2H-pyran-4-yl)methoxy)benzoate (250 mg), palladium on carbon (10 mg) and 15 mL of anhydrous methanol. The system was provided with a hydrogen balloon, and the mixture was purged with hydrogen gas three times and reacted at room temperature for 4 h. A sample was taken, and TLC detection showed that the spots of the raw materials disappeared. The resulting mixture was filtered through celite and the solvent was removed by rotary evaporation under reduced pressure, so as to obtain 190 mg of the title compound (MS(ESI) m/z 489.0 [M+1]$^+$).

28.9 (S)-5-((6-ethyl-2-methyl-3,4-dihydro-1,7-naphthyridin-1(2H)-yl)sulfonyl)-2-((tetrahydro-2H-pyran-4-yl)methoxy)benzyl Alcohol A 25 mL single-necked flask was charged with methyl (S)-5-((6-ethyl-2-methyl-3,4-dihydro-1,7-naphthyridin-1(2H)-yl)sulfonyl)-2-((tetrahydro-2H-pyran-4-yl)methoxy)benzoate (180 mg) and 10 mL of anhydrous tetrahydrofuran. The mixture was purged with nitrogen gas three times and cooled to 0° C. in an ice bath. Lithium aluminum hydride (40 mg) was added to the reaction solution in portions, and the reaction proceeded at 0° C. for 0.5 h. A sample was taken, and TLC detection showed that the spots of the raw materials disappeared. The sample was subjected to LC-MS detection, and a peak of the product (461.0[M+1]$^+$) was detected. The reaction was quenched by ice water, and the resulting mixture was extracted with ethyl acetate (50 mL×3). Excess aqueous potassium hydroxide solution was added. The aqueous phase was extracted with ethyl acetate (20 mL×3), and the organic phases were dried over anhydrous sodium sulfate and concentrated by rotary evaporation under reduced pressure, so as to obtain 177 mg of an oily liquid, which was purified by prep-HPLC and concentrated to obtain 12 mg of the title compound (HPLC purity: 90.7%).

MS(ESI) m/z 461.0[M+1]$^+$.

1H NMR (400 MHz, CDCl3) δ 8.80 (s, 1H), 7.61 (d, J=1.9 Hz, 1H), 7.45 (dd, J=8.6, 2.2 Hz, 1H), 6.81 (d, J=8.6 Hz, 2H), 4.65 (s, 2H), 4.44 (dd, J=12.3, 6.0 Hz, 1H), 4.02 (dd, J=11.3, 3.8 Hz, 2H), 3.88 (d, J=6.3 Hz, 2H), 3.45 (t, J=11.0 Hz, 2H), 2.76 (q, J=7.6 Hz, 2H), 2.56-2.43 (m, 1H), 2.12-2.07 (m, 1H), 2.01 (s, 2H), 1.80-1.74 (m, 2H), 1.54-1.31 (m, 4H), 1.30-1.24 (m, 6H).

Example 29

Synthesis of (S)-1-(5-((7-ethyl-2-methyl-3,4-dihydroquinolin-1(2H)-yl)sulfonyl)-2-((tetrahydro-2H-pyran-4-yl)methoxy)phenyl)cyclopropanol

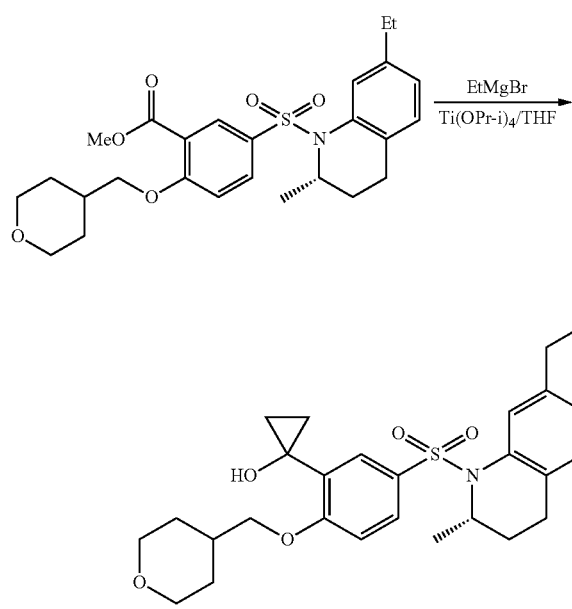

A 50 mL three-necked flask was charged with methyl (S)-5-((7-ethyl-2-methyl-3,4-dihydroquinolin-1(2H)-yl)sulfonyl)-2-((tetrahydro-2H-pyran-4-yl)methoxy)benzoate (213 mg, Example 27), titanium tetraisopropoxide (173 mg) and anhydrous tetrahydrofuran (9 mL). The mixture was purged with nitrogen gas three times. The reaction mixture was cooled to 0° C. in an ice bath. Ethylmagnesium bromide (1.22 mL, 1 M) was added dropwise to the reaction solution within 30 minutes, and the reaction mixture was gradually warmed to room temperature and reacted at room temperature for 36.5 h. A sample was taken and subjected to LC-MS detection, and a peak of the product (486.0[M+1]$^+$) was detected. The reaction was quenched with saturated ammonium chloride solution (2.5 mL). The resulting mixture was filtered through celite, the filtrate was concentrated under reduced pressure, and the crude product was purified by pre-HPLC, so as to obtain 22 mg of the title compound (HPLC purity: 99.86%).

MS(ESI) m/z 486.0[M+1]$^+$.

$^1$H NMR (400 MHz, CDCl$_3$) δ 7.59 (s, 1H), 7.44 (s, 1H), 7.24-7.09 (m, 1H), 7.08-6.61 (m, 3H), 4.30 (br. s, 1H), 4.13-3.75 (m, 4H), 3.60-3.31 (m, 2H), 3.27-3.03 (m, 1H), 2.85-2.54 (m, 2H), 2.42-2.26 (m, 1H), 2.22-2.04 (m, 1H), 1.83-1.39 (m, 7H), 1.36-1.16 (m, 6H), 1.08-0.91 (m, 2H), 0.78-0.56 (m, 2H)).

Example 30

Synthesis of 5-((2,6-diethyl-3,4-dihydroquinolin-1(2H)-yl)sulfonyl)-2-((tetrahydro-2H-pyran-4-yl)methoxy)benzonitrile

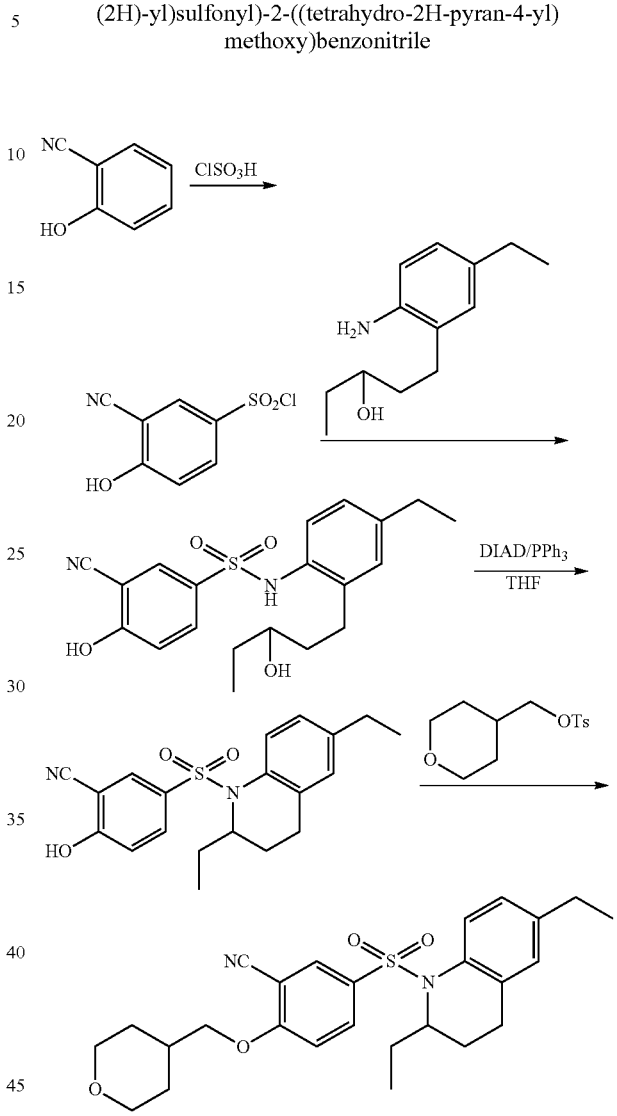

30.1 3-Cyano-4-hydroxybenzenesulfonyl Chloride

A 50 mL single-necked flask was charged with 2-cyanophenol (2.0 g) and 10 mL of thionyl chloride, cooled in an ice bath, and chlorosulfonic acid (2.9 g) was added dropwise. After the completion of the dropwise addition, the mixture was warmed to room temperature and stirred overnight. A sample was taken, and TLC detection showed that the spots of the raw materials disappeared. The sample was subjected to LC-MS detection, and peaks of the product (216.0, 218.0 [M+1]$^+$) was detected. Post-treatment: the reaction solution was added dropwise into 150 mL of ice water to quench the reaction. The aqueous phase was extracted with ethyl acetate (20 mL×3). The organic phases were combined, washed with 50 mL of saturated saline and dried over anhydrous sodium sulfate, and the solvent was removed by rotary evaporation under reduced pressure to obtain 1.6 g of 3-cyano-4-hydroxybenzenesulfonyl chloride.

30.2 3-Cyano-N-(4-ethyl-2-(3-hydroxypentyl)phenyl)-4-hydroxybenzenesulfonamide A 50 mL single-necked flask was charged with 1-(2-amino-5-ethylphenyl)-3-pentanol (600 mg), and 10 mL of pyridine was added to dissolve the former. The mixture was cooled in an ice bath, and 3-cyano-4-hydroxybenzenesulfonyl chloride (1.0 g) was added in portions. After the completion of the dropwise addition, the mixture was warmed to room temperature and stirred overnight. A sample was taken, and TLC detection showed that the reaction of the raw materials was complete. The sample was subjected to LC-MS detection 387.1[M+1]$^+$. Post-treatment: 50 mL of water was added, and the resulting mixture was extracted with ethyl acetate (20 mL×3). The organic phases were combined, washed with 50 mL of saturated saline and dried over anhydrous sodium sulfate, and the solvent was removed by rotary evaporation under reduced pressure, so as to obtain an oil, which was purified by passing through a column to obtain 550 mg of the title compound.

30.3 5-((2,6-diethyl-3,4-dihydroquinolin-1(2H)-yl)sulfonyl)-2-hydroxybenzonitrile A 50 mL three-necked flask was charged with triphenylphosphine (1.1 g), and 4 ml of anhydrous tetrahydrofuran was added to dissolve the former. The mixture was purged with nitrogen gas three times and cooled to 0° C. in an ice bath. A solution of diisopropyl azodicarboxylate (573 mg) in tetrahydrofuran (2 mL) was added dropwise. After the completion of the dropwise addition, the mixture was stirred for 20 min in an ice bath, followed by dropwise addition of a solution of 3-cyano-N-(4-ethyl-2-(3-hydroxypentyl) phenyl)-4-hydroxybenzenesulfonamide (550 mg) in tetrahydrofuran (4 mL). After the completion of the dropwise addition, the mixture was warmed to room temperature and stirred overnight. A sample was taken, and TLC detection showed that the spots of the raw materials disappeared. The sample was subjected to LC-MS detection, and a peak of the product (369.0[M−1]$^+$) was detected. The resulting product was purified by passing through a column, so as to obtain 1.0 g of the title compound.

30.4 5-((2,6-diethyl-3,4-dihydroquinolin-1(2H)-yl)sulfonyl)-2-((tetrahydro-2H-pyran-4-yl)methoxy)benzonitrile A 50 mL single-necked flask was charged with 1.0 g of 5-((2,6-diethyl-3,4-dihydroquinolin-1(2H)-yl)sulfonyl)-2-hydroxybenzonitrile, and 15 mL of N,N-dimethyl formamide was added to dissolve the former. Then, p-toluenesulfonate-4-methyl pyran (870 mg) and potassium carbonate (750 mg) were added. The mixture was reacted overnight in an oil bath at 70° C. A sample was taken, and TLC detection showed that the spots of the raw materials disappeared. The sample was subjected to LC-MS detection, and a peak of the product (491.2[M+Na]$^+$) was detected. Post-treatment: 50 mL of water was added, and the resulting mixture was extracted with ethyl acetate (20 mL×3). The organic phases were combined, washed with 50 mL of saturated saline and dried over anhydrous sodium sulfate, and the solvent was removed by rotary evaporation under reduced pressure, so as to obtain 1.6 g of an oil. 500 mg of the oil was taken and subjected to Prep-HPLC, so as to prepare and obtain 30 mg of the title compound.

$^1$H NMR (400 MHz, CDCl3) δ 7.69 (d, J=2.1 Hz, 1H), 7.67-7.58 (m, 2H), 7.09 (d, J=8.2 Hz, 1H), 6.90 (d, J=8.9 Hz, 1H), 6.85 (s, 1H), 4.27-4.09 (m, 1H), 4.04 (dd, J=11.4, 3.8 Hz, 2H), 3.94 (d, J=6.7 Hz, 2H), 3.47 (t, J=11.1 Hz, 2H), 2.63 (q, J=7.6 Hz, 2H), 2.52-2.39 (m, 1H), 2.28-2.11 (m, 1H), 1.91-1.72 (m, 4H), 1.69-1.62 (m, 1H), 1.54-1.41 (m, 4H), 1.25 (t, J=7.6 Hz, 3H), 0.97 (t, J=7.4 Hz, 3H).

Example 31

Synthesis of 2,6-diethyl-1-((3-nitro-4-((tetrahydro-2H-pyran-4-yl)methoxy)phenyl) sulfonyl)-1,2,3,4-tetrahydroquinoline

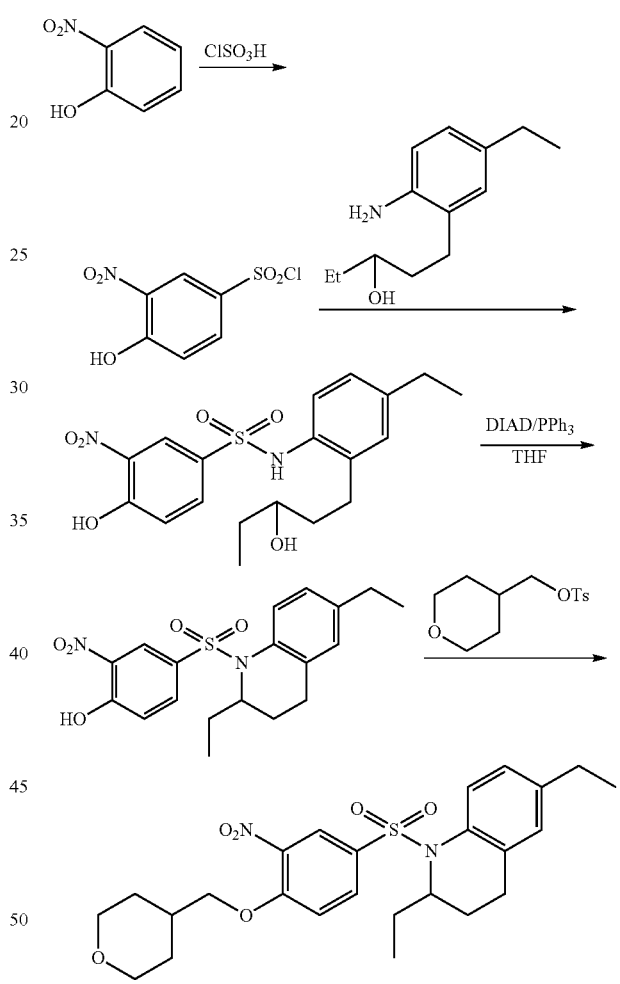

30 mg of the title compound was prepared and obtained with reference to the synthesis method of Example 30 (purity: 98.4%).

MS(ESI) m/z: 511.0[M+Na]$^+$).

$^1$H NMR (400 MHz, CDCl$_3$) δ 7.92 (s, 1H), 7.62 (d, J=8.2 Hz, 1H), 7.57 (d, J=8.6 Hz, 1H), 7.07 (d, J=7.9 Hz, 1H), 7.00 (d, J=8.7 Hz, 1H), 6.83 (s, 1H), 4.24-4.14 (m, 1H), 4.02 (d, J=8.6 Hz, 2H), 3.95 (d, J=6.2 Hz, 2H), 3.44 (t, J=11.5 Hz, 2H), 2.60 (dd, J=14.6, 7.2 Hz, 2H), 2.50-2.39 (m, 1H), 2.13 (m, 1H), 1.93-1.79 (m, 2H), 1.76 (d, J=13.3 Hz, 2H), 1.61 (dd, J=13.5, 6.6 Hz, 1H), 1.51-1.40 (m, 4H), 1.22 (t, J=7.5 Hz, 3H), 0.95 (t, J=7.1 Hz, 3H).

Example 32

Synthesis of (S)-5-((-2-ethyl-6-trifluoromethyl-3,4-dihydroquinolin-1(2H)-yl)sulfonyl)-2-((tetrahydro-2H-pyran-4-yl)methoxy)benzyl Alcohol

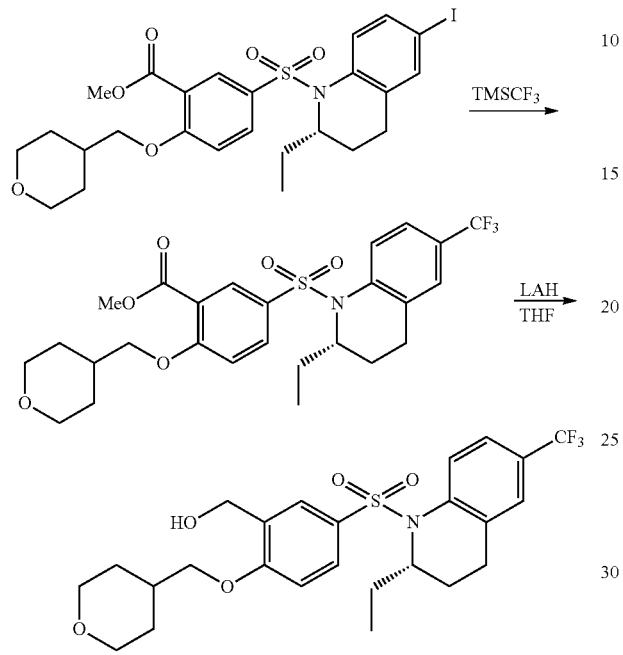

32.1 Methyl (S)-5-((-2-ethyl-6-trifluoromethyl-3,4-dihydroquinolin-1(2H)-yl)sulfonyl)-2-((tetrahydro-2H-pyran-4-yl)methoxy)benzoate A 250 mL three-necked flask was charged with methyl (S)-5-((6-iodo-2-ethyl-3,4-dihydroquinolin-1(2H)-yl)sulfonyl)-2-((tetrahydro-2H-pyran-4-yl)methoxy)benzoate (300 mg, Example 24.6), potassium fluoride (150 mg), cuprous iodide (40 mg), and 1,10-phenanthroline (30 mg), which were dissolved in anhydrous dimethyl sulfoxide. The mixture was purged with nitrogen gas and protected thereby. (Trifluoromethyl)trimethylsilane (360 mg) and trimethyl borate (260 mg) dissolved in anhydrous dimethyl sulfoxide were injected. The mixture was stirred at 60° C. overnight. LC-MS detection showed that the spots of the raw materials disappeared. Water and ethyl acetate were added to the system to perform extraction. The organic layer was dried and concentrated to obtain the title compound (400 mg of a crude product).

32.2 (S)-5-((-2-ethyl-6-trifluoromethyl-3,4-dihydroquinolin-1(2H)-yl)sulfonyl)-2-((tetrahydro-2H-pyran-4-yl)methoxy)benzyl Alcohol A 25 mL single-necked flask was charged with methyl (S)-5-((-2-ethyl-6-trifluoromethyl-3,4-dihydroquinolin-1(2H)-yl)sulfonyl)-2-((tetrahydro-2H-pyran-4-yl)methoxy)benzoate (400 mg) and 10 mL of anhydrous tetrahydrofuran. The mixture was purged with nitrogen gas three times and cooled to 0° C. in an ice bath. Lithium aluminum hydride (80 mg) was added to the reaction solution in portions. The mixture was kept at 0° C. to react for 0.5 h. A sample was taken, and TLC detection showed that the spots of the raw materials disappeared. The sample was subjected to LC-MS detection, and a peak of the product (514.0[M+1]$^+$) was detected. The reaction was quenched with ice water, and the resulting mixture was extracted with ethyl acetate (50 mL×3).

An aqueous solution of sodium hydroxide was added in an excessive amount. The aqueous phase was extracted with ethyl acetate (20 mL×3), and the organic phases were dried over anhydrous sodium sulfate and subjected to rotary evaporation and concentration under reduced pressure, so as to obtain 200 mg of an oily liquid, which was purified by prep-HPLC and concentrated to obtain 37 mg of the title compound (HPLC purity: 98.2%), MS(ESI) m/z: 514.0[M+1]t 1H NMR (400 MHz, CDCl3) δ 7.91 (d, J=8.6 Hz, 1H), 7.60 (d, J=2.0 Hz, 1H), 7.45 (d, J=8.8 Hz, 1H), 7.41 (dd, J=8.7, 2.2 Hz, 1H), 7.26-7.24 (m, 1H), 6.80 (d, J=8.7 Hz, 1H), 4.65 (d, J=5.8 Hz, 2H), 4.35-4.21 (m, 1H), 4.02 (dd, J=11.4, 3.6 Hz, 2H), 3.87 (d, J=6.3 Hz, 2H), 3.44 (t, J=11.0 Hz, 2H), 2.64-2.48 (m, 1H), 2.23-2.04 (m, 2H), 2.00 (t, J=6.2 Hz, 1H), 1.78-1.65 (m, 3H), 1.60-1.41 (m, 5H), 0.95 (t, J=7.4 Hz, 3H).

Example 33

Synthesis of (S)-5-((2,5,7-trimethyl-3,4-dihydroquinolin-1(2H)-yl)sulfonyl)-2-((tetrahydro-2H-pyran-4-yl)methoxy)benzyl Alcohol

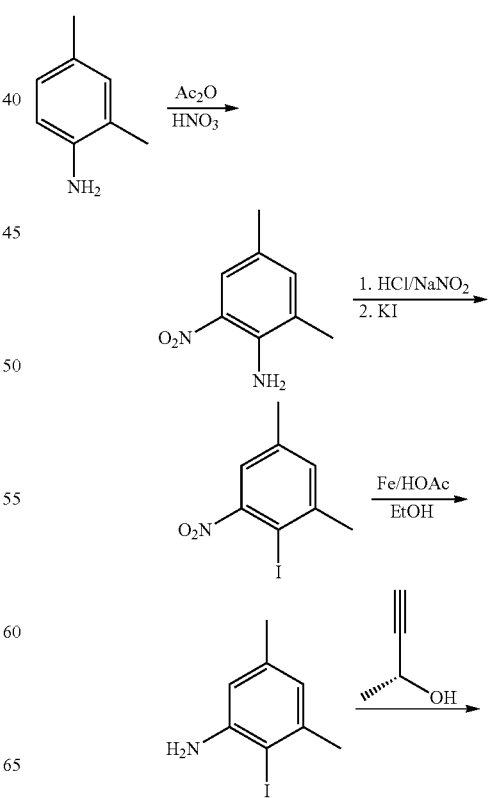

-continued
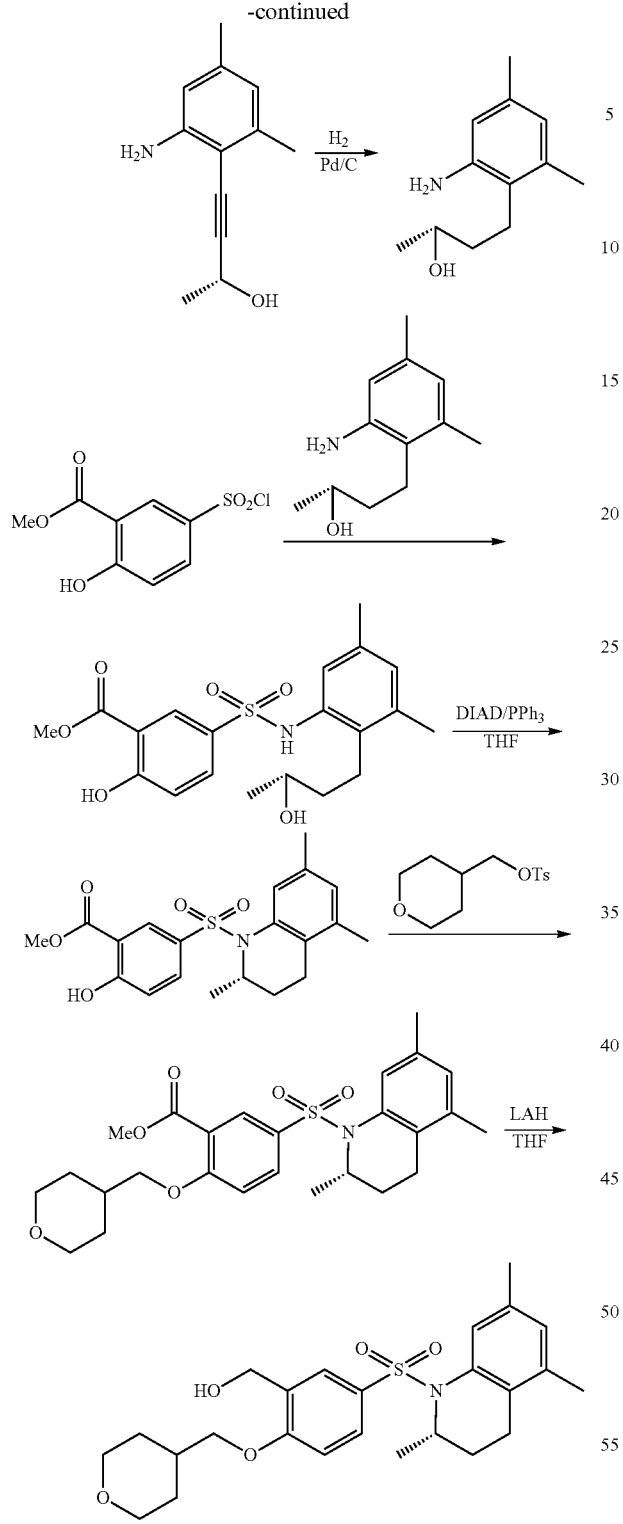
120 mg of the title compound (HPLC purity: 99.9%) was prepared and obtained with reference to the method in Example 27.
$^1$H NMR (400 MHz, CDCl$_3$) δ 7.50 (s, 1H), 7.42 (s, 1H), 7.40 (s, 1H), 6.82-6.78 (m, 2H), 4.61 (d, J=5.4 Hz, 2H), 4.41 (dd, J=11.9, 5.9 Hz, 1H), 4.02 (d, J=8.0 Hz, 2H), 3.87 (d, J=6.2 Hz, 2H), 3.44 (t, J=11.5 Hz, 2H), 2.38 (dd, J=16.4, 8.4 Hz, 1H), 2.31 (s, 3H), 2.11 (s, 3H), 2.08 (m, 1H), 1.93-1.78 (m, 1H), 1.72 (m, 4H), 1.59-1.43 (m, 2H), 1.43-1.35 (m, 1H), 1.19 (d, J=6.5 Hz, 3H).
Example 34
Synthesis of 5-((6-isopropyl-2-ethyl-3,4-dihydroquinolin-1(2H)-yl)sulfonyl)-2-((tetrahydro-2H-pyran-4-yl)methoxy)benzyl Alcohol
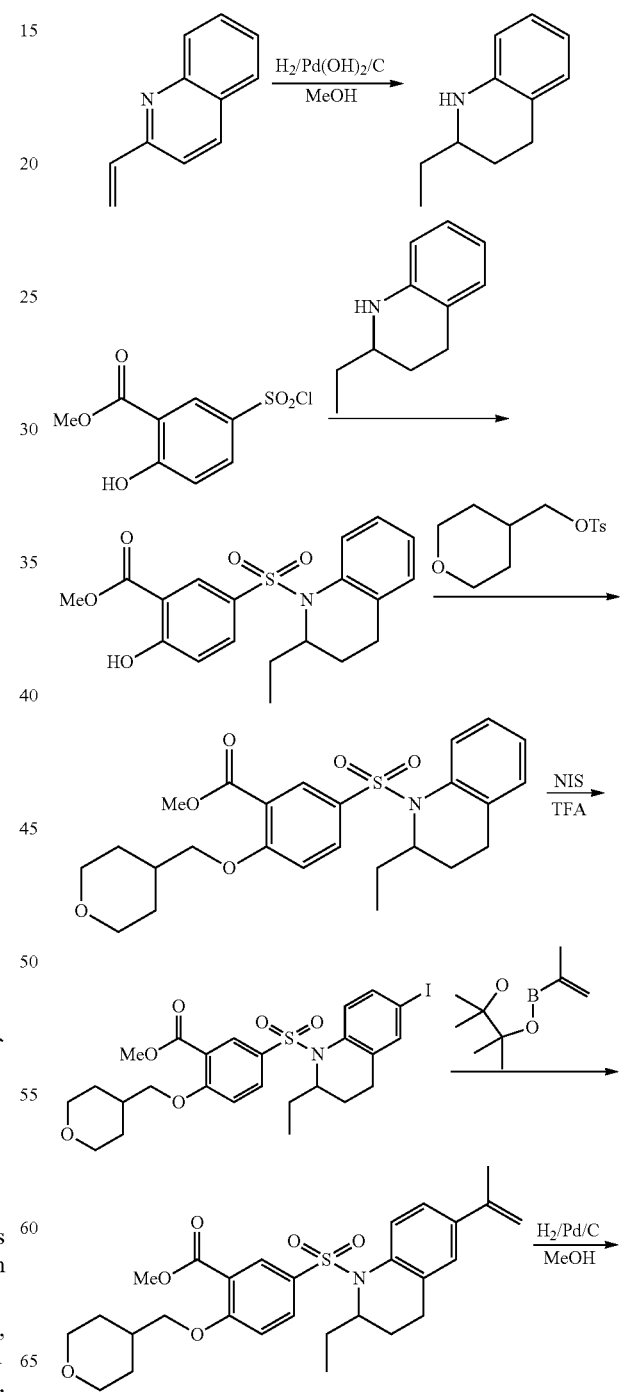

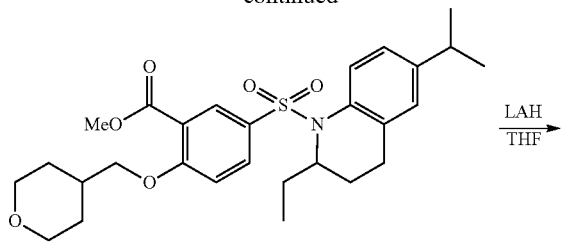

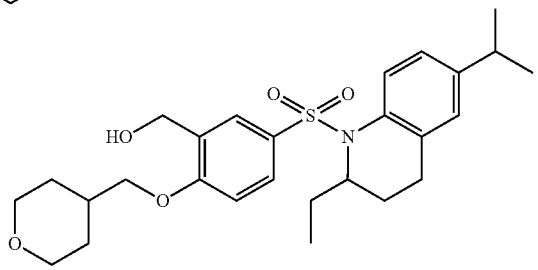

34.1 2-Ethyl-1,2,3,4-tetrahydroquinoline

A single-necked flask was charged with 2-vinylquinoline (2.1 g, Example 24.1), 25 mL of methanol was added to dissolve the former, and 560 mg of palladium hydroxide on carbon was added. The mixture was purged with hydrogen gas three times and stirred for 48 h in an external bath at 50° C. A sample was taken, and TLC detection showed that the reaction of the raw materials was complete. 162.2 [M+1]$^+$ was detected by LC-MS. Post-treatment: The resulting mixture was filtered, mixed with silica gel and stirred, purified by passing through a column, and eluted with petroleum ether as an eluent. The product was collected and concentrated under reduced pressure to obtain 1.9 g of 2-ethyl-1,2,3,4-tetrahydroquinoline.

34.2 Methyl 5-((6-iodo-2-ethyl-3,4-dihydroquinolin-1(2H)-yl)sulfonyl)-2-((tetrahydro-2H-pyran-4-yl)methoxy)benzoate 1.1 g of the title compound was prepared and obtained with reference to the synthesis methods in steps 24.4 to 24.6 of Example 24.

34.3 Methyl 5-((6-isopropenyl-2-ethyl-3,4-dihydroquinolin-1(2H)-yl)sulfonyl)-2-((tetrahydro-2H-pyran-4-yl)methoxy)benzoate A single-necked flask was charged with methyl 5-((6-iodo-2-ethyl-3,4-dihydroquinolin-1(2H)-yl)sulfonyl)-2-((tetrahydro-2H-pyran-4-yl)methoxy)benzoate (1.1 g), and 1,4-dioxane (10 mL) was added to dissolve the former. Isopropenylboronic acid pinacol ester (453 mg), cesium carbonate (1.17 g) and 3 mL of water were added. After the mixture was purged with nitrogen gas three times, tetrakis(triphenylphosphine)palladium (416 mg) was added. The mixture was purged with nitrogen gas three times again and stirred overnight in an external bath at 90° C. A sample was taken, and TLC detection showed that the spots of the raw materials disappeared. The sample was subjected to LC-MS detection, 514.1[M+1]$^+$. Post-treatment: 50 mL of water was added, and the resulting mixture was extracted three times with ethyl acetate (20 mL×3). The organic phases were combined, washed with saturated saline, dried over anhydrous sodium sulfate, filtered and concentrated under reduced pressure, so as to obtain an oil, which was purified by passing through a column to obtain 400 mg of the title compound.

34.4 5-((6-Isopropyl-2-ethyl-3,4-dihydroquinolin-1(2H)-yl)sulfonyl)-2-((tetrahydro-2H-pyran-4-yl)methoxy)benzyl Alcohol 35 mg of the title compound (HPLC purity: 99.0%) was prepared and obtained with reference to the synthesis methods in steps 24.8 to 24.9 of Example 24.

$^1$H NMR (400 MHz, CDCl$_3$) δ 7.67 (d, J=8.4 Hz, 1H), 7.50-7.40 (m, 2H), 7.10 (dd, J=8.4, 1.7 Hz, 1H), 6.83-6.80 (m, 2H), 4.61 (d, J=6.5 Hz, 2H), 4.26-4.11 (m, 1H), 4.04 (dd, J=11.3, 3.6 Hz, 2H), 3.89 (d, J=6.4 Hz, 2H), 3.46 (dd, J=11.6, 10.3 Hz, 2H), 2.87 (dt, J=13.8, 6.9 Hz, 1H), 2.51-2.32 (m, 1H), 2.20-2.06 (m, 1H), 1.96-1.83 (m, 2H), 1.76 (m, 2H), 1.68-1.61 (m, 2H), 1.48 (m, 4H), 1.26 (d, J=8.7 Hz, 6H), 0.96 (t, J=7.4 Hz, 3H).

Example 35

Synthesis of (S)-5-((7-trifluoromethyl-2-methyl-3,4-dihydroquinolin-1(2H)-yl)sulfonyl)-2-((tetrahydro-2H-pyran-4-yl)methoxy)benzyl Alcohol

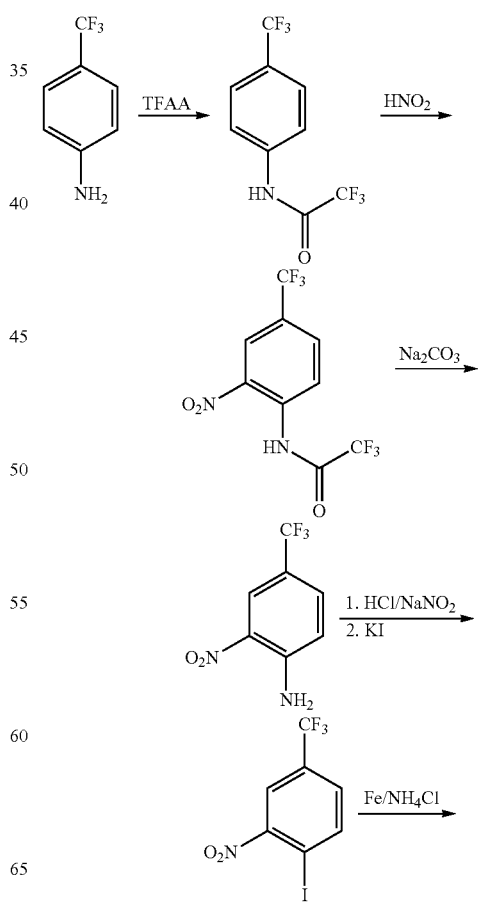

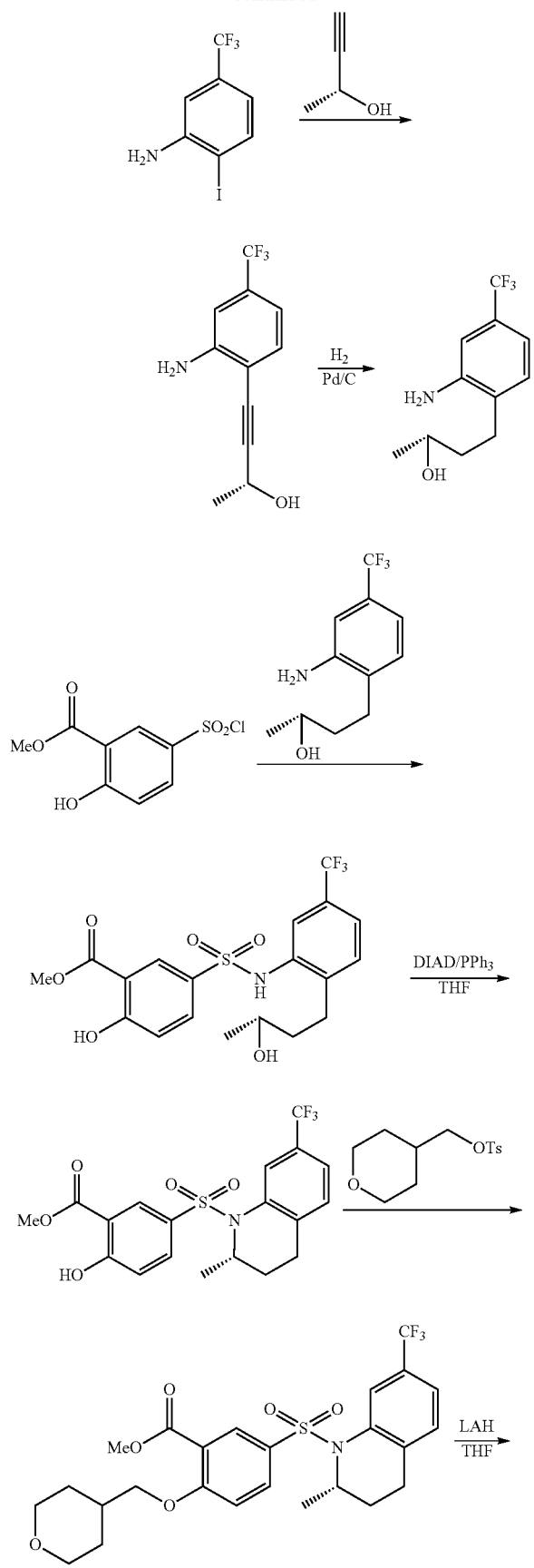

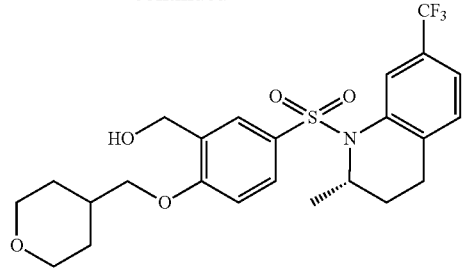

35.1 2,2,2-Trifluoro-N-(4-trifluoromethylphenyl)acetamide

A 250 mL single-necked flask was charged with 4-trifluoromethylaniline (5.0 g), dichloromethane (90 mL) was added to dissolve the former, and triethylamine (9.4 g) was added. The mixture was cooled in an ice bath. Under nitrogen protection, trifluoroacetic anhydride (9.8 g) was added dropwise. After the completion of the dropwise addition, the mixture was stirred overnight at room temperature. The raw materials disappeared as detected by TLC, and a peak of the product (256.0[M+1]$^+$) was detected by LC-MS. Post-treatment: 50 mL of water was added to quench the reaction and the resulting mixture was subjected to liquid-liquid separation. The aqueous phase was extracted with dichloromethane (20 mL×2). The organic phases were combined, washed with 50 mL of saturated saline and dried over anhydrous sodium sulfate, and the solvent was removed by rotary evaporation under reduced pressure, so as to obtain 9.0 g of 2,2,2-trifluoro-N-(4-trifluoro methylphenyl)acetamide.

35.2 2,2,2-Trifluoro-N-(2-nitro-4-trifluoromethylphenyl)acetamide

A single-necked flask was charged with 2,2,2-trifluoro-N-(4-trifluoromethylphenyl) acetamide (9.0 g), and 40 mL of concentrated sulfuric acid was added to dissolve the former. The mixture was cooled in an ice bath, and fuming nitric acid (2.65 g) was added dropwise thereto. After the completion of the dropwise addition, the mixture was stirred for 10 min in the ice bath. The raw materials disappeared as detected by TLC. Post-treatment: 100 mL of water was added dropwise to quench the reaction, and the resulting mixture was extracted with ethyl acetate (30 mL×4). The organic phases were combined, washed with a saturated aqueous sodium carbonate solution, washed with saline and dried over anhydrous sodium sulfate, and the solvent was removed by rotary evaporation under reduced pressure, so as to obtain 8.9 g of the title compound.

35.3 2-Nitro-4-trifluoromethylaniline

A single-necked flask was charged with 2,2,2-trifluoro-N-(2-nitro-4-trifluoro methylphenyl)acetamide (8.9 g), 20 mL of methanol was added to dissolve the former, and sodium carbonate (4.7 g) was added. The mixture was stirred for 30 min at room temperature. The raw materials disappeared as detected by TLC. Post-treatment: The resulting mixture was filtered by suction, the filtrate was mixed with silica gel, stirred, and purified by passing through a column, so as to obtain 5.8 g of 2-nitro-4-trifluoromethylaniline.

35.4 (S)-5-((7-trifluoromethyl-2-methyl-3,4-dihydroquinolin-1(2H)-yl)sulfonyl)-2-((tetrahydro-2H-pyran-4-yl)methoxy)benzyl Alcohol 123 mg of the title compound (HPLC purity: 97.8%) was prepared and obtained with reference to the synthesis methods in steps 27.2 to 27.6 of Example 27.

$^1$H NMR (400 MHz, CDCl$_3$) δ 8.05 (s, 1H), 7.59 (d, J=2.1 Hz, 1H), 7.42 (dd, J=8.6, 2.3 Hz, 1H), 7.34 (d, J=7.9 Hz, 1H), 7.13 (d, J=7.9 Hz, 1H), 6.81 (d, J=8.7 Hz, 1H), 4.65 (s, 2H), 4.47 (dd, J=12.7, 6.4 Hz, 1H), 4.04 (dd, J=11.4, 3.8 Hz, 2H), 3.89 (d, J=6.3 Hz, 2H), 3.46 (t, J=11.0 Hz, 2H), 2.64-2.43 (m, 1H), 2.03-1.95 (m, 1H), 1.89-1.81 (m, 1H), 1.91-1.83 (m, 1H), 1.74 (d, J=12.7 Hz, 2H), 1.57-1.38 (m, 3H), 1.29 (d, J=6.6 Hz, 3H).

Example 36

Synthesis of 5-((6-isopropenyl-2-ethyl-3,4-dihydroquinolin-1(2H)-yl)sulfonyl)-2-((tetrahydro-2H-pyran-4-yl)methoxy)benzyl Alcohol

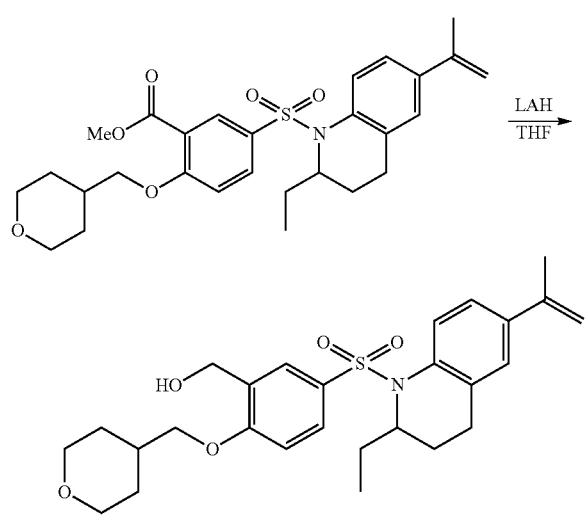

A 100 mL single-necked flask was charged with methyl 5-((6-isopropenyl-2-ethyl-3,4-dihydroquinolin-1(2H)-yl)sulfonyl)-2-((tetrahydro-2H-pyran-4-yl)methoxy)benzoate (80 mg, Example 34.3), and 5 mL of anhydrous tetrahydrofuran was added to dissolve the former. The mixture was cooled in an ice bath, and lithium tetrahydroaluminate (15 mg) was added in portions. After the completion of the addition, the mixture was stirred for 30 min in an ice bath. The reaction was complete as detected by TLC. LC-MS, 486.1[M+1]$^+$. 0.03 mL of water and 0.03 mL of 15% aqueous sodium hydroxide solution were added, and 0.09 mL of water was added to quench the reaction. 10 mL of ethyl acetate was further added, followed by drying over anhydrous sodium sulfate. The resulting mixture was filtered and concentrated under reduced pressure, so as to obtain 50 mg of an oil, which was subjected to Prep-HPLC to prepare and obtain 6.5 mg of the title compound (HPLC purity: 99.39%).

$^1$H NMR (400 MHz, CDCl$_3$) δ 7.72 (d, J=8.5 Hz, 1H), 7.53 (d, J=1.8 Hz, 1H), 7.40 (dd, J=8.6, 2.1 Hz, 1H), 7.33 (dd, J=8.5, 1.7 Hz, 1H), 7.08 (s, 1H), 6.77 (d, J=8.7 Hz, 1H), 5.35 (s, 1H), 5.06 (s, 1H), 4.62 (d, J=6.2 Hz, 2H), 4.19 (dd, J=12.8, 6.3 Hz, 1H), 4.02 (dd, J=11.4, 3.8 Hz, 2H), 3.86 (d, J=6.3 Hz, 2H), 3.44 (t, J=11.2 Hz, 2H), 2.52-2.41 (m, 1H), 2.13 (s, 3H), 2.08 (m, 1H), 2.02-1.96 (m, 1H), 1.94 (m, 1H), 1.71 (dd, J=17.7, 7.3 Hz, 3H), 1.64 (m, 1H), 1.53-1.41 (m, 4H), 0.94 (t, J=7.4 Hz, 3H).

Example 37

Synthesis of 5-((6-ethyl-4-hydroxy-2-methyl-3,4-dihydroquinolin-1(2H)-yl)sulfonyl)-2-((tetrahydro-2H-pyran-4-yl)methoxy)benzyl Alcohol

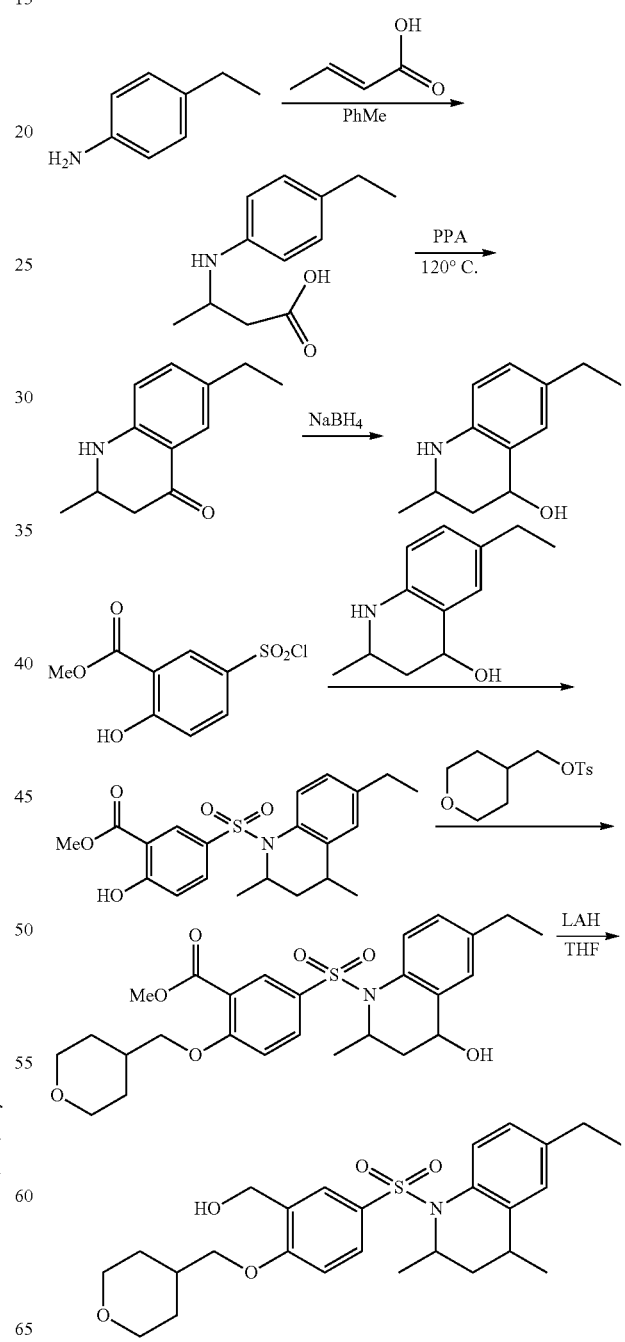

37.1 3-(4-Ethylanilino)butyric Acid

A 100 mL single-necked flask was charged with crotonic acid (3.0 g) and p-ethylaniline (3.8 g), and toluene (30 mL) was added as a reaction solvent. The mixture was reacted at 110° C. for 16 h. A sample was taken, and the raw materials disappeared as monitored by TLC. The sample was subjected to LC-MS detection, and a peak of the product (208 [M+H]$^+$) was detected. The reaction mixture was naturally cooled to room temperature and concentrated under reduced pressure to remove toluene. The residue was diluted with ethyl acetate (80 mL) and washed five times with a saturated sodium bicarbonate solution (30 mL×5). The alkaline aqueous phases were combined, adjusted to pH 3 to 4 with 2 N hydrochloric acid, and extracted three times with ethyl acetate (50 mL×3). The organic phases were combined, washed twice with saturated sodium chloride solution (60 mL×2), dried over anhydrous sodium sulfate, and concentrated, so as to obtain 3.7 g of 3-(4-ethylanilino)butyric acid, MS(ESI) m/z: 208.0[M+1]$^+$.

37.2 6-Ethyl-2-methyl-2,3-dihydroquinolin-4(1H)-one

A 50 mL single-necked flask was charged with 3-(4-ethylanilino)butyric acid (2.6 g) and toluene (10 mL), and polyphosphoric acid (20.7 g) was added under stirring. The mixture was reacted at 120° C. for 3 h, a sample was taken, and the spots of the raw materials disappeared as monitored by TLC. The sample was subjected to LC-MS detection, and a peak of the product (190 [M+H]$^+$) was detected. The reaction mixture was naturally cooled to room temperature. The reaction solution was slowly poured into ice water (100 mL), stirred for 10 minutes, and extracted three times with ethyl acetate (50 mL×2). The organic phases were combined, washed twice with a saturated sodium chloride solution (60 mL×2), dried over anhydrous sodium sulfate, and concentrated. The residue was mixed with silica gel, stirred, and purified by column chromatography, so as to obtain 630 mg of 6-ethyl-2-methyl-2,3-dihydroquinolin-4(1H)-one (MS(ESI) m/z: 190.0[M+1]$^+$).

37.3 6-Ethyl-2-methyl-1,2,3,4-tetrahydroquinolin-4-ol

A 50 mL single-necked flask was charged with 6-ethyl-2-methyl-2,3-dihydroquinolin-4(1H)-one (0.2 g) and methanol (10 mL), and cooled in an ice bath. The compound sodium borohydride (0.704 g) was added in portions. After the completion of the addition, the ice bath was removed, and the mixture was stirred and reacted at room temperature for 3 h. A sample was taken, and TLC detection showed that the spots of the raw materials disappeared. The sample was subjected to LC-MS detection, and a peak of the product (192 [M+H]$^+$) was detected. The reaction system was adjusted to have a pH of 3 to 4 by addition of 1 N hydrochloric acid, and then extracted three times with ethyl acetate (30 mL×3). The organic phases were combined, washed twice with saturated saline (40 mL×2), dried over anhydrous sodium sulfate and concentrated, so as to obtain 500 mg of a solid as a crude product, which was directly used in the reaction of the next step without purification (MS(ESI) m/z: 192.0[M+H]$^+$).

37.4 5-((6-Ethyl-4-hydroxy-2-methyl-3,4-dihydroquinolin-1(2H)-yl)sulfonyl)-2-((tetrahydro-2H-pyran-4-yl)methoxy)benzyl alcohol The rest reaction steps proceeded with reference to the corresponding synthesis method in Example 3, so as to prepare and obtain 120 mg of the title compound (MS(ESI) m/z: 476.0 [M+H]$^+$).

$^1$H NMR (400 MHz, CDCl$_3$) δ 7.61 (d, J=7.9 Hz, 1H), 7.41 (d, J=1.8 Hz, 1H), 7.36 (dd, J=8.6, 2.1 Hz, 1H), 7.19 (s, 1H), 7.17 (s, 1H), 6.78 (d, J=8.6 Hz, 1H), 4.66-4.55 (m, 2H), 4.26 (dq, J=13.1, 6.7 Hz, 1H), 4.04 (dd, J=11.3, 3.7 Hz, 2H), 3.88 (d, J=6.2 Hz, 2H), 3.67-3.59 (m, 1H), 3.46 (t, J=11.1 Hz, 2H), 2.67 (q, J=7.5 Hz, 2H), 2.31 (m, 1H), 2.29-2.17 (m, 2H), 2.15-2.05 (m, 1H), 1.73 (d, J=11.9 Hz, 2H), 1.51 (ddd, J=25.1, 12.4, 4.5 Hz, 2H), 1.39 (d, J=6.4 Hz, 3H), 1.26 (t, J=7.6 Hz, 3H).

Example 38

Synthesis of 2,6-diethyl-1-((3-(methyl sulfonyl)-4-((tetrahydro-2H-pyran-4-yl)methoxy) phenyl)sulfonyl)-1,2,3,4-tetrahydroquinoline

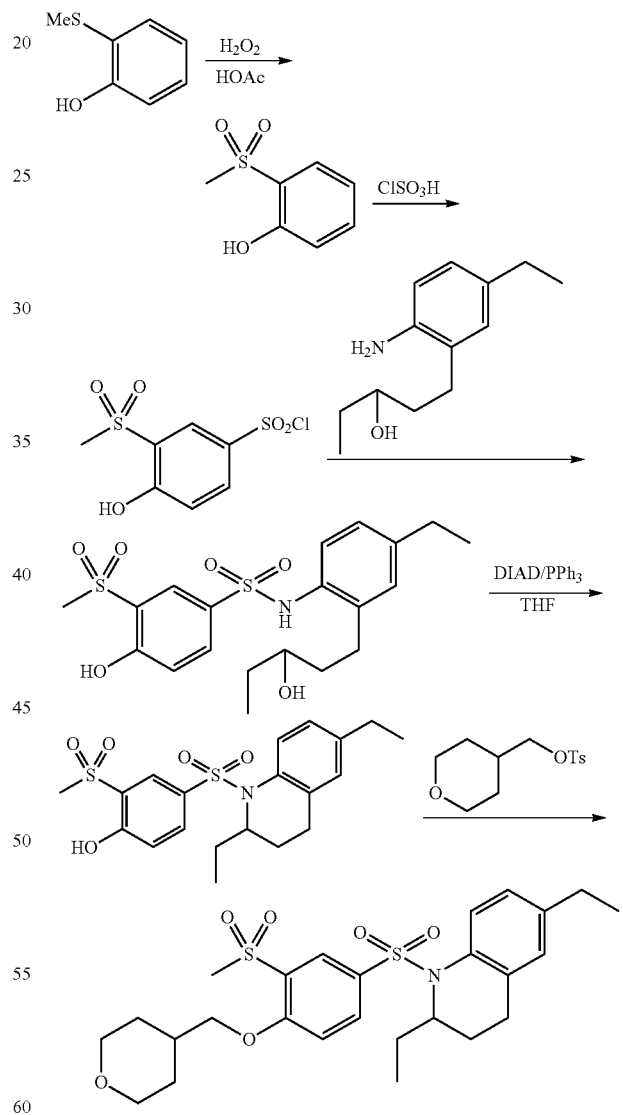

38.1 2-(Methylsulfonyl)phenol

A 50 mL single-necked flask was charged with 2-hydroxythioanisole (0.5 g) and glacial acetic acid (5 mL), to which 30% hydrogen peroxide (1.3 mL) was slowly added dropwise while the mixture was stirred at room temperature. The mixture was reacted for 4 h at 100° C., a sample was taken, and the raw materials disappeared as monitored by TLC. The sample was subjected to LC-MS detection, and a peak of the product (171 [M+H]$^+$) was detected. The reaction mixture was naturally cooled to room temperature. The reaction solution was slowly poured into water (60 mL), and extracted three times with ethyl acetate (20 mL×3). The organic phases were combined, washed twice with a saturated sodium bicarbonate solution (20 mL×2), washed twice with a saturated sodium chloride solution (20 mL×2), dried over anhydrous sodium sulfate, and concentrated, so as to obtain 480 mg of 2-(methylsulfonyl) phenol (MS(ESI) m/: 171.0[M+1]$^+$).

38.2 Synthesis of 2,6-diethyl-1-((3-(methyl sulfonyl)-4-((tetrahydro-2H-pyran-4-yl) methoxy)phenyl) sulfonyl)-1,2,3,4-tetrahydroquinoline The rest steps proceeded with reference to the synthesis methods in steps 30.1 to 30.4 of Example 30, so as to prepare and obtain 22 mg of the title compound (MS(ESI) m/z: 522.0[M+H]$^+$).

$^1$H NMR (400 MHz, CDCl$_3$) δ 8.18 (d, J=1.7 Hz, 1H), 7.65-7.56 (m, 2H), 7.06 (d, J=8.0 Hz, 1H), 6.94 (d, J=8.8 Hz, 1H), 6.81 (s, 1H), 4.26-4.17 (m, 1H), 4.07-3.96 (m, 4H), 3.45 (t, J=11.4 Hz, 2H), 3.14 (s, 3H), 2.59 (q, J=7.5 Hz, 2H), 2.48-2.38 (m, 1H), 2.17 (m, 1H), 1.93-1.74 (m, 4H), 1.58 (m, 1H), 1.47 (m, 4H), 1.22 (t, J=7.6 Hz, 3H), 0.95 (t, J=7.3 Hz, 3H).

Example 39

Synthesis of (6-((2,6-diethyl-3,4-dihydroquinolin-1 (2H)-yl)sulfonyl)-3-((tetrahydro-2H-pyran-4-yl) methoxy)pyridin-2-yl)methanol

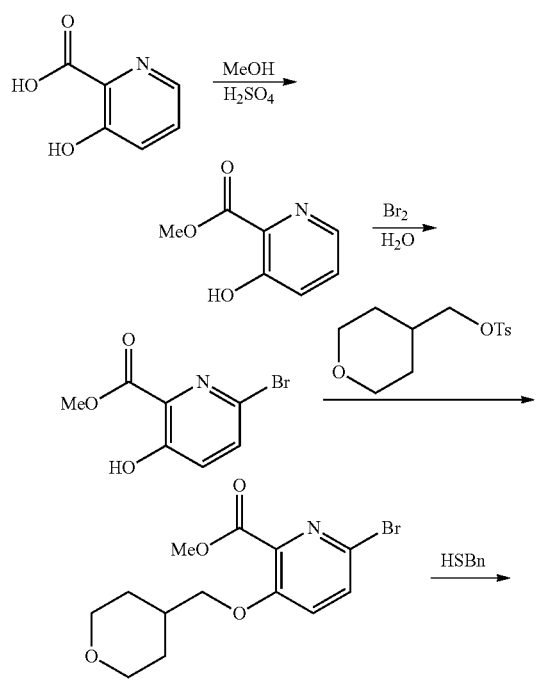

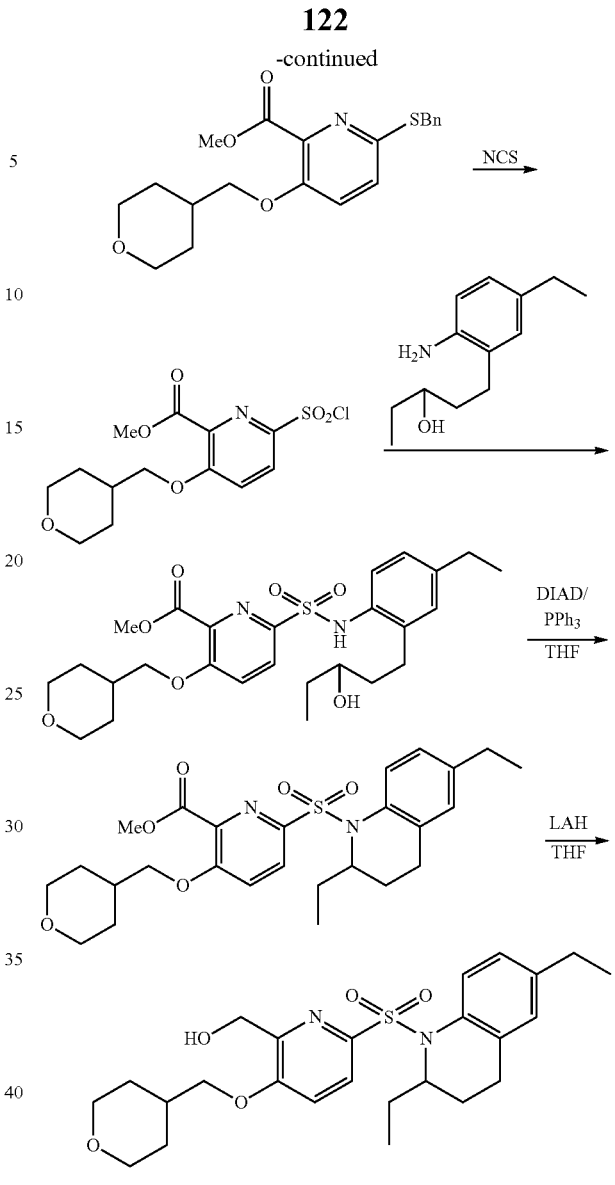

39.1 Methyl 3-hydroxy-2-picolinate

A 250 mL single-necked flask was charged with 3-hydroxy-2-picolinic acid (5.0 g) and 100 mL of anhydrous methanol. The mixture was cooled in an ice-salt bath, and 2 mL of concentrated sulfuric acid was added at 0° C. After the addition, the ice bath was removed, and the mixture was reacted for 16 h in an oil bath at 80° C. A sample was taken, and TLC detection showed that the spots of the raw materials disappeared. After concentration, 50 mL of water was added, and the resulting mixture was extracted with ethyl acetate (20 mL×3), washed with 50 mL of saturated saline, dried over anhydrous sodium sulfate and concentrated, so as to obtain 3.65 g of methyl 3-hydroxy-2-picolinate.

39.2 Methyl 6-bromo-3-hydroxy-2-picolinate

A 250 mL single-necked flask was charged with methyl 3-hydroxy-2-picolinate (3.00 g), bromine (4.70 g) and 80 mL of water, which were reacted at room temperature for 6 h. A sample was taken, and TLC detection showed that the spots of the raw materials disappeared. The mixture was extracted with ethyl acetate (50 mL×3), washed with 100 mL of saturated saline, dried over anhydrous sodium sulfate, concentrated, and subjected to column chromatography (PE:EA=7:1), so as to obtain 3.5 g of methyl 6-bromo-3-hydroxy-2-picolinate.

39.3 Methyl 6-bromo-3-((tetrahydro-2H-pyran-4-yl)methoxy)-2-picolinate

A 25 mL single-necked flask was charged with methyl 6-bromo-3-hydroxy-2-picolinate (1.50 g), p-toluenesulfonate-4-methyl pyran (1.92 g), potassium carbonate (2.68 g), tetrabutylammonium iodide (0.24 g) and 15 mL of dimethylformamide (DMF). The mixture was purged with nitrogen gas three times and then reacted in an oil bath at 80° C. for 16 h. A sample was taken, and TLC detection showed that the spots of the raw materials disappeared. 50 mL of water was added, and the resulting mixture was extracted with ethyl acetate (25 mL×3), washed with 30 mL of saturated saline, dried over anhydrous sodium sulfate, and subjected to column chromatography (PE:EA=5:1), so as to obtain 1.30 g of methyl 6-bromo-3-((tetrahydro-2H-pyran-4-yl)methoxy)-2-picolinate.

39.4 Methyl 6-benzylthio-3-((tetrahydro-2H-pyran-4-yl)methoxy)-2-picolinate

A 50 mL single-necked flask was successively charged with methyl 6-bromo-3-((tetrahydro-2H-pyran-4-yl)methoxy)-2-picolinate (700 mg), tris(dibenzylideneacetone)dipalladium (101 mg), 4,5-bis(diphenylphosphino)-9,9-dimethylxanthene (128 mg), N,N-diisopropylethylamine (822 mg) and 10 mL of 1,4-dioxane, and benzyl mercaptan (395 mg) was finally added. After being purged with nitrogen gas three times, the mixture was reacted for 16 h in an oil bath at 100° C. A sample was taken, and TLC showed that the spots of the raw materials disappeared. The sample was subjected to LC-MS detection, and a peak of the product (374.1[M+1]$^+$) was detected. 20 mL of saturated saline was added, and the resulting mixture was extracted with ethyl acetate (20 mL×3). The organic phases were combined, washed with saturated saline (20 mL×3), dried over anhydrous sodium sulfate, concentrated, and subjected to column chromatography (PE:EA=5:1), so as to obtain 840 mg of methyl 6-benzylthio-3-((tetrahydro-2H-pyran-4-yl)methoxy)-2-picolinate (MS(ESI) m/z 374.1 [M+1]$^+$).

39.5 Methyl 6-chlorosulfonyl-3-((tetrahydro-2H-pyran-4-yl)methoxy)-2-picolinate A 25 mL single-necked flask was charged with methyl 6-benzylthio-3-((tetrahydro-2H-pyran-4-yl)methoxy)-2-picolinate (840 mg), 9 mL of glacial acetic acid and 3 mL of water, which were cooled to 0° C. in an ice-salt bath. N-chlorosuccinimide (900 mg) was added in portions, and the mixture was naturally warmed to room temperature and reacted for 16 h. TLC detection showed that the spots of the raw materials disappeared. The sample was subjected to LC-MS detection, and a peak of the product (350.0[M+1]$^+$) was detected. 15 mL of water was added, and the resulting mixture was extracted with ethyl acetate (20 mL×3), washed with saturated saline (50 mL), dried over anhydrous sodium sulfate, concentrated, and subjected to column chromatography (PE:EA=3:1), so as to obtain 680 mg of methyl 6-chlorosulfonyl-3-((tetrahydro-2H-pyran-4-yl)methoxy)-2-picolinate (MS(ESI) m/z 350.0 [M+1]$^+$).

39.6 Methyl 6-(N-(4-ethyl-2-(3-hydroxypentyl)phenyl)aminosulfonyl)-3-((tetrahydro-2H-pyran-4-yl)methoxy)-2-picolinate A 10 mL single-necked flask was charged with methyl 6-chlorosulfonyl-3-((tetrahydro-2H-pyran-4-yl)methoxy)-2-picolinate (680 mg), 1-(2-amino-5-ethylphenyl)-3-pentanol (524 mg) and 3 mL of pyridine, which were reacted at room temperature for 16 h. A sample was taken, and TLC detection showed that the spots of the raw materials disappeared. The sample was subjected to LC-MS detection, and a peak of the product (521.2[M+1]$^+$) was detected. The mixture was concentrated and subjected to column chromatography (PE:EA=3:1), so as to obtain 1.0 g of the title compound (MS(ESI) m/z 521.2 [M+1]$^+$).

39.7 Methyl 6-((2,6-diethyl-3,4-dihydroquinolin-1(2H)-yl)sulfonyl)-3-((tetrahydro-2H-pyran-4-yl)methoxy)-2-picolinate A 100 mL single-necked flask was charged with triphenylphosphine (1.26 g) and 20 mL of anhydrous tetrahydrofuran. The mixture was purged with nitrogen gas three times, and cooled to 0° C. in an ice bath. Diisopropyl azodicarboxylate (0.78 g) was dissolved in 5 mL of anhydrous tetrahydrofuran and then was slowly added to the reaction solution, and a large amount of white solid precipitated after 5 min. Methyl 6-(N-(4-ethyl-2-(3-hydroxypentyl)phenyl)aminosulfonyl)-3-((tetrahydro-2H-pyran-4-yl)methoxy)-2-picolinate (1.00 g) was dissolved in 5 mL of tetrahydrofuran, and then was slowly added to the reaction solution. The resulting mixture was naturally warmed to room temperature and reacted for 4 h. A sample was taken, and TLC detection showed that the spots of the raw materials disappeared. The sample was subjected to LC-MS detection, and a peak of the product (503.2 [M+1]$^+$) was detected. The mixture was directly concentrated and subjected to column chromatography (PE:EA=1:10), so as to obtain 1.20 g of the title compound (MS(ESI) m/z 503.2[M+1]$^+$).

39.8 6-((2,6-Diethyl-3,4-dihydroquinolin-1(2H)-yl)sulfonyl)-3-((tetrahydro-2H-pyran-4-yl)methoxy)-2-pyridinemethanol A 25 mL single-necked flask was charged with methyl 6-((2,6-diethyl-3,4-dihydroquinolin-1(2H)-yl)sulfonyl)-3-((tetrahydro-2H-pyran-4-yl)methoxy)-2-picolinate (1.20 g) and 20 mL of anhydrous tetrahydrofuran. The mixture was purged with nitrogen gas three times and cooled to 0° C. in an ice bath; lithium aluminum hydride (0.27 g) was added to the reaction solution in portions, and the reaction proceeded for 2 h at 0° C. A sample was taken, and TLC detection showed that the spots of the raw materials disappeared. The sample was subjected to LC-MS detection, and a peak of the product (475.2 [M+1]$^+$) was detected. The reaction was quenched by ice water, and the resulting mixture was extracted with ethyl acetate (20 mL×3). The organic phase was dried over anhydrous sodium sulfate, concentrated, and subjected to column chromatography (PE:EA=3:1), so as to obtain 261 mg of an oily liquid, which was subjected to prep-HPLC for purification and then concentrated to obtain 93 mg of the title compound (HPLC purity: 99.30%, MS(ESI) m/z 475.2[M+1]$^+$).

$^1$H NMR (400 MHz, CDCl$_3$): δ 7.73 (d, J=8.5 Hz, 1H), 7.65 (d, J=8.3 Hz, 1H), 7.09 (d, J=8.5 Hz, 1H), 7.01 (d, J=7.4 Hz, 1H), 6.83 (s, 1H), 4.75-4.60 (m, 2H), 4.45-4.36 (m, 1H), 4.02 (dd, J=11.4, 3.7 Hz, 2H), 3.86 (d, J=6.4 Hz, 2H), 3.44

(t, J=11.0 Hz, 2H), 3.32 (m, 1H), 2.62-2.48 (m, 3H), 2.23-2.04 (m, 2H), 1.94-1.84 (m, 1H), 1.73 (m, 1H), 1.62 (dd, J=14.4, 7.1 Hz, 2H), 1.48 (tdd, J=16.9, 13.0, 5.2 Hz, 4H), 1.20 (t, J=7.6 Hz, 3H), 0.94 (t, J=7.4 Hz, 3H).

Example 40

Synthesis of 5-((2,6-diethyl-3,4-dihydroquinolin-1 (2H)-yl)sulfonyl)-2-((tetrahydro-2H-pyran-4-yl) methoxy)benzenesulfonamide

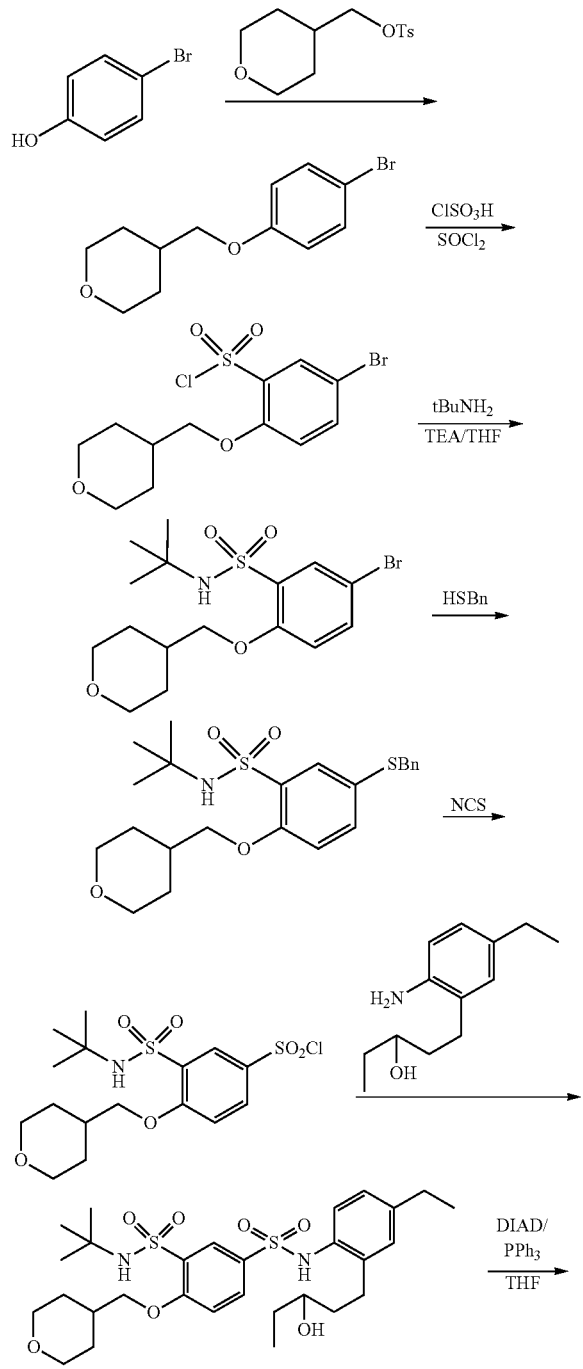

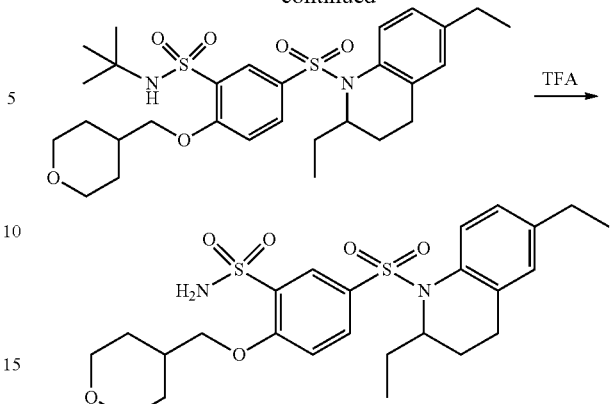

40.1 4-((4-Bromophenoxy)methyl)tetrahydro-2H-pyran

A 25 mL single-necked flask was charged with 4-bromophenol (2 g), p-toluenesulfonate-4-methyl pyran (3.6 g), potassium carbonate (4.8 g), tetrabutylammonium iodide (200 mg) and 10 mL of dimethylformamide. The mixture was purged with nitrogen gas three times and reacted at 70° C. overnight. TLC detection showed that the spots of the raw materials disappeared. The sample was subjected to LC-MS detection, and no peak of the product was detected. The oil bath was removed; the reaction mixture was naturally cooled, filtered by suction, diluted with 20 mL of ethyl acetate, washed with 1N hydrochloric acid and saturated saline respectively, and dried over anhydrous sodium sulfate; and the solvent was removed by rotary evaporation under reduced pressure, so as to obtain 3.4 g of 4-((4-bromophenoxy)methyl)tetrahydro-2H-pyran.

40.2 5-Bromo-2-((tetrahydro-2H-pyran-4-yl) methoxy)benzenesulfonyl Chloride

In an ice bath, a 50 mL single-necked flask was charged with Compound 3 (2.4 g), chlorosulfonic acid (2.1 g) and 20 mL of thionyl chloride, and then was transferred to an environment at room temperature to react for 16 h. A sample was taken and TLC detection showed that the spots of the raw materials disappeared. The reaction solution was added dropwise onto an ice cube and extracted with dichloromethane (25 mL×3). The organic layers were dried over anhydrous sodium sulfate, filtered and concentrated under reduced pressure, so as to obtain 2 g of the title compound.

40.3 5-Bromo-N-tert-butyl-2-((tetrahydro-2H-pyran-4-yl)methoxy)benzenesulfonamide A 50 mL single-necked flask was charged with 5-bromo-2-((tetrahydro-2H-pyran-4-yl) methoxy)benzenesulfonyl chloride (2 g) and 30 mL of tetrahydrofuran. In an ice bath, triethylamine (5 mL) and tert-butylamine (2 mL) were added dropwise, and the mixture was transferred to an environment at room temperature and reacted for 16 h. A sample was taken and TLC detection showed that the spots of the raw materials disappeared. The reaction solution was added dropwise onto an ice cube and extracted with dichloromethane (25 mL×3). The organic layers were dried over anhydrous sodium sulfate, filtered and concentrated under reduced pressure, so as to obtain 2 g of an oil. The reaction was complete as detected by TLC, and a peak of the product (430.0[M+Na]+) was detected. The system was concentrated, and the resultant was dissolved by adding 30 mL of dichloromethane and then washed with dilute hydrochloric acid (20 mL×3). The organic phases were dried over anhydrous sodium sulfate and filtered, and the filtrate was concentrated and subjected to column chromatography (PE:EA=1:1), so as to give 1 g of the title compound. MS(ESI) m/z 430.0 [M+Na]+.

40.4 5-Benzylthio-N-tert-butyl-2-((tetrahydro-2H-pyran-4-yl)methoxy)benzene Sulfonamide A 50 mL single-necked flask was charged with 5-bromo-N-tert-butyl-2-((tetrahydro-2H-pyran-4-yl)methoxy)benzenesulfonamide (3.3 g), benzyl mercaptan (1.5 mL), tris(dibenzylideneacetone)dipalladium (0.75 g), 4,5-bis(diphenylphosphino)-9,9-dimethylxanthene (0.46 g), N,N-diisopropylethylamine (6 mL) and 30 mL of tetrahydrofuran. After being purged with nitrogen gas three times, the mixture was reacted at 100° C. overnight. A sample was taken, and TLC detection showed that the spots of the raw materials disappeared. The sample was subjected to LC-MS detection, and a peak of the product (449.8 [M+1]+) was detected. The solvent was removed by rotary evaporation under reduced pressure, and the resulting mixture was subjected to column chromatography, so as to obtain 3.5 g of the title compound. MS(ESI) m/z 449.8[M+1]+.

40.5 3-(N-(tert-butyl)sulfamoyl)-4-((tetrahydro-2H-pyran-4-yl)methoxy)benzenesulfonyl Chloride A 25 mL single-necked flask was charged with 5-benzylthio-N-tert-butyl-2-((tetrahydro-2H-pyran-4-yl)methoxy)benzenesulfonamide (2 g), N-chlorosuccinimide (1.8 g), acetic acid (10 mL) and 2 mL of water. After being purged with nitrogen gas three times, the mixture was reacted at room temperature overnight. TLC detection showed that the spots of the raw materials disappeared. A sample was subjected to LC-MS detection, and a peak of the product (424.0[M−1]−) was detected. The reaction mixture was diluted with 50 mL of ethyl acetate, washed with ice water (20 mL×3) and dried over anhydrous sodium sulfate, and the solvent was removed by rotary evaporation under reduced pressure, so as to obtain 2 g of the title compound, MS(ESI) m/z 424.0 [M−1]−.

40.6 $N^3$-(tert-butyl)-$N^1$-(4-ethyl-2-(3-hydroxypentyl)phenyl)-4-((tetrahydro-2H-pyran-4-yl)methoxy)benzene-1,3-disulfonamide A 50 mL single-necked flask was charged with 3-(N-(tert-butyl)sulfamoyl)-4-((tetrahydro-2H-pyran-4-yl)methoxy)benzenesulfonyl chloride (1 g), 1-(2-amino-5-ethyl phenyl)-3-pentanol (0.35 g) and 10 mL of pyridine. After being purged with nitrogen gas three times, the mixture was reacted at room temperature overnight. A sample was taken, and TLC detection showed that the spots of the raw materials disappeared. The sample was subjected to LC-MS detection, and a peak of the product (595.0[M−1]−) was detected. The solvent was removed by rotary evaporation under reduced pressure. The resulting mixture was diluted by adding 50 mL of ethyl acetate, followed by washing with 1N hydrochloric acid and saturated saline, respectively. The organic phase was dried over anhydrous sodium sulfate and filtered, and the filtrate was concentrated and subjected to column chromatography, so as to obtain 1.3 g of the title compound, MS(ESI) m/z 595.0[M−1]−.

40.7 N-(tert-butyl)-5-((2,6-diethyl-3,4-dihydroquinolin-1(2H)-yl)sulfonyl)-2-((tetrahydro-2H-pyran-4-yl)methoxy)benzenesulfonamide A 25 mL single-necked flask was charged with triphenylphosphine (1 g) and 5 mL of anhydrous tetrahydrofuran. The mixture was purged with nitrogen gas three times and cooled to 0° C. in an ice bath. Diisopropyl azodicarboxylate (400 mg) was dissolved in 2 mL of tetrahydrofuran and slowly added to the reaction solution. After 5 minutes, a large amount of white solid precipitated. $N^3$-(tert-butyl)-$N^1$-(4-ethyl-2-(3-hydroxypentyl)phenyl)-4-((tetrahydro-2H-pyran-4-yl)methoxy)benzene-1,3-disulfonamide (0.6 g) was dissolved in 3 mL of tetrahydrofuran and slowly added to the reaction solution, which was naturally warmed to room temperature and reacted for 4 h. A sample was taken and TLC detection showed that the spots of the raw materials disappeared. The solvent was directly removed by rotary evaporation under reduced pressure, and the resulting mixture was subjected to column chromatography, so as to obtain 630 mg of the title compound, MS(ESI) m/z 579.0 $[M+1]^+$.

40.8 5-((2,6-Diethyl-3,4-dihydroquinolin-1(2H)-yl)sulfonyl)-2-((tetrahydro-2H-pyran-4-yl)methoxy)benzenesulfonamide A 25 mL single-necked flask was charged with N-(tert-butyl)-5-((2,6-diethyl-3,4-dihydroquinolin-1(2H)-yl)sulfonyl)-2-((tetrahydro-2H-pyran-4-yl)methoxy)benzenesulfonamide (600 mg) and 10 mL of trifluoroacetic acid, which were stirred at room temperature for 12 h. A sample was taken, and TLC detection showed that the spots of the raw materials disappeared. The sample was subjected to LC-MS detection, and a peak of the product (523.2[M+1]$^+$) was detected. The reaction was quenched with ice water, and the resulting mixture was extracted with ethyl acetate (50 mL×3). An aqueous sodium hydroxide solution was added in an excessive amount, the aqueous phase was extracted with ethyl acetate (20 mL×3), and the organic phases were dried over anhydrous sodium sulfate and concentrated by rotary evaporation under reduced pressure, so as to obtain 300 mg of an oily liquid, which was purified by prep-HPLC and concentrated to obtain 56 mg of the title compound (HPLC purity: 99.8%, MS(ESI) m/z 523.2[M+1]$^+$).

1H NMR (400 MHz, CDCl3) δ 8.01 (d, J=2.0 Hz, 1H), 7.59 (d, J=8.3 Hz, 1H), 7.45 (dd, J=8.7, 2.0 Hz, 1H), 7.05 (d, J=8.2 Hz, 1H), 6.92 (d, J=8.8 Hz, 1H), 6.80 (s, 1H), 5.11 (s, 2H), 4.22-4.10 (m, 1H), 4.03 (p, J=8.7 Hz, 4H), 3.45 (t, J=11.3 Hz, 2H), 2.59 (q, J=7.6 Hz, 2H), 2.47-2.33 (m, 1H), 2.18 (m, 1H), 1.91-1.68 (m, 4H), 1.59-1.53 (m, 1H), 1.45 (ddd, J=19.8, 11.9, 4.9 Hz, 4H), 1.22 (t, J=7.6 Hz, 3H), 0.93 (t, J=7.3 Hz, 3H).

Example 41

Synthesis of 5-((6-vinyl-2-ethyl-3,4-dihydroquinolin-1(2H)-yl)sulfonyl)-2-((tetrahydro-2H-pyran-4-yl)methoxy)benzyl Alcohol

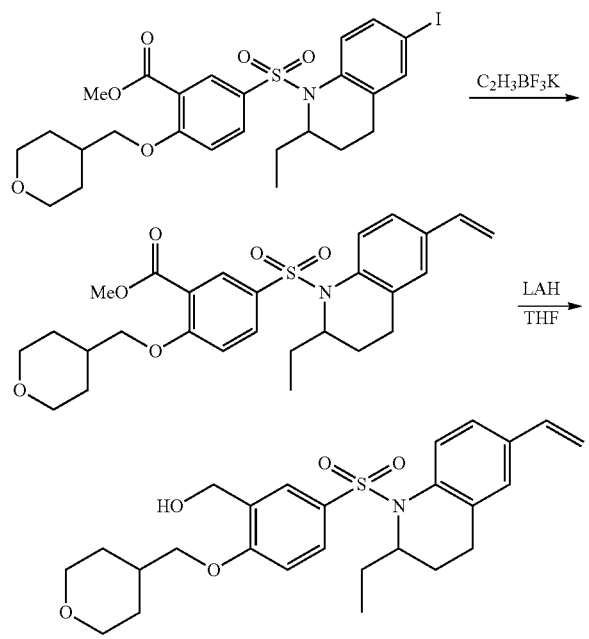

41.1 Methyl 5-((6-vinyl-2-ethyl-3,4-dihydroquinolin-1(2H)-yl)sulfonyl)-2-((tetrahydro-2H-pyran-4-yl)methoxy)benzoate A single-necked flask was charged with methyl 5-((6-iodo-2-ethyl-3,4-dihydroquinolin-1(2H)-yl)sulfonyl)-2-((tetrahydro-2H-pyran-4-yl)methoxy)benzoate (1.0 g, Example 34.2), 15 mL of 1,4-dioxane was added to dissolve the former, followed by addition of potassium vinyltrifluoroborate (335 mg), cesium carbonate (1.1 g) and 5 mL of water. The mixture was purged with nitrogen gas three times, and tetrakis(triphenylphosphine) palladium (392 mg) was added. The resulting mixture was purged with nitrogen gas three times again and stirred in an oil bath at 90° C. overnight. A sample was taken, and TLC detection showed that the spots of the raw materials disappeared. The sample was subjected to LC-MS detection, 500.1[M+1]$^+$. Post-treatment: 50 mL of water was added, and the mixture was extracted three times with ethyl acetate (20 mL×3). The organic phases were combined, washed with saturated saline, and dried over anhydrous sodium sulfate. The resulting mixture was filtered and concentrated under reduced pressure to obtain an oil, which was purified by passing through a column. The product was collected and concentrated under reduced pressure to obtain the title compound (230 mg).

41.2 5-((6-Vinyl-2-ethyl-3,4-dihydroquinolin-1(2H)-yl)sulfonyl)-2-((tetrahydro-2H-pyran-4-yl)methoxy)benzyl Alcohol A 100 mL single-necked flask was charged with methyl 5-((6-vinyl-2-ethyl-3,4-dihydroquinolin-1(2H)-yl)sulfonyl)-2-((tetrahydro-2H-pyran-4-yl)methoxy)benzoate (230 mg), and 5 mL of anhydrous THF was added to dissolve the former. The mixture was cooled in an ice bath, and then lithium tetrahydroaluminate (52 mg) was added in portions. After the addition was complete, the mixture was stirred for 30 min in an ice bath. The reaction was complete as detected by TLC, LC-MS, 472[M+1]$^+$. 0.05 mL of water and 0.05 mL of 15% NaOH aqueous solution were added. The reaction was quenched with 0.15 mL of water. The mixture was further added with 10 mL of ethyl acetate and dried over anhydrous sodium sulfate. The resulting mixture was filtered and concentrated under reduced pressure to obtain 180 mg of an oil. 34 mg of the title compound (HPLC purity: 99.77%) was obtained by analysis and preparation.

$^1$H NMR (400 MHz, CDCl$_3$) δ 7.73 (d, J=8.4 Hz, 1H), 7.54 (s, 1H), 7.39 (d, J=8.7 Hz, 1H), 7.29 (s, 1H), 7.02 (s, 1H), 6.77 (d, J=8.7 Hz, 1H), 6.65 (dd, J=17.6, 10.9 Hz, 1H), 5.70 (d, J=17.6 Hz, 1H), 5.22 (d, J=10.9 Hz, 1H), 4.62 (d, J=6.0 Hz, 2H), 4.28-4.15 (m, 1H), 4.02 (dd, J=11.3, 3.8 Hz, 2H), 3.86 (d, J=6.3 Hz, 2H), 3.44 (t, J=11.4 Hz, 2H), 2.53-2.39 (m, 1H), 2.07 (d, J=18.5 Hz, 1H), 2.02-1.89 (m, 2H), 1.79-1.66 (m, 3H), 1.63 (d, J=7.3 Hz, 1H), 1.53-1.39 (m, 4H), 0.94 (t, J=7.4 Hz, 3H).

Example 42

Synthesis of 5-((2,6-diethyl-5-fluoro-3,4-dihydroquinolin-1(2H)-yl)sulfonyl)-2-((tetrahydro-2H-pyran-4-yl)methoxy)benzyl Alcohol

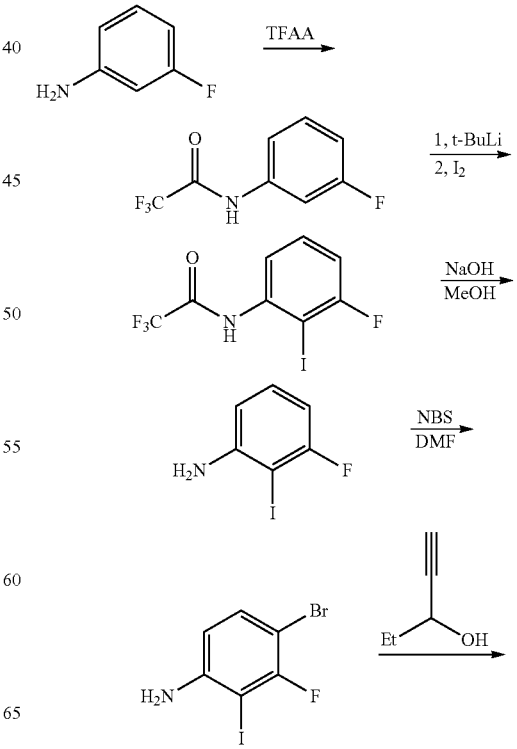

-continued

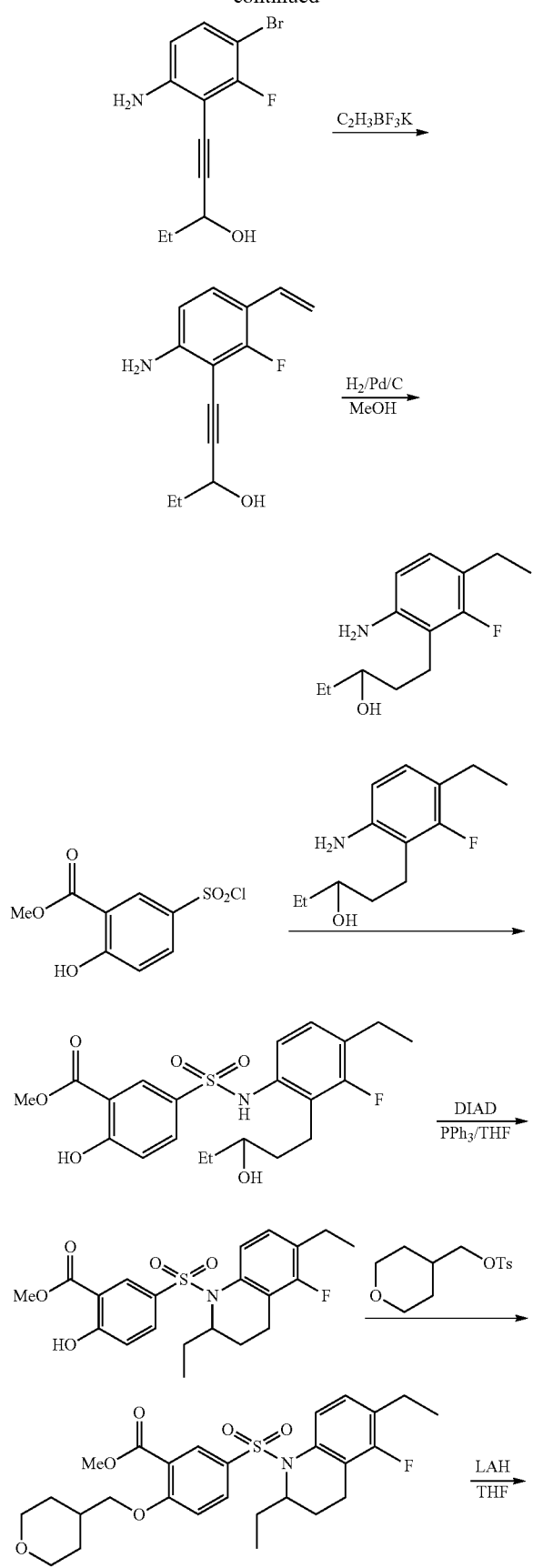

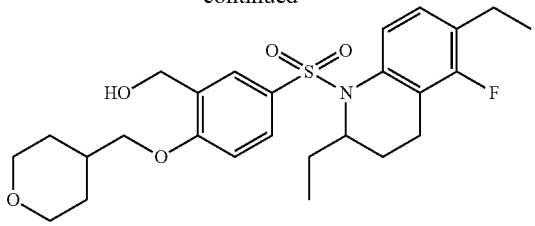

42.1 2,2,2-Trifluoro-N-(3-fluorophenyl)acetamide

A 250 mL single-necked flask was successively charged with 3-fluoroaniline (5.00 g), 100 mL of dichloromethane and 27.5 mL of triethylamine. The mixture was cooled to 0° C. in an ice-salt bath, and trifluoroacetic anhydride (9.4 mL) was slowly added dropwise to the reaction solution. After the completion of the dropwise addition, the mixture was naturally warmed to room temperature and reacted for about 16 h. A sample was taken and TLC detection showed that the spots of the raw materials disappeared. The sample was subjected to LC-MS detection, and a peak of the product (206.1[M−1]$^-$) was detected. 100 mL of saturated aqueous sodium hydroxide solution was added and the resulting mixture was subjected to liquid-liquid separation. The aqueous phase was extracted with dichloromethane (50 mL×3). The organic phases were combined, washed with 100 mL of saturated saline, and dried over anhydrous sodium sulfate. The solvent was removed by rotary evaporation under reduced pressure, and the resulting mixture was subjected to column chromatography (PE:EA=10:1), so as to obtain 5.60 g of 2,2,2-trifluoro-N-(3-fluorophenyl)acetamide (MS(ESI) m/z 206.1 [M−1]$^-$).

42.2 2,2,2-Trifluoro-N-(3-fluoro-2-iodophenyl)acetamide

A 250 mL single-necked flask was successively charged with tetramethylethylenediamine (6.73 g) and 100 mL of anhydrous tetrahydrofuran. The mixture was purged with nitrogen gas three times and cooled to −78° C. in an acetone-dry ice bath, and a solution of tert-butyllithium in n-hexane (45.0 mL, 1.3 M) was slowly added dropwise. The mixture was kept at −78° C. and stirred for 10 min. Then, a solution of 2,2,2-trifluoro-N-(3-fluorophenyl)acetamide (4.00 g) in anhydrous tetrahydrofuran (10 mL) was added dropwise. The mixture was kept at −78° C. and stirred for 40 min. 40 mL of a solution of iodine (7.35 g) in tetrahydrofuran was added dropwise. The mixture was kept at −78° C. and stirred for 1 h, and then was naturally warmed to room temperature. 200 mL of water was added to quench the reaction. The mixture was subjected to liquid-liquid separation. The aqueous phase was extracted with ethyl acetate (50 mL×3). The organic phases were combined, washed with 20 mL of saturated saline, dried over anhydrous sodium sulfate, concentrated, and subjected to column chromatography (PE:EA=20:1), so as to obtain 4.00 g of 2,2,2-trifluoro-N-(3-fluoro-2-iodophenyl)acetamide (MS(ESI) m/z 331.9 [M−1]).

42.3 3-Fluoro-2-iodoaniline

A 50 mL single-necked flask was charged with 4.00 g of 2,2,2-trifluoro-N-(3-fluoro-2-iodophenyl)acetamide and 20 mL of anhydrous methanol, and 5 mL of an aqueous solution of sodium hydroxide (1.44 g) was added thereto. The mixture was heated to reflux in an oil bath and reacted for 16 h. A sample was taken and TLC detection showed that the spots of the raw materials disappeared. The sample was subjected to LC-MS detection, and a peak of the product (237.9[M+1]$^+$) was detected. The mixture was added with 10 mL of water and extracted with ethyl acetate (20 mL×3). The organic phases were combined, dried over anhydrous sodium sulfate, concentrated, and subjected to column chromatography (PE:EA=10:1), so as to obtain 1.72 g of 3-fluoro-2-iodoaniline (MS(ESI) m/z 237.9 [M+1]$^+$).

42.4 4-Bromo-3-fluoro-2-iodoaniline

A 50 mL single-necked flask was charged with 3-fluoro-2-iodoaniline (1.72 g) and 15 mL of dimethylformamide (DMF). The mixture was cooled to −30° C., and NBS (1.04 g) was added thereto in portions. The mixture was kept at −30° C. and reacted for 2 h. A sample was taken and TLC detection showed that the spots of the raw materials disappeared. The sample was subjected to LC-MS detection, and a peak of the product (317.8[M+1]$^+$) was detected. About 20 mL of a saturated aqueous sodium sulfite solution was added in an excessive amount, and then the mixture was extracted with ethyl acetate (20 mL×3), washed with 50 mL of saturated saline, dried over anhydrous sodium sulfate, concentrated, and subjected to column chromatography (PE:EA=10:1), so as to obtain 1.76 g of 4-bromo-3-fluoro-2-iodoaniline (MS(ESI) m/z 317.8[M+1]$^+$).

42.5 1-(6-Amino-3-bromo-2-fluorophenyl)pentyn-3-ol

A 100 mL single-necked flask was charged with 4-bromo-3-fluoro-2-iodoaniline (1.76 g), 1-pentyn-3-ol (0.70 g), bis(triphenylphosphine)palladium (II) chloride (0.20 g), cuprous iodide (0.11 g) and 20 mL of triethylamine. The mixture was purged with nitrogen gas three times and then reacted for 16 h in an oil bath at 80° C. A sample was taken and TLC detection showed that the spots of the raw materials disappeared. The sample was subjected to LC-MS detection, and a peak of the product (270.0[M−1]) was detected. The resulting mixture was filtered through celite, concentrated and subjected to column chromatography (PE:EA=1:1), so as to obtain 1.55 g of 1-(6-amino-3-bromo-2-fluorophenyl)pentyn-3-ol (MS(ESI) m/z 270.0 [M−1]$^-$).

42.6 1-(6-Amino-3-vinyl-2-fluorophenyl)pentyn-3-ol

A 100 mL single-necked flask was charged with 1-(6-amino-3-bromo-2-fluorophenyl) pentyn-3-ol (1.55 g), potassium vinyltrifluoroborate (1.15 g), tetrakis(triphenylphosphine)palladium (0.34 g), cesium carbonate (5.57 g), 20 mL of 1,4-dioxane and 5 mL of water. The mixture was purged with nitrogen gas three times and reacted for 16 h in an oil bath at 90° C. A sample was taken and TLC detection showed that the spots of the raw materials disappeared. The sample was subjected to LC-MS detection, and a peak of the product (218.1[M−1]$^-$) was detected. The mixture was filtered through celite, and 10 mL of water was added. The resulting mixture was extracted with ethyl acetate (25 mL×3), washed with 30 mL of saturated saline, dried over anhydrous sodium sulfate, filtered and concentrated, so as to obtain 1.90 g of the title compound (MS(ESI) m/z 218.1 [M−1]).

42.7 1-(6-Amino-3-ethyl-2-fluorophenyl)-3-pentanol

A 50 mL single-necked flask was successively charged with 1-(6-amino-3-vinyl-2-fluorophenyl)pentyn-3-ol (1.90 g), palladium hydroxide on carbon (0.40 g) and 15 mL of methanol. The mixture was purged with nitrogen gas three times and reacted for 16 h at room temperature. A sample was taken and TLC showed that the spots of the raw materials disappeared. The sample was subjected to LC-MS detection, and a peak of the product (226.1[M+1]$^+$) was detected. The mixture was filtered through celite, concentrated, and subjected to column chromatography (PE:EA=3:1), so as to obtain 380 mg of 1-(6-amino-3-ethyl-2-fluorophenyl)-3-pentanol (MS(ESI) m/z 226.1[M+1]$^+$).

42.8 5-((2,6-Diethyl-5-fluoro-3,4-dihydro quinolin-1(2H)-yl)sulfonyl)-2-((tetrahydro-2H-pyran-4-yl)methoxy)benzyl Alcohol The rest synthesis steps proceeded with reference to the corresponding synthesis method in Example 12, so as to prepare and obtain 8.7 mg of the title compound (HPLC purity: 97.13%, MS(ESI) m/z 492.2[M+1]$^+$).
$^1$H NMR (400 MHz, CDCl3) δ 7.60 (s, 1H), 7.56 (d, J=8.5 Hz, 1H), 7.45 (dd, J=8.6, 1.9 Hz, 1H), 7.06 (t, J=8.5 Hz, 1H), 6.81 (d, J=8.7 Hz, 1H), 4.66 (d, J=5.2 Hz, 2H), 4.27 (td, J=10.5, 5.1 Hz, 1H), 4.04 (dd, J=11.3, 3.7 Hz, 2H), 3.89 (d, J=6.3 Hz, 2H), 3.46 (t, J=11.5 Hz, 2H), 2.64 (q, J=7.5 Hz, 2H), 2.59-2.45 (m, 1H), 2.22-2.18 (m, 1H), 2.18-2.08 (m, 1H), 1.74 (d, J=12.7 Hz, 2H), 1.59-1.50 (m, 4H), 1.48 (d, J=4.5 Hz, 1H), 1.28 (m, 2H), 1.23 (t, J=7.6 Hz, 3H), 0.96 (t, J=7.3 Hz, 3H).

Example 43

Synthesis of 5-((6-isopropyl-2-ethyl-3,4-dihydroquinolin-1(2H)-yl)sulfonyl)-2-((tetrahydro-2H-pyran-4-yl)methoxy)benzene Deuterated Methanol

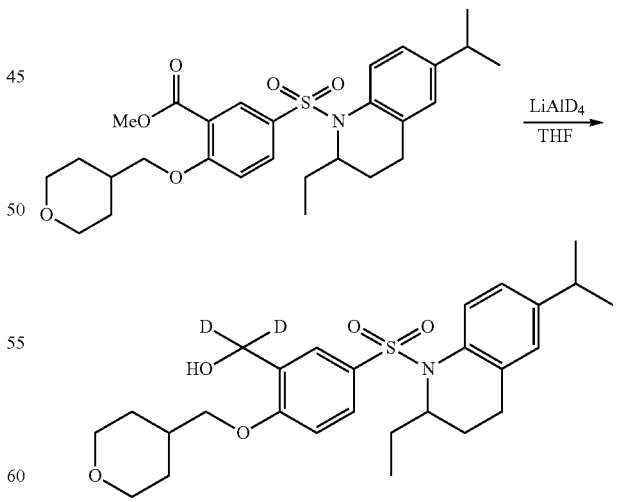

A 100 mL single-necked flask was charged with methyl 5-((6-isopropyl-2-ethyl-3,4-dihydroquinolin-1(2H)-yl)sulfonyl)-2-((tetrahydro-2H-pyran-4-yl)methoxy)benzoate (120 mg, an intermediate in Example 34), and 5 mL of anhydrous tetrahydrofuran was added to dissolve the former.

The mixture was cooled in an ice bath, and deuterated lithium tetrahydroaluminate (30 mg) was added in portions. After the completion of the addition, the mixture was stirred for 30 min in an ice bath. The reaction was complete as detected by TLC. 0.03 mL of water and 0.03 mL of 15% NaOH aqueous solution were added successively, and 0.09 mL of water was added to quench the reaction. 10 mL of ethyl acetate was additionally added thereto. The resulting mixture was dried over anhydrous sodium sulfate, filtered and concentrated under reduced pressure to obtain 80 mg of an oil. 25 mg of the title compound (490.2[M+1]$^+$, HPLC purity: 99.16%) was obtained by analysis and preparation.

$^1$H NMR (400 MHz, CDCl$_3$) δ 7.67 (d, J=8.4 Hz, 1H), 7.49-7.34 (m, 2H), 7.10 (d, J=8.3 Hz, 1H), 6.92-6.72 (m, 2H), 4.25-4.10 (m, 1H), 4.04 (dd, J=11.4, 3.8 Hz, 2H), 3.89 (d, J=6.4 Hz, 2H), 3.46 (t, J=11.2 Hz, 2H), 2.87 (dt, J=13.7, 6.9 Hz, 1H), 2.50-2.32 (m, 1H), 2.11 (dd, J=9.5, 5.5 Hz, 1H), 1.95-1.82 (m, 2H), 1.74 (d, J=11.9 Hz, 2H), 1.68-1.58 (m, 2H), 1.55-1.40 (m, 4H), 1.25 (d, J=6.9 Hz, 6H), 0.96 (t, J=7.4 Hz, 3H).

Example 44

Synthesis of 5-((6-(1,1-difluoroethyl)-2-ethyl-3,4-dihydroquinolin-1(2H)-yl)sulfonyl)-2-((tetrahydro-2H-pyran-4-yl)methoxy)benzyl Alcohol

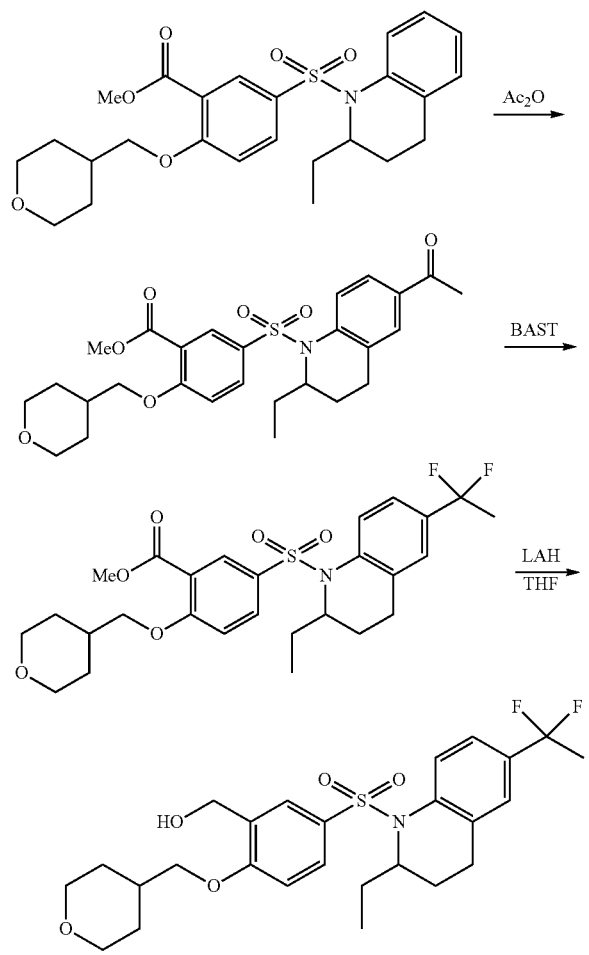

44.1 Methyl 5-((6-acetyl-2-ethyl-3,4-dihydroquinolin-1(2H)-yl)sulfonyl)-2-((tetrahydro-2H-pyran-4-yl)methoxy)benzoate A 100 mL single-necked flask was charged with aluminum trichloride (580 mg) and 10 mL of dichloromethane. The mixture was purged with nitrogen gas and protected thereby. Acetic anhydride (214 mg) was added while the mixture was kept in an ice bath. The mixture was stirred at room temperature for 30 min. The system was cooled to 0° C. again, and methyl 5-((2-ethyl-3,4-dihydroquinolin-1(2H)-yl)sulfonyl)-2-((tetrahydro-2H-pyran-4-yl)methoxy)benzoate (200 mg, an intermediate in Example 34) was added thereto. The mixture was stirred at room temperature overnight. The reaction was complete as detected by TLC, and a peak of the product (516.0[M+1]$^+$) was detected. The system was cooled to 0° C. again, and 30 mL of ice water was added to quench the reaction. The resulting mixture was extracted with dichloromethane (25 mL×3). The organic layers were combined, washed three times with saturated saline, dried over anhydrous sodium sulfate, and subjected to column chromatography, so as to obtain 200 mg of the title compound (MS(ESI) m/z 516.0[M+1]$^+$).

44.2 Methyl 5-((6-(1,1-difluoroethyl)-2-ethyl-3,4-dihydroquinolin-1(2H)-yl)sulfonyl)-2-((tetrahydro-2H-pyran-4-yl)methoxy)benzoate A 50 mL three-necked flask was charged with methyl 5-((6-acetyl-2-ethyl-3,4-dihydroquinolin-1(2H)-yl)sulfonyl)-2-((tetrahydro-2H-pyran-4-yl)methoxy)benzoate (180 mg) and bis(2-methoxyethyl)aminosulfur trifluoride (3 mL), and ethanol (1.6 mg) was added thereto. The mixture was purged with nitrogen gas and protected thereby, and was stirred at 80° C. overnight. LC-MS detection showed that the spots of the raw materials disappeared. Water and ethyl acetate were added to the system to perform extraction. The organic layer was dried and concentrated to obtain 200 mg of the title compound.

44.3 Synthesis of 5-((6-(1,1-difluoroethyl)-2-ethyl-3,4-dihydroquinolin-1(2H)-yl) sulfonyl)-2-((tetrahydro-2H-pyran-4-yl)methoxy)benzyl Alcohol A 25 mL single-necked flask was charged with methyl 5-((6-(1,1-difluoroethyl)-2-ethyl-3,4-dihydroquinolin-1(2H)-yl)sulfonyl)-2-((tetrahydro-2H-pyran-4-yl)methoxy)benzoate (200 mg) and 10 mL of anhydrous tetrahydrofuran. The mixture was purged with nitrogen gas three times and then was cooled to 0° C. in an ice bath. Lithium aluminum hydride (71 mg) was added to the reaction solution in portions, and the reaction solution was kept at 0° C. and reacted for 0.5 h. A sample was taken and TLC detection showed that the spots of the raw materials disappeared. The sample was subjected to LC-MS detection, and a peak of the product (510.0[M+1]$^+$) was detected. The reaction was quenched with ice water, and the mixture was extracted with ethyl acetate (50 mL×3). An aqueous sodium hydroxide solution was added in an excessive amount, and the aqueous phase was extracted with ethyl acetate (20 mL×3). The organic phases were dried over anhydrous sodium sulfate and concentrated by rotary evaporation under reduced pressure, so as to obtain 200 mg of an oily liquid, which was purified by prep-HPLC and concentrated to obtain 38 mg of the title compound (HPLC purity: 99.0%, MS(ESI) m/z 510.0[M+1]$^+$).

1H NMR (400 MHz, CDCl3) δ 7.82 (d, J=8.5 Hz, 1H), 7.54 (s, 1H), 7.40 (d, J=8.5 Hz, 1H), 7.33 (d, J=8.4 Hz, 1H), 7.14 (s, 1H), 6.79 (d, J=8.7 Hz, 1H), 4.63 (s, 2H), 4.33-4.16 (m, 1H), 4.02 (dd, J=11.3, 3.7 Hz, 2H), 3.87 (d, J=6.3 Hz, 2H), 3.44 (t, J=11.6 Hz, 2H), 2.58-2.45 (m, 1H), 2.18-2.03 (m, 2H), 1.91 (t, J=18.2 Hz, 3H), 1.74 (m, 2H), 1.71-1.62 (m, 2H), 1.58 (dd, J=14.2, 7.2 Hz, 1H), 1.54-1.38 (m, 4H), 0.98-0.87 (m, 3H).

Example 45

Synthesis of 5-(((6-ethyl-2-trifluoromethyl-3,4-dihydroquinolin-1(2H)-yl)sulfonyl)-2-((tetrahydro-2H-pyran-4-yl)methoxy)benzyl Alcohol

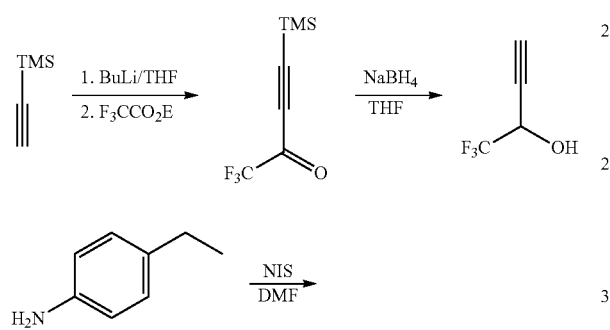

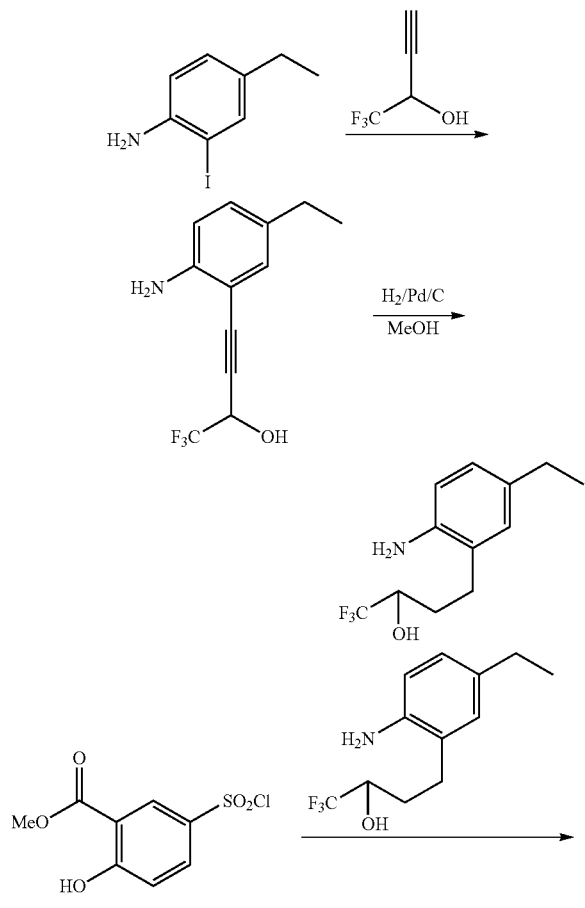

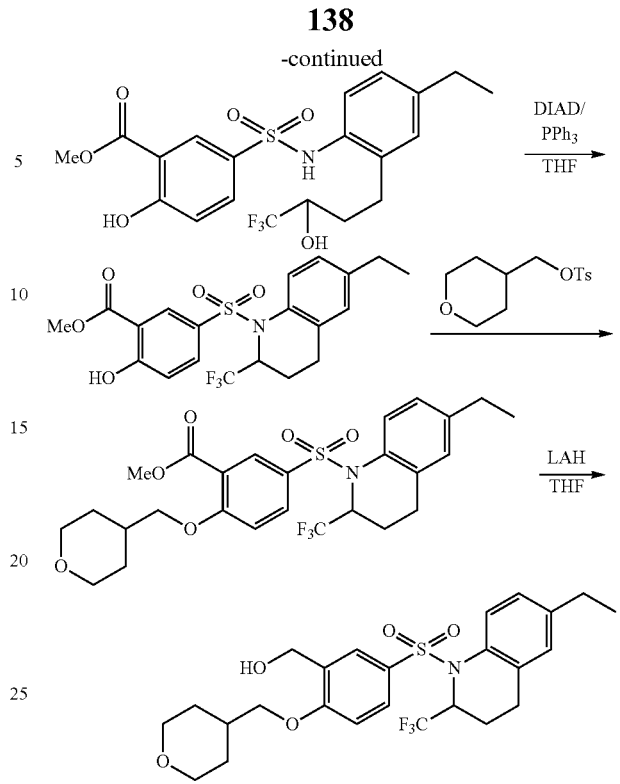

45.1 1,1,1-Trifluoro-3-butyn-2-ol

A 150 mL three-necked reaction flask was charged with trimethylsilylacetylene (2.0 g), and tetrahydrofuran (20 mL) was added thereto. Under nitrogen protection, butyl lithium (9 mL) was added dropwise under a condition of −78° C. After the completion of the addition, the mixture was kept at this temperature and reacted for 1 h. Ethyl trifluoroacetate (4.3 g) was slowly added dropwise. After the completion of the addition, the mixture was reacted at this temperature for 2 h. A sample was taken, and the reaction was complete as monitored by TLC. The mixture was slowly warmed to room temperature and diluted by adding methanol (20 mL), and sodium tetrahydroborate was added thereto at 0° C. The mixture was reacted for 16 h at room temperature. The reaction was complete as monitored by TLC. The reaction was quenched by adding saturated ammonium chloride solution. The resulting mixture was extracted three times with methyl tert-butyl ether (30 mL×3). The organic phases were combined, washed twice with saturated sodium chloride solution (40 mL×2), dried over anhydrous sodium sulfate, and concentrated. The residue was distilled under reduced pressure to obtain 900 mg of 1,1,1-trifluoro-3-butyn-2-ol.

45.2 Synthesis of 5-(((6-ethyl-2-trifluoromethyl-3,4-dihydroquinolin-1(2H)-yl)sulfonyl)-2-((tetrahydro-2H-pyran-4-yl)methoxy)benzyl Alcohol The rest synthesis steps proceeded with reference to the corresponding synthesis method in Example 12, so as to prepare and obtain 50 mg of the title compound (MS(ESI) m/z: 514.0 [M+H]$^+$).

$^1$H NMR (400 MHz, CDCl$_3$) δ 7.48 (d, J=8.1 Hz, 1H), 7.44 (s, 1H), 7.36-7.30 (m, 1H), 7.10 (d, J=8.1 Hz, 1H), 6.81 (s, 1H), 6.76 (d, J=8.7 Hz, 1H), 4.84 (dt, J=15.0, 7.4 Hz, 1H), 4.60 (d, J=4.8 Hz, 2H), 4.02 (dd, J=11.2, 3.4 Hz, 2H), 3.87 (d, J=6.3 Hz, 2H), 3.44 (t, J=11.5 Hz, 2H), 2.60 (q, J=7.5 Hz, 2H), 2.28 (m, 2H), 2.14-2.01 (m, 2H), 1.75-1.67 (m, 3H), 1.48 (dt, J=15.4, 7.9 Hz, 3H), 1.22 (t, J=7.6 Hz, 3H).

Example 46

2,6-Diethyl-1-((4-((tetrahydro-2H-pyran-4-yl)methoxy)-3-trifluoromethylphenyl)sulfonyl)-1,2,3,4-tetrahydroquinoline

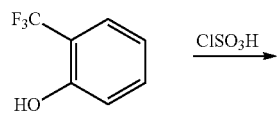

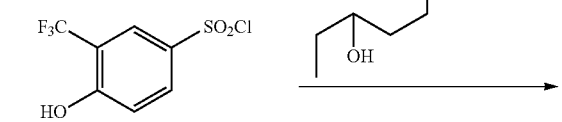

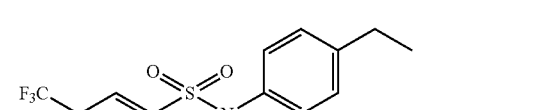

60 mg of the title compound (HPLC purity: 97.99%) was prepared and obtained with reference to the synthesis method of Example 30.

¹H NMR (400 MHz, CDCl₃) δ 7.71-7.51 (m, 3H), 7.09 (d, J=8.3 Hz, 1H), 6.92 (d, J=9.3 Hz, 1H), 6.83 (s, 1H), 4.17 (td, J=12.9, 6.8 Hz, 1H), 4.04 (dd, J=11.3, 3.8 Hz, 2H), 3.92 (d, J=6.4 Hz, 2H), 3.47 (t, J=11.1 Hz, 2H), 2.61 (q, J=7.6 Hz, 2H), 2.42 (dt, J=9.0, 6.0 Hz, 1H), 2.13 (m, 1H), 1.89-1.71 (m, 4H), 1.70-1.61 (m, 1H), 1.47 (ddd, J=20.5, 13.5, 8.1 Hz, 4H), 1.24 (t, J=7.6 Hz, 3H), 0.97 (t, J=7.4 Hz, 3H).

Example 47

Synthesis of 5-((6-ethyl-4-methyl-3,4-dihydroquinolin-1(2H)-yl)sulfonyl)-2-((tetrahydro-2H-pyran-4-yl)methoxy)benzyl Alcohol

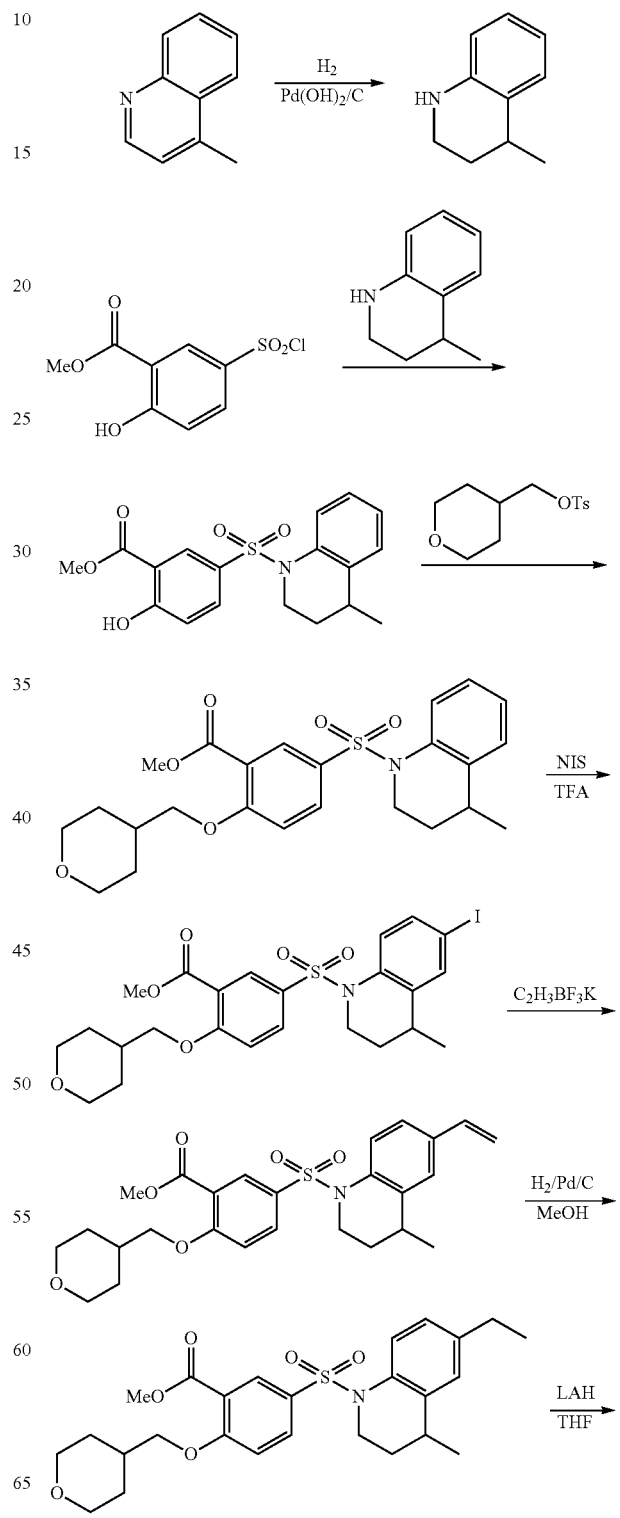

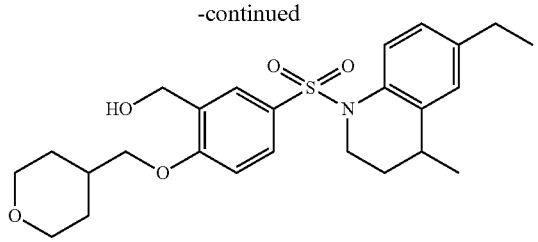

47.1 4-Methyl-1,2,3,4-tetrahydroquinoline

A 10 mL single-necked flask was successively charged with 4-methyl-quinoline (700 mg), palladium hydroxide on carbon (344 mg), and methanol (5 mL). The mixture was purged with hydrogen gas three times and reacted at room temperature for 16 h. A sample was taken, and TLC showed that the spots of the raw materials disappeared. The sample was subjected to LC-MS detection, and a peak of the product (148.2[M+1]$^+$) was detected. The resulting mixture was filtered through celite, concentrated and subjected to column chromatography (PE:EA=10:1), so as to obtain 4-methyl-1,2,3,4-tetrahydroquinoline (432 mg, MS(ESI) m/z 148.2[M+1]$^+$).

47.2 5-((6-Ethyl-4-methyl-3,4-dihydroquinolin-1 (2H)-yl)sulfonyl)-2-((tetrahydro-2H-pyran-4-yl) methoxy)benzyl Alcohol The rest synthesis steps proceeded with reference to the corresponding synthesis method in Example 24, so as to prepare and obtain 14 mg of the title compound (MS(ESI) m/z 208.2[M+1]$^+$).

$^1$H NMR (400 MHz, CDCl$_3$) δ 7.70 (d, J=8.4 Hz, 1H), 7.58 (s, 1H), 7.51 (dd, J=8.6, 2.0 Hz, 1H), 7.04 (d, J=8.4 Hz, 1H), 6.96 (s, 1H), 6.83 (d, J=8.7 Hz, 1H), 4.64 (d, J=5.9 Hz, 2H), 4.04 (dd, J=11.3, 3.8 Hz, 2H), 3.89 (d, J=6.4 Hz, 2H), 3.80 (ddd, J=12.5, 7.6, 4.6 Hz, 2H), 3.46 (t, J=11.3 Hz, 2H), 2.68-2.53 (m, 3H), 2.19-2.07 (m, 1H), 2.00 (t, J=6.4 Hz, 1H), 1.75 (t, J=12.5 Hz, 3H), 1.56-1.40 (m, 3H), 1.24 (t, J=7.6 Hz, 3H), 1.06 (d, J=7.0 Hz, 3H).

Example 48

Synthesis of (R)-5-((6-isopropyl-2-ethyl-3,4-dihydroquinolin-1(2H)-yl)sulfonyl)-2-((tetrahydro-2H-pyran-4-yl)methoxy)benzyl Alcohol

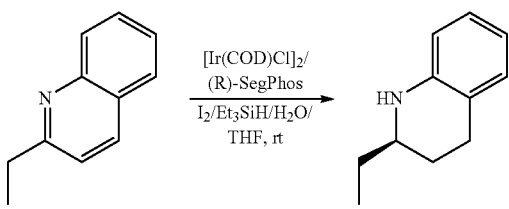

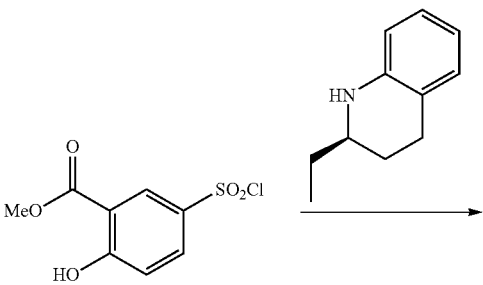

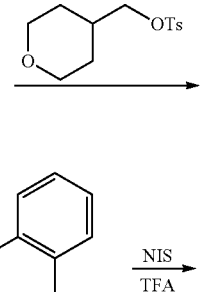

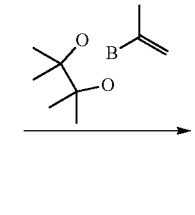

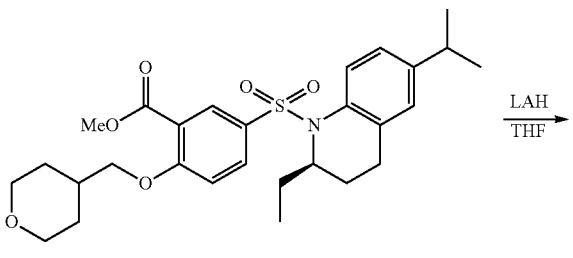

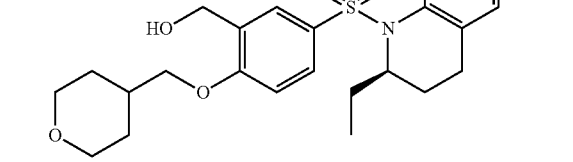

48.1 (R)-2-ethyl-1,2,3,4-tetrahydroquinoline

A 100 mL three-necked flask was charged with 1,5-cyclooctadiene-iridium chloride dimer (141 mg) and (R)-(−)-5,5'-bis(diphenylphosphino)-4,4'-di-1,3-benzodioxole (256 mg), and 40 mL of tetrahydrofuran was added to dissolve the formers. The mixture was purged with nitrogen gas and protected thereby, and was stirred for 15 min at room temperature. Under nitrogen protection, elemental iodine (533 mg) was added, and the mixture was stirred at room temperature for 15 min. Under nitrogen protection, 2-ethyl-quinoline (3.3 g, Example 24.2) and triethylsilane (14.6 g) were added, and the mixture was stirred at room temperature for 10 min. Water (756 mg) was added, and the mixture was stirred at room temperature overnight. The reaction was complete as detected by TLC, and a peak of the product (162.0[M+1]$^+$) was detected. 50 mL of water was added, and the resulting mixture was extracted with ethyl acetate (100 mL×2). The organic layer was washed three times with saturated saline, dried over anhydrous sodium sulfate, filtered and concentrated under reduced pressure, so as to obtain (R)-2-ethyl-1,2,3,4-tetrahydroquinoline (8.2 g, crude product).

48.2 (R)-5-((6-isopropyl-2-ethyl-3,4-dihydroquinolin-1(2H)-yl)sulfonyl)-2-((tetrahydro-2H-pyran-4-yl)methoxy)benzyl Alcohol The rest synthesis steps proceeded with reference to the corresponding synthesis method in Example 34, so as to prepare and obtain the title compound (8 mg, HPLC purity: 98.9%).

$^1$H NMR (400 MHz, CDCl$_3$) δ 7.67 (d, J=8.4 Hz, 1H), 7.43 (m, 2H), 7.10 (d, J=6.9 Hz, 1H), 6.90-6.70 (m, 2H), 4.61 (d, J=5.2 Hz, 2H), 4.24-4.13 (m, 1H), 4.05 (dd, J=11.2, 3.8 Hz, 2H), 3.89 (d, J=6.3 Hz, 2H), 3.46 (t, J=11.2 Hz, 2H), 2.87 (dt, J=13.7, 6.8 Hz, 1H), 2.48-2.35 (m, 1H), 2.18-2.05 (m, 1H), 1.96-1.82 (m, 2H), 1.74 (m, 2H), 1.68-1.58 (m, 2H), 1.54-1.39 (m, 4H), 1.25 (d, J=6.9 Hz, 6H), 0.96 (t, J=7.4 Hz, 3H).

Example 49

Synthesis of (R)-5-((2,6-diethyl-3,4-dihydroquinolin-1(2H)-yl)sulfonyl)-2-((tetrahydro-2H-pyran-4-yl)methoxy)benzyl Alcohol

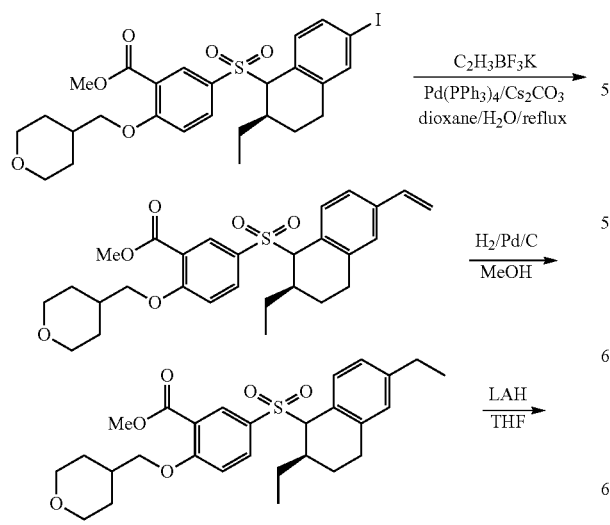

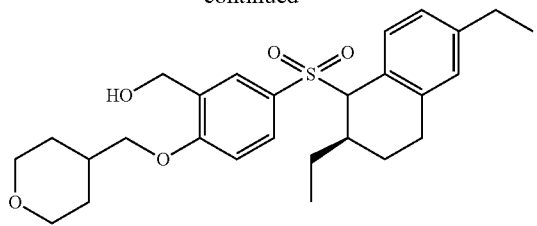

67 mg of the title compound (HPLC purity: 99.17%) was prepared and obtained with reference to the corresponding synthesis method in Example 48.

$^1$H NMR (400 MHz, CDCl$_3$) δ 7.66 (d, J=8.3 Hz, 1H), 7.48 (d, J=2.0 Hz, 1H), 7.40 (dd, J=8.6, 2.2 Hz, 1H), 7.07 (d, J=8.3 Hz, 1H), 6.81-6.74 (m, 2H), 4.62 (d, J=6.3 Hz, 2H), 4.26-4.11 (m, 1H), 4.04 (dd, J=11.4, 3.9 Hz, 2H), 3.88 (d, J=6.4 Hz, 2H), 3.46 (t, J=11.1 Hz, 2H), 2.61 (q, J=7.6 Hz, 2H), 2.48-2.34 (m, 1H), 2.10 (m, 1H), 1.98 (t, J=6.5 Hz, 1H), 1.89 (dt, J=16.0, 6.4 Hz, 1H), 1.75 (dd, J=16.6, 10.6 Hz, 2H), 1.67-1.57 (m, 2H), 1.56-1.35 (m, 4H), 1.24 (t, J=7.6 Hz, 3H), 0.96 (t, J=7.4 Hz, 3H).

Example 50

Synthesis of 1-(4-((2,6-diethyl-3,4-dihydroquinolin-1(2H)-yl)sulfonyl)-2-hydroxymethyl phenyl)-2-(tetrahydro-2H-pyran-4-yl)ethanol

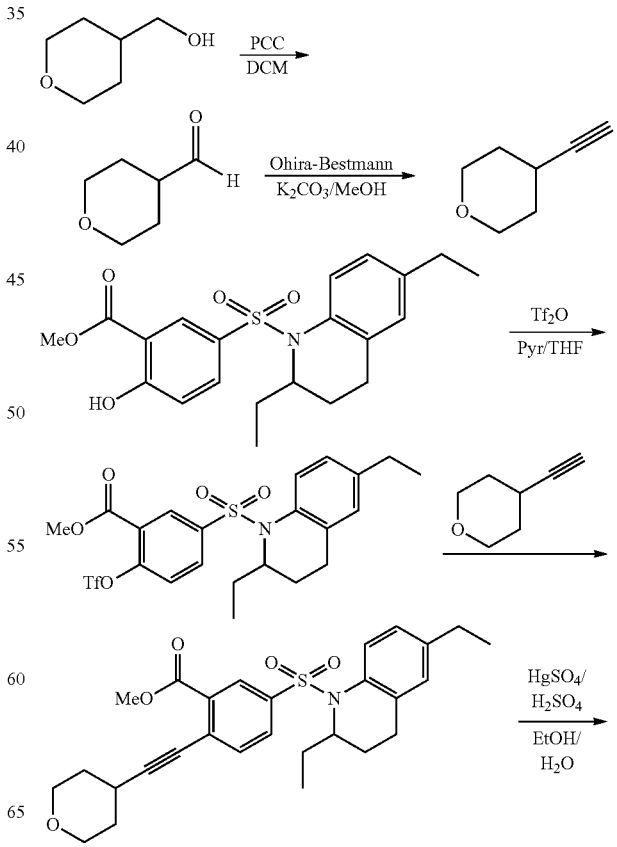

-continued

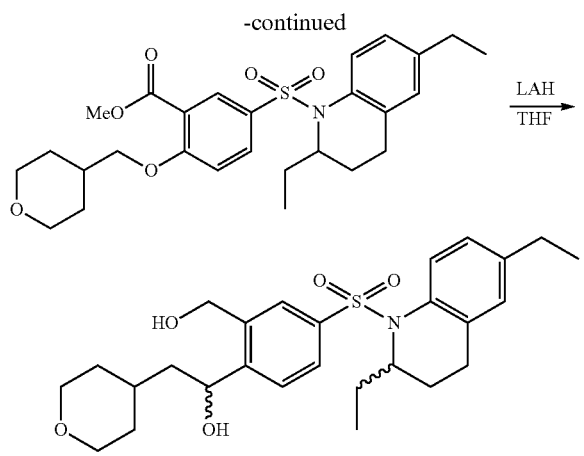

50.1 Tetrahydro-2H-pyran-4-carbaldehyde

A 100 mL round-bottom flask was charged with (tetrahydro-2H-pyran-4-yl)methanol (1.00 g), which was dissolved with dichloromethane (30 mL). The mixture was stirred in an ice bath. Dess-Martin periodinane (5.48 g) was slowly added to the reaction system in portions. After the completion of the addition, the reaction mixture was stirred at room temperature for 5 h. A sample was taken, and TLC detection showed that the raw materials disappeared and the reaction was complete. The reaction was quenched with a saturated sodium thiosulfate solution (80 mL), and the resulting mixture was diluted with dichloromethane (120 mL). The separated organic phase was washed with a saturated sodium thiosulfate solution (60 mL×2), washed with a saturated sodium bicarbonate solution (60 mL×2), washed with saturated saline (30 mL), dried over anhydrous sodium sulfate, filtered, and dried by rotary evaporation under reduced pressure, so as to obtain a crude product, which was subjected to silica gel column chromatography (eluent: PE:EA=10:0 to 5:1) to obtain tetrahydro-2H-pyran-4-carbaldehyde (433 mg).

50.2 4-Ethynyltetrahydro-2H-pyran

A 50 mL single-necked flask was charged with tetrahydro-2H-pyran-4-carbaldehyde (433 mg), potassium carbonate (1050 mg) and methanol (10.8 mL). The reaction system was stirred at room temperature. Ohira-Bestmann reagent (948 mg) was added to the reaction solution. The reaction solution was stirred at room temperature for 8 h. A sample was taken, and TLC detection showed that the raw materials disappeared and the reaction was complete. The reaction solution was filtered through celite, and the filtrate was dried by rotary evaporation under reduced pressure to obtain a crude product, which was subjected to silica gel column chromatography (eluent: PE:EA=10:0 to 10:1) to obtain 400 mg of 4-ethynyltetrahydro-2H-pyran.

50.3 Methyl 5-((2,6-diethyl-3,4-dihydroquinolin-1 (2H)-yl)sulfonyl)-2-(trifluoromethane sulfonyloxy) benzoate A 25 mL single-necked flask was charged with methyl 2-hydroxy-5-((2,6-diethyl-3,4-dihydroquinolin-1(2H)-yl) sulfonyl)benzoate (750 mg), which was then dissolved in dichloromethane (8 mL). The mixture was cooled at 0° C., and pyridine (530 mg) and trifluoromethanesulfonic anhydride (787 mg) were added dropwise thereto. The resulting reaction solution was stirred at 0° C. for 1 h and then stirred at room temperature for 23 h. A sample was taken and subjected to LC-MS detection, and a peak of the product (558.2[M+Na]$^+$) was detected. The reaction solution was diluted with dichloromethane (150 mL) and washed with saturated saline (40 mL×3). The organic layer was dried over anhydrous sodium sulfate and filtered, the solvent was removed by rotary evaporation under reduced pressure, and the resulting mixture was subjected to silica gel column chromatography (eluent: PE:EA=10:0 to 10:1)), so as to obtain the title compound (960 mg, MS(ESI) m/z 536.0[M+1]$^+$).

50.4 Methyl 5-((2,6-diethyl-3,4-dihydroquinolin-1 (2H)-yl)sulfonyl)-2-((tetrahydro-2H-pyran-4-yl) ethynyl)benzoate A 25 mL single-necked flask was charged with methyl 5-((2,6-diethyl-3,4-dihydroquinolin-1(2H)-yl)sulfonyl)-2-(trifluoromethanesulfonyloxy)benzoate (200 mg), 4-ethynyl tetrahydro-2H-pyran (82.3 mg), cuprous iodide (7.1 mg), N,N-diisopropylethylamine (96.7 mg), and dichloromethane (6 mL). The reaction system was purged with nitrogen gas three times, and tetrakis(triphenylphosphine)palladium (46.5 mg) was rapidly added thereto. Then, the system was purged with nitrogen gas three times again. The reaction solution was stirred at room temperature for 24 h. The reaction solution was dried by rotary evaporation under reduced pressure and subjected to silica gel column chromatography (eluent: PE:EA=10:0 to 2:1), so as to obtain the title compound (173 mg, MS(ESI) m/z 496.2[M+1]$^+$).

50.5 Methyl 5-((2,6-diethyl-3,4-dihydroquinolin-1 (2H)-yl)sulfonyl)-2-(2-(tetrahydro-2H-pyran-4-yl) acetyl)benzoate A 25 mL single-necked flask was charged with methyl 5-((2,6-diethyl-3,4-dihydroquinolin-1(2H)-yl)sulfonyl)-2-((tetrahydro-2H-pyran-4-yl)ethynyl)benzoate (136 mg), which was dissolved with 95% ethanol (9 mL). Mercury sulfate (8.2 mg) and sulfuric acid (2.7 mg) were added thereto, and the resulting reaction solution was stirred at 70° C. for 14 h. A sample was taken and subjected to LC-MS detection, and a peak of the product (514.2[M+1]$^+$) was detected. The reaction solution was filtered through celite, and the solvent was removed by rotary evaporation under reduced pressure. A crude product was purified by pre-HPLC to obtain the title compound (63 mg).

50.6 1-(4-((2,6-Diethyl-3,4-dihydroquinolin-1(2H)-yl)sulfonyl)-2-hydroxymethylphenyl)-2-(tetrahydro-2H-pyran-4-yl)ethanol A 10 mL three-necked flask was charged with methyl 5-((2,6-diethyl-3,4-dihydroquinolin-1(2H)-yl)sulfonyl)-2-(2-(tetrahydro-2H-pyran-4-yl)acetyl)benzoate (213 mg), which was dissolved with anhydrous tetrahydrofuran (1.5 mL). The mixture was purged with nitrogen gas three times and was cooled to 0° C. in an ice bath. Lithium tetrahydroaluminate (14 mg) was added, and the reaction solution was stirred at 0° C. for 1 h. A sample was taken and subjected to LC-MS detection, and a peak of the product (488.2[M+1]$^+$) was detected. The reaction was quenched with water (30 μL) in an ice bath, and then 10% aqueous sodium hydroxide solution (20 μL) was added dropwise. The reaction solution was diluted with tetrahydrofuran (40 mL), and then water (60 µL) was added dropwise. The mixture was stirred at room temperature for 5 min. An appropriate amount of anhydrous magnesium sulfate was added to dry the mixture. The resulting mixture was stirred for 5 min and filtered through celite, and the filtrate was concentrated under reduced pressure. A crude product was purified by pre-HPLC to obtain 13.6 mg of the title compound (HPLC purity: 99.76%, MS(ESI) m/z 488.2[M+1]$^+$).

$^1$H NMR (400 MHz, CDCl$_3$): δ 7.61 (d, J=8.0 Hz, 1H), 7.49-7.38 (m, 1H), 7.27-7.14 (m, 2H), 7.06 (d, J=8.0 Hz, 1H), 6.79 (s, 1H), 4.76-4.58 (m, 1H), 4.46-4.25 (m, 1H), 4.21-4.08 (m, 1H), 4.08-3.93 (m, 2H), 3.73-3.52 (m, 1H), 3.52-3.42 (m, 1H), 3.43-3.33 (m, 2H), 3.03 (br s, 1H), 2.87-2.71 (m, 2H), 2.59 (q, J=7.6 Hz, 2H), 2.42-2.25 (m, 1H), 1.80-1.56 (m, 6H), 1.51-1.32 (m, 4H), 1.22 (t, J=7.6 Hz, 3H), 0.93 (t, J=7.2 Hz, 3H).

Example 51

Synthesis of 5-((6-ethyl-2-isopropyl-3,4-dihydroquinolin-1(2H)-yl)sulfonyl)-2-((tetrahydro-2H-pyran-4-yl)methoxy)benzyl Alcohol

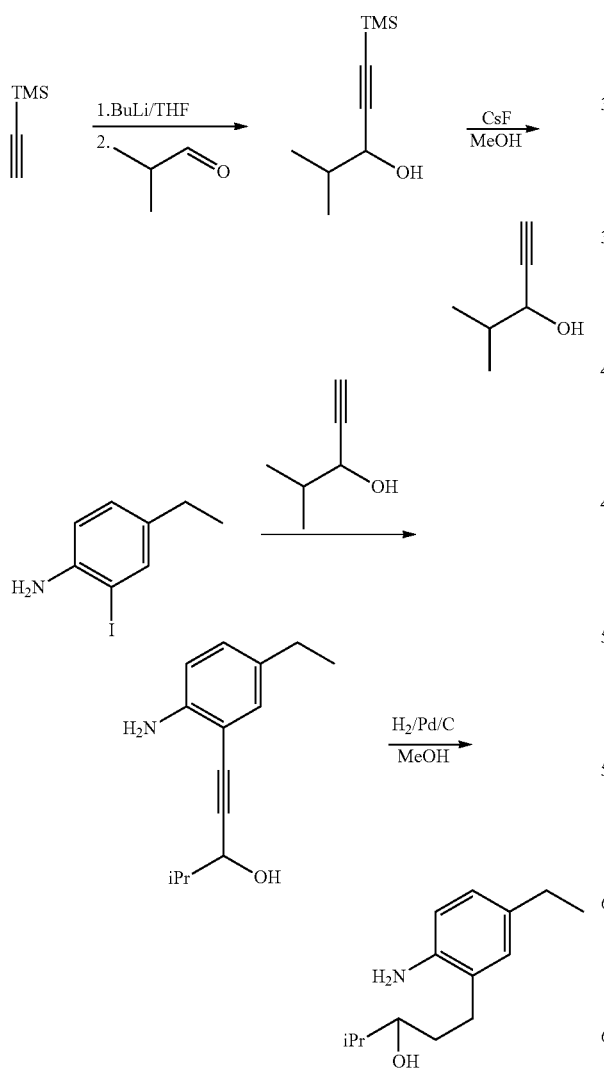

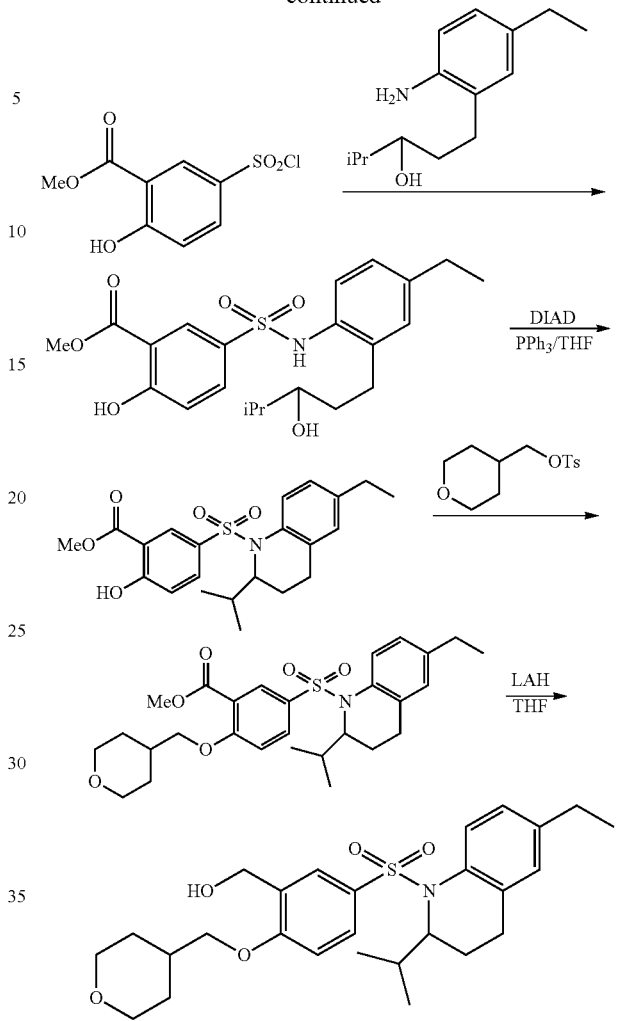

51.1 4-Methyl-1-trimethylsilylpentyn-3-ol

A 250 mL single-necked flask was successively charged with trimethylsilylacetylene (5.0 g) and anhydrous tetrahydrofuran (100 mL). The mixture was purged with nitrogen gas three times and cooled to −79° C. in an acetone-dry ice bath. n-Butyllithium (22.4 mL) was slowly added dropwise. After the completion of the addition, the mixture was stirred at −79° C. for 30 min, and isopropylaldehyde (3.98 g) was added dropwise. After the completion of the addition, the mixture was naturally warmed to room temperature. A saturated aqueous ammonium chloride solution (100 mL) was added, and the mixture was subjected to liquid-liquid separation. The aqueous phase was extracted with dichloromethane (50 mL×3). The organic phases were washed with saturated saline (20 mL), dried over anhydrous sodium sulfate, concentrated and distilled under reduced pressure, so as to obtain 4-methyl-1-trimethylsilylpentyn-3-ol (8.63 g).

51.2 4-Methyl-1-pentyn-3-ol

A 250 mL single-necked flask was charged with 4-methyl-1-trimethylsilylpentyn-3-ol (8.63 g), cesium fluoride (9.24 g) and 100 mL of methanol. The mixture was reacted at room temperature for 16 h. TLC detection (basic potassium permanganate was used for color development) showed that the spots of the raw materials disappeared. The reaction mixture was concentrated and subjected to column chromatography (PE:EA=10:1), so as to obtain 3.30 g of 4-methyl-1-pentyn-3-ol.

51.3 5-((6-ethyl-2-isopropyl-3,4-dihydroquinolin-1(2H)-yl)sulfonyl)-2-((tetrahydro-2H-pyran-4-yl)methoxy)benzyl Alcohol The rest synthesis steps proceeded with reference to the corresponding synthesis method in Example 12, so as to prepare and obtain 60 mg of the title compound (MS(ESI) m/z 488.2[M+1]$^+$).

$^1$H NMR (400 MHz, CDCl$_3$) δ 7.66 (d, J=8.2 Hz, 1H), 7.45 (s, 1H), 7.38 (d, J=8.5 Hz, 1H), 7.07 (d, J=7.9 Hz, 1H), 6.80 (s, 1H), 6.78 (d, J=8.7 Hz, 1H), 4.61 (d, J=5.6 Hz, 2H), 4.04 (dd, J=11.2, 3.4 Hz, 2H), 3.96 (dd, J=14.1, 6.3 Hz, 1H), 3.88 (d, J=6.3 Hz, 2H), 3.46 (t, J=11.4 Hz, 2H), 2.61 (q, J=7.5 Hz, 2H), 2.43-2.30 (m, 1H), 2.19-2.08 (m, 1H), 1.90-1.77 (m, 2H), 1.74 1.71 (m, 2H), 1.71-1.62 (m, 2H), 1.59-1.43 (m, 3H), 1.23 (t, J=7.6 Hz, 3H), 1.00 (d, J=6.7 Hz, 3H), 0.88 (d, J=6.7 Hz, 3H).

Example 52

Synthesis of 4-(4-((2,6-diethyl-3,4-dihydroquinolin-1(2H)-yl)sulfonyl)-2-hydroxy methylphenoxy)tetrahydro-2H-thiopyran 1,1-dioxide

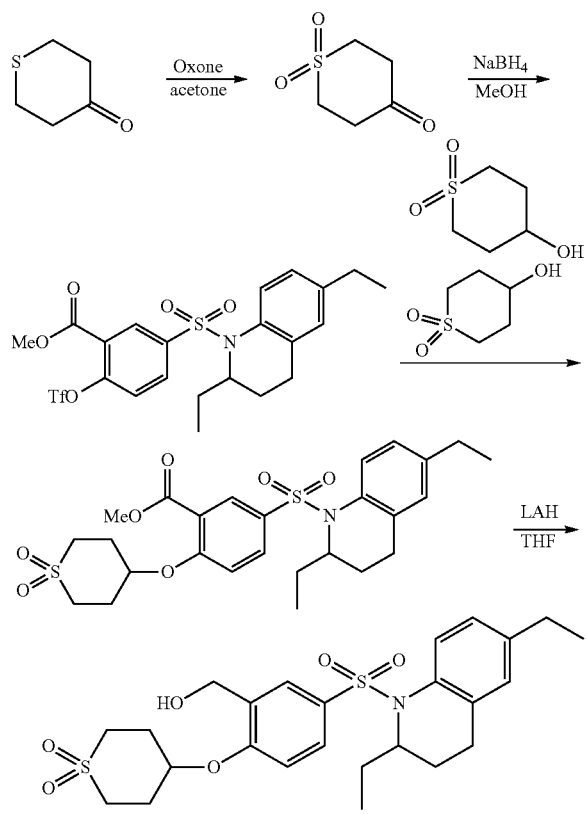

52.1 Dihydro-2H-thiopyran-4(3H)-one 1,1-dioxide

A 100 mL single-necked flask was charged with tetrahydrothiopyran-4-one (1.0 g), acetone (20 mL) was added as a reaction solvent, and potassium monopersulphate triple salt (10.6 g) was added thereto under stirring. After the completion of the addition, the mixture was stirred and reacted at room temperature for 16 h. A sample was taken, and TLC detection showed that the spots of the raw materials disappeared and the reaction was complete. The mixture was filtered by suction, the filter cake was washed with an appropriate amount of acetone, and the filtrate was concentrated, so as to obtain 1.0 g of dihydro-2H-thiopyran-4(3H)-one 1,1-dioxide.

52.2 4-Hydroxytetrahydro-2H-thiopyran 1,1-dioxide

A 50 mL single-necked reaction flask was charged with dihydro-2H-thiopyran-4(3H)-one 1,1-dioxide (1.0 g), and methanol (10 mL) was added thereto. Sodium borohydride (0.39 g) was added in portions while the mixture was stirred in an ice bath. The mixture was reacted at room temperature for 2 h. A sample was taken, and TLC detection showed that the spots of the raw materials disappeared and the reaction was complete. The mixture was concentrated to dryness under reduced pressure and purified by column chromatography, so as to obtain 1.0 g of 4-hydroxytetrahydro-2H-thiopyran 1,1-dioxide.

52.3 Methyl 5-((2,6-diethyl-3,4-dihydroquinolin-1(2H)-yl)sulfonyl)-2-((1,1-di oxo tetrahydro-2H-pyran-4-yl)oxy)benzoate A 10 mL three-necked flask was charged with methyl 2-hydroxy-5-((2,6-diethyl-3,4-dihydroquinolin-1(2H)-yl)sulfonyl)benzoate (0.14 g), 4-hydroxytetrahydro-2H-thiopyran 1,1-dioxide (0.068 g) and triphenylphosphine (0.27 g), and anhydrous tetrahydrofuran (4 mL) was added thereto. The mixture was purged with nitrogen gas three times, and diisopropyl azodicarboxylate (0.18 g) was added dropwise under ice bath condition. After the completion of the addition, the mixture was naturally warmed and reacted for 16 h. A sample was taken, and TLC detection showed that the spots of the raw materials disappeared. The sample was subjected to LC-MS detection, and a peak of the product (558 [M+Na]$^+$) was detected. Ethyl acetate (60 mL) was added to the reaction system to dilute the mixture. The resulting mixture was washed twice with water (20 mL×2), washed three times with saturated saline (20 mL×2), dried over anhydrous sodium sulfate, concentrated, and purified by column chromatography, so as to obtain 0.3 g of the title compound, which contained a certain amount of triphenylphosphine oxide and was directly used for reduction in the next step (MS(ESI) m/z: 558.0[M+Na]$^+$).

52.4 4-(4-((2,6-Diethyl-3,4-dihydroquinolin-1(2H)-yl)sulfonyl)-2-hydroxymethyl-phenoxy)tetrahydro-2H-thiopyran 1,1-dioxide A 25 mL single-necked flask was charged with methyl 5-((2,6-diethyl-3,4-dihydroquinolin-1(2H)-yl)sulfonyl)-2-((1,1-dioxotetrahydro-2H-pyran-4-yl)oxy)benzoate (0.30 g) and anhydrous tetrahydrofuran (5 mL). The mixture was cooled to 0° C. in an ice bath; and lithium tetrahydroaluminate (0.04 g) was added in portions. After the completion of the addition, the mixture was reacted for 1 h at this temperature. A sample was taken, and the spots of the raw materials disappeared as monitored by TLC. The sample was subjected to LC-MS detection, and a peak of the product (508 [M+H]$^+$) was detected. Under ice bath condition, water was added to quench the reaction, and the mixture was extracted three times with ethyl acetate (20 mL×3). The organic phases were combined, washed twice with saturated saline (20 mL×2), dried over anhydrous sodium sulfate and concentrated, so as to obtain 300 mg of a residue, which was directly subjected to perp-HPLC. Finally, 20 mg of the title compound (MS(ESI) m/z: 508.0[M+H]$^+$) was prepared and obtained.

$^1$H NMR (400 MHz, CDCl$_3$) δ 7.60 (d, J=8.3 Hz, 1H), 7.52 (d, J=2.2 Hz, 1H), 7.34 (dd, J=8.6, 2.3 Hz, 1H), 7.05 (dd, J=8.3, 1.5 Hz, 1H), 6.80 (s, 1H), 6.78 (s, 1H), 4.76 (s, 1H), 4.62 (s, 2H), 4.14 (p, J=6.3 Hz, 1H), 3.38 (dt, J=16.7, 3.7 Hz, 2H), 2.94 (d, J=14.4 Hz, 2H), 2.59 (q, J=7.6 Hz, 2H), 2.51-2.33 (m, 5H), 2.07 (m, 1H), 1.84 (dt, J=15.9, 6.4 Hz, 1H), 1.73 (td, J=13.7, 6.0 Hz, 1H), 1.66-1.52 (m, 1H), 1.43 (qt, J=13.0, 6.7 Hz, 2H), 1.22 (t, J=7.6 Hz, 3H), 0.93 (t, J=7.4 Hz, 3H).

Example 53

Synthesis of 5-((6-isopropyl-3,3-dimethyl-3,4-dihydroquinolin-1(2H)-yl)sulfonyl)-2-((tetrahydro-2H-pyran-4-yl)methoxy)benzyl Alcohol

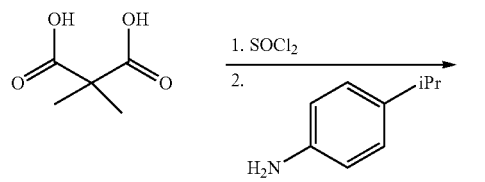

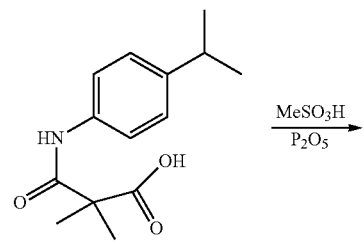

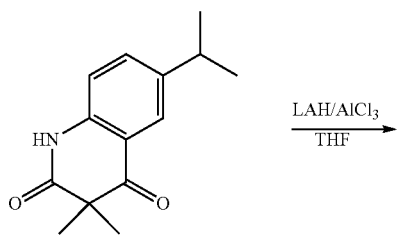

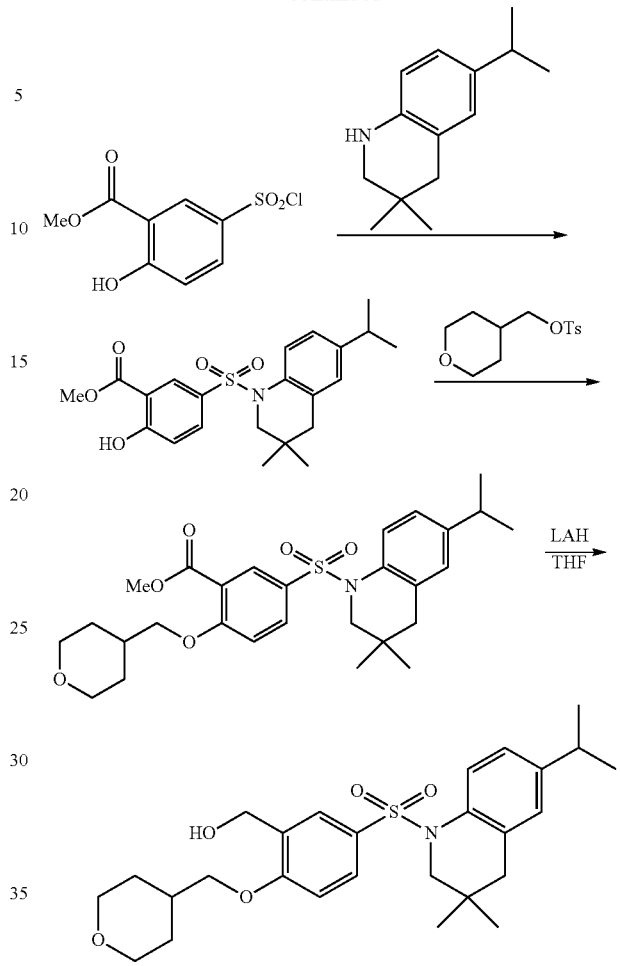

52 mg of the title compound (MS(ESI) m/z: 488.0[M+H]$^+$) was prepared and obtained with reference to the corresponding synthesis method in Example 17.

$^1$H NMR (400 MHz, CDCl$_3$) δ 7.76 (dd, J=12.6, 4.0 Hz, 2H), 7.44 (d, J=8.6 Hz, 1H), 6.93 (d, J=8.6 Hz, 1H), 6.90-6.83 (m, 2H), 4.68 (s, 2H), 4.02 (dd, J=11.3, 3.6 Hz, 2H), 3.89 (d, J=6.3 Hz, 2H), 3.58 (s, 2H), 3.44 (t, J=11.2 Hz, 2H), 2.78 (dt, J=13.8, 6.9 Hz, 1H), 2.44 (s, 2H), 2.20 (m, 1H), 2.09 (m, 1H), 1.72 (m, 2H), 1.47 (qd, J=12.4, 4.4 Hz, 2H), 1.18 (d, J=6.9 Hz, 6H), 1.04 (s, 6H).

Example 54

Synthesis of 5-((6-isopropyl-3,3-dimethyl-3,4-dihydroquinolin-1(2H)-yl)sulfonyl)-2-((tetrahydro-2H-pyran-4-yl)methoxy)benzene Deuterated Methanol

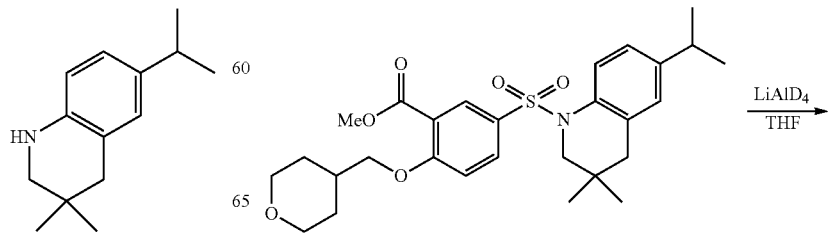

-continued

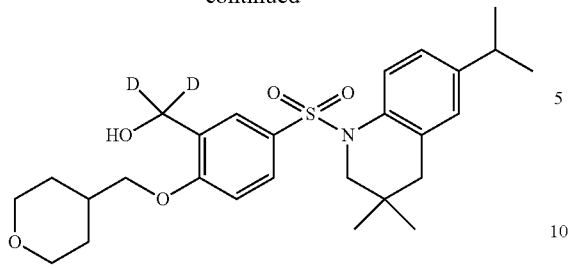

A 50 mL single-necked flask was charged with methyl 5-((6-isopropyl-3,3-dimethyl-3,4-dihydroquinolin-1(2H)-yl)sulfonyl)-2-((tetrahydro-2H-pyran-4-yl)methoxy)benzoate (400 mg, an intermediate in Example 53) and anhydrous tetrahydrofuran (8 mL). The mixture was cooled to 0° C. in an ice bath; and deuterated lithium tetrahydroaluminate (90 mg) was added in portions. The mixture was reacted for 0.5 h at this temperature. A sample was taken, and the spots of the raw materials disappeared as monitored by TLC. The sample was subjected to LC-MS detection, and a peak of the product (490 [M+H]$^+$) was detected. The reaction was quenched while the resulting mixture was cooled in an ice bath, and the mixture was extracted three times with ethyl acetate (20 mL×3). The organic phases were combined, washed twice with saturated saline (15 mL×2), and dried over anhydrous sodium sulfate. The filtrate was concentrated to obtain 300 mg of a crude product, which was directly subjected to prep-HPLC for purification, followed by concentration, so as to obtain 170 mg of the title compound (MS(ESI) m/z: 490.0[M+H]$^+$).

$^1$H NMR (400 MHz, CDCl$_3$) δ 7.79 (d, J=2.1 Hz, 1H), 7.74 (dd, J=8.6, 2.2 Hz, 1H), 7.44 (d, J=8.6 Hz, 1H), 6.93 (d, J=8.6 Hz, 1H), 6.90-6.83 (m, 2H), 4.01 (dd, J=11.3, 3.5 Hz, 2H), 3.88 (d, J=6.3 Hz, 2H), 3.58 (s, 2H), 3.43 (t, J=11.4 Hz, 2H), 2.77 (dt, J=13.8, 6.9 Hz, 1H), 2.44 (m, 3H), 2.09 (m, 1H), 1.72 (m, 2H), 1.46 (qd, J=12.5, 4.4 Hz, 2H), 1.17 (d, J=6.9 Hz, 6H), 1.04 (s, 6H).

Example 55

Synthesis of 2-(2-ethyl-1-((3-hydroxymethyl-4-((tetrahydro-2H-pyran-4-yl)methoxy) phenyl)sulfonyl)-1,2,3,4-tetrahydroquinolin-6-yl)2-propanol

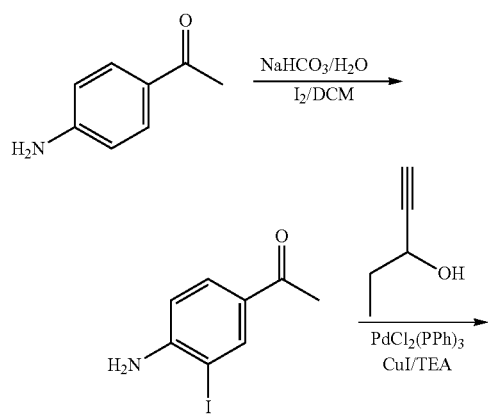

-continued

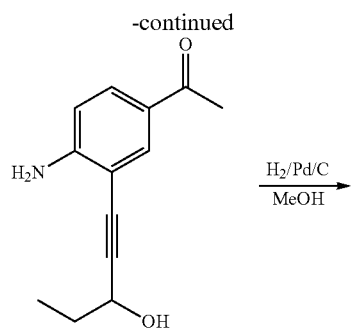

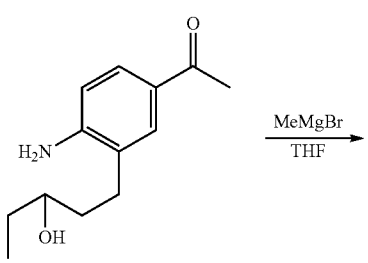

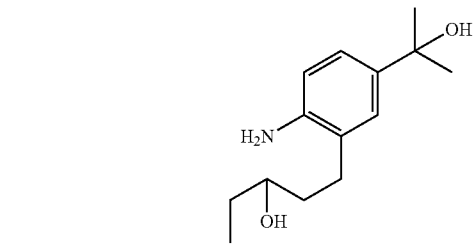

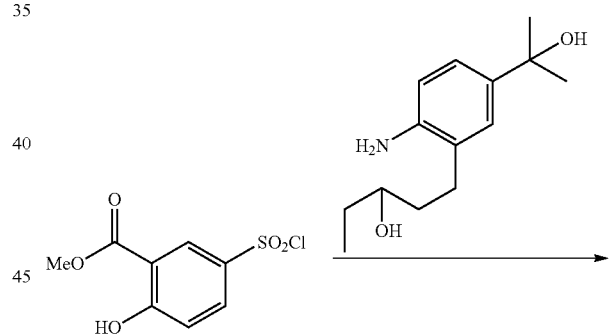

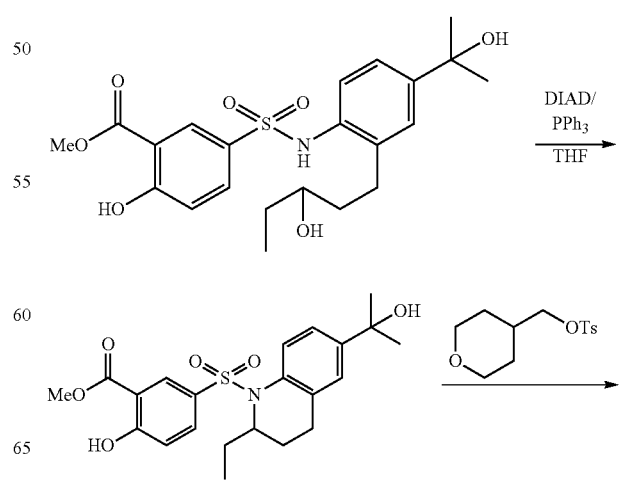

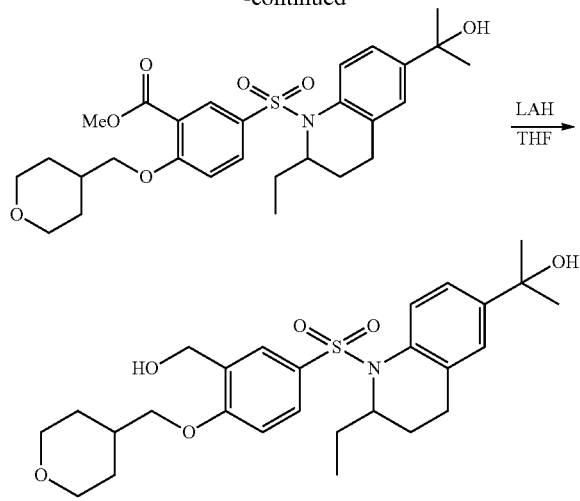

55.1 1-(4-Amino-3-iodophenyl)ethanone

A 250 mL single-necked flask was charged with 1-(4-aminophenyl)ethanone (10.0 g), which was dissolved in 50 mL of dichloromethane. A solution of sodium bicarbonate (9.3 g) in 100 mL of water was added, iodine (19.7 g) was added, and the resulting mixture was stirred at room temperature overnight. TLC detection showed that the raw materials disappeared, and LC-MS detected a peak of the product (262.1[M+1]$^+$). Post-treatment: saturated aqueous sodium sulfite solution was added, and the mixture was subjected to liquid-liquid separation. The aqueous phase was extracted with dichloromethane (50 mL×2). The organic phases were combined, washed with 50 mL of saturated saline and dried over anhydrous sodium sulfate, and the solvent was removed by rotary evaporation under reduced pressure, so as to obtain an oil, which was purified by passing through a column. The product was collected and concentrated under reduced pressure to obtain 1-(4-amino-3-iodophenyl)ethanone (12.7 g).

55.2 1-(4-Amino-3-(3-hydroxy-1-pentyn-1-yl)phenyl)ethanone

A single-necked flask was charged with 1-(4-amino-3-iodophenyl)ethanone (5.0 g), and 60 mL of triethylamine was added to dissolve the former. 1-Pentyn-3-ol (2.0 g), cuprous iodide and bis(triphenylphosphine)palladium (II) dichloride (673 mg) were added. The mixture was purged with nitrogen gas three times and stirred at room temperature overnight. A sample was taken, and TLC detection showed that the reaction of the raw materials was complete. 218.0 [M+1]+ was detected by LC-MS. Post-treatment: 50 mL of water was added, and the mixture was extracted three times with ethyl acetate (50 mL×3). The organic phases were combined, washed with a saturated aqueous sodium chloride solution, dried over anhydrous sodium sulfate and filtered, and the filtrate was concentrated under reduced pressure to obtain an oil, which was purified by passing through a column. The product was collected and concentrated under reduced pressure to obtain 1.3 g of 1-(4-amino-3-(3-hydroxy-1-pentyn-1-yl) phenyl)ethenone.

55.3 1-(4-Amino-3-(3-hydroxypentyl)phenyl)ethanone

A single-necked flask was charged with 1-(4-amino-3-(3-hydroxy-1-pentyn-1-yl)phenyl) ethanone (1.3 g), which was dissolved by methanol. 260 mg of palladium on carbon was added thereto. The mixture was purged with hydrogen gas three times and stirred at room temperature overnight. TLC detection showed the completion of the reaction. A peak of the product (222.1[M+1]$^+$) was detected by LC-MS. The reaction mixture was filtered and concentrated under reduced pressure to obtain 1.0 g of 1-(4-amino-3-(3-hydroxypentyl)phenyl)ethanone.

55.4 1-(2-Amino-5-(2-hydroxypropan-2-yl)phenyl)-3-pentanol

A single-necked flask was charged with 1-(4-amino-3-(3-hydroxypentyl)phenyl) ethanone (1.0 g), and 25 mL of tetrahydrofuran was added to dissolve the former. The mixture was cooled in an ice bath, and 3.0 mol/L methylmagnesium bromide (9 mL) was added thereto dropwise. After the completion of the addition, the mixture was heated to room temperature and stirred overnight. A sample was taken, and TLC detection showed that the raw materials disappeared. A peak of the product (238.1 [M+1]$^+$) was detected by LC-MS. Post-treatment: the reaction was quenched by addition of 30 mL of a saturated aqueous ammonium chloride solution, and the mixture was extracted with ethyl acetate (20 mL×3). The organic phases were combined, washed with 20 mL of saturated saline, and dried over anhydrous sodium sulfate. The resulting mixture was filtered and subjected to rotary evaporation under reduced pressure to remove the solvent and obtain an oil, which was purified by passing through a column. The product was collected and concentrated under reduced pressure to obtain 350 mg of the title compound.

55.5 2-(2-Ethyl-1-((3-hydroxymethyl-4-((tetrahydro-2H-pyran-4-yl)methoxy)phenyl) sulfonyl)-1,2,3,4-tetrahydroquinolin-6-yl)2-propanol The rest synthesis steps proceeded with reference to the corresponding synthesis method in Example 12, so as to prepare and obtain 104.3 mg of the title compound (HPLC purity: 98.9%).

$^1$H NMR (400 MHz, CDCl$_3$) δ 7.71 (d, J=8.5 Hz, 1H), 7.47 (dd, J=8.6, 2.3 Hz, 1H), 7.30 (dd, J=8.7, 2.1 Hz, 2H), 7.13 (d, J=1.8 Hz, 1H), 6.78 (d, J=8.7 Hz, 1H), 4.66-4.48 (m, 2H), 4.25-4.10 (m, 1H), 4.02 (dd, J=11.4, 3.7 Hz, 2H), 3.86 (d, J=6.3 Hz, 2H), 3.44 (t, J=11.0 Hz, 2H), 2.52-2.35 (m, 1H), 2.09 (m, 1H), 1.99 (m, 2H), 1.88 (dt, J=16.1, 6.3 Hz, 1H), 1.79-1.68 (m, 3H), 1.58 (d, J=7.6 Hz, 6H), 1.45 (ddt, J=30.3, 12.9, 6.5 Hz, 4H), 0.95 (t, J=7.4 Hz, 3H).

Example 56

Synthesis of 2-(4-((2,6-diethyl-3,4-dihydroquinolin-1(2H)-yl)sulfonyl)-2-(hydroxymethyl)phenyl)-2-morpholinoethanol and 1-(4-((2,6-diethyl-3,4-dihydroquinolin-1(2H)-yl) sulfonyl)-2-(hydroxymethyl)phenyl)-2-morpholinoethanol

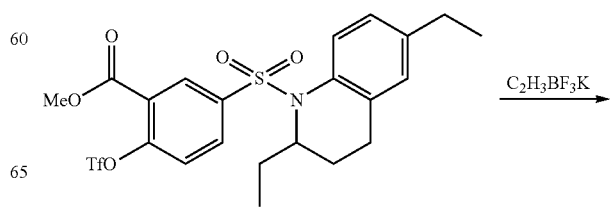

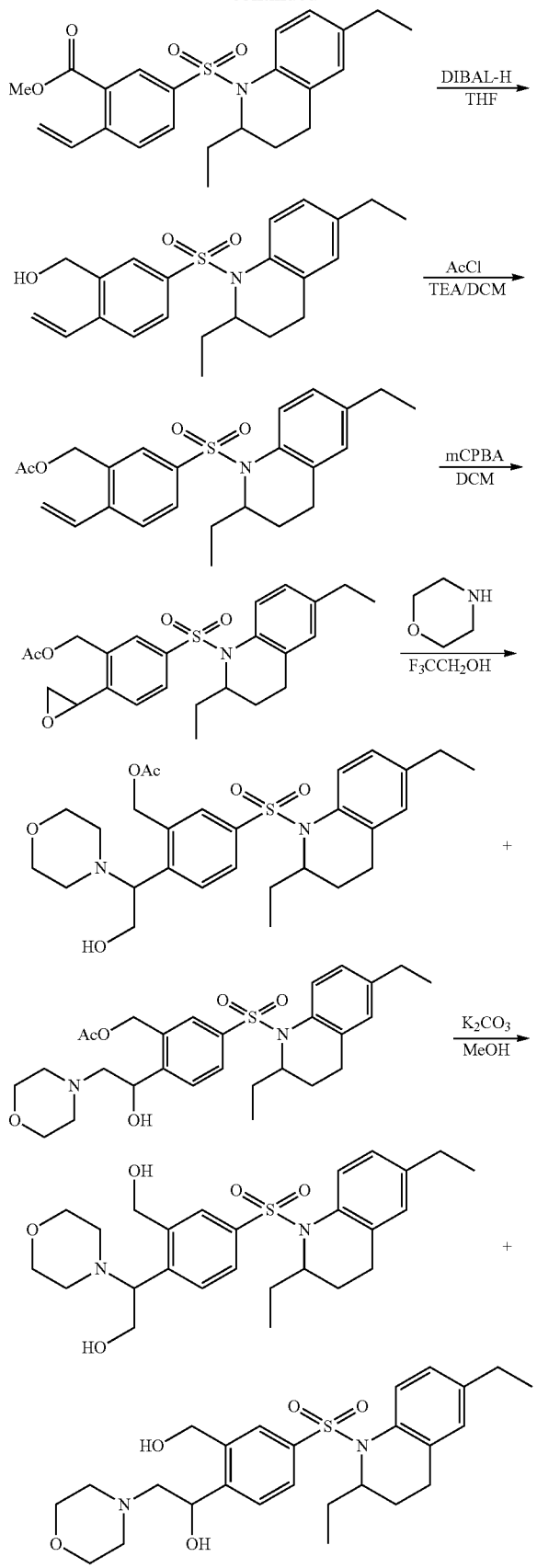

56.1 Methyl 5-((2,6-diethyl-3,4-dihydroquinolin-1(2H)-yl)sulfonyl)-2-vinylbenzoate A 50 mL round-bottom flask was charged with methyl 5-((2,6-diethyl-3,4-dihydroquinolin-1(2H)-yl)sulfonyl)-2-(trifluoromethanesulfonyl oxy)benzoate (400 mg, Example 52.3), potassium vinyltrifluoroborate (200 mg) and cesium carbonate (243 mg). The mixture was dissolved with 1,4-dioxane (18 mL) and water (3 mL), and purged with nitrogen gas three times. Tetrakis(triphenylphosphine)palladium (186 mg) was added thereto, and the mixture was purged with nitrogen gas three times again. The resulting reaction solution was heated in an oil bath at 85° C. for 5 h. A sample was taken and subjected to LC-MS detection, and a peak of the product (414.2[M+1]$^+$) was detected. The reaction solution was diluted with ethyl acetate (200 mL) and washed with saturated saline (30 mL×3). The organic phases were dried over anhydrous sodium sulfate, filtered and dried by rotary evaporation under reduced pressure, so as to obtain a crude product, which was subjected to silica gel column chromatography to obtain 342 mg of the title compound.

56.2 5-((2,6-Diethyl-3,4-dihydroquinolin-1(2H)-yl)sulfonyl)-2-vinylbenzyl Alcohol A 10 mL single-necked flask was charged with methyl 5-((2,6-diethyl-3,4-dihydroquinolin-1(2H)-yl)sulfonyl)-2-vinylbenzoate (150 mg) as a substrate, and tetrahydrofuran (4.5 mL). A solution of diisobutylaluminum hydride (0.72 mL) was added dropwise at −40° C. The resulting reaction mixture was stirred at 0° C. for 10 h. A sample was taken and subjected to LC-MS detection, and a peak of the product (386.2[M+1]$^+$) was detected. The reaction was complete, and a saturated ammonium chloride solution (1.2 mL) was added to the reaction solution to quench the reaction. The reaction solution was diluted with tetrahydrofuran and filtered through celite. The filtrate was dried by rotary evaporation under reduced pressure, then diluted with ethyl acetate (80 mL), and washed with water (20 mL) and saturated saline (20 mL). The organic phase was dried over anhydrous sodium sulfate, filtered and dried by rotary evaporation under reduced pressure to obtain 141 mg of the title compound.

56.3 5-((2,6-Diethyl-3,4-dihydroquinolin-1(2H)-yl)sulfonyl)-2-vinylbenzyl Acetate A 10 mL single-necked flask was charged with 5-((2,6-diethyl-3,4-dihydroquinolin-1(2H)-yl)sulfonyl)-2-vinylbenzyl alcohol (191 mg), which was dissolved in dichloromethane (3 mL), and the reaction system was cooled in an ice bath. Triethylamine (60.2 mg) was added to the reaction system, and then acetyl chloride (46.7 mg) was added. The reaction solution was gradually warmed to room temperature and stirred for 5 h. A sample was taken, and TLC detection showed that the raw materials disappeared and the reaction was complete. The reaction solution was diluted with dichloromethane (100 mL), and washed with saturated sodium bicarbonate solution (20 mL×2) and saturated saline (30 mL). The organic phase was dried over anhydrous sodium sulfate and filtered, and the filtrate was dried by rotary evaporation under reduced pressure and subjected to silica gel column chromatography (eluent: PE:EA=10:0 to 5:1), so as to obtain 128 mg of the title compound.

56.4 5-((2,6-Diethyl-3,4-dihydroquinolin-1(2H)-yl)sulfonyl)-2-oxiranylbenzyl Acetate A 10 mL single-necked flask was charged with 5-((2,6-diethyl-3,4-dihydroquinolin-1(2H)-yl)sulfonyl)-2-vinylbenzyl acetate (98 mg), which was dissolved in dichloromethane (3.2 mL). The mixture was cooled at 0° C., and m-chloroperoxybenzoic acid (158 mg) was added thereto in portions. The reaction solution was stirred at 0° C. for 30 min and then stirred at room temperature for 22 h. A sample was taken and subjected to LC-MS detection, and a peak of the product (443.9[M+1]$^+$) was detected. The reaction was complete. The reaction solution was diluted with dichloromethane (80 mL), washed with saturated sodium bicarbonate solution (15 mL), and washed with saturated saline (20 mL×2). The organic phase was dried over anhydrous sodium sulfate, filtered, and subjected to silica gel column chromatography (eluent: PE:EA=10:0 to 10:3), so as to obtain 80 mg of the title compound.

56.5 A mixture of 5-((2,6-diethyl-3,4-dihydroquinolin-1(2H)-yl)sulfonyl)-2-(2-hydroxy-1-morpholinoethyl)benzyl Acetate and 5-((2,6-diethyl-3,4-dihydroquinolin-1(2H)-yl)sulfonyl)-2-(1-hydroxy-2-morpholinoethyl)benzyl Acetate A 10 mL single-necked flask was charged with 5-((2,6-diethyl-3,4-dihydroquinolin-1(2H)-yl)sulfonyl)-2-oxiranyl-benzyl acetate (63 mg) as a substrate, which was dissolved with trifluoroethanol (4 mL). Morpholine (618.6 mg) was added to the mixture, and the resulting mixed solution was heated and stirred at 50° C. for 6 h. A sample was taken and subjected to LC-MS detection, and a peak of the product (530.9[M+1]$^+$) was detected. The reaction was complete, and the reaction solution was dried by rotary evaporation under reduced pressure, so as to obtain 92 mg of the title mixture, which was directly charged in the next step.

56.6 2-(4-((2,6-diethyl-3,4-dihydroquinolin-1(2H)-yl)sulfonyl)-2-(hydroxymethyl)phenyl)-2-morpholinoethanol and 1-(4-((2,6-diethyl-3,4-dihydroquinolin-1(2H)-yl)sulfonyl)-2-(hydroxymethyl)phenyl)-2-morpholinoethanol A 25 mL single-necked flask was charged with a mixture (92 mg) of 5-((2,6-diethyl-3,4-dihydroquinolin-1(2H)-yl)sulfonyl)-2-(2-hydroxy-1-morpholinoethyl) benzyl acetate and 5-((2,6-diethyl-3,4-dihydroquinolin-1(2H)-yl)sulfonyl)-2-(1-hydroxy-2-m orpholinoethyl) benzyl acetate, potassium carbonate (71.8 mg) and methanol (2 mL). The resulting mixed solution was stirred at room temperature for 5 h. A sample was taken and subjected to LC-MS detection, and a peak of the product (488.9[M+1]$^+$) was detected. The reaction was complete, the reaction solution was filtered through celite, and the filtrate was concentrated under reduced pressure. A crude product was separated and purified by pre-HPLC to obtain 6.2 mg of compound 2-(4-((2,6-diethyl-3,4-dihydroquinolin-1(2H)-yl)sulfonyl)-2-(hydroxymethyl) phenyl)-2-morpholinoethanol (HPLC purity: 99.74%, MS(ESI) m/z 489.0[M+1]$^+$) and 22.1 mg of 1-(4-((2,6-diethyl-3,4-dihydroquinolin-1(2H)-yl)sulfonyl)-2-(hydroxymethyl)phenyl)-2-morpholinoethanol (HPLC purity: 100.0%, MS(ESI) m/z 489.0[M+1]$^+$).

2-(4-((2,6-diethyl-3,4-dihydroquinolin-1(2H)-yl)sulfonyl)-2-(hydroxymethyl)phenyl)-2-morpholinoethanol (56-1)

$^1$H NMR (400 MHz, CDCl$_3$): δ 7.62 (d, J=8.4 Hz, 1H), 7.48-7.35 (m, 3H), 7.07 (d, J=9.2 Hz, 1H), 6.78 (d, J=8.8 Hz, 1H), 4.90 (br s, 1H), 4.68-4.50 (m, 2H), 4.23-4.07 (m, 2H), 4.03-3.91 (m, 1H), 3.88-3.76 (m, 1H), 3.72-3.53 (m, 4H), 2.66-2.54 (m, 4H), 2.52-2.43 (m, 2H), 2.39-2.29 (m, 1H), 2.19-1.96 (m, 1H), 1.75-1.58 (m, 3H), 1.51-1.32 (m, 2H), 1.22 (t, J=7.6 Hz, 3H), 0.93 (t, J=7.6 Hz, 3H).

1-(4-((2,6-diethyl-3,4-dihydroquinolin-1(2H)-yl)sulfonyl)-2-(hydroxymethyl)phenyl)-2-morpholinoethanol (56-2)

$^1$H NMR (400 MHz, CDCl$_3$): δ 7.63 (d, J=7.6 Hz, 1H), 7.53 (t, J=7.6 Hz, 1H), 7.49-7.42 (m, 1H), 7.37 (s, 1H), 7.06 (d, J=7.6 Hz, 1H), 6.78 (m, 1H), 5.10-4.95 (m, 1H), 4.72-4.59 (m, 1H), 4.57-4.39 (m, 1H), 4.23-4.09 (s, 1H), 3.88-3.56 (m, 5H), 2.66-2.41 (m, 8H), 2.40-2.29 (m, 1H), 1.84-1.56 (m, 3H), 1.51-1.34 (m, 2H), 1.22 (t, J=6.8 Hz, 3H), 0.93 (t, J=6.8 Hz, 3H).

Example 57

Synthesis of 54(2-ethyl-6-trifluoromethyl-3,4-dihydroquinolin-1(2H)-yl)sulfonyl)-2-((tetrahydro-2H-pyran-4-yl)methoxy)benzyl Alcohol

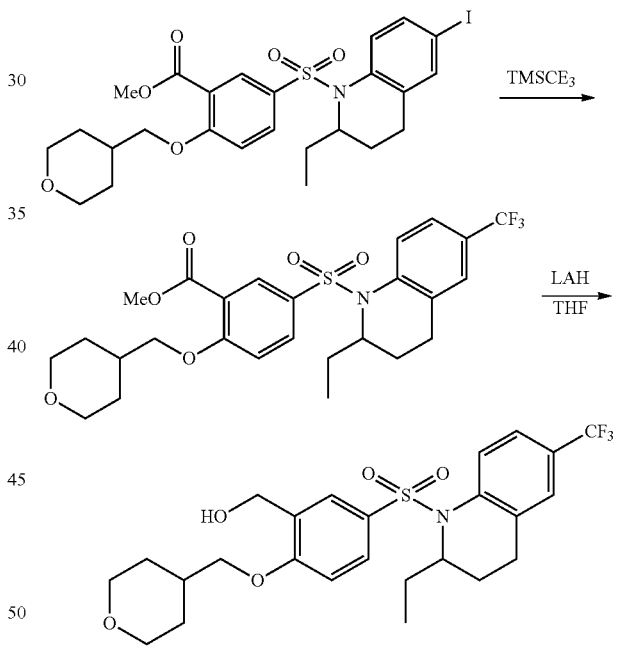

128.2 mg of the title compound (HPLC purity: 99.1%) was prepared and obtained by using the corresponding intermediate in Example 34 as a raw material with reference to the corresponding synthesis method in Example 32.

$^1$H NMR (400 MHz, CDCl$_3$) δ 7.91 (d, J=8.6 Hz, 1H), 7.60 (d, J=2.3 Hz, 1H), 7.45 (d, J=8.6 Hz, 1H), 7.40 (dd, J=8.6, 2.4 Hz, 1H), 7.26-7.24 (m, 1H), 6.80 (d, J=8.7 Hz, 1H), 4.65 (d, J=6.0 Hz, 2H), 4.34-4.21 (m, 1H), 4.03 (dd, J=11.3, 3.7 Hz, 2H), 3.87 (d, J=6.4 Hz, 2H), 3.44 (td, J=11.9, 1.8 Hz, 2H), 2.65-2.49 (m, 1H), 2.21-2.04 (m, 2H), 1.97 (t, J=6.4 Hz, 1H), 1.69 (m, 3H), 1.58-1.41 (m, 5H), 0.95 (t, J=7.4 Hz, 3H).

Example 58

Synthesis of 5-((6-tert-butyl-2-ethyl-3,4-dihydroquinolin-1(2H)-yl)sulfonyl)-2-((tetrahydro-2H-pyran-4-yl)methoxy)benzyl Alcohol

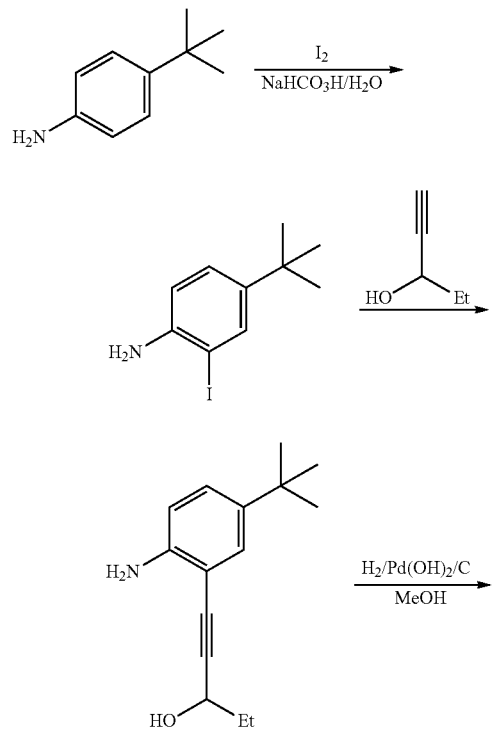

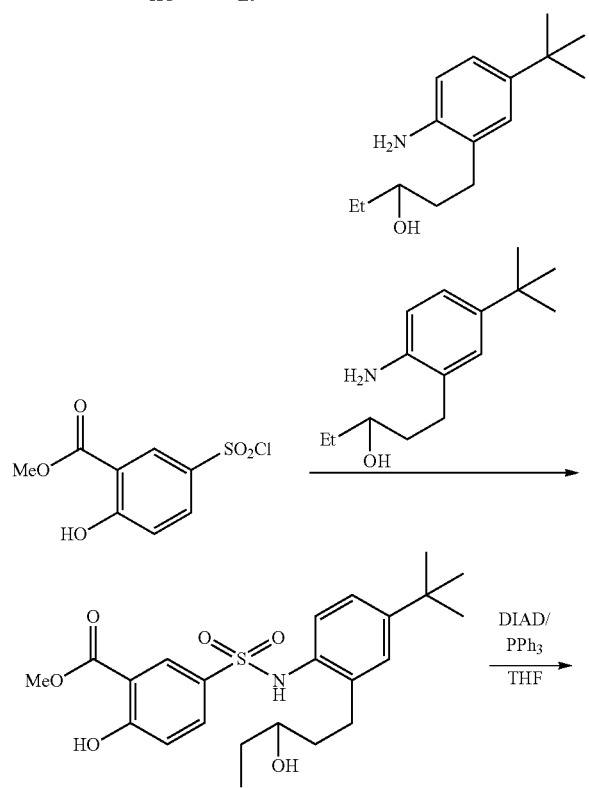

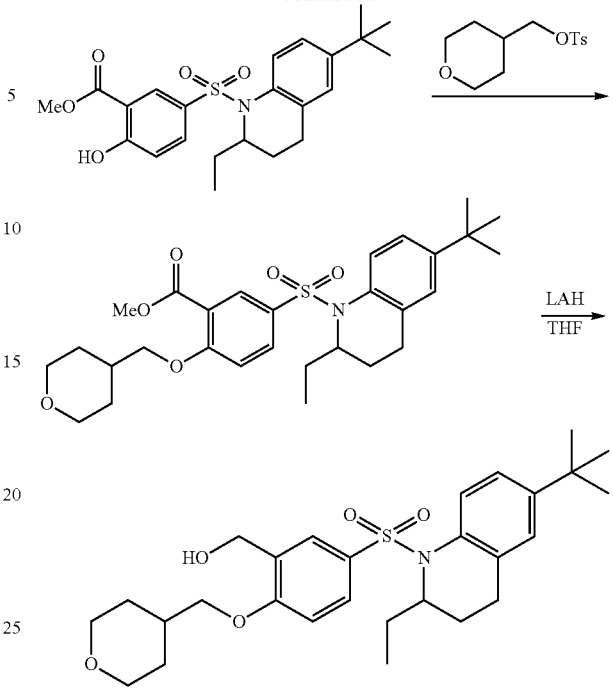

28 mg of the title compound (MS(ESI) m/z 501.9[M+1]⁺) was prepared and obtained, with reference to the corresponding synthesis method in Example 15.

$^1$H NMR (400 MHz, CDCl$_3$) δ 7.67 (d, J=8.6 Hz, 1H), 7.46-7.39 (m, 2H), 7.26 (dd, J=8.6, 2.3 Hz, 1H), 6.97 (d, J=2.1 Hz, 1H), 6.80 (d, J=8.5 Hz, 1H), 4.60 (s, 2H), 4.20-4.12 (m, 1H), 4.04 (dd, J=11.3, 3.7 Hz, 2H), 3.89 (d, J=6.3 Hz, 2H), 3.55-3.36 (m, 2H), 2.49-2.38 (m, 1H), 2.17-2.07 (m, 1H), 1.91 (dt, J=16.2, 6.2 Hz, 2H), 1.76-1.59 (m, 4H), 1.54-1.41 (m, 4H), 1.31 (s, 9H), 0.96 (t, J=7.4 Hz, 3H).

Example 59

Synthesis of (R)-5-((2-ethyl-6-trifluoromethyl-3,4-dihydroquinolin-1(2H)-yl)sulfonyl)-2-((tetrahydro-2H-pyran-4-yl)methoxy)benzyl Alcohol

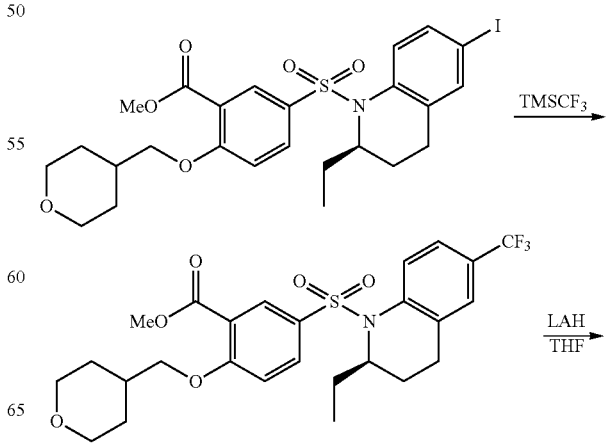

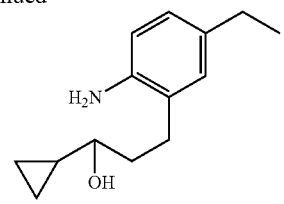

34 mg of the title compound (HPLC purity: 99.4%) was prepared and obtained by using the corresponding intermediate in Example 48 as a raw material, with reference to the corresponding synthesis method in Example 32.

$^1$H NMR (400 MHz, CDCl$_3$) δ 7.91 (d, J=8.6 Hz, 1H), 7.60 (d, J=2.2 Hz, 1H), 7.45 (d, J=8.5 Hz, 1H), 7.40 (dd, J=8.7, 2.3 Hz, 1H), 7.26-7.24 (m, 1H), 6.80 (d, J=8.7 Hz, 1H), 4.65 (d, J=6.3 Hz, 2H), 4.34-4.23 (m, 1H), 4.03 (dd, J=11.2, 3.8 Hz, 2H), 3.87 (d, J=6.4 Hz, 2H), 3.45 (dd, J=11.7, 10.1 Hz, 2H), 2.64-2.50 (m, 1H), 2.24-2.03 (m, 2H), 1.93 (t, J=6.4 Hz, 1H), 1.81-1.64 (m, 3H), 1.64-1.58 (m, 1H), 1.57-1.39 (m, 4H), 0.95 (t, J=7.4 Hz, 3H).

Example 60

Synthesis of 5-((2-cyclopropyl-6-ethyl-3,4-dihydroquinolin-1(2H)-yl)sulfonyl)-2-((tetrahydro-2H-pyran-4-yl)methoxy)benzyl Alcohol

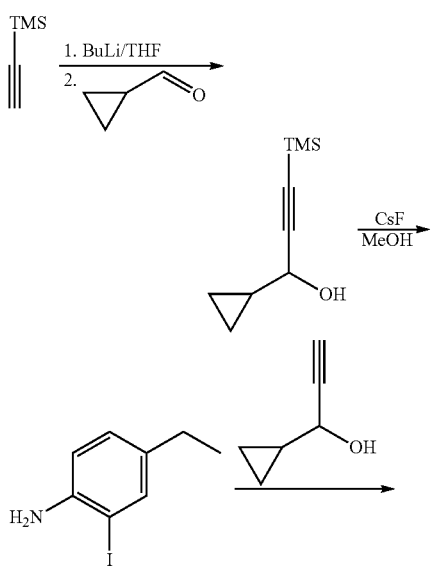

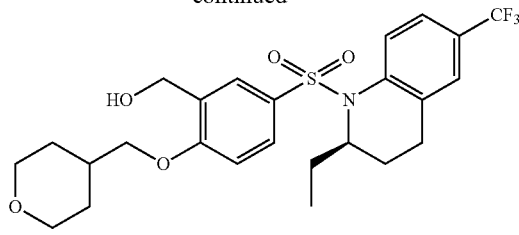

55 mg of the title compound (MS(ESI) m/z: 486.0[M+H]$^+$) was prepared and obtained with reference to the corresponding synthesis method in Example 51.

$^1$H NMR (400 MHz, CDCl$_3$) δ 7.65 (d, J=8.3 Hz, 1H), 7.48 (d, J=2.2 Hz, 1H), 7.37 (dd, J=8.6, 2.3 Hz, 1H), 7.04 (dd, J=8.3, 1.7 Hz, 1H), 6.83 (s, 1H), 6.76 (d, J=8.7 Hz, 1H), 4.60 (d, J=5.4 Hz, 2H), 4.02 (dd, J=11.3, 3.6 Hz, 2H), 3.86 (d, J=6.4 Hz, 2H), 3.64 (dt, J=8.5, 5.6 Hz, 1H), 3.44 (td, J=11.8, 1.5 Hz, 2H), 2.63-2.51 (m, 3H), 2.03 (ddd, J=16.8, 16.3, 5.0 Hz, 3H), 1.76-1.68 (m, 3H), 1.65-1.55 (m, 1H), 1.47 (qd, J=12.4, 4.5 Hz, 2H), 1.22 (t, J=7.6 Hz, 3H), 0.95-0.86 (m, 1H), 0.55-0.42 (m, 3H), 0.38-0.31 (m, 1H).

Example 61

Synthesis of 54(2-ethyl-6-(2,2,2-trifluoroethyl)-3,4-dihydroquinolin-1(2H)-yl)sulfonyl)-2-((tetrahydro-2H-pyran-4-yl)methoxy)benzyl Alcohol

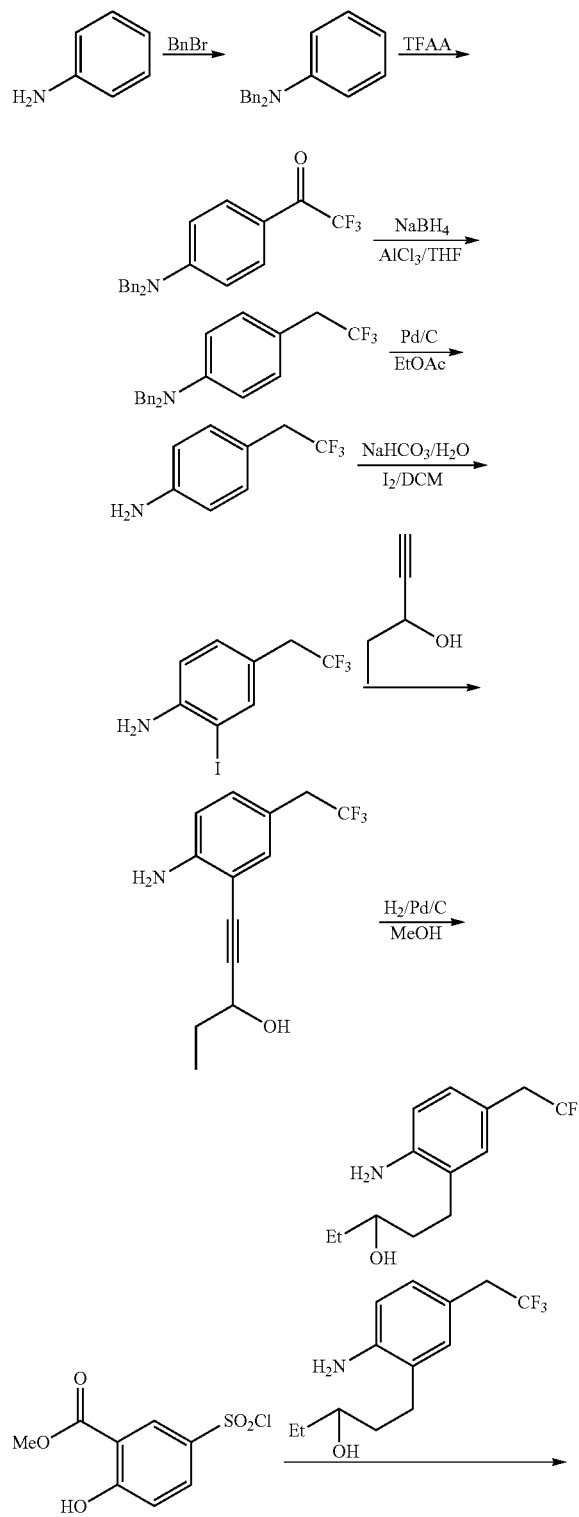

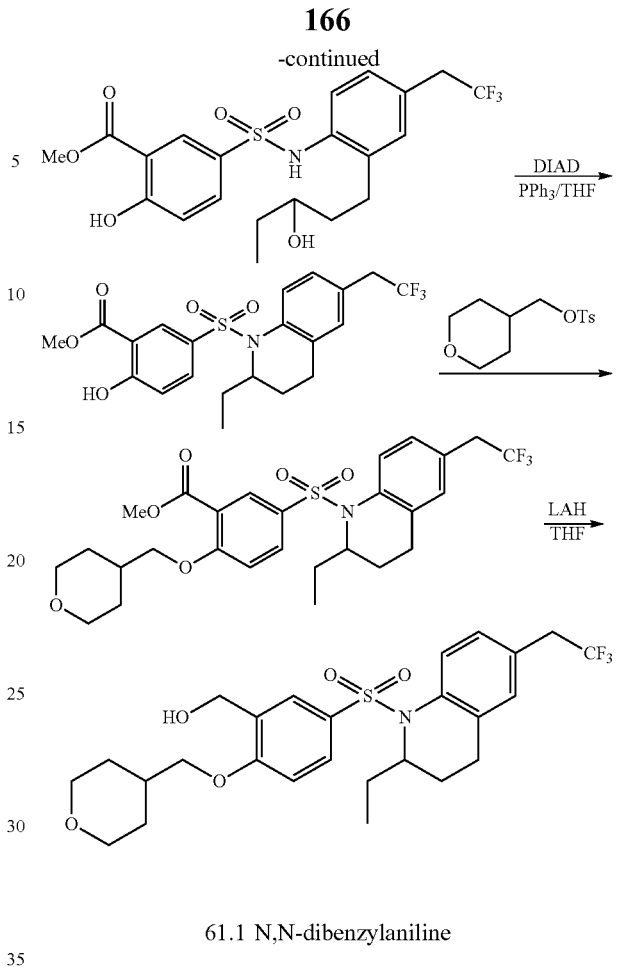

61.1 N,N-dibenzylaniline

A 100 mL single-necked flask was charged with aniline (5 g), benzyl bromide (16 mL), potassium carbonate (22 g), and N, N-dimethylformamide (15 mL). Under nitrogen protection, the mixture was reacted at 80° C. overnight. A sample was taken, and the spots of the raw materials disappeared as monitored by TLC. The sample was subjected to LC-MS detection, and a peak of the product (274.0 [M+H]$^+$) was detected. The reaction solution was slowly poured into water (50 mL), and the mixture was extracted three times with ethyl acetate (50 mL×3). The organic phases were combined, washed twice with saturated sodium chloride solution (30 mL×2), dried over anhydrous sodium sulfate, and concentrated. The residue was mixed with silica gel, stirred, and purified by column chromatography, so as to obtain 9.0 g of N,N-dibenzylaniline (MS(ESI) m/z: 274.0[M+1]$^+$).

61.2 1-(4-(dibenzylamino)phenyl)-2,2,2-trifluoroethanone

A 100 mL single-necked flask was charged with N,N-dibenzylaniline (8 g), pyridine (12.3 mL) and chloroform (15 mL), and then trifluoroacetic anhydride (12.3 mL) was added dropwise to the mixture in an ice bath. Under nitrogen protection, the mixture was reacted at room temperature overnight. A sample was taken, and the spots of the raw materials disappeared as monitored by TLC. The sample was subjected to LC-MS detection, and a peak of the product (370.0 [M+H]$^+$) was detected. 1N aqueous sodium hydroxide solution (20 mL) was slowly added dropwise to the reaction solution, and the mixture was extracted three times with ethyl acetate (50 mL×3). The organic phases were combined, washed twice with saturated sodium chloride solution (30 mL×2), dried over anhydrous sodium sulfate, and concentrated. The residue was mixed with silica gel, stirred, and purified by column chromatography, so as to obtain 7.0 g of 1-(4-(dibenzylamino)phenyl)-2,2,2-trifluoroethanone (MS(ESI) m/z: 370.0 [M+H]⁺).

61.3 N,N-dibenzyl-4-(2,2,2-trifluoroethyl)aniline

A 100 mL single-necked flask was charged with 1-(4-(dibenzylamino)phenyl)-2,2,2-trifluoroethanone (7 g) and tetrahydrofuran (20 mL), followed by addition of sodium borohydride (5.6 g); then, aluminum trichloride (12 g) was added in portions. Under nitrogen protection, the mixture was reacted at 70° C. overnight. A sample was taken, and the spots of the raw materials disappeared as monitored by TLC. The sample was subjected to LC-MS detection, and a peak of the product (356.0 [M+H]⁺) was detected. The reaction solution was slowly poured into water (50 mL), and the mixture was extracted three times with ethyl acetate (50 mL×3). The organic phases were combined, washed twice with saturated sodium chloride solution (30 mL×2), dried over anhydrous sodium sulfate, and concentrated. The residue was mixed with silica gel, stirred, and purified by column chromatography, so as to finally obtain 7.4 g of N,N-dibenzyl-4-(2,2,2-trifluoroethyl)aniline (MS(ESI) m/z: 356.0 [M+1]⁺).

61.4 4-(2,2,2-Trifluoroethyl)aniline

A 100 mL single-necked flask was charged with N,N-dibenzyl-4-(2,2,2-trifluoroethyl) aniline (7.4 g), palladium on carbon (450 mg) and 60 mL of ethyl acetate. The system was provided with a hydrogen balloon and purged with hydrogen gas three times, and then the mixture was reacted at room temperature overnight. A sample was taken, and TLC detection showed that the spots of the raw materials disappeared. The resulting mixture was filtered through celite, and the solvent was removed by rotary evaporation under reduced pressure, so as to obtain 3.6 g of 4-(2,2,2-trifluoroethyl)aniline (MS(ESI) m/z 176.0[M+1]⁺).

61.5 2-Iodo-4-(2,2,2-trifluoroethyl)aniline

A 100 mL single-necked flask was charged with 4-(2,2,2-trifluoroethyl)aniline (1 g) and dichloromethane (30 mL), followed by addition of sodium bicarbonate (1 g) and water (15 mL); then, elemental iodine (1.45 g) was added thereto. Under nitrogen protection, the mixture was stirred at room temperature overnight. A sample was taken, and the spots of the raw materials disappeared as monitored by TLC. The sample was subjected to LC-MS detection, and a peak of the product (301.8[M+H]⁺) was detected. The reaction solution was slowly poured into water (50 mL), and the mixture was extracted three times with ethyl acetate (25 mL×3). The organic phases were combined, washed twice with saturated sodium bisulfite solution (30 mL×2), washed twice with saturated sodium chloride solution (30 mL×2), dried over anhydrous sodium sulfate, and concentrated. The residue was mixed with silica gel, stirred, and purified by column chromatography, so as to finally obtain 1.28 g of 2-iodo-4-(2,2,2-trifluoroethyl)aniline (MS(ESI) m/z: 301.8[M+1]⁺).

61.6 5-((2-ethyl-6-(2,2,2-trifluoroethyl)-3,4-dihydroquinolin-1(2H)-yl)sulfonyl)-2-((tetrahydro-2H-pyran-4-yl)methoxy)benzyl Alcohol The rest synthesis steps proceeded with reference to the corresponding synthesis method in Example 12, so as to prepare and obtain 50 mg of the title compound (yield: 12%, MS(ESI) m/z: 527.0[M+H]⁺).

¹H NMR (400 MHz, CDCl₃) 1H NMR (400 MHz, CDCl3) δ 7.76 (d, J=8.3 Hz, 1H), 7.47 (d, J=2.0 Hz, 1H), 7.39 (dd, J=8.6, 2.2 Hz, 1H), 7.15 (d, J=8.2 Hz, 1H), 6.91 (s, 1H), 6.77 (d, J=8.7 Hz, 1H), 4.60 (d, J=6.4 Hz, 2H), 4.27-4.14 (m, 1H), 4.03 (dd, J=11.3, 3.8 Hz, 2H), 3.87 (d, J=6.4 Hz, 2H), 3.45 (t, J=11.1 Hz, 2H), 3.31 (q, J=10.8 Hz, 2H), 2.53-2.38 (m, 1H), 2.09 (m, 1H), 1.93 (ddd, J=19.2, 11.6, 6.5 Hz, 2H), 1.77-1.70 (m, 2H), 1.66-1.55 (m, 2H), 1.54-1.40 (m, 4H), 0.95 (t, J=7.4 Hz, 3H).

Example 62

Synthesis of 5-((6-cyclobutyl)-2-ethyl-3,4-dihydroquinolin-1(2H)-yl)sulfonyl)-2-((tetrahydro-2H-pyran-4-yl)methoxy)benzyl Alcohol

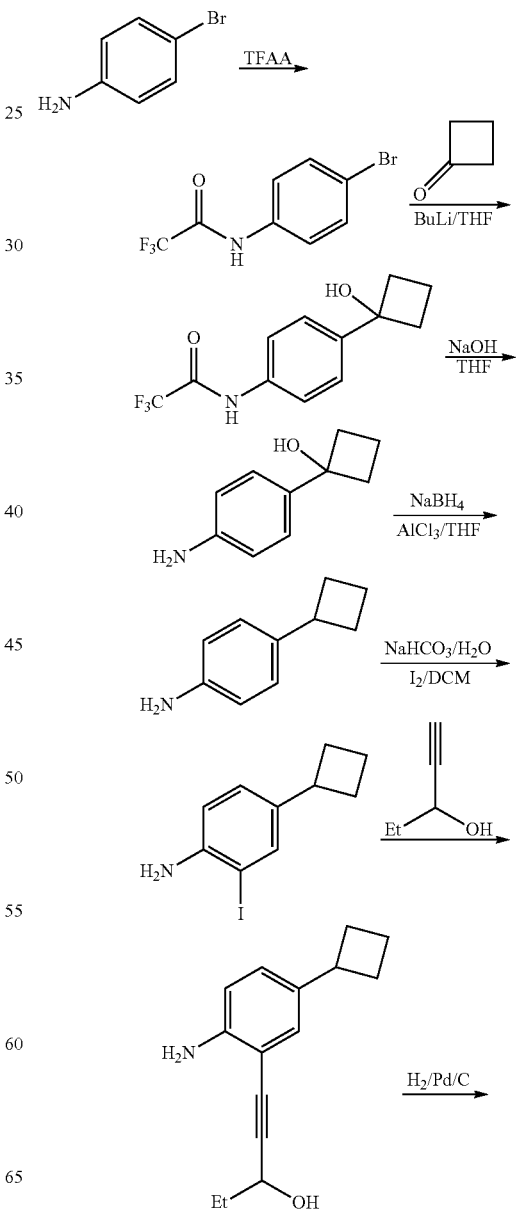

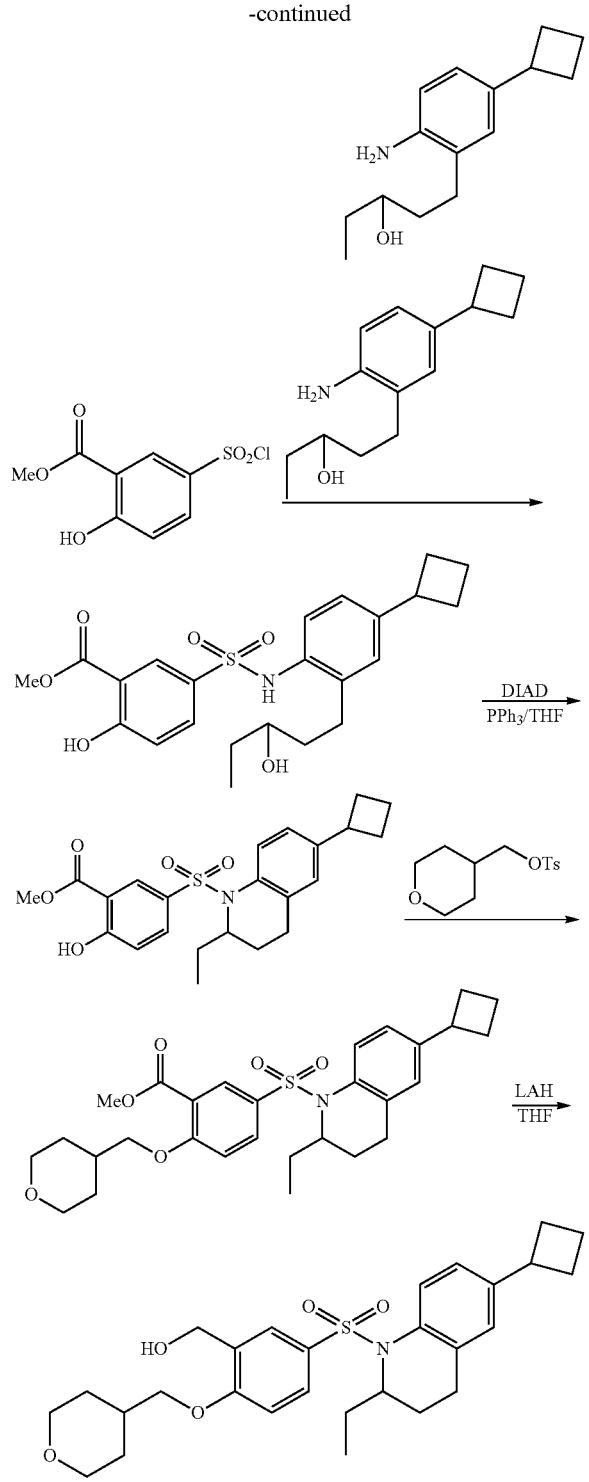

62.1 N-(4-bromophenyl)-2,2,2-trifluoroacetamide

A 100 mL single-necked flask was charged with p-bromoaniline (10 g), triethylamine (23.5 mL) and dichloromethane (30 mL), and trifluoroacetic anhydride (12.3 mL) was added dropwise to the mixture in an ice bath. Under nitrogen protection, the mixture was reacted at room temperature overnight. A sample was taken, and the spots of the raw materials disappeared as monitored by TLC. The sample was subjected to LC-MS detection, and a peak of the product (265.9/267.9 [M−H]$^-$) was detected. 1N aqueous sodium hydroxide solution (20 mL) was slowly added dropwise into the reaction solution. The mixture was extracted three times with ethyl acetate (50 mL×3). The organic phases were combined, washed twice with saturated sodium chloride solution (30 mL×2), dried over anhydrous sodium sulfate, concentrated, and purified by column chromatography, so as to obtain 15 g of N-(4-bromophenyl)-2,2,2-trifluoroacetamide.

62.2 2,2,2-Trifluoro-N-(4-(1-hydroxycyclobutyl)phenyl)acetamide

A 150 mL three-necked reaction flask was charged with N-(4-bromophenyl)-2,2,2-trifluoroacetamide (5 g), and tetrahydrofuran (20 mL) was added thereto. Under nitrogen protection, butyl lithium (15 mL) was added dropwise under a condition of −78° C. After the completion of the addition, the mixture was kept at this temperature and reacted for 1 h. Cyclobutanone (1.43 g) was slowly added dropwise. After the completion of the addition, the mixture was reacted at this temperature for 2 h. A sample was taken, and the reaction was complete as monitored by TLC. The sample was subjected to LC-MS detection, and a peak of the product (260.0 [M+1-1]$^+$) was detected. The mixture was slowly warmed to room temperature, and saturated ammonium chloride solution was added to quench the reaction. The resulting mixture was extracted three times with methyl tert-butyl ether (50 mL×3). The organic phases were combined, washed twice with saturated sodium chloride solution (20 mL×2), dried over anhydrous sodium sulfate, and concentrated. The residue was mixed with silica gel, stirred, and purified by column chromatography, so as to obtain 4.5 g of the title compound.

62.3 1-(4-Aminophenyl)cyclobutanol

A 100 mL single-necked flask was charged with 2,2,2-trifluoro-N-(4-(1-hydroxycyclobutyl)phenyl)acetamide (4.5 g), 1N aqueous sodium hydroxide solution (15 mL) and methanol (30 mL). The mixture was reacted at room temperature overnight. A sample was taken, and the spots of the raw materials disappeared as monitored by TLC. The sample was subjected to LC-MS detection, and a peak of the product (164.0 [M+H]$^+$) was detected. The system was concentrated to until no liquid dripped and extracted three times with dichloromethane (50 mL×3). The organic phases were combined, washed twice with saturated sodium chloride solution (30 mL×2), dried over anhydrous sodium sulfate, and concentrated. The residue was mixed with silica gel, stirred, and purified by column chromatography, so as to obtain 2.2 g of 1-(4-aminophenyl)cyclobutanol (MS(ESI) m/z: 164 0.0 [M+1]$^+$).

62.4 4-Cyclobutylaniline

A 100 mL single-necked flask was charged with 1-(4-aminophenyl)cyclobutanol (1.1 g) and tetrahydrofuran (15 mL), followed by addition of sodium borohydride (1.45 g); then, aluminum trichloride (2.7 g) was added in portions. Under nitrogen protection, the mixture was reacted at 70° C. overnight. A sample was taken, and the spots of the raw materials disappeared as monitored by TLC. The sample was subjected to LC-MS detection, and a peak of the product (148.0 [M+H]$^+$) was detected. The reaction solution was slowly poured into water (20 mL). The resulting mixture was extracted three times with ethyl acetate (50 mL×3). The organic phases were combined, washed twice with saturated sodium chloride solution (20 mL×2), dried over anhydrous sodium sulfate, and concentrated. The residue was purified by column chromatography to obtain 580 mg of 4-cyclobutylaniline.

62.5 5-((6-Cyclobutyl)-2-ethyl-3,4-dihydroquinolin-1(2H)-yl)sulfonyl)-2-((tetrahydro-2H-pyran-4-yl)methoxy)benzyl Alcohol The rest synthesis steps proceeded with reference to the corresponding synthesis method in Example 61, so as to prepare and obtain 80 mg of the title compound (yield: 22%, MS(ESI) m/z: [M+H]+ 499.9).

$^1$H NMR (400 MHz, CDCl$_3$) 1H NMR (400 MHz, CDCl3) δ 7.66 (d, J=8.3 Hz, 1H), 7.45 (d, J=2.0 Hz, 1H), 7.39 (dd, J=8.6, 2.2 Hz, 1H), 7.11-7.04 (m, 1H), 6.83-6.74 (m, 2H), 4.60 (d, J=6.5 Hz, 2H), 4.22-4.09 (m, 1H), 4.03 (dd, J=11.4, 3.7 Hz, 2H), 3.87 (d, J=6.4 Hz, 2H), 3.54-3.36 (m, 3H), 2.39 (m, 1H), 2.31 (dt, J=8.0, 4.3 Hz, 2H), 2.06 (ddd, J=24.1, 19.3, 9.5 Hz, 4H), 1.92-1.80 (m, 3H), 1.76-1.69 (m, 2H), 1.59 (dd, J=12.6, 8.6 Hz, 2H), 1.53-1.36 (m, 4H), 0.93 (t, J=7.4 Hz, 3H).

Example 63

Synthesis of (R)-5-((6-(1,1-difluoroethyl)-2-ethyl-3,4-dihydroquinolin-1(2H)-yl)sulfonyl)-2-((tetrahydro-2H-pyran-4-yl)methoxy)benzyl Alcohol

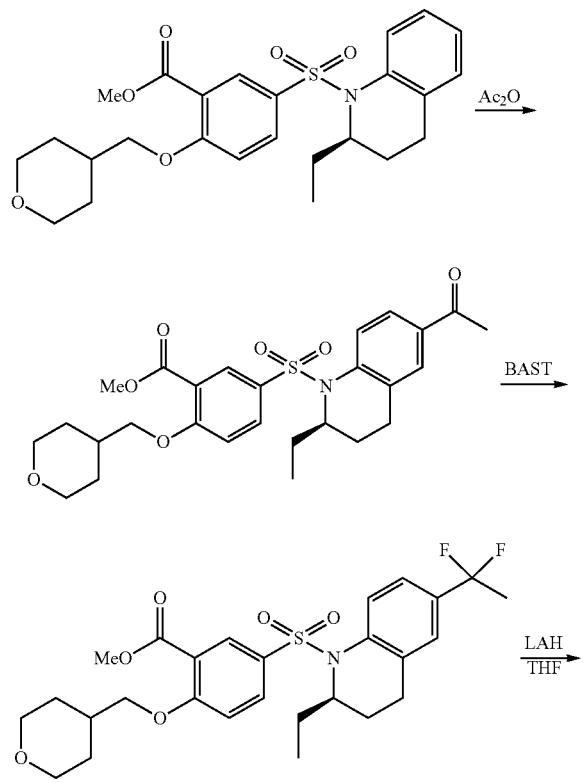

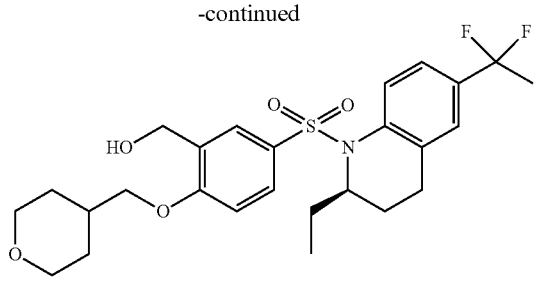

40 mg of the title compound (HPLC: 98.87%) was prepared and obtained using the corresponding intermediate in Example 48 as a raw material, with reference to the corresponding synthesis method in Example 44.

$^1$H NMR (400 MHz, CDCl$_3$) δ 7.83 (d, J=7.9 Hz, 1H), 7.54 (s, 1H), 7.41 (d, J=8.1 Hz, 1H), 7.33 (d, J=8.1 Hz, 1H), 7.14 (s, 1H), 6.79 (d, J=8.5 Hz, 1H), 4.63 (s, 2H), 4.23 (m, 1H), 4.02 (d, J=11.3 Hz, 2H), 3.87 (s, 2H), 3.44 (t, J=11.5 Hz, 2H), 2.51 (m, 1H), 2.09 (m, 2H), 2.01 (m, 1H), 1.92 (t, J=18.0 Hz, 4H), 1.72 (m, 3H), 1.48 (m, 4H), 0.94 (t, 3H).

Example 64

Synthesis of 5-((6-ethyl-2-isobutyl-3,4-dihydroquinolin-1(2H)-yl)sulfonyl)-2-((tetrahydro-2H-pyran-4-yl)methoxy)benzyl Alcohol

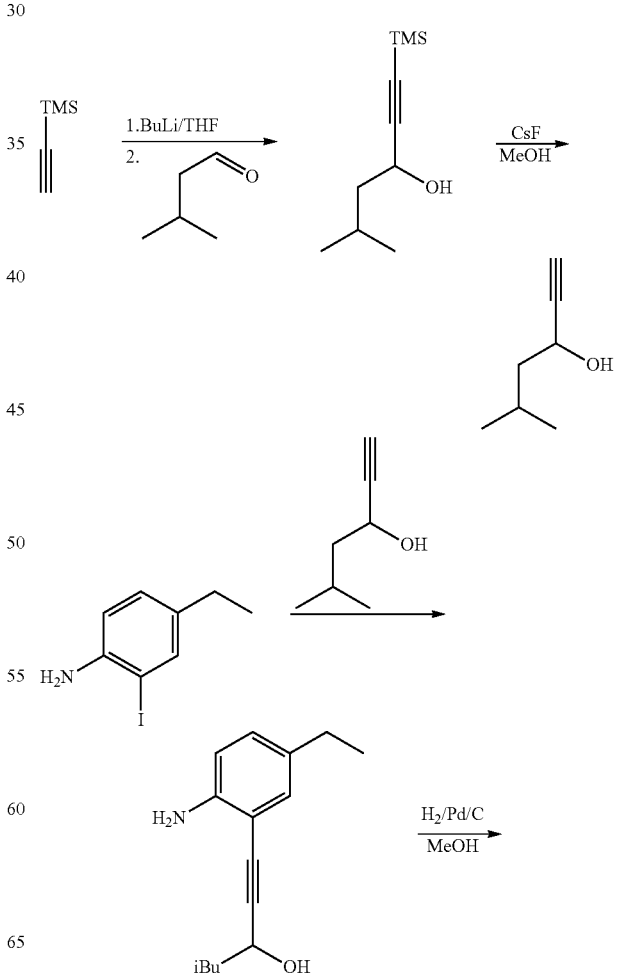

Example 65

Synthesis of (S)-5-((6-ethyl-2-(2,2,2-trifluoroethyl)-3,4-dihydroquinolin-1(2H)-yl) sulfonyl)-2-((tetrahydro-2H-pyran-4-yl)methoxy)benzyl Alcohol

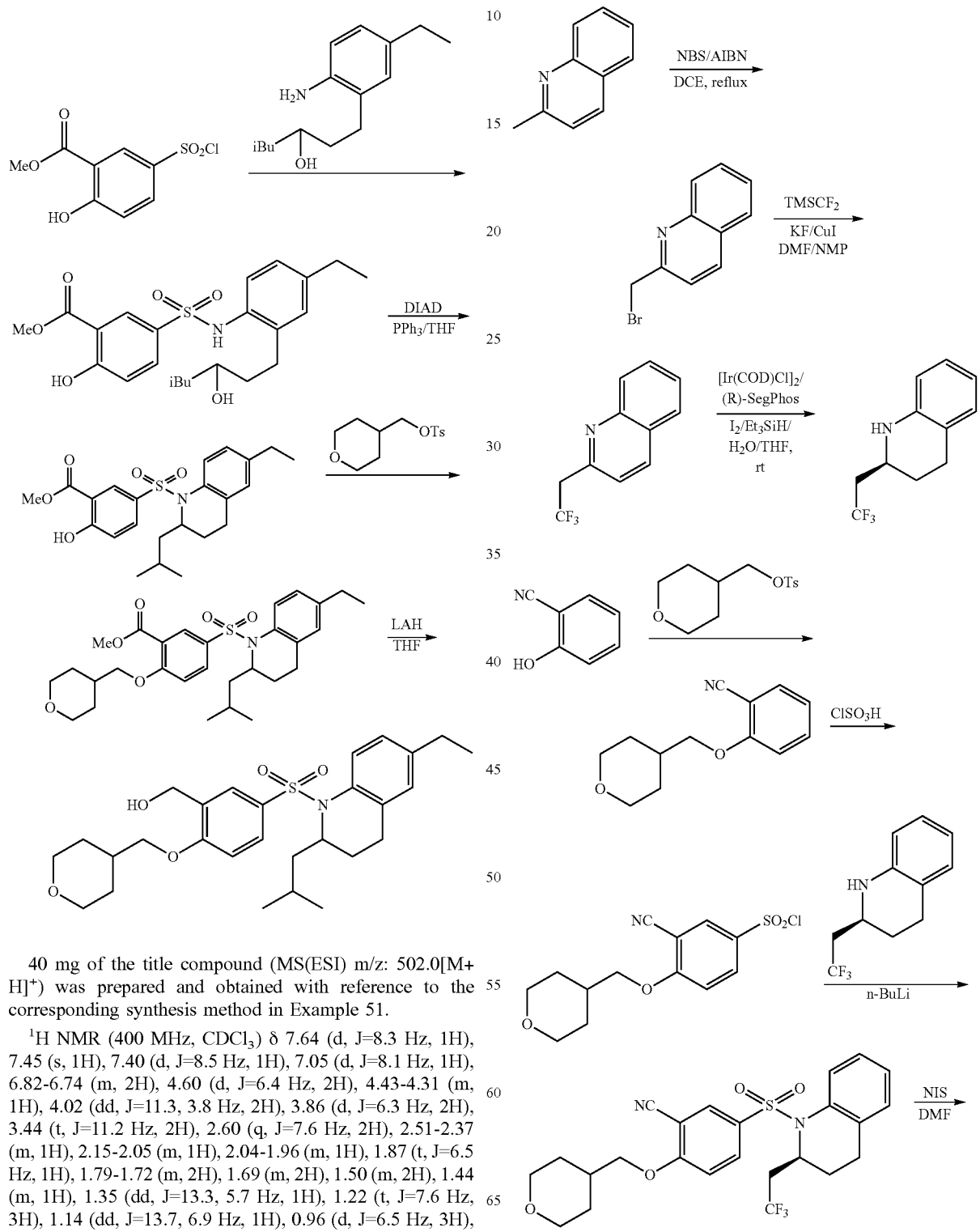

40 mg of the title compound (MS(ESI) m/z: 502.0[M+H]⁺) was prepared and obtained with reference to the corresponding synthesis method in Example 51.

$^1$H NMR (400 MHz, CDCl$_3$) δ 7.64 (d, J=8.3 Hz, 1H), 7.45 (s, 1H), 7.40 (d, J=8.5 Hz, 1H), 7.05 (d, J=8.1 Hz, 1H), 6.82-6.74 (m, 2H), 4.60 (d, J=6.4 Hz, 2H), 4.43-4.31 (m, 1H), 4.02 (dd, J=11.3, 3.8 Hz, 2H), 3.86 (d, J=6.3 Hz, 2H), 3.44 (t, J=11.2 Hz, 2H), 2.60 (q, J=7.6 Hz, 2H), 2.51-2.37 (m, 1H), 2.15-2.05 (m, 1H), 2.04-1.96 (m, 1H), 1.87 (t, J=6.5 Hz, 1H), 1.79-1.72 (m, 2H), 1.69 (m, 2H), 1.50 (m, 2H), 1.44 (m, 1H), 1.35 (dd, J=13.3, 5.7 Hz, 1H), 1.22 (t, J=7.6 Hz, 3H), 1.14 (dd, J=13.7, 6.9 Hz, 1H), 0.96 (d, J=6.5 Hz, 3H), 0.88 (d, J=6.6 Hz, 3H).

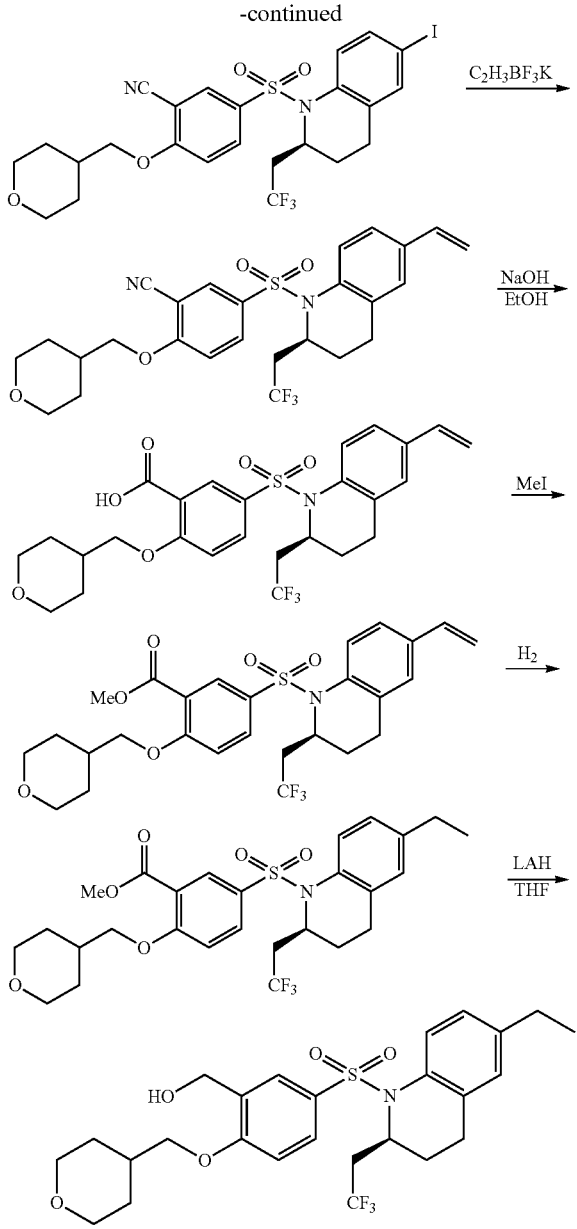

65.1 2-Bromomethylquinoline

A 100 mL single-necked flask was charged with methylquinoline (3.0 g) and azobisisobutyronitrile (207 mg). The mixture was dissolved with dichloroethane (25 mL). The reaction system was protected by nitrogen gas, and N-bromosuccinimide (3.918 g) was added to the mixture in portions. The reaction solution was stirred under reflux for 4 h. A sample was taken, and the appearance of a new spot was apparent as shown by TLC detection. The reaction solution was diluted with dichloromethane (150 mL) and washed with saturated saline (30 mL×3). The organic phase was dried over anhydrous sodium sulfate and filtered, and the filtrate was dried by rotary evaporation under reduced pressure and subjected to silica gel column chromatography (eluent: PE:EA=10:0 to 10:1), so as to obtain 2.0 g of 2-bromomethyl quinoline (MS(ESI) m/z 221.9, 223.8[M+1]$^+$).

65.2 2-(2,2,2-Trifluoromethyl)quinoline

A 50 mL round-bottom flask was charged with 2-bromomethylquinoline (2.0 g), potassium fluoride (785 mg) and cuprous iodide (2.57 g), and N,N-dimethylformamide (10 mL) and N-methylpyrrolidone (10 mL) were added as solvent to dissolve the formers. The system was protected by nitrogen gas. The mixture was stirred at room temperature, and trifluoromethyltrimethylsilane (1.92 g) was added dropwise thereto. The reaction mixture was stirred and reacted at 55° C. for 11 h. A sample was taken and subjected to LC-MS detection, and a peak of the product (211.9[M+1]$^+$) was detected. The reaction solution was filtered through celite, and the filtrate was diluted with ethyl acetate (200 mL), washed with water (50 mL) and washed with saturated saline (50 mL×2). The organic phase was dried over anhydrous sodium sulfate, and the filtrate was dried by rotary evaporation under reduced pressure and subjected to silica gel column chromatography (eluent: PE:EA=10:0 to 10:1), so as to obtain 814 mg of 2-(2,2,2-trifluoromethyl)quinoline (MS(ESI) m/z 211.9[M+1]$^+$).

65.3 (S)-2-(2,2,2-trifluoroethyl)-1,2,3,4-tetrahydroquinoline

A 50 mL round-bottom flask was charged with 1,5-cyclooctadiene-iridium chloride dimer (26 mg), (R)-SegPhos (51.8 mg) and tetrahydrofuran (8 mL). The reaction system was protected by nitrogen gas and stirred at room temperature for 20 min. Iodine (97.9 mg) was added thereto, and the mixture was stirred at room temperature for 20 min. Further, 2-(2,2,2-trifluoromethyl)quinoline (814 mg) and triethylsilane (2.69 g) were added, and the mixture was stirred at room temperature for 10 min. Water (138.9 mg) was added to the system, and the resulting reaction solution was stirred at room temperature for 23 h. A sample was taken and subjected to LC-MS detection, and a peak of the product (216.0[M+1]$^+$) was detected. Water (50 mL) was added to the reaction solution, and the resulting mixture was extracted with ethyl acetate (60 mL×3). The organic phases were combined and washed with saturated saline (50 mL). The organic phase was dried over anhydrous sodium sulfate, and the filtrate was dried by rotary evaporation under reduced pressure and subjected to silica gel column chromatography (eluent: PE:EA=10:0 to 10:1), so as to obtain 680 mg of a yellow solid (MS(ESI) m/z 216.0[M+1]$^+$).

65.4 2-((Tetrahydro-2H-pyran-4-yl)methoxy)benzonitrile

A 100 mL round-bottom flask was charged with 2-hydroxybenzonitrile (2.0 g), p-toluenesulfonate-4-methyl pyran (5.4 g), potassium carbonate (6.95 g), and potassium iodide (278 mg). The mixture was dissolved with N,N-dimethylformamide (30 mL), and was stirred and reacted in an oil bath at 80° C. A sample was taken and subjected to LC-MS detection, and a peak of the product (218.0[M+1]$^+$) was detected. The reaction solution was diluted with ethyl acetate (150 mL) and washed with saturated saline (40 mL×3). The organic phase was dried over anhydrous sodium sulfate and filtered, and the filtrate was dried by rotary evaporation under reduced pressure and subjected to silica gel column chromatography (eluent: PE:EA=10:0 to 10:2), so as to obtain 3.2 g of 2-((tetrahydro-2H-pyran-4-yl)methoxy) benzonitrile (MS(ESI) m/z 218.0 [M+1]$^+$).

65.5 3-Cyano-4-((tetrahydro-2H-pyran-4-yl)methoxy)benzenesulfonyl Chloride

A 50 mL round-bottom flask was charged with 2-((tetrahydro-2H-pyran-4-yl)methoxy) benzonitrile (1.9 g) and thionyl chloride (5.7 mL). The mixture was cooled in an ice bath, and chlorosulfonic acid (1.52 g) was added dropwise thereto. After the completion of the addition, the reaction solution was stirred at room temperature for 24 h. A sample was taken, and TLC detection showed that the reaction of the raw materials was complete. The reaction solution was slowly added dropwise into an ice-water mixture, and the resulting mixture was then extracted with ethyl acetate (50 mL×3). The organic phases were combined and washed with saturated saline (50 mL). The organic phase was dried over anhydrous sodium sulfate and filtered, and the filtrate was dried by rotary evaporation under reduced pressure and subjected to silica gel column chromatography (eluent: PE:EA=10:0 to 2:1), so as to obtain 680 mg of 3-cyano-4-((tetrahydro-2H-pyran-4-yl)methoxy)benzenesulfonyl chloride.

65.6 (S)-2-((tetrahydro-2H-pyran-4-yl)methoxy)-5-((2-(2,2,2-trifluoroethyl)-3,4-dihydro quinolin-1(2H)-yl)sulfonyl)benzonitrile (S)-2-(2,2,2-trifluoroethyl)-1,2,3,4-tetrahydroquinoline (273 mg) was dissolved in tetrahydrofuran (3 mL). The system was cooled at −78° C., and a solution of n-butyl-lithium (0.56 mL) was added dropwise to the reaction solution. The mixture was stirred for 30 min, and a solution of 3-cyano-4-((tetrahydro-2H-pyran-4-yl)methoxy)benzene sulfonyl chloride (610 mg) in tetrahydrofuran (3 mL) was added dropwise thereto. The resulting reaction solution was stirred at −78° C. for 1 h and then heated to −30° C. and stirred for 1 h. A sample was taken and subjected to LC-MS detection, and a peak of the product (494.8[M+1]$^+$) was detected. The reaction solution was quenched with saturated ammonium chloride solution (0.6 mL), diluted with ethyl acetate (100 mL), and washed with saturated saline (30 mL×3). The organic phase was dried over anhydrous sodium sulfate and filtered, and the filtrate was dried by rotary evaporation under reduced pressure and purified by pre-HPLC, so as to obtain 52 mg of the title compound (MS (ESI) m/z 494.8[M+1]$^+$).

65.7 (S)-5-((6-iodo-2-(2,2,2-trifluoroethyl)-3,4-dihydroquinolin-1(2H)-yl)sulfonyl)-2-((tetrahydro-2H-pyran-4-yl)methoxy)benzonitrile A 10 mL single-necked flask was charged with (S)-2-((tetrahydro-2H-pyran-4-yl) methoxy)-5-((2-(2,2,2-trifluoroethyl)-3,4-dihydroquinolin-1(2H)-yl)sulfonyl)benzonitrile (52 mg) and trifluoroacetic acid (1.5 mL). The mixture was cooled in an ice bath, and N-iodosuccinimide (28.4 mg) was added to the reaction solution. After the completion of the addition, the reaction mixture was stirred at room temperature for 22 h. A sample was taken and subjected to LC-MS detection, and a peak of the product (620.7[M+1]$^+$) was detected. The reaction solution was diluted with dichloromethane (80 mL), washed with saturated sodium bicarbonate solution (20 mL×3), and washed with saturated saline (20 mL). The organic phase was dried over anhydrous sodium sulfate and filtered, and the filtrate was dried by rotary evaporation under reduced pressure, so as to obtain 65 mg of the title compound (crude product), MS(ESI) m/z 620.7[M+1]$^+$.

65.8 (S)-2-((tetrahydro-2H-pyran-4-yl)methoxy)-5-((2-(2,2,2-trifluoroethyl)-6-vinyl-3,4-dihydroquinolin-1(2H)-yl)sulfonyl)benzonitrile A 10 mL round-bottom flask was charged with (S)-5-((6-iodo-2-(2,2,2-trifluoroethyl)-3,4-dihydroquinolin-1(2H)-yl) sulfonyl)-2-((tetrahydro-2H-pyran-4-yl)methoxy)benzonitrile (65 mg), potassium vinyltrifluoroborate (28.1 mg), cesium carbonate (68.3 mg), 1,4-dioxane (4 mL) and water (0.7 mL). The mixture was purged with nitrogen gas three times, and tetrakis(triphenylphosphine)palladium (26.1 mg) was added thereto. The mixture was purged with nitrogen gas three times, and heated and stirred in an external bath at 85° C. for 6 h. A sample was taken and subjected to LC-MS detection, and a peak of the product (520.7[M+1]$^+$) was detected. The reaction solution was filtered through celite, and the filtrate was dried by rotary evaporation under reduced pressure. The residual solution was diluted with ethyl acetate (80 mL) and washed with saturated saline (30 mL×2). The organic phase was dried over anhydrous sodium sulfate and filtered, and the filtrate was dried by rotary evaporation under reduced pressure and purified by pre-HPLC, so as to obtain 29 mg of the title compound (MS (ESI) m/z 521.0[M+1]$^+$).

65.9 (S)-2-((tetrahydro-2H-pyran-4-yl)methoxy)-5-((2-(2,2,2-trifluoroethyl)-6-vinyl-3,4-dihydroquinolin-1(2H)-yl)sulfonyl)benzoic Acid A 10 mL round-bottom flask was charged with (S)-2-((tetrahydro-2H-pyran-4-yl) methoxy)-5-((2-(2,2,2-trifluoroethyl)-6-vinyl-3,4-dihydroquinolin-1(2H)-yl)sulfonyl) benzonitrile (29 mg) and ethanol (1 mL), and 5N aqueous sodium hydroxide solution (50 μL) was added thereto. The resulting mixture was heated and stirred at 65° C. for 22 h. A sample was taken and subjected to LC-MS detection, and a peak of the product was detected. The reaction solution was dried by rotary evaporation under reduced pressure and diluted with water (15 mL). The mixture was adjusted to pH 3 with 1N hydrochloric acid and extracted with ethyl acetate (30 mL×3). The organic phases were combined and washed with saturated saline (30 mL). The organic phase was dried over anhydrous sodium sulfate and filtered. The filtrate was dried by rotary evaporation under reduced pressure to obtain 27 mg of the title compound (MS(ESI) m/z 539.8[M+1]$^+$).

65.10 Methyl (S)-2-((tetrahydro-2H-pyran-4-yl)methoxy)-5-((2-(2,2,2-trifluoroethyl)-6-vinyl-3,4-dihydroquinolin-1(2H)-yl)sulfonyl)benzoate A 10 mL round-bottom flask was charged with (S)-2-((tetrahydro-2H-pyran-4-yl) methoxy)-5-((2-(2,2,2-trifluoroethyl)-6-vinyl-3,4-dihydroquinolin-1(2H)-yl)sulfonyl) benzoic acid (27 mg), sodium bicarbonate (6 mg) and N,N-dimethylformamide (1 mL), and iodomethane (8.5 mg) was added thereto. The resulting reaction mixture was stirred at 30° C. for 3 h. A sample was taken and subjected to LC-MS detection, and a peak of the product (553.8[M+1]$^+$) was detected. The reaction solution was diluted with ethyl acetate (50 mL) and washed with saturated saline (15 mL×3). The organic phase was dried over anhydrous sodium sulfate and filtered. The filtrate was dried by rotary evaporation under reduced pressure to obtain 35 mg of the title compound (crude product), which was directly charged in the next step.

65.11 Methyl (S)-2-((tetrahydro-2H-pyran-4-yl)methoxy)-5-((2-(2,2,2-trifluoroethyl)-6-ethyl-3,4-dihydroquinolin-1(2H)-yl)sulfonyl)benzoate A 10 mL round-bottom flask was charged with methyl (S)-2-((tetrahydro-2H-pyran-4-yl) methoxy)-5-((2-(2,2,2-trifluoroethyl)-6-vinyl-3,4-dihydroquinolin-1(2H)-yl)sulfonyl) benzoate (35 mg), palladium hydroxide on carbon (9 mg) and methanol (1 mL), and the mixture was purged with hydrogen gas three times. The resulting reaction mixture was stirred at room temperature for 21 h. A sample was taken and subjected to LC-MS detection, and a peak of the product (555.8[M+1]$^+$) was detected. The reaction solution was filtered through celite, and the filtrate was concentrated under reduced pressure, so as to obtain 36 mg of the title compound (crude product), which was directly charged in the next step.

65.12 (S)-2-((tetrahydro-2H-pyran-4-yl)methoxy)-5-((2-(2,2,2-trifluoroethyl)-6-ethyl-3,4-dihydroquinolin-1(2H)-yl)sulfonyl)benzyl Alcohol A 10 mL round-bottom flask was charged with methyl (S)-2-((tetrahydro-2H-pyran-4-yl) methoxy)-5-((2-(2,2,2-trifluoroethyl)-6-ethyl-3,4-dihydroquinolin-1(2H)-yl)sulfonyl)benzoate (36 mg) and anhydrous tetrahydrofuran (1 mL). The mixture was cooled at 0° C., lithium aluminum hydride (7.4 mg) was added thereto, and the reaction solution was stirred at 0° C. for 1 h. A sample was taken and subjected to LC-MS detection, and a peak of the product (527.9[M+1]$^+$) was detected. In an ice bath, the reaction was quenched with water (0.01 mL), and then 15% aqueous sodium hydroxide solution (0.01 mL) was added dropwise. Water (0.03 mL) was further added dropwise, and the mixture was stirred at room temperature for 5 min. The reaction solution was diluted with tetrahydrofuran (10 mL), and an appropriate amount of anhydrous magnesium sulfate was added. The mixture was stirred for 15 min and filtered through celite. The filtrate was concentrated under reduced pressure, and the crude product was purified by pre-HPLC to obtain 2.5 mg of the title compound (HPLC purity: 99.850%), MS(ESI) m/z 527.8 [M+1]$^+$.
$^1$H NMR (400 MHz, CDCl$_3$): δ 7.61 (d, J=8.4 Hz, 1H), 7.48-7.37 (m, 2H), 7.08 (d, J=8.8 Hz, 1H), 6.82 (s, 1H), 6.80 (d, J=8.4 Hz, 1H), 4.61 (d, J=5.6 Hz, 2H), 4.57-4.50 (m, 1H), 4.03 (dd, J=11.4, 2.4 Hz, 2H), 3.88 (d, J=6.4 Hz, 2H), 3.45 (t, J=10.4 Hz, 2H), 2.74-2.64 (m, 1H), 2.60 (q, J=7.6 Hz, 2H), 2.44-2.36 (m, 1H), 2.28-2.20 (m, 1H), 2.14-2.06 (m, 1H), 2.01-1.93 (m, 1H), 1.89-1.80 (m, 2H), 1.76-1.69 (m, 2H), 1.52-1.41 (m, 3H), 1.22 (t, J=7.6 Hz, 3H).

Example 66

Synthesis of (2-((2,6-diethyl-3,4-dihydroquinolin-1(2H)-yl)sulfonyl)-3-((tetrahydro-2H-pyran-4-yl)methoxy)pyridin-4-yl)methanol

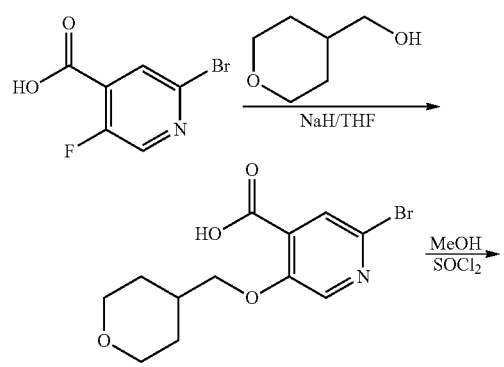

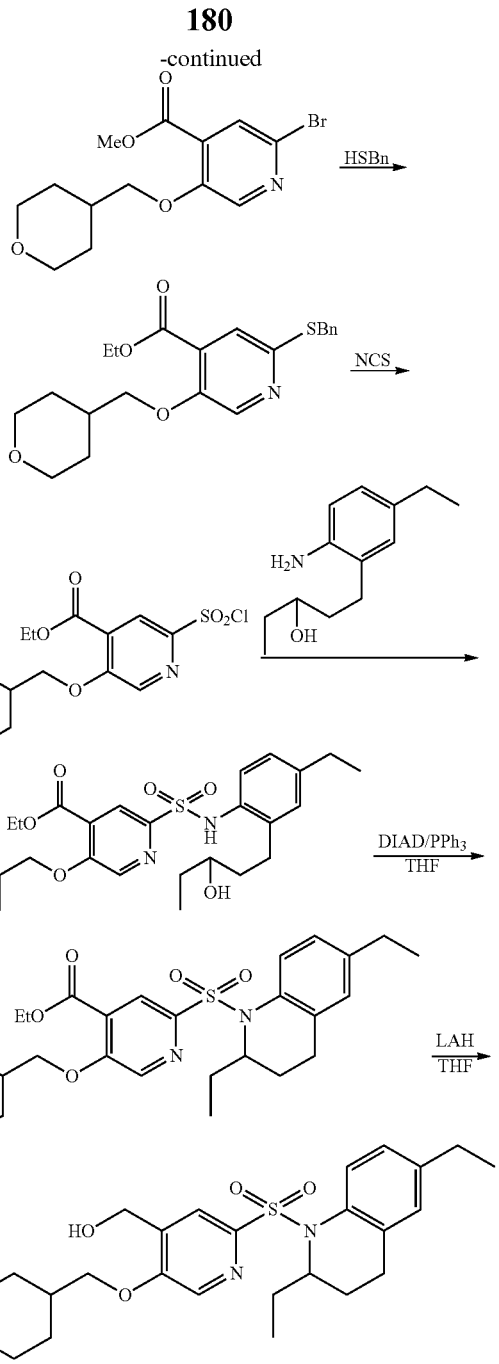

66.1 2-Bromo-5-((tetrahydro-2H-pyran-4-yl)methoxy)pyridine-4-formic Acid

A 50 mL single-necked flask was charged with (tetrahydro-2H-pyran-4-yl)methanol (0.8 g), and tetrahydrofuran (10 mL) was added thereto simultaneously. Under nitrogen protection, sodium hydride (0.8 g) was added to the mixture under a condition of ice bath. After the completion of the addition, the mixture was reacted for 1 h in the ice bath, and then a solution of 2-bromo-5-fluoro-4-picolinic acid (1.0 g) in tetrahydrofuran (5 mL) was added dropwise. After the completion of the dropwise addition, the mixture was naturally warmed and reacted for 16 h. A sample was taken and the spots of the raw materials disappeared as monitored by TLC. The sample was subjected to LC-MS detection, and

181 peaks of the product (315.8 and 317.8 [M+H]+) were detected. The reaction was terminated and quenched by pouring the reaction solution into ice water. The mixture was adjusted to have a pH value of 5 to 6 with 2N HCl and extracted four times with ethyl acetate (15 mL×4). The organic phases were combined, dried over anhydrous sodium sulfate and concentrated, so as to obtain 1.0 g of the title compound (MS(ESI) m/z: 315.8 and 317.8 [M+H]+).

66.2 Methyl 2-bromo-5-((tetrahydro-2H-pyran-4-yl)methoxy)pyridine-4-formate

A 25 mL single-necked flask was charged with 2-bromo-5-((tetrahydro-2H-pyran-4-yl) methoxy)pyridine-4-formic acid (1.0 g), and methanol (12 mL) was added thereto. Thionyl chloride (0.4 mL) was added dropwise under a condition of an ice bath. The mixture was reacted for 2 h under a condition of 65° C. A sample was taken and the spots of the raw materials disappeared as monitored by TLC. The sample was subjected to LC-MS detection, and peaks of the product (330 and 332 [M+H]+) were detected. The reaction solution was concentrated under reduced pressure to remove the reaction solvent. The residue was diluted with ethyl acetate (50 mL), washed twice with saturated sodium bicarbonate solution (20 mL×2), washed once with saturated saline (20 mL×1), dried over anhydrous sodium sulfate, and concentrated, so as to obtain 700 mg of the title compound (MS(ESI) m/z: 330 and 332 [M+1]+).

66.3 (2-((2,6-Diethyl-3,4-dihydroquinolin-1(2H)-yl)sulfonyl)-3-((tetrahydro-2H-pyran-4-yl)methoxy)pyridin-4-yl)methanol The rest synthesis steps proceeded with reference to the corresponding synthesis method in Example 39, so as to prepare and obtain 25 mg of the title compound (MS(ESI) m/z: 475.0 [M+H]+).

$^1$H NMR (400 MHz, CDCl$_3$) δ 8.14 (s, 1H), 7.79 (s, 1H), 7.62 (d, J=8.3 Hz, 1H), 6.99 (dd, J=8.3, 1.7 Hz, 1H), 6.79 (s, 1H), 4.72-4.60 (m, 2H), 4.47-4.38 (m, 1H), 4.02 (dd, J=11.5, 4.0 Hz, 2H), 3.98 (d, J=6.3 Hz, 2H), 3.44 (dd, J=11.6, 10.4 Hz, 2H), 2.55 (dd, J=15.1, 7.5 Hz, 2H), 2.51-2.43 (m, 2H), 2.19-2.05 (m, 2H), 1.99 (ddd, J=19.8, 8.3, 6.0 Hz, 1H), 1.77-1.69 (m, 2H), 1.64-1.56 (m, 1H), 1.48 (ddd, J=26.7, 13.6, 6.2 Hz, 4H), 1.18 (t, J=7.6 Hz, 3H), 0.91 (t, J=7.4 Hz, 3H).

Example 67

Synthesis of (S)-5-((2-methyl-6-trifluoromethyl-3,4-dihydroquinolin-1(2H)-yl)sulfonyl)-2-tetrahydro-2H-pyran-4-yl)methoxy)benzyl Alcohol

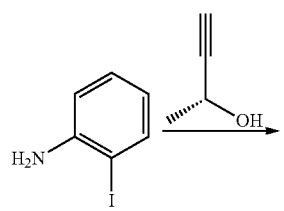

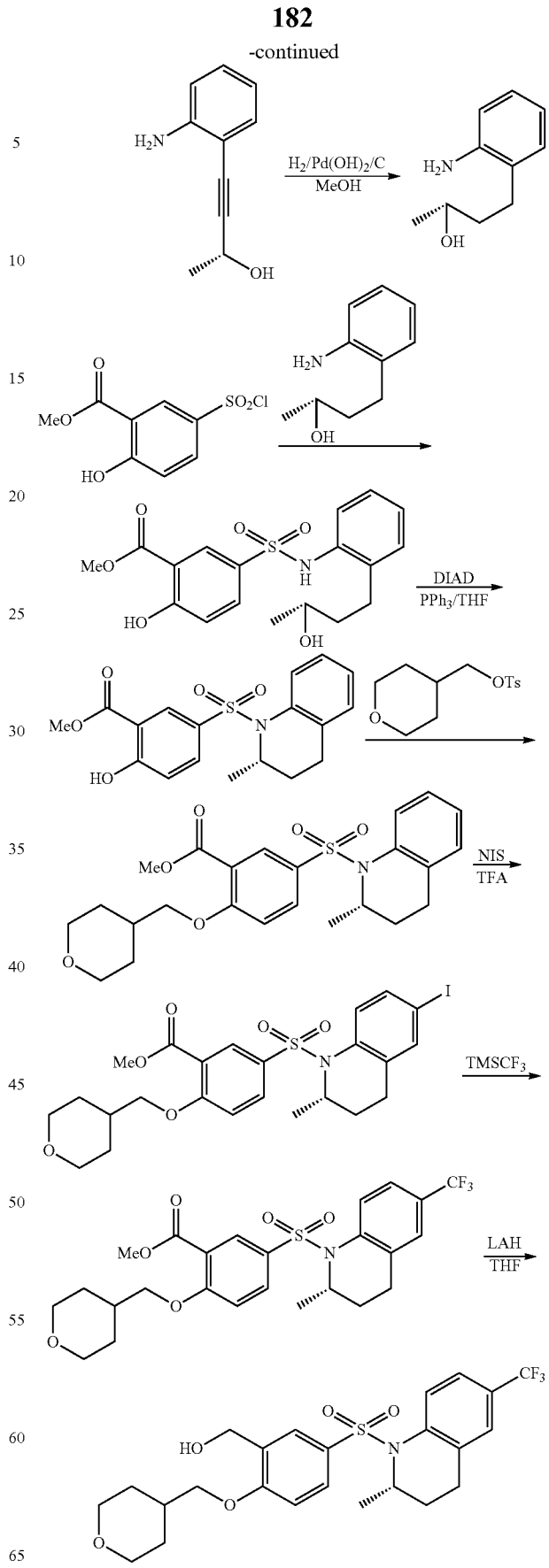

67.1 Methyl (S)-5-((2-methyl-3,4-dihydroquinolin-1(2H)-yl)sulfonyl)-2-((tetrahydro-2H-pyran-4-yl)methoxy)benzoate 2.1 g of the title compound was prepared and obtained with reference to the synthesis methods in steps 12.2 to 12.6 of Example 12.

67.2 Methyl (S)-5-((2-methyl-6-iodo-3,4-dihydroquinolin-1(2H)-yl)sulfonyl)-2-((tetrahydro-2H-pyran-4-yl)methoxy)benzoate A 50 mL single-necked flask was charged with methyl (S)-5-((2-methyl-3,4-dihydroquinolin-1(2H)-yl)sulfonyl)-2-((tetrahydro-2H-pyran-4-yl)methoxy)benzoate (860 mg), and 5 mL of trifluoroacetic acid was added to dissolve the former. The mixture was cooled in an ice bath, and N-iodosuccinimide (442 mg) was added in portions. After the completion of the addition, the mixture was warmed to room temperature and stirred overnight. A sample was taken and TLC detection showed that the spots of the raw materials disappeared. Post-treatment: 20 mL of water was added, and the mixture was extracted three times with ethyl acetate (30 mL×3). The organic phases were combined, washed with an aqueous solution of sodium sulfite, washed with an aqueous solution of sodium carbonate, washed with saturated saline, and dried over anhydrous sodium sulfate, and the solvent was removed by rotary evaporation under reduced pressure, so as to obtain 1.0 g of the title compound.

67.3 (S)-5-((2-methyl-6-trifluoromethyl-3,4-dihydroquinolin-1(2H)-yl)sulfonyl)-2-((tetrahydro-2H-pyran-4-yl)methoxy)benzyl Alcohol The rest synthesis steps proceeded with reference to the corresponding synthesis method in Example 32, so as to prepare and obtain 26 mg of the title compound (HPLC purity: 98.10%, MS(ESI) m/z: 499.9[M+1]+).

$^1$H NMR (400 MHz, CDCl$_3$) δ 7.85 (d, J=8.6 Hz, 1H), 7.60 (d, J=2.0 Hz, 1H), 7.43 (d, J=8.6 Hz, 1H), 7.36 (dd, J=8.6, 2.2 Hz, 1H), 7.25 (d, J=4.4 Hz, 1H), 6.78 (d, J=8.7 Hz, 1H), 4.63 (s, 2H), 4.45 (dt, J=12.5, 6.3 Hz, 1H), 3.99 (dd, J=11.3, 3.7 Hz, 2H), 3.85 (d, J=6.3 Hz, 2H), 3.42 (t, J=11.1 Hz, 2H), 2.63-2.49 (m, 1H), 2.34 (s, 1H), 2.09 (dt, J=11.2, 6.2 Hz, 2H), 1.79 (ddt, J=14.0, 8.7, 5.6 Hz, 1H), 1.70 (d, J=11.7 Hz, 2H), 1.52-1.38 (m, 3H), 1.25 (d, J=6.6 Hz, 3H).

Example 68

Synthesis of (S)-5-((2-methyl-6-trifluoromethyl-3,4-dihydroquinolin-1(2H)-yl)sulfonyl)-2-((tetrahydro-2H-pyran-4-yl)methoxy)benzene Deuterated Methanol

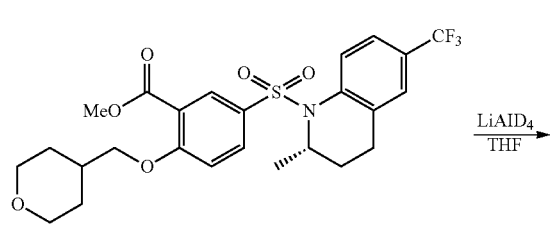

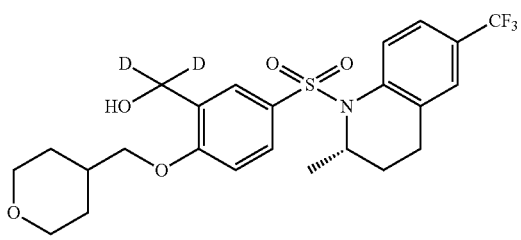

17 mg of the title compound (MS(ESI) m/z: 501.9[M+1]+) was prepared and obtained with reference to the synthesis method in Example 43.

$^1$H NMR (400 MHz, CDCl$_3$) δ 7.88 (d, J=8.6 Hz, 1H), 7.60 (d, J=2.0 Hz, 1H), 7.46 (d, J=8.6 Hz, 1H), 7.41 (d, J=8.6 Hz, 1H), 7.26 (s, 1H), 6.80 (d, J=8.7 Hz, 1H), 4.47 (dt, J=12.6, 6.2 Hz, 1H), 4.02 (dd, J=11.4, 3.9 Hz, 2H), 3.87 (d, J=6.3 Hz, 2H), 3.44 (t, J=11.6 Hz, 2H), 2.63-2.50 (m, 1H), 2.10 (dt, J=16.0, 5.9 Hz, 2H), 2.00 (s, 1H), 1.88-1.77 (m, 1H), 1.72 (d, J=12.9 Hz, 2H), 1.49 (dt, J=21.2, 8.9 Hz, 3H), 1.27 (d, J=6.6 Hz, 3H).

Example 69

Synthesis of 4-((4-((2,6-diethyl-3,4-dihydroquinolin-1(2H)-yl)sulfonyl)-2-(hydroxy methyl)phenoxy)methyl)tetrahydro-2H-thiopyran 1,1-dioxide

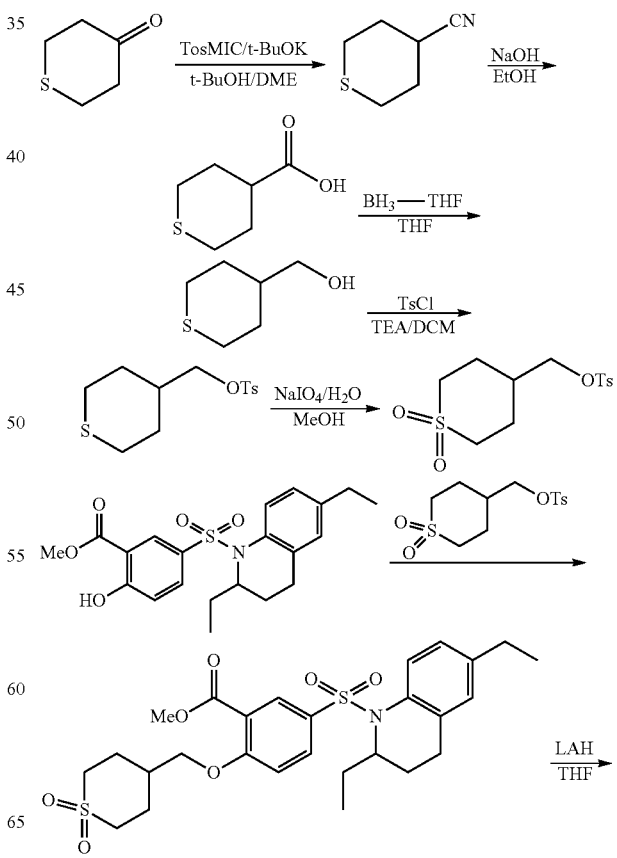

-continued

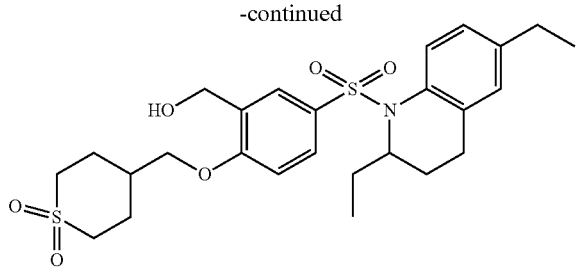

69.1 Tetrahydrothiopyran-4-carbonitrile

A 150 mL single-necked flask was charged with potassium tert-butoxide (3.33 g), and anhydrous tetrahydrofuran (20 mL) and tert-butanol (10 mL) were added at the same time. Under nitrogen protection, a solution of tetrahydrothiopyran-4-one (1.5 g) and p-toluenesulfonylmethyl isocyanide (3.0 g) in ethylene glycol dimethyl ether (30 mL) were added dropwise under a condition of an ice bath. After the completion of the addition, the mixture was reacted at room temperature for 3 h. A sample was taken, and the spots of the raw materials disappeared and the reaction was complete as monitored by TLC. Methyl tert-butyl ether (200 mL) was added to the reaction system. The resulting mixture was washed twice with saturated sodium bicarbonate solution (50 mL×2), dried over anhydrous sodium sulfate, concentrated, and purified by column chromatography, so as to obtain 1.1 g of tetrahydrothiopyran-4-carbonitrile.

69.2 Tetrahydrothiopyran-4-formic Acid

A 25 mL single-necked flask was charged with tetrahydrothiopyran-4-carbonitrile (0.35 g), and ethanol (5 mL) was added thereto. While the mixture was stirred at room temperature, 5N NaOH aqueous solution (3 mL) was added thereto, and the resulting mixture was reacted at 90° C. for 3 h. A sample was taken, and the spots of the raw materials disappeared and the reaction was complete as monitored by TLC. The reaction solution was concentrated to remove ethanol which was the reaction solvent, and the residue was diluted with water (20 mL). The mixture was adjusted to have a pH value of 1 to 2 with 2N HCl and extracted three times with ethyl acetate (15 mL×3). The organic phases were combined, dried over anhydrous sodium sulfate and concentrated, so as to obtain 0.36 g of tetrahydrothiopyran-4-formic acid.

69.3 Tetrahydrothiopyran-4-methanol

A 25 mL single-necked flask was charged with tetrahydrothiopyran-4-formic acid (0.36 g), and anhydrous tetrahydrofuran (5 mL) as the reaction solvent. Under a condition of room temperature, a solution of borane in tetrahydrofuran (1 M, 3.7 mL) was added dropwise. After the completion of the addition, the mixture was reacted at 70° C. for 2 h. A sample was taken, and TLC detection showed that the spots of the raw materials disappeared and the reaction was complete. Methanol was added dropwise to the reaction system to quench the reaction. The resulting mixture was concentrated under reduced pressure to obtain 0.34 g of tetrahydrothiopyran-4-methanol (crude product), which was directly used for the reaction in the next step.

69.4 Methyl 4-tetrahydrothiopyran-p-toluenesulfonate

A 25 mL single-necked flask was charged with tetrahydrothiopyran-4-methanol (0.34 g, crude product), and dichloromethane (5 mL) and triethylamine (0.5 mL) were added thereto as reaction solvents. Under a condition of ice bath, p-toluenesulfonyl chloride (0.52 g) was added in portions. After the completion of the addition, the mixture was naturally warmed to room temperature and reacted for 16 h. A sample was taken, and the spots of the raw materials disappeared and the reaction was complete as monitored by TLC. The reaction was terminated, and the reaction system was diluted by adding dichloromethane (30 mL), washed twice with water (15 mL×2), washed twice with saturated saline (15 mL×2), dried over anhydrous sodium sulfate, and concentrated, so as to obtain 780 mg of methyl 4-tetrahydrothiopyran-p-toluenesulfonate (crude product), which was directly used for the reaction in the next step.

69.5 Methyl (1,1-dioxothiotetrahydropyran)-4-p-toluenesulfonate

A 50 mL single-necked reaction flask was charged with sodium periodate (1.05 g), and water (10 mL) was added to dissolve the former under stirring. Then, a solution of methyl 4-tetrahydrothiopyran-p-toluenesulfonate (780 mg, crude product) in methanol (6 mL) was added dropwise. The mixture was reacted at 60° C. for 2 h. A sample was taken, and the spots of the raw materials disappeared and the reaction was complete as monitored by TLC. The reaction solution was concentrated under reduced pressure to remove methanol, and the residue was diluted with water (10 mL) and extracted three times with ethyl acetate (30 mL×3). The organic phases were combined, washed twice with saturated saline (20 mL×2), dried over anhydrous sodium sulfate, and concentrated, so as to obtain 630 mg of methyl (1,1-dioxothiotetrahydropyran)-4-p-toluene sulfonate.

69.6 Synthesis of 4-((4-((2,6-diethyl-3,4-dihydroquinolin-1(2H)-yl)sulfonyl)-2-(hydroxymethyl)phenoxy)methyl)tetrahydro-2H-thiopyran 1,1-dioxide The rest synthesis steps proceeded with reference to the synthesis methods in Examples 3.6 to 3.7, so as to prepare and obtain 40 mg of the title compound (MS(ESI) m/z: 521.9 [M+H]$^+$).

$^1$H NMR (400 MHz, CDCl$_3$) δ 7.62 (d, J=8.3 Hz, 1H), 7.49 (s, 1H), 7.34 (d, J=8.5 Hz, 1H), 7.05 (d, J=8.0 Hz, 1H), 6.79 (s, 1H), 6.72 (d, J=8.6 Hz, 1H), 4.59 (s, 2H), 4.19-4.10 (m, 1H), 3.90 (d, J=5.4 Hz, 2H), 3.07 (dt, J=25.8, 13.1 Hz, 4H), 2.59 (q, J=7.5 Hz, 2H), 2.43-2.34 (m, 1H), 2.26 (d, J=12.1 Hz, 2H), 2.17-1.97 (m, 4H), 1.90-1.80 (m, 1H), 1.77-1.71 (m, 1H), 1.58 (td, J=14.4, 7.3 Hz, 1H), 1.42 (ddt, J=26.2, 13.0, 6.7 Hz, 2H), 1.22 (t, J=7.6 Hz, 3H), 0.93 (t, J=7.3 Hz, 3H).

Example 70

Synthesis of 5-((2,6-diethyl-3,4-dihydroquinolin-1(2H)-yl)sulfonyl)-2-((4-(methyl sulfonyl)cyclohexyl)oxy)benzyl Alcohol

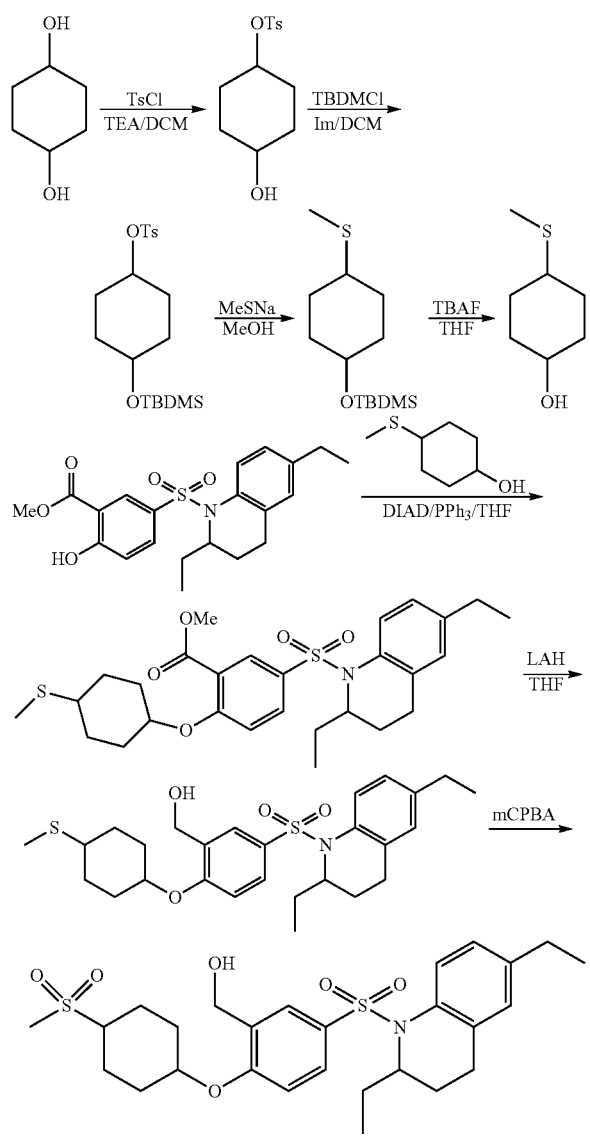

70.1 4-Hydroxycyclohexyl P-toluenesulfonate

A 250 mL single-necked reaction flask was charged with 1,4-cyclohexanediol (10.0 g), and dichloromethane (50 mL) and triethylamine (26 mL) were added thereto. Under nitrogen protection, the system was cooled to 0° C. Then, p-toluenesulfonyl chloride (16.4 g) was added. After the completion of the addition, the mixture was naturally warmed to room temperature and reacted overnight. The reaction was complete as monitored by TLC. The mixture was subjected to purification by column chromatography to obtain 12 g of 4-hydroxycyclohexyl p-toluenesulfonate.

70.2 4-((Tert-butyldimethylsilyl)oxy)cyclohexyl P-toluenesulfonate

A 100 mL single-necked flask was charged with 4-hydroxycyclohexyl p-toluenesulfonate (5 g) and dichloromethane (30 mL), followed by addition of imidazole (3.2 g) and tert-butyldimethylchlorosilane (4.4 g). Under nitrogen protection, the mixture was stirred at room temperature overnight. A sample was taken, and the reaction was complete as monitored by TLC. The mixture was purified by column chromatography to obtain 5.2 g of 4-((tert-butyl dimethyl silyl)oxy)cyclohexyl p-toluenesulfonate.

70.3 Tert-butyldimethyl((4-(methylthio)cyclohexyl)oxy)silane

A 50 mL single-necked flask was charged with 4-((tert-butyldimethylsilyl)oxy) cyclohexyl p-toluenesulfonate (7 g) and methanol (20 mL), followed by addition of 20% aqueous sodium thiomethoxide solution (25 mL). Under nitrogen protection, the mixture was stirred and reacted at 70° C. overnight. A sample was taken and TLC detection showed that the spots of the raw materials disappeared. The reaction system was distilled under reduced pressure until no liquid dripped, extracted with ethyl acetate (35 mL×3), washed twice with saturated saline (20 mL×2), dried over anhydrous sodium sulfate, concentrated, and purified by column chromatography, so as to obtain 2.25 g of the title compound.

70.4 4-(Methylthio)cyclohexanol

A 50 mL single-necked reaction flask was charged with tert-butyldimethyl((4-(methylthio)cyclohexyl)oxy)silane (1.15 g), and anhydrous tetrahydrofuran (20 mL) was added thereto. The mixture was stirred, and tetrabutylammonium fluoride (2.3 g) was added simultaneously. Under nitrogen protection, the mixture was stirred and reacted at room temperature overnight. A sample was taken, and TLC detection showed that the spots of the raw materials disappeared and the reaction was complete. The mixture was concentrated and purified by column chromatography to obtain 440 mg of 4-(methylthio)cyclohexanol.

70.5 Methyl 5-((2,6-diethyl-3,4-dihydroquinolin-1(2H)-yl)sulfonyl)-2-((4-(methylthio) cyclohexyl)oxy)benzoate A 50 mL three-necked flask was charged with triphenylphosphine (2 g), and tetrahydrofuran (15 mL) was added thereto. The mixture was purged with nitrogen gas three times. Under a condition of ice bath, diisopropyl azodicarboxylate (0.75 g) was added dropwise. After the completion of the addition, the mixture was stirred at this temperature for 0.5 h. A solution of 4-(methylthio)cyclohexanol (0.37 g) and methyl 2-hydroxy-5-((2,6-diethyl-3,4-dihydroquinolin-1(2H)-yl)sulfonyl)benzoate (0.5 g) in tetrahydrofuran (5 mL) was added. After the completion of the addition, the mixture was naturally warmed and reacted overnight. A sample was taken and TLC detection showed that the spots of the raw materials disappeared. The sample was subjected to LC-MS detection, and a peak of the product (531.8 [M+H]$^+$) was detected. The reaction system was diluted by adding ethyl acetate (60 mL), washed twice with water (20 mL×2), washed three times with saturated saline (20 mL×3), dried over anhydrous sodium sulfate, concentrated, and purified by column chromatography, so as to obtain 270 mg of the title compound (MS(ESI) m/z: 531.8 [M+H]⁺).

70.6 5-((2,6-diethyl-3,4-dihydroquinolin-1(2H)-yl)sulfonyl)-2-((4-(methylthio)cyclo hexyl)oxy)benzyl Alcohol A 25 mL single-necked flask was charged with compound 7 (250 mg) and anhydrous tetrahydrofuran (6 mL). The mixture was cooled to 0° C. in an ice bath, and lithium tetrahydroaluminate (58 mg) was added in portions. After the completion of the addition, the mixture was reacted at this temperature for 10 min. A sample was taken, and the spots of the raw materials disappeared as monitored by TLC. The sample was subjected to LC-MS detection, and a peak of the product (503.8 [M+H]⁺) was detected. Under a condition of ice bath, water was added to quench the reaction, and the mixture was extracted three times with ethyl acetate (20 mL×3). The organic phases were combined, washed twice with saturated saline (20 mL×2), dried over anhydrous sodium sulfate, and concentrated, so as to obtain 245 mg of the title compound (crude product, MS(ESI) m/z: 503.8 [M+H]⁺).

70.7 5-((2,6-diethyl-3,4-dihydroquinolin-1(2H)-yl)sulfonyl)-2-((4-(methyl sulfonyl)cyclo hexyl)oxy)benzyl Alcohol A 25 mL single-necked flask was charged with 5-((2,6-diethyl-3,4-dihydroquinolin-1(2H)-yl)sulfonyl)-2-((4-(methylthio)cyclohexyl)oxy)benzyl alcohol (240 mg), methanol (10 mL) and water (2 mL) were added thereto as reaction solvents, and potassium peroxymonosulfonate (600 mg) was added under stirring. Under nitrogen protection, the mixture was stirred and reacted at room temperature for 6 h. A sample was taken and the spots of the raw materials disappeared as monitored by TLC. The sample was subjected to LC-MS detection, and a peak of the product (535.9 [M+H]+) was detected. The system was filtered, and the filtrate was concentrated and purified via pre-HPLC, so as to prepare and obtain 60 mg of the title compound (MS(ESI) m/z: [M+H]⁺ 535.9).

¹H NMR (400 MHz, CDCl₃): δ 7.62 (d, J=8.3 Hz, 1H), 7.46 (d, J=2.3 Hz, 1H), 7.37 (dd, J=8.6, 2.3 Hz, 1H), 7.06 (d, J=1.7 Hz, 1H), 6.78 (d, J=8.8 Hz, 2H), 4.55 (d, J=5.9 Hz, 2H), 4.32 (s, 1H), 4.22-4.09 (m, 1H), 2.98-2.88 (m, 1H), 2.87 (s, 3H), 2.59 (q, J=7.6 Hz, 2H), 2.37-2.24 (m, 4H), 1.96 (t, J=6.4 Hz, 1H), 1.90-1.70 (m, 4H), 1.64-1.60 (m, 2H), 1.57-1.49 (m, 2H), 1.42 (ddt, J=26.4, 19.5, 6.5 Hz, 2H), 1.21 (t, J=7.6 Hz, 3H), 0.93 (t, J=7.4 Hz, 3H).

Example 71

Synthesis of (S)-5-((6-(1,1-difluoroethyl)-2-methyl-3,4-dihydroquinolin-1(2H)-yl) sulfonyl)-2-((tetrahydro-2H-pyran-4-yl)methoxy)benzyl Alcohol

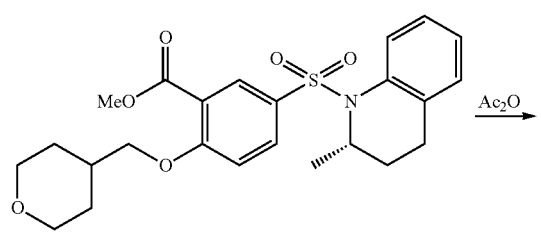

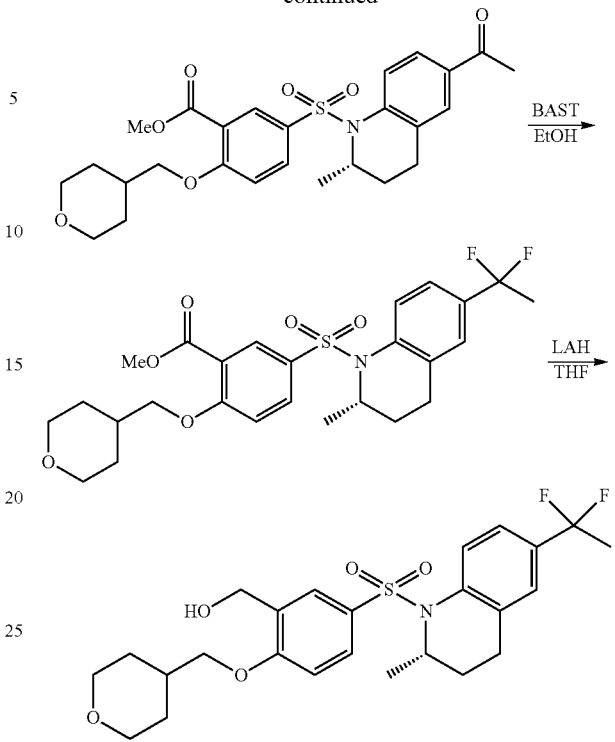

15 mg of the title compound (HPLC: 99.5%) was prepared and obtained using the corresponding intermediate in Example 67 as a raw material, with reference to the corresponding synthesis method in Example 44.

¹H NMR (400 MHz, CDCl₃) δ 7.81 (d, J=8.5 Hz, 1H), 7.54 (d, J=2.3 Hz, 1H), 7.42 (dd, J=8.6, 2.4 Hz, 1H), 7.35 (d, J=8.6 Hz, 1H), 7.16 (s, 1H), 6.80 (d, J=8.7 Hz, 1H), 4.64 (d, J=6.4 Hz, 2H), 4.42 (dt, J=13.0, 6.5 Hz, 1H), 4.03 (dd, J=11.0, 3.6 Hz, 2H), 3.88 (d, J=6.4 Hz, 2H), 3.45 (td, J=11.9, 1.8 Hz, 2H), 2.59-2.44 (m, 1H), 2.11 (s, 1H), 2.06-1.97 (m, 1H), 1.92 (dd, J=24.4, 12.0 Hz, 3H), 1.86-1.79 (m, 1H), 1.73 (d, J=11.1 Hz, 2H), 1.46 (m, 4H), 1.28 (d, J=6.6 Hz, 3H).

Example 72

Synthesis of (R)-5-((6-cyclobutyl)-2-ethyl-3,4-dihydroquinolin-1(2H)-yl)sulfonyl)-2-((tetrahydro-2H-pyran-4-yl)methoxy)benzyl Alcohol

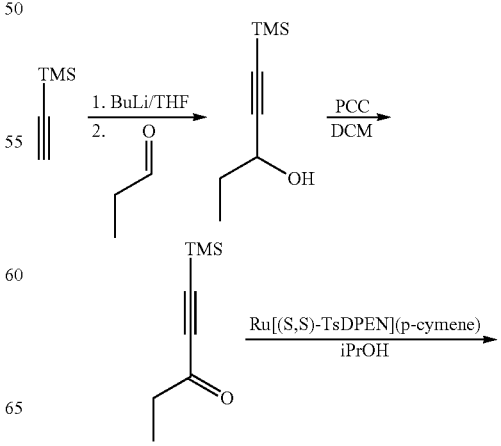

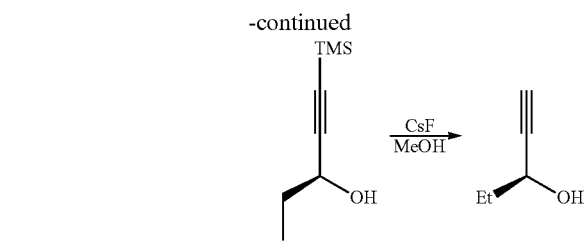

72.1 1-Trimethylsilyl-1-pentyn-3-ol

A 500 mL three-necked flask was successively charged with trimethylsilylacetylene (7.00 g) and anhydrous tetrahydrofuran (100 mL). The mixture was purged with nitrogen gas three times and cooled to below −70° C. in an ethanol-dry ice bath, and a solution of n-butyllithium in n-hexane (31.4 mL, 2.5 M) was added dropwise. After the completion of the dropwise addition, the mixture was stirred at a low temperature for about 30 min. n-Propionaldehyde (5.7 mL) was added dropwise. After the completion of the dropwise addition, the mixture was naturally warmed to room temperature. The reaction was quenched by adding a saturated aqueous ammonium chloride solution. The mixture was extracted with ethyl acetate (50 mL×3), rinsed with saturated saline (20 mL), dried over anhydrous sodium sulfate, concentrated, and distilled under reduced pressure, so as to obtain 1-trimethylsilyl-1-pentyn-3-ol (6.96 g). $^1$H NMR (400 MHz, CDCl$_3$) δ 4.30 (d, J=4.8 Hz, 1H), 1.91 (d, J=4.8 Hz, 1H), 1.76-1.66 (m, 2H), 1.00 (t, J=7.4 Hz, 3H), 0.23-0.03 (m, 9H).

72.2 1-(Trimethyl silyl)-1-pentyn-3-one

A 250 mL single-necked flask was charged with 1-trimethylsilyl-1-pentyn-3-ol (6.00 g), which was diluted with 100 mL of dichloromethane. The mixture was cooled in an ice bath, silica gel (20 g) was added, and pyridinium chlorochromate (9.10 g) was added in portions. After the completion of the dropwise addition, the mixture was reacted at room temperature for 16 h. TLC detection showed that the spots of the raw materials disappeared. The mixture was filtered through celite and distilled under reduced pressure, so as to obtain 1-(trimethylsilyl)-1-pentyn-3-one (5.00 g). $^1$H NMR (400 MHz, CDCl$_3$) δ 2.57 (q, J=7.4 Hz, 2H), 1.12 (t, J=7.4 Hz, 3H), 0.22 (s, 9H).

72.3 (S)-1-trimethylsilyl-1-pentyn-3-ol

A 250 mL single-necked flask was charged with 1-(trimethylsilyl)-1-pentyn-3-one (2.00 g) and anhydrous isopropanol (12 mL), and a solution of (S,S)-Noyori's catalyst (1.02 g, prepared with reference to the following literature: Chem. Eur. J. 21(32), 11387-392, 2015) in 6 mL of anhydrous isopropanol was added thereto. The mixture was reacted at room temperature for 0.5 h. TLC detection showed that the spots of the raw materials disappeared. The solvent was removed by rotary evaporation under reduced pressure. The above procedures were repeated in three batches. The resulting mixtures were combined and purified by column chromatography to obtain (S)-1-trimethylsilyl-1-pentyn-3-ol (7.50 g). $^1$H NMR (400 MHz, CDCl$_3$) δ 4.29 (t, J=6.4 Hz, 1H), 2.16 (s, 1H), 1.75-1.62 (m, 2H), 0.98 (t, J=7.4 Hz, 3H), 0.15 (s, 9H).

72.4 (S)-1-pentyn-3-ol

A 100 mL single-necked flask was charged with (S)-1-trimethylsilyl-1-pentyn-3-ol (7.50 g) and methanol (50 mL), and cesium fluoride (8.00 g) was added in portions. After the completion of the addition, the mixture was reacted at room temperature for 16 h. TLC detection showed that the spots of the raw materials disappeared. The solvent was removed by rotary evaporation under reduced pressure. The resulting mixture was subjected to column chromatography to obtain (S)-1-pentyn-3-ol (4.50 g).

72.5 (R)-5-((6-cyclobutyl)-2-ethyl-3,4-dihydroquinolin-1(2H)-yl)sulfonyl)-2-((tetrahydro-2H-pyran-4-yl)methoxy)benzyl Alcohol The rest synthesis steps proceeded with reference to the corresponding synthesis method in Example 62, so as to prepare and obtain 13 mg of the title compound (MS(ESI) m/z: 499.9 [M+H]$^+$).
$^1$H NMR (400 MHz, CDCl$_3$) δ 7.65 (d, J=8.3 Hz, 1H), 7.46 (d, J=2.0 Hz, 1H), 7.40 (dd, J=8.6, 2.2 Hz, 1H), 7.07 (d, J=6.9 Hz, 1H), 6.85-6.73 (m, 2H), 4.60 (d, J=6.2 Hz, 2H), 4.24-4.10 (m, 1H), 4.02 (dd, J=11.5, 3.8 Hz, 2H), 3.87 (d, J=6.4 Hz, 2H), 3.46 (dt, J=17.9, 11.0 Hz, 3H), 2.48-2.36 (m, 1H), 2.31 (dt, J=8.0, 4.3 Hz, 2H), 2.18-1.98 (m, 4H), 1.97-1.82 (m, 3H), 1.75-1.69 (m, 2H), 1.57 (d, J=7.5 Hz, 2H), 1.44 (m, 4H), 0.93 (t, J=7.4 Hz, 3H).

Example 73

Synthesis of 5-((trans-6-ethyl-3-hydroxy-2-methyl-3,4-dihydroquinolin-1(2H)-yl) sulfonyl)-2-((tetrahydro-2H-pyran-4-yl)methoxy)benzyl Alcohol

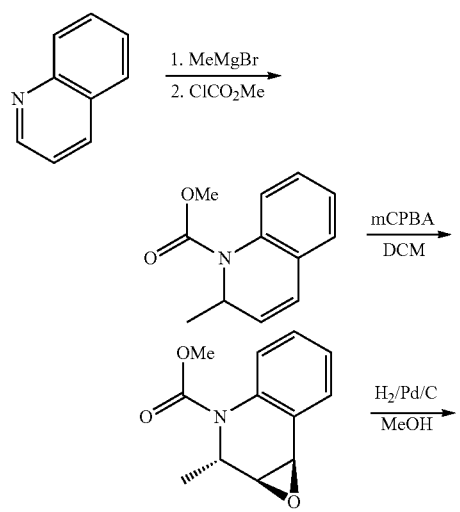

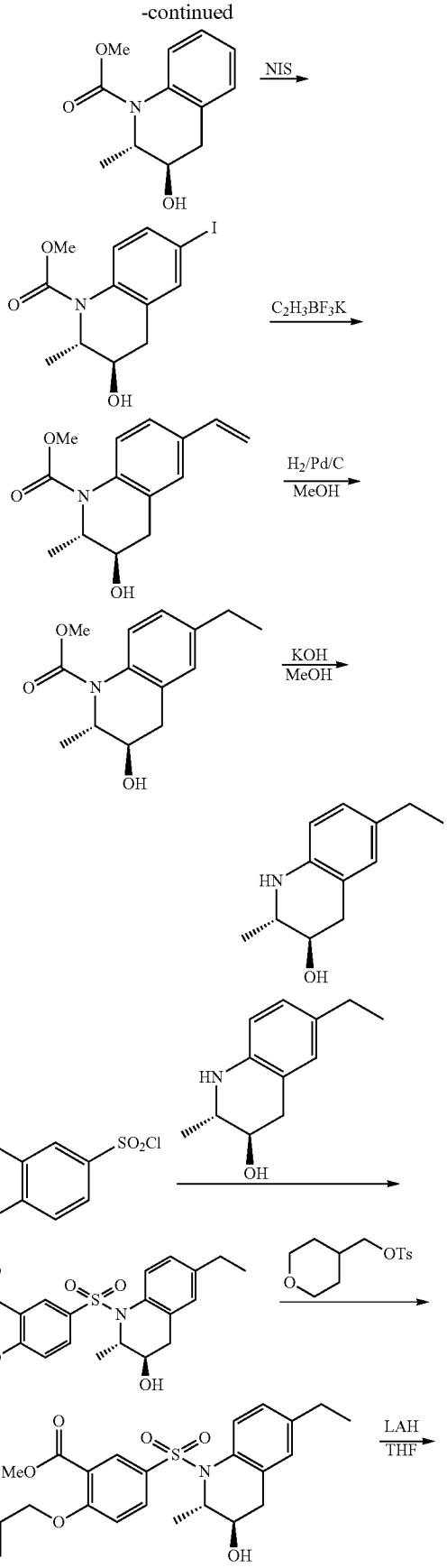

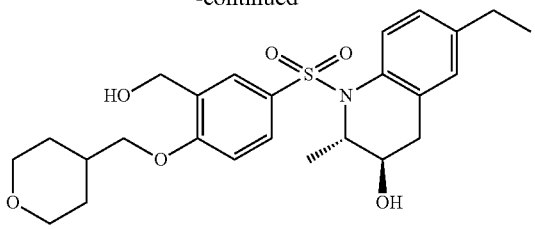

73.1 Methyl 2-methyl quinoline-1(2H)-carboxylate

A 250 mL single-necked flask was charged with quinoline (2.4 mL), and anhydrous dichloromethane (80 mL) was added simultaneously. Under nitrogen protection, the mixture was stirred at −20° C. for 10 min. Methyl magnesium bromide (8 mL) was added dropwise. After the completion of the addition, the mixture was reacted at this temperature for 0.5 h, and methyl chloroformate (17.6 mL) was added dropwise. After the completion of the addition, the mixture was reacted at this temperature for 1 h. A sample was taken, and the spots of the raw materials disappeared and the reaction was complete as monitored by TLC. A saturated ammonium chloride solution was added to the reaction system to quench the reaction, and the resulting mixture was washed twice with saturated sodium chloride solution (20 mL×2), dried over anhydrous sodium sulfate, concentrated and purified by column chromatography, so as to obtain 3.2 g of methyl 2-methylquinoline-1(2H)-carboxylate (MS(ESI) m/z: 204 [M+H]$^+$).

73.2 Methyl trans-2-methyl-3,4-epoxy-3,4-dihydro-quinoline-1(2H)-carboxylate A 100 mL single-necked flask was charged with methyl 2-methylquinoline-1(2H)-carboxylate (3.2 g), and dichloromethane (50 mL) was added thereto. When the mixture was stirred in an ice bath, m-chloroperoxybenzoic acid (3.8 g) was added. After the completion of the addition, the ice bath was removed, and the mixture was reacted at room temperature for 16 h. A sample was taken, and the spots of the raw materials disappeared and the reaction was complete as monitored by TLC. The reaction solution was directly filtered by suction, and the filter cake was washed with an appropriate amount of dichloromethane. The filtrate was washed three times with saturated sodium bicarbonate solution (30 mL×3), washed twice with saturated saline (30 mL×2), dried over anhydrous sodium sulfate, concentrated, and purified by column chromatography, so as to obtain 2.0 g of methyl trans-2-methyl-3,4-epoxy-3,4-dihydroquinoline-1(2H)-carboxylate (MS(ESI) m/z: 220 [M+H]$^+$).

73.3 Methyl trans-2-methyl-3-hydroxy-3,4-dihydro-quinoline-1(2H)-carboxylate A 50 mL single-necked flask was charged with methyl trans-2-methyl-3,4-epoxy-3,4-dihydroquinoline-1(2H)-carboxylate (2.0 g). Under nitrogen protection, 10% palladium on carbon (0.2 g) and anhydrous methanol (20 mL) were added. After the completion of the addition, the mixture was purged with hydrogen gas three times and reacted at 35° C. for 16 h. A sample was taken and TLC detection showed that the spots of the raw materials disappeared. The sample was subjected to LC-MS detection, and a peak of the product (222 [M+H]$^+$) was detected. The reaction was terminated. The resulting mixture was directly filtered by suction, washed with an appropriate amount of ethyl acetate, and concentrated, so as to obtain methyl trans-2-methyl-3-hydroxy-3,4-dihydroquinoline-1(2H)-carboxylate (1.5 g, crude product), which was directly used for the reaction in the next step.

73.4 Methyl trans-6-iodo-2-methyl-3-hydroxy-3,4-dihydroquinoline-1(2H)-carboxylate A 50 mL single-necked flask was charged with methyl trans-2-methyl-3-hydroxy-3,4-dihydroquinoline-1(2H)-carboxylate (1.5 g, crude product), and acetonitrile (20 mL) and trifluoroacetic acid (4 mL) were added. Under a condition of ice bath, N-iodosuccinimide (1.6 g) was added in portions. After the completion of the addition, the mixture was reacted at this temperature for 2 h. A sample was taken, and the spots of the raw materials disappeared and the reaction was complete as monitored by TLC. The reaction system was diluted by adding ethyl acetate (100 mL). The resulting mixture was washed twice with water (20 mL×2), washed twice with saturated sodium bisulfite solution (20 mL×2), washed twice with saturated saline (20 mL×2), dried over anhydrous sodium sulfate, concentrated, and purified by column chromatography, so as to obtain 1.14 g of methyl trans-6-iodo-2-methyl-3-hydroxy-3,4-dihydroquinoline-1(2H)-carboxylate (MS(ESI) m/z: 348 [M+H]$^+$).

73.5 Methyl trans-6-vinyl-2-methyl-3-hydroxy-3,4-dihydroquinoline-1(2H)-carboxylate A 100 mL single-necked reaction flask was charged with methyl trans-6-iodo-2-methyl-3-hydroxy-3,4-dihydroquinoline-1(2H)-carboxylate (1.14 g), potassium vinyltrifluoroborate (0.66 g), tetrakis(triphenylphosphine)palladium (0.38 g) and potassium carbonate (1.14 g), and dioxane (20 mL) and water (4 mL) were added simultaneously. The mixture was purged with nitrogen gas three times and reacted at 70° C. for 16 h. A sample was taken, and the spots of the raw materials disappeared and the reaction was complete as monitored by TLC. The reaction system was diluted by adding ethyl acetate (80 mL). The resulting mixture was washed twice with water (30 mL×2), washed twice with saturated saline (30 mL×2), dried over anhydrous sodium sulfate, concentrated, and purified by column chromatography, so as to obtain methyl trans-6-vinyl-2-methyl-3-hydroxy-3,4-dihydroquinoline-1(2H)-carboxylate (450 mg, MS (ESI) m/z: 248 [M+H]$^+$).

73.6 Methyl trans-6-ethyl-2-methyl-3-hydroxy-3,4-dihydroquinoline-1(2H)-carboxylate A 25 mL single-necked reaction flask was charged with methyl trans-6-vinyl-2-methyl-3-hydroxy-3,4-dihydroquinoline-1(2H)-carboxylate (0.45 g), and methanol (8 mL) and palladium hydroxide on carbon (51 mg) were added simultaneously. The mixture was purged with hydrogen gas three times and reacted at room temperature for 16 h. A sample was taken, and the spots of the raw materials disappeared as monitored by TLC. The sample was subjected to LC-MS detection, and a peak of the product (250 [M+H]$^+$) was detected. The mixture was directly filtered by suction, washed with an appropriate amount of ethyl acetate, and concentrated under reduced pressure, so as to obtain methyl trans-6-ethyl-2-methyl-3-hydroxy-3,4-dihydroquinoline-1

(2H)-carboxylate (370 mg, MS(ESI) m/z: 250 [M+H]⁺), which was directly used for the reaction in the next step.

73.7 trans-6-ethyl-2-methyl-3-hydroxy-1,2,3,4-tetra-hydroquinoline

A 25 mL single-necked reaction flask was charged with methyl trans-6-ethyl-2-methyl-3-hydroxy-3,4-dihydroquinoline-1(2H)-carboxylate (0.37 g), and anhydrous methanol (10 mL) was added simultaneously. Potassium hydroxide (0.5 g) was added, and the mixture was reacted at 55° C. for 16 h. A sample was taken, and TLC detection showed that the spots of the raw materials disappeared. The reaction mixture was concentrated under reduced pressure to remove excess reaction solvent methanol, and the residue was diluted with water and extracted three times with ethyl acetate (30 mL×3). The organic phases were combined, washed twice with saturated saline (20 mL×2), dried over anhydrous sodium sulfate and concentrated, so as to obtain trans-6-ethyl-2-methyl-3-hydroxy-1,2,3,4-tetrahydroquinoline (0.27 g, MS(ESI) m/z: 192 [M+H]⁺), which was directly used for the reaction in the next step.

73.8 5-((trans-6-ethyl-3-hydroxy-2-methyl-3,4-dihydroquinolin-1(2H)-yl)sulfonyl)-2-((tetrahydro-2H-pyran-4-yl)methoxy)benzyl Alcohol The rest reaction steps proceeded with reference to the corresponding synthesis method in Example 3, so as to prepare and obtain 21 mg of the title compound (MS(ESI) m/z: 475.9 [M+H]⁺).

¹H NMR (400 MHz, CDCl₃) δ 7.78 (d, J=1.6 Hz, 1H), 7.56 (d, J=8.3 Hz, 1H), 7.43 (dd, J=8.6, 2.0 Hz, 1H), 7.03 (d, J=7.4 Hz, 1H), 6.82 (s, 1H), 6.76 (d, J=8.7 Hz, 1H), 4.64 (dd, J=43.4, 13.9 Hz, 2H), 4.21 (p, J=6.3 Hz, 1H), 4.01 (dd, J=11.2, 3.4 Hz, 2H), 3.89-3.81 (m, 2H), 3.57 (s, 1H), 3.44 (t, J=11.2 Hz, 2H), 3.06 (d, J=20.7 Hz, 2H), 2.64 (dd, J=15.2, 4.3 Hz, 1H), 2.57 (q, J=7.6 Hz, 2H), 2.08 (d, J=4.0 Hz, 1H), 1.89 (dd, J=15.2, 7.8 Hz, 1H), 1.71 (d, J=12.7 Hz, 2H), 1.48 (qd, J=12.5, 4.2 Hz, 2H), 1.31 (d, J=6.6 Hz, 3H), 1.19 (t, J=7.6 Hz, 3H).

Example 74

Synthesis of (S)-5-((2-cyclopropyl-6-ethyl-3,4-dihydroquinolin-1(2H)-yl)sulfonyl)-2-((tetrahydro-2H-pyran-4-yl)methoxy)benzyl Alcohol

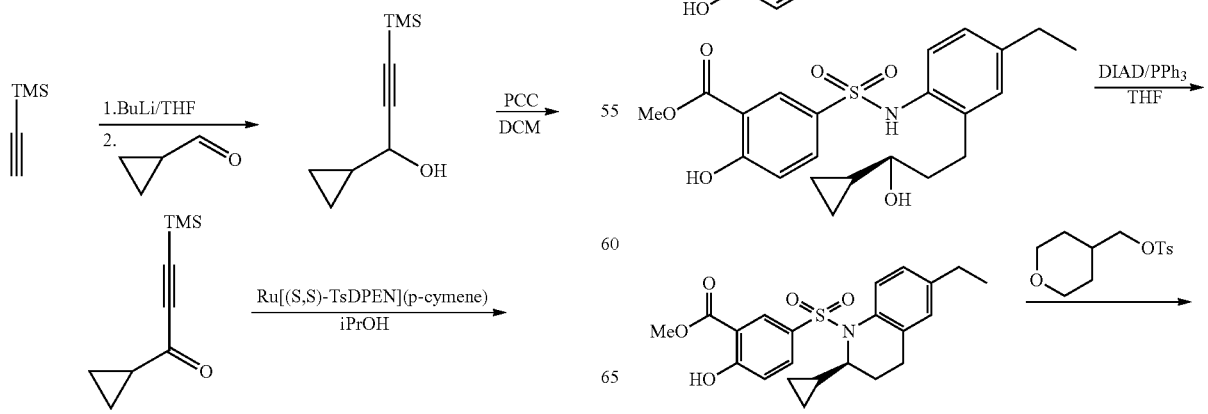

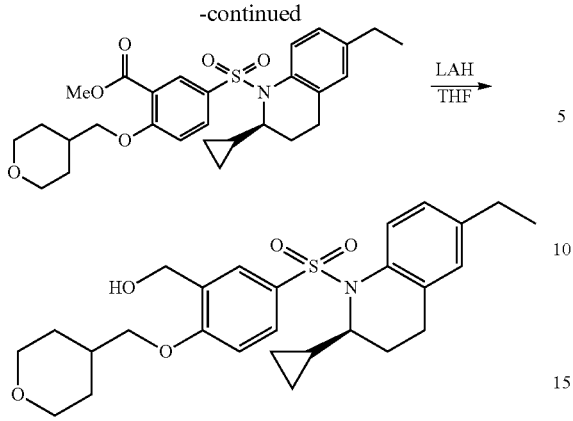

68 mg of the title compound (MS(ESI) m/z: [M+H]+ 486) was prepared and obtained with reference to the corresponding synthesis method in Example 72.

$^1$H NMR (400 MHz, CDCl$_3$) δ 7.65 (d, J=8.3 Hz, 1H), 7.48 (d, J=1.9 Hz, 1H), 7.38 (dd, J=8.6, 2.1 Hz, 1H), 7.04 (d, J=8.2 Hz, 1H), 6.83 (s, 1H), 6.76 (d, J=8.7 Hz, 1H), 4.60 (s, 2H), 4.02 (dd, J=11.3, 3.8 Hz, 2H), 3.86 (d, J=6.3 Hz, 2H), 3.65 (dt, J=8.4, 5.6 Hz, 1H), 3.44 (t, J=11.2 Hz, 2H), 2.59 (dd, J=15.1, 7.5 Hz, 2H), 2.54 (d, J=8.4 Hz, 1H), 2.17-2.06 (m, 2H), 2.01 (dt, J=16.3, 6.2 Hz, 1H), 1.74 (m, 3H), 1.60 (m, 1H), 1.47 (ddd, J=25.0, 12.4, 4.4 Hz, 2H), 1.22 (t, J=7.6 Hz, 3H), 0.95-0.86 (m, 1H), 0.55-0.43 (m, 3H), 0.38-0.31 (m, 1H).

Example 75

Synthesis of 5-((2-cyclobutyl-6-ethyl-3,4-dihydro-quinolin-1(2H)-yl)sulfonyl)-2-((tetrahydro-2H-pyran-4-yl)methoxy)benzyl Alcohol

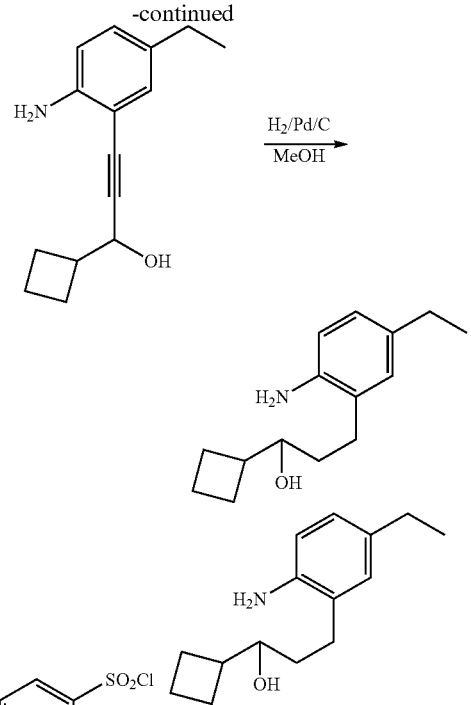

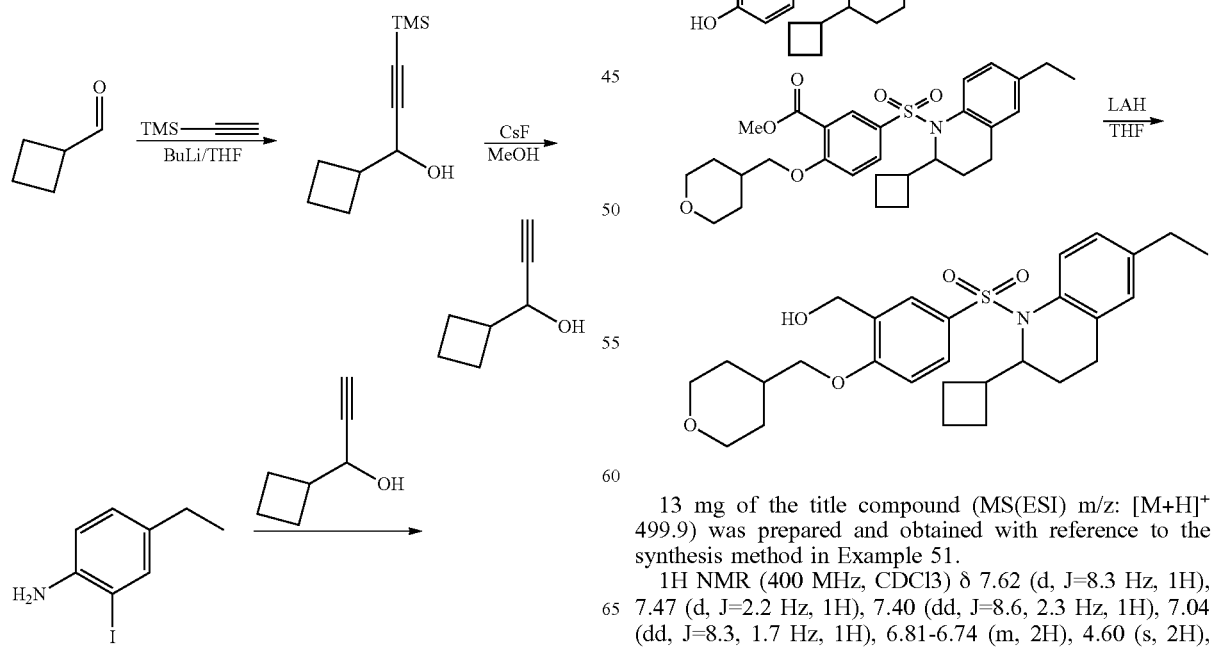

13 mg of the title compound (MS(ESI) m/z: [M+H]+ 499.9) was prepared and obtained with reference to the synthesis method in Example 51.

1H NMR (400 MHz, CDCl3) δ 7.62 (d, J=8.3 Hz, 1H), 7.47 (d, J=2.2 Hz, 1H), 7.40 (dd, J=8.6, 2.3 Hz, 1H), 7.04 (dd, J=8.3, 1.7 Hz, 1H), 6.81-6.74 (m, 2H), 4.60 (s, 2H), 4.26-4.18 (m, 1H), 4.02 (dd, J=11.3, 3.7 Hz, 2H), 3.86 (d,

J=6.4 Hz, 2H), 3.44 (td, J=11.8, 1.7 Hz, 2H), 2.59 (q, J=7.6 Hz, 2H), 2.44-2.25 (m, 2H), 2.09 (s, 1H), 2.01-1.89 (m, 4H), 1.80-1.72 (m, 4H), 1.55 (dd, J=14.6, 6.2 Hz, 1H), 1.51-1.35 (m, 3H), 1.27 (d, J=12.1 Hz, 2H), 1.22 (t, J=7.6 Hz, 3H).

Example 76

Synthesis of 5-((2-cyclopropyl-6,8-dimethyl-3,4-dihydroquinolin-1(2H)-yl)sulfonyl)-2-((tetrahydro-2H-pyran-4-yl)methoxy)benzyl Alcohol

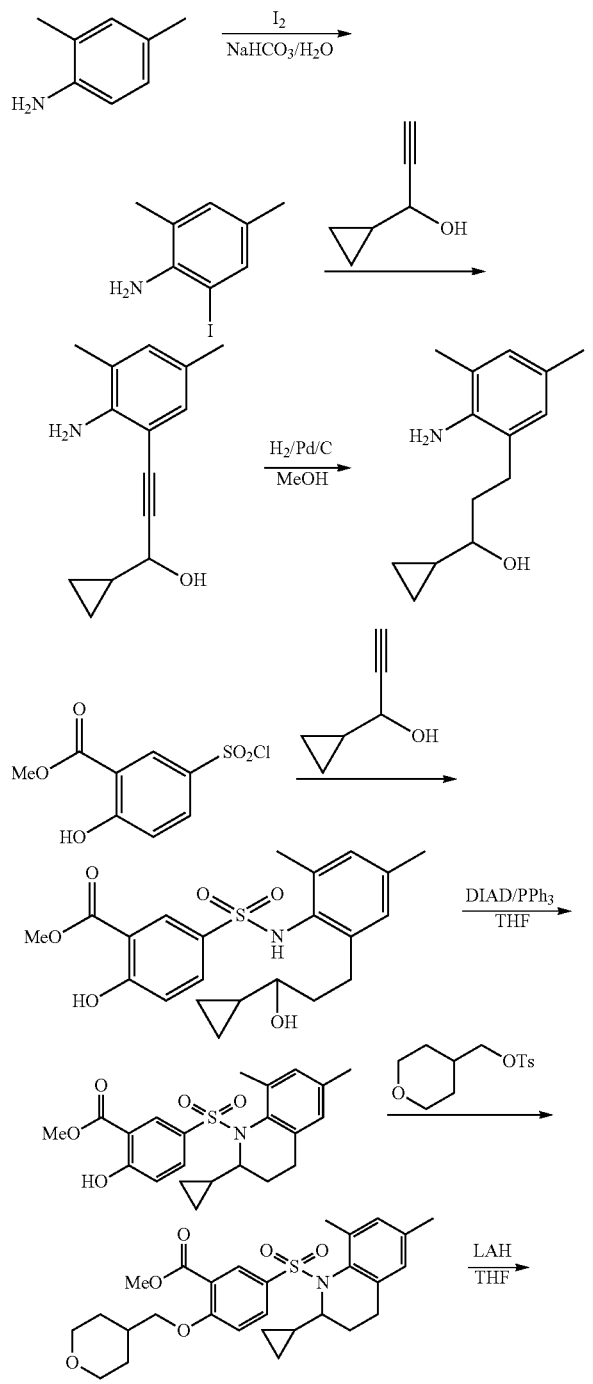

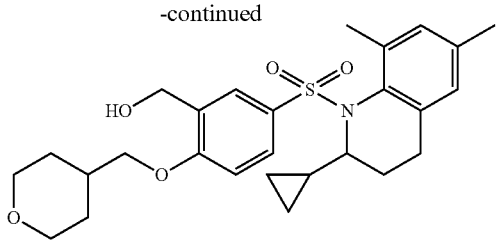

72.91 mg of the title compound (HPLC purity: 99.72%) was prepared and obtained with reference to the corresponding synthesis method in Example 60.

¹H NMR (400 MHz, CDCl₃) δ 7.56 (d, J=2.2 Hz, 1H), 7.42 (dd, J=8.6, 2.3 Hz, 1H), 7.01 (s, 1H), 6.82 (d, J=8.7 Hz, 1H), 6.65 (s, 1H), 4.66 (s, 2H), 4.05 (dd, J=11.3, 3.7 Hz, 2H), 3.91 (d, J=6.3 Hz, 2H), 3.74-3.64 (m, 1H), 3.47 (td, J=11.8, 1.7 Hz, 2H), 2.51 (s, 3H), 2.30 (s, 3H), 2.21-2.07 (m, 3H), 2.07-1.99 (m, 1H), 1.76 (d, J=12.7 Hz, 2H), 1.50 (qd, J=12.5, 4.5 Hz, 2H), 1.39-1.30 (m, 1H), 1.29-1.21 (m, 1H), 0.85-0.73 (m, 1H), 0.55-0.35 (m, 4H).

Example 77

Synthesis of 5-((2-cyclopropyl-6-isopropyl-3,4-dihydroquinolin-1(2H)-yl)sulfonyl)-2-((tetrahydro-2H-pyran-4-yl)methoxy)benzyl Alcohol

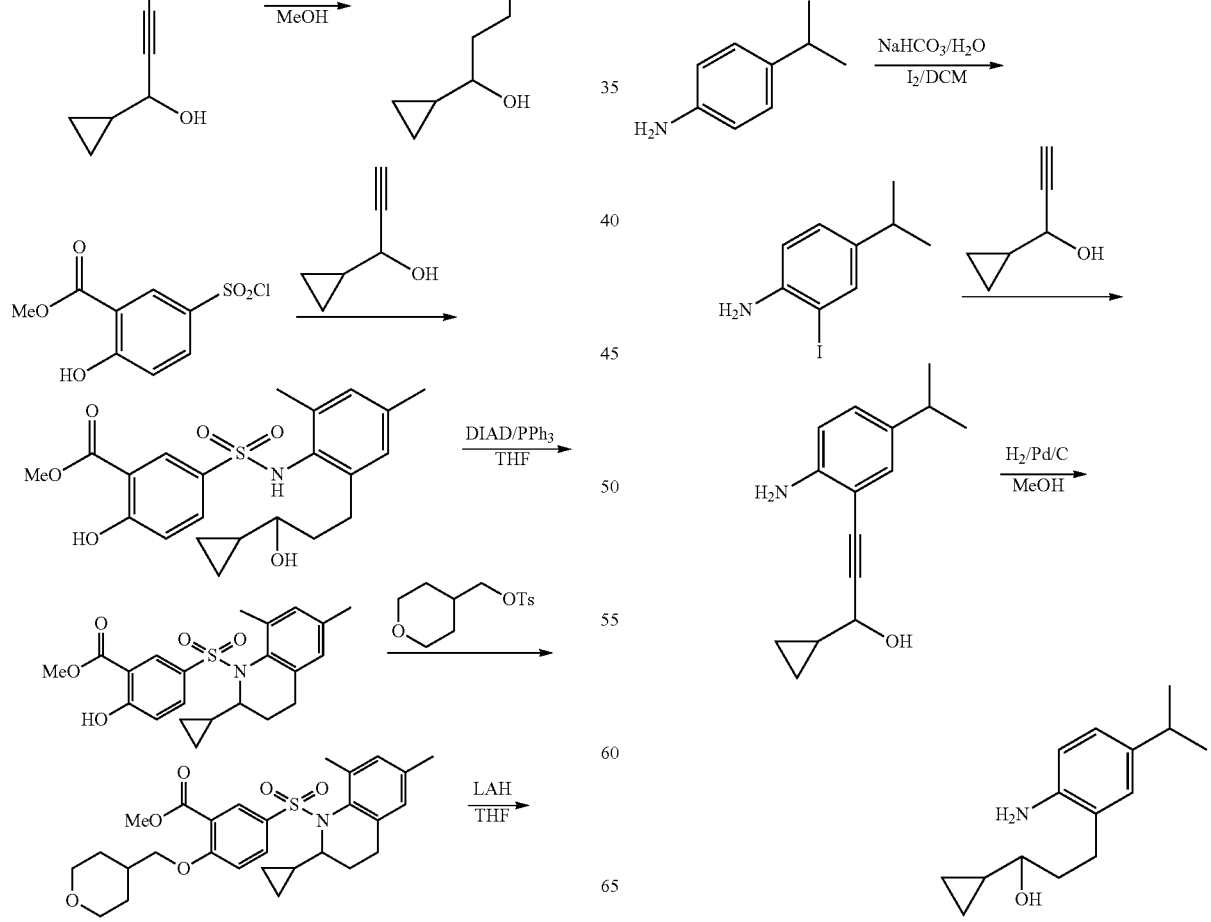

204

Example 78

Synthesis of 6-ethyl-1-((3-(hydroxymethyl)-4-(tetrahydro-2H-pyran-4-yl)methoxy) phenyl)sulfonyl)-2-methyl-2,3-dihydroquinolin-4(1H)-one

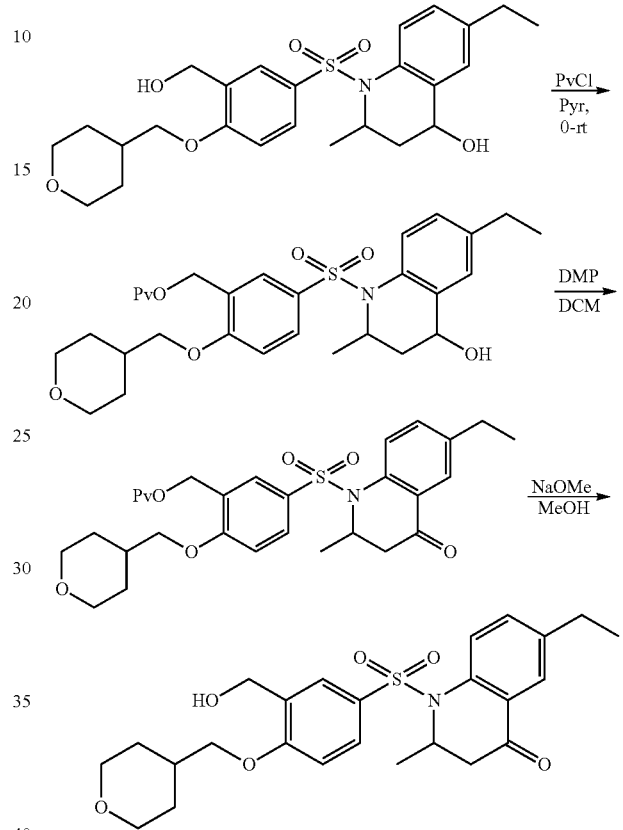

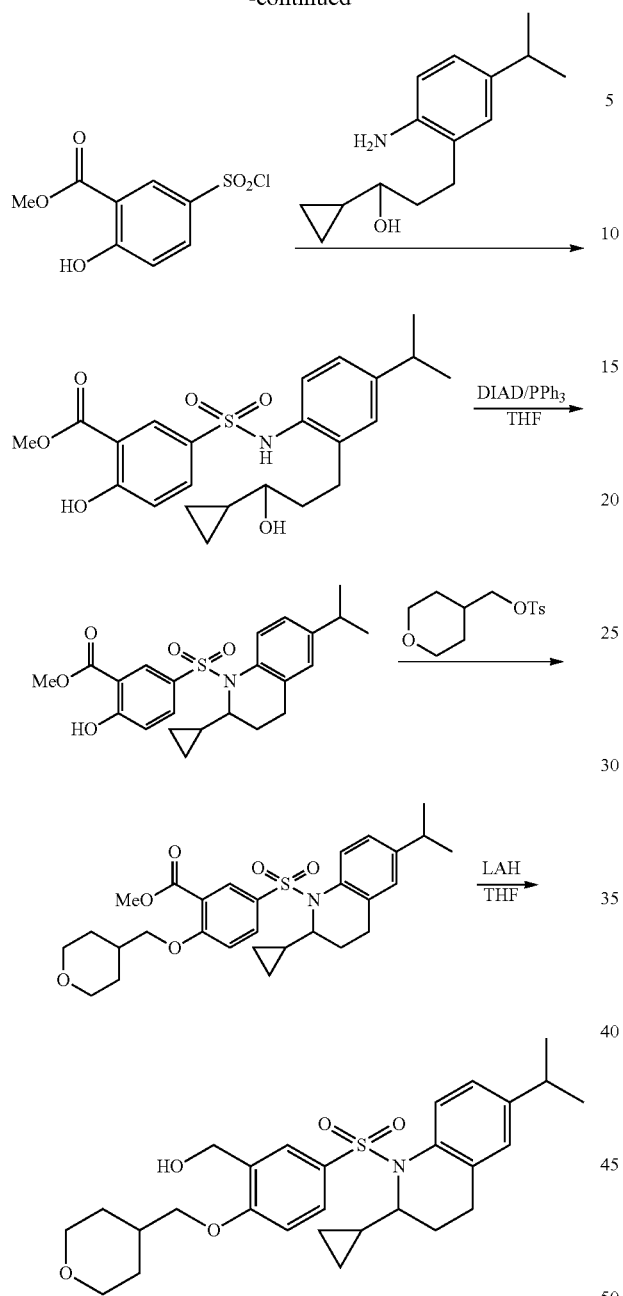

25.2 mg of the title compound (HPLC purity: 99.73%, MS(ESI) m/z 500.3[M+1]$^+$) was prepared and obtained with reference to the corresponding synthesis method in Example 60.

$^1$H NMR (400 MHz, CDCl$_3$) δ 7.65 (d, J=8.4 Hz, 1H), 7.49-7.38 (m, 2H), 7.07 (d, J=8.4 Hz, 1H), 6.84 (s, 1H), 6.76 (d, J=8.4 Hz, 1H), 4.58 (d, J=4.5 Hz, 2H), 4.01 (dd, J=11.3, 3.6 Hz, 2H), 3.86 (d, J=6.3 Hz, 2H), 3.64 (dt, J=8.5, 5.6 Hz, 1H), 3.44 (t, J=11.6 Hz, 2H), 2.84 (dt, J=13.8, 6.9 Hz, 1H), 2.63-2.48 (m, 1H), 2.16-2.05 (m, 1H), 2.05-1.92 (m, 2H), 1.72 (m, 3H), 1.60 (m, 1H), 1.47 (ddd, J=25.0, 12.4, 4.4 Hz, 2H), 1.22 (d, J=6.9 Hz, 6H), 0.94-0.87 (m, 1H), 0.55-0.41 (m, 3H), 0.33 (m, 1H).

78.1 5-((6-Ethyl-4-hydroxy-2-methyl-3,4-dihydroquinolin-1(2H)-yl)sulfonyl)-2-((tetrahydro-2H-pyran-4-yl)methoxy)benzyl pivalate A 10 mL single-necked flask was charged with 5-((6-ethyl-4-hydroxy-2-methyl-3,4-dihydroquinolin-1(2H)-yl)sulfonyl)-2-((tetrahydro-2H-pyran-4-yl)methoxy)benzyl alcohol (0.24 g, Example 37.4), and pyridine (3 mL) was added thereto. Under a condition of 0° C., pivaloyl chloride (0.1 mL) was added. The mixture was reacted at room temperature for 16 h. A sample was taken, and the raw materials disappeared as monitored by TLC. The reaction mixture was concentrated under reduced pressure to remove pyridine. The residue was diluted with ethyl acetate (60 mL), washed twice with saturated sodium chloride solution (20 mL×2), dried over anhydrous sodium sulfate, and concentrated, so as to obtain the title compound (350 mg, crude product, MS(ESI) m/z: 542 [M–OH]$^+$), which was directly used for the reaction in the next step without purification.

78.2 5-((6-Ethyl-2-methyl-4-oxo-3,4-dihydroquinolin-1(2H)-yl)sulfonyl)-2-((tetrahydro-2H-pyran-4-yl)methoxy)benzyl Pivalate A 10 mL single-necked flask was charged with 5-((6-ethyl-4-hydroxy-2-methyl-3,4-dihydroquinolin-1(2H)-yl)sulfonyl)-2-((tetrahydro-2H-pyran-4-yl)methoxy)benzyl pivalate (0.35 g, crude product) and dichloromethane (6 mL), and Dess-Martin periodinane (0.32 g) was added while the mixture was stirred in an ice bath. The mixture was reacted at room temperature for 2 h. A sample was taken, and the spots of the raw materials disappeared as monitored by TLC. The reaction solution was directly filtered by suction and washed with an appropriate amount of dichloromethane. The organic phase was washed twice with saturated sodium chloride solution (10 mL×2), dried over anhydrous sodium sulfate, and concentrated, so as to obtain the title compound (400 mg, crude product), which was directly used for the reaction in the next step without purification.

78.3 Synthesis of 6-ethyl-1-((3-(hydroxymethyl)-4-(tetrahydro-2H-pyran-4-yl)methoxy) phenyl)sulfonyl)-2-methyl-2,3-dihydroquinolin-4(1H)-one A 50 mL single-necked flask was charged with 5-((6-ethyl-2-methyl-4-oxo-3,4-dihydroquinolin-1(2H)-yl)sulfonyl)-2-((tetrahydro-2H-pyran-4-yl)methoxy)benzyl pivalate (0.40 g, crude product), and methanol (6 mL) was added thereto. The mixture was cooled in an ice bath, and sodium methoxide (0.041 g) was added thereto. After the completion of the addition, the ice bath was removed, and the mixture was stirred and reacted at room temperature for 16 h. A sample was taken and TLC detection showed that the spots of the raw materials disappeared. The sample was subjected to LC-MS detection, and a peak of the product (473.8 [M+H]$^+$) was detected. The reaction system was diluted by adding ethyl acetate (60 mL), washed twice with saturated saline (20 mL×2), dried over anhydrous sodium sulfate, and concentrated. The crude product was directly subjected to HPLC-preparation, so as to finally obtain 8 mg of the title compound (MS(ESI) m/z: 474.0 [M+H]$^+$).

$^1$H NMR (400 MHz, CDCl$_3$) δ 7.79 (d, J=8.4 Hz, 1H), 7.74 (d, J=1.7 Hz, 1H), 7.67 (d, J=2.0 Hz, 1H), 7.48 (dd, J=8.6, 2.2 Hz, 1H), 7.45 (dd, J=8.5, 1.9 Hz, 1H), 6.80 (d, J=8.7 Hz, 1H), 4.91-4.82 (m, 1H), 4.63 (s, 2H), 4.02 (dd, J=11.2, 3.8 Hz, 2H), 3.86 (d, J=6.3 Hz, 2H), 3.44 (t, J=11.0 Hz, 2H), 2.67 (q, J=7.6 Hz, 2H), 2.40 (dd, J=17.9, 5.9 Hz, 1H), 2.22 (d, J=17.9 Hz, 1H), 2.09 (m, 2H), 1.73 (s, 2H), 1.54-1.42 (m, 2H), 1.26 (dd, J=13.5, 7.1 Hz, 6H).

Example 79

Synthesis of (S)-5-((6-cyclobutyl)-2-cyclopropyl-3,4-dihydroquinolin-1(2H)-yl)sulfonyl)-2-((tetrahydro-2H-pyran-4-yl)methoxy)benzyl Alcohol

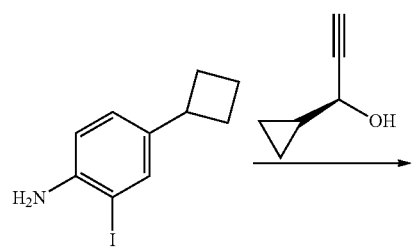

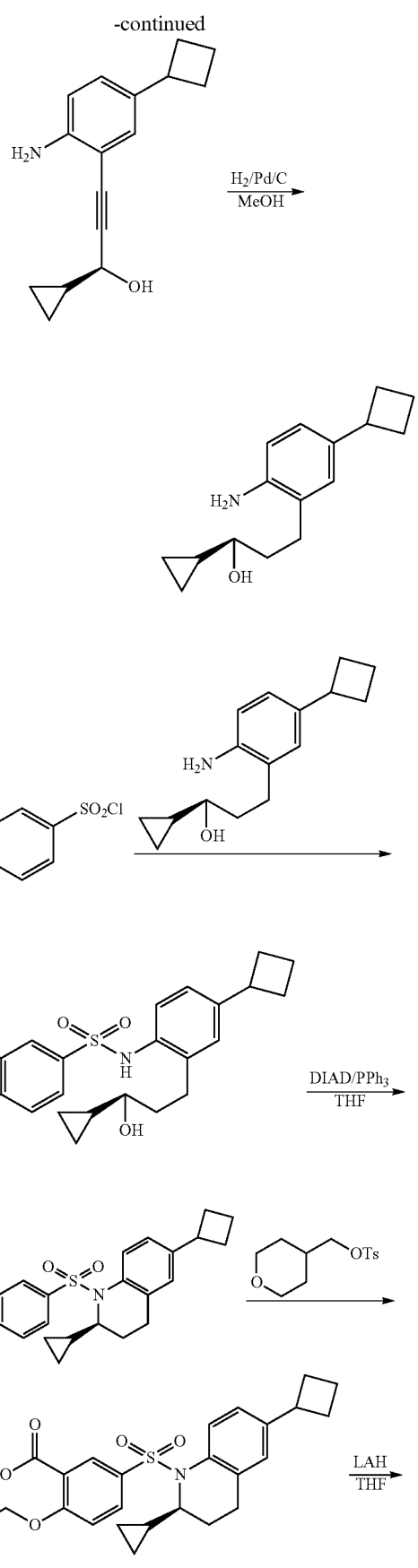

207

-continued

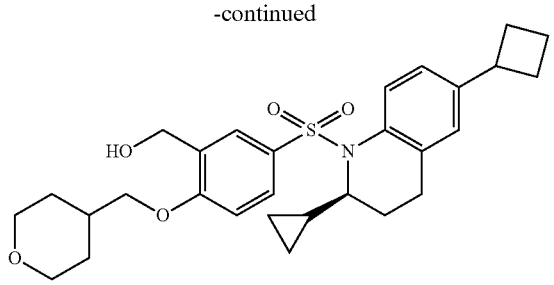

38.29 mg of the title compound (MS(ESI) m/z: 512.1 [M+H]$^+$) was prepared and obtained using (S)-1-cyclopropylpropynol in Example 74 as a raw material, with reference to the corresponding synthesis method in Example 62.

$^1$H NMR (400 MHz, CDCl$_3$) δ 7.66 (d, J=8.4 Hz, 1H), 7.50 (d, J=1.4 Hz, 1H), 7.39 (d, J=8.6 Hz, 1H), 7.07 (d, J=8.4 Hz, 1H), 6.85 (s, 1H), 6.77 (d, J=8.7 Hz, 1H), 4.61 (s, 2H), 4.02 (dd, J=11.3, 3.7 Hz, 2H), 3.87 (d, J=6.3 Hz, 2H), 3.66 (dt, J=8.5, 5.6 Hz, 1H), 3.54-3.40 (m, 3H), 2.65-2.53 (m, 1H), 2.33 (ddd, J=13.7, 8.1, 4.2 Hz, 2H), 2.20-1.98 (m, 6H), 1.85 (dd, J=19.2, 8.8 Hz, 1H), 1.77-1.68 (m, 3H), 1.62 (dq, J=12.0, 6.0 Hz, 1H), 1.48 (qd, J=12.4, 4.5 Hz, 2H), 0.91 (m, 1H), 0.57-0.41 (m, 3H), 0.40-0.32 (m, 1H).

Example 80

Synthesis of 5-((2,6-diethyl-3,4-dihydro-1,8-naphthyridin-1(2H)-yl)sulfonyl)-2-((tetrahydro-2H-pyran-4-yl)methoxy)benzyl Alcohol

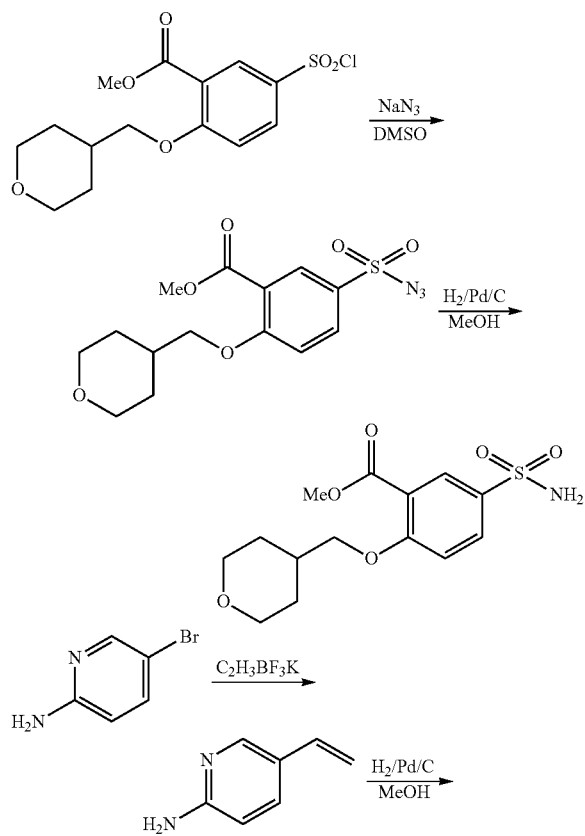

208

-continued

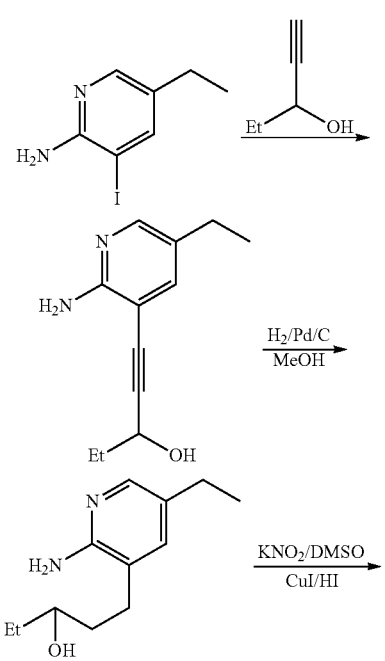

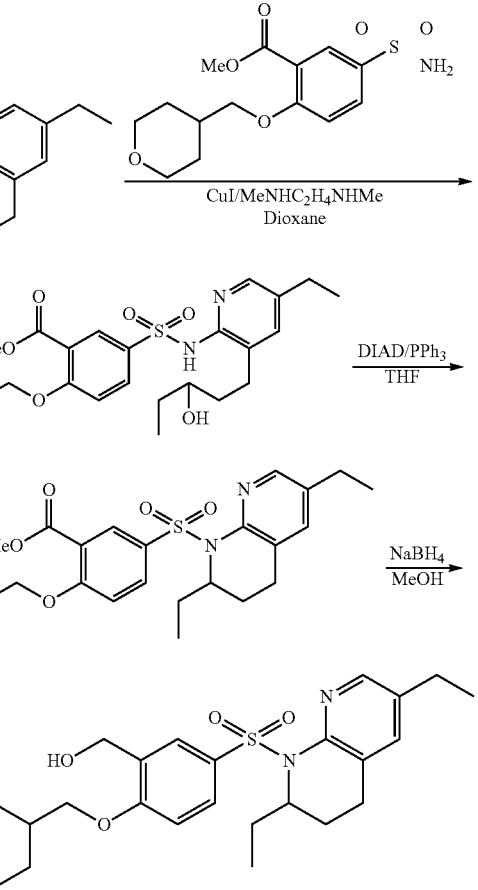

80.1 Methyl 5-azidosulfonyl-2-((tetrahydro-2H-pyran-4-yl)methoxy)benzoate

A 50 mL single-necked flask was charged with sodium azide (1.0 g), and dimethylsulfoxide (20 mL) was added thereto. A solution of methyl 5-chlorosulfonyl-2-((tetrahydro-2H-pyran-4-yl)methoxy)benzoate (3.2 g, an intermediate in Example 1.4) in dichloromethane (10 mL) was added under stirring. After the completion of the addition, the mixture was reacted at room temperature for 16 h. A sample was taken and TLC detection showed that the spots of the raw materials disappeared. The reaction was terminated, and ethyl acetate (80 mL) was added to the reaction system to dilute the mixture. The resulting mixture was washed twice with water (20 mL×2), washed twice with saturated saline (20 mL×2), dried over anhydrous sodium sulfate, concentrated, and purified by column chromatography, so as to obtain the title compound (1.6 g, MS(ESI) m/z: 356 [M+H]$^+$).

80.2 Methyl 5-aminosulfonyl-2-((tetrahydro-2H-pyran-4-yl)methoxy)benzoate

A 50 mL single-necked reaction flask was charged with methyl 5-azidosulfonyl-2-((tetrahydro-2H-pyran-4-yl)methoxy)benzoate (1.6 g). Under nitrogen protection, 10% palladium on carbon (0.1 g) was added, and methanol (16 mL) was added simultaneously as the reaction solvent. The resulting mixture was purged with hydrogen gas three times and reacted at room temperature for 16 h. A sample was taken and TLC detection showed that the spots of the raw materials disappeared. The reaction solution was directly filtered by suction, washed with an appropriate amount of ethyl acetate, and concentrated under reduced pressure, so as to obtain 1.4 g of a solid (MS(ESI) m/z: 330 [M+H]$^+$).

80.3 5-Vinyl-2-pyridylamine

A single-necked flask was charged with 5-bromo-2-pyridylamine (5.1 g), and potassium vinyltrifluoroborate (5.1 g), 1,4-dioxane (90 mL) and cesium carbonate (19.2 g) were added thereto, followed by addition of water (20 mL) and tetrakis(triphenylphosphine)palladium (680 mg). The mixture was purged with nitrogen gas three times and stirred overnight in an oil bath at 80° C. A sample was taken and TLC detection showed that the reaction of the raw materials was complete. LC-MS detection: 121.0 [M+1]$^+$. Post-treatment: 50 mL of water was added, and the mixture was extracted three times with ethyl acetate (50 mL×3). The organic phases were combined, washed with saturated aqueous sodium chloride solution, dried over anhydrous sodium sulfate and filtered, and the filtrate was concentrated under reduced pressure, so as to obtain 5-vinyl-2-pyridylamine (5.7 g).

80.4 5-Ethyl-2-pyridylamine

A single-necked flask was charged with 5-vinyl-2-pyridylamine (5.7 g), which was dissolved in methanol (60 mL). Palladium hydroxide on carbon (1.1 g) was added, and the mixture was purged with hydrogen gas three times and stirred at room temperature overnight. LC-MS detected a peak of the product (123.1[M+1]$^+$), and the reaction of the raw materials was complete. The resulting mixture was filtered and concentrated under reduced pressure to obtain 5-ethyl-2-pyridylamine (3.9 g).

80.5 1-(2-Amino-5-ethyl-3-pyridyl)-3-pentanol 1-(2-Amino-5-ethyl-3-pyridyl)-3-pentanol (1.5 g, 209 [M+1]$^+$) was prepared and obtained with reference to the synthesis steps in Examples 12.1 to 12.3.

80.6 1-(2-Iodo-5-ethyl-3-pyridyl)-3-pentanol

A single-necked flask was charged with 1-(2-amino-5-ethyl-3-pyridyl)-3-pentanol (1.0 g), sodium nitrite (663 mg) was added, and dimethylsulfoxide (10 mL) was added. Then, the mixture was stirred and dissolved, and a solution of potassium iodide (4.0 g) and hydroiodic acid (2.5 g) in dimethylsulfoxide (10 mL) was added dropwise. After the completion of the dropwise addition, the mixture was purged with nitrogen gas three times and stirred overnight in an oil bath at 55° C. A sample was taken and TLC detection showed that the spots of the raw materials disappeared. LC-MS detection: 320[M+1]+. Post-treatment: the reaction solution was poured into 100 mL of a saturated solution of potassium carbonate in ice water, and the resulting mixture was extracted three times with ethyl acetate (30 mL×3). The organic phases were combined, washed with saturated saline, dried over anhydrous sodium sulfate, filtered, and concentrated under reduced pressure, so as to obtain an oil, which was subjected to column chromatography and eluted with an eluent (ethyl acetate:petroleum ether=0% to 30%). The product was collected and concentrated under reduced pressure to obtain 1-(2-iodo-5-ethyl-3-pyridyl)-3-pentanol (230 mg).

80.7 Methyl 5-(N-(5-ethyl-3-(3-hydroxypentyl)-2-pyridyl)aminosulfonyl)-2-((tetrahydro-2H-pyran-4-yl)methoxy)benzoate A 50 mL single-necked flask was charged with 1-(2-iodo-5-ethyl-3-pyridyl)-3-pentanol (170 mg), methyl 5-aminosulfonyl-2-((tetrahydro-2H-pyran-4-yl)methoxy)benzoate (263 mg) was added, and 1,4-dioxane (5 mL) was added to dissolve the formers, followed by addition of cuprous iodide (20 mg) and N,N'-dimethylethylenediamine (10 mg). The mixture was stirred at room temperature overnight. A sample was taken and TLC detection showed that there were few spots of the raw materials left. The sample was subjected to LC-MS detection, and a peak of the product (521[M+1]$^+$) was detected. Post-treatment: 20 mL of water was added, and the mixture was extracted three times with ethyl acetate (30 mL×3). The organic phases were combined, washed with 50 mL of saturated saline, and dried over anhydrous sodium sulfate. The solvent was removed by rotary evaporation under reduced pressure, so as to obtain an oil, which was subjected to column chromatography and eluted with an eluent (ethyl acetate:petroleum ether=0% to 30%). The product was collected and concentrated under reduced pressure to obtain the title compound (170 mg).

80.8 Methyl 5-((2,6-diethyl-3,4-dihydro-1,8-naphthyridin-1(2H)-yl)sulfonyl)-2-((tetrahydro-2H-pyran-4-yl)methoxy)benzoate A 250 mL three-necked flask was charged with triphenylphosphine (260 mg), and anhydrous tetrahydrofuran (3 mL) was added to dissolve the former. The mixture was purged with nitrogen gas three times and cooled to 0° C. in an ice bath. Diisopropyl azodicarboxylate (165 mg) was added dropwise. After the completion of the dropwise addition, the mixture was stirred for 30 min in an ice bath, and a solution of methyl 5-(N-(5-ethyl-3-(3-hydroxypentyl)-2-pyridyl)aminosulfonyl)-2-((tetrahydro-2H-pyran-4-yl)methoxy)benzoate (170 mg) in tetrahydrofuran (2 mL) was added dropwise. After the completion of the dropwise addition, the mixture was warmed to room temperature and stirred overnight. A sample was taken and TLC detection showed that there were few spots of the raw materials left. LC-MS detected a peak of the product (503.1[M+1]$^+$). 20 mL of water was added, and the mixture was extracted three times with ethyl acetate (30 mL×3). The organic phases were combined, washed with 20 mL of saturated saline, and dried over anhydrous sodium sulfate. The solvent was removed by rotary evaporation under reduced pressure, so as to obtain an oil, which was subjected to column chromatography and eluted with an eluent (ethyl acetate:petroleum ether=0% to 30%). The product was collected and concentrated under reduced pressure to obtain the title compound (360 mg).

80.9 5-((2,6-Diethyl-3,4-dihydro-1,8-naphthyridin-1(2H)-yl)sulfonyl)-2-((tetrahydro-2H-pyran-4-yl)methoxy)benzyl Alcohol A 100 mL single-necked flask was charged with methyl 5-((2,6-diethyl-3,4-dihydro-1,8-naphthyridin-1(2H)-yl)sulfonyl)-2-((tetrahydro-2H-pyran-4-yl)methoxy)benzoate (320 mg), and methanol (10 mL) was added to dissolve the former. The mixture was heated to reflux, and sodium borohydride (120 mg) was added thereto in portions. After the completion of the addition, the mixture was refluxed for 30 min. The reaction was complete as detected by TLC. 450 mL of water was added, and the mixture was extracted three times with ethyl acetate (40 mL×3). The organic phases were combined, washed with 50 mL of saturated saline, dried over anhydrous sodium sulfate, filtered, and concentrated under reduced pressure, so as to obtain 60 mg of an oil, which was subjected to Prep-HPLC preparation to obtain the title compound (45.6 mg), MS(ESI) m/z: 475[M+1]$^+$.

$^1$H NMR (400 MHz, CDCl$_3$) δ 8.09 (d, J=2.2 Hz, 1H), 8.06 (dd, J=8.6, 2.3 Hz, 1H), 7.98 (d, J=1.8 Hz, 1H), 7.18 (d, J=1.3 Hz, 1H), 6.88 (d, J=8.7 Hz, 1H), 4.77 (dt, J=11.3, 3.8 Hz, 1H), 4.71 (s, 2H), 4.03 (dd, J=11.3, 3.7 Hz, 2H), 3.91 (d, J=6.3 Hz, 2H), 3.45 (td, J=11.8, 1.6 Hz, 2H), 2.86-2.73 (m, 1H), 2.72-2.62 (m, 1H), 2.52 (q, J=7.6 Hz, 2H), 2.32 (s, 1H), 2.18-2.06 (m, 1H), 2.05-1.95 (m, 2H), 1.74 (dd, J=12.9, 1.6 Hz, 2H), 1.65 (td, J=14.4, 7.3 Hz, 1H), 1.56-1.41 (m, 3H), 1.18 (t, J=7.6 Hz, 3H), 0.93 (t, J=7.4 Hz, 3H).

Biological Activity Test
Luciferase Assay

This assay method used luciferase as a reporter gene to detect the expression of cells transfected with a gene recombinant plasmid at gene transcription level, wherein the recombinant plasmid was constructed by the promoter of a target gene and a luciferase gene. The experiment was primarily related to the transfection of the recombinant plasmid hRORγt ("RORgt"). The transfection needed 27.75 micrograms of DNA, 18 mL of cells, culture medium, and a 125 mL shake flask.

I. Reagents and Materials:
1. Cells: Chinese hamster ovary cells (CHO—S, Invitrogen, Cat #R80007), suspension-cultured in CD-CHO culture medium containing 8 mM L-glutamine and 1×HT.
2. Culture medium:
a) To CD-CHO (Invitrogen, Cat #10743029) culture medium, 1×HT (Invitrogen, Cat #11067030) and L-glutamine (Invitrogen, Cat #25030149)] were added;

Penicillin-Streptomycin 100× (Invitrogen, Cat #10378016) was only used in passage and not used in transfection.
b) Opti-MEM (Invitrogen, Cat #51985034) was a serum-reduced culture medium that was used during the formation of the transfection complex.
3. DNA:
a) Luciferase reporter gene plasmid pG5-luc: reporter plasmid (Promega).
b) Target gene plasmid pM-hRORγt: human RORgamma.
4. Transfection reagent: TransIT-CHO transfection kit (Minis Bio Co.) containing Trans-It reagent and Mojo reagent (Minis, MIR2170).
5. Culture plate: white cell culture plate (VWR, Catalog #29444-041).
6. Compound plate: polypropylene 96-well round-bottom plate (VWR, Catalog #29444-104).
7. Luciferase kit: (Promega ONE-Glo, 100 ml, Catalog #E6120): containing luciferase substrate (Coenzyme A, ATP and luciferin) and a reaction buffer.
8. Shake flask.
II. Specific Experimental Steps
A Cell culture
1. Cell seeding: 18 to 24 h before transfection, a 125 mL shake flask was charged with CHO—S cells having a concentration of 0.5×10$^6$ cells/mL to 0.6×10$^6$ cells/mL, and CD-CHO culture medium (the culture medium only contained L-glutamine and an HT supplement) was added thereto to a final volume of 18 mL. The shake flask was placed on a shaker, and the cells were passaged overnight under a condition of 120 rpm, 37° C. and 8% CO$_2$.
2. Cell transfection: At this time, the cell concentration of the above-mentioned solution should be 1.2×10$^6$ cells/mL to 1.5×10$^6$ cells/mL. CD-CHO culture medium (containing L-glutamine and an HT supplement) was used for dilution until the cell concentration reached 1×10$^6$ cells/mL.
B. Preparation of transfection reagent (TransIT-CHO: Mojo: DNA complex), which was formulated immediately before transfection.
1. Trans-IT reagent was warmed to room temperature in advance and shaken to be uniformly mixed before use.
2. Preparation for DNA transfection: the following reagents were mixed in a 1.5 mL sterile centrifuge tube:
27 μg of luciferase reporter gene plasmid pG5-luc: 27 μL, 1 mg/mL solution,
0.75 μg of the expression plasmid of the target gene (pM-hRORγt, 7.5 μL, 0.1 mg/mL solution).
3. The following reagents were charged into a 15 mL sterile centrifuge tube:
2.8 mL of Opti-MEM
83 μL of TransIT-CHO reagent
the DNA complex prepared in step 2
4. The mixture was mixed well and placed at room temperature for 5 min.
5. 13.9 μL of Mojo reagent was charged into a sterile centrifuge tube, mixed slightly, and placed at room temperature for 20 min to form a transfection complex.
C. Cell transfection:
1. A 125 mL shake flask was charged with the transfection complex prepared in step B dropwise while being shaken slowly.
2. The cells were cultured for 4 h in a shaker under a condition of 37° C. and 8% carbon dioxide.
3. After 4 h, the cells were transferred to a 50 mL sterile centrifuge tube, centrifuged at 1200 rpm for 4 min, and the supernatant was aspirated.

4. The cells were re-suspended in 6 mL of a freezing medium (CD-CHO, L-glutamine, HT supplement, and 10% DMSO), and the cell density should be $3\times10^6$ cells/ml at this time.

5. The mixture was dispensed into 12 tubes with 0.5 mL in each tube. The tubes were placed in a refrigerator at −80° C. to be slowly frozen overnight, and then were transferred into liquid nitrogen for long-term storage.

D. Luciferase activity assay (96-well flat plate)

1. The cells were thawed at 37° C.

2. The cells ($1.5\times10^6$ cells/0.5 mL) were diluted with 2 mL of freshly formulated culture medium (CD-CHO, L-glutamine and an HT supplement) to a volume of 2.5 mL, and then were transferred to a 15 mL sterile centrifuge tube.

3. Cell counting: If the cells were completely viable, a concentration of $6\times10^5$ cells/mL should be achieved. Generally, a viability of 65% to 70% should be achieved, and the cell density should be $4\times10^5$ cells/mL. If necessary, the cells were diluted with culture medium.

4. Cell seeding: 100 µl cells ($4\times10^4$ cells) were added to each well.

5. Each well was charged with 1 µl of a compound to be tested (dissolved in 100% DMSO), and a plate prepared in advance which contained the compounds to be test with 100-fold concentration was used.

6. The cells were cultured overnight at 37° C. under an atmosphere of 5% carbon dioxide.

7. ONE-Glo luciferase (4:1) was fresh formulated by diluting with the culture medium on the next day, and 50 µl of the resultant was transferred to the cell plate and mixed well by using a multi-channel pipette.

8. The cell plate was shaken and the mixture therein was mixed evenly for 5 min.

9. The luciferase activity was measured by a fluorometer.

Settings of the fluorometer Wallac Trilux luminometer:
Protocol: Luciferase luminescence
Reading time: 1 sec/well, 6 wells/read
Design and arrangement for 96-well plate luciferase experiment:

A white opaque 96-well plate was used in this experiment.

B1 referred to the blank control group: sterile deionized water

S referred to the positive control group (100% inhibition): 2 µM ursolic acid in DMSO D referred to the negative control group (100% activity): DMSO C1 to C8 referred to groups of the compounds to be tested: compounds to be tested at different concentrations or repeated experimental groups.

|   | 1 | 2 | 3 | 4 | 5 | 6 | 7 | 8 | 9 | 10 | 11 | 12 |
|---|---|---|---|---|---|---|---|---|---|----|----|----|
| A | Bl | Bl | Bl | Bl | Bl | Bl | Bl | Bl | Bl | Bl | Bl | Bl |
| B | Bl | S | D | C1 | C2 | C3 | C4 | C5 | C6 | C7 | C8 | Bl |
| C | Bl | S | D | C1 | C2 | C3 | C4 | C5 | C6 | C7 | C8 | Bl |
| D | Bl | S | D | C1 | C2 | C3 | C4 | C5 | C6 | C7 | C8 | Bl |
| E | Bl | S | D | C1 | C2 | C3 | C4 | C5 | C6 | C7 | C8 | Bl |
| F | Bl | S | D | C1 | C2 | C3 | C4 | C5 | C6 | C7 | C8 | Bl |
| G | Bl | S | D | C1 | C2 | C3 | C4 | C5 | C6 | C7 | C8 | Bl |
| H | Bl | Bl | Bl | Bl | Bl | Bl | Bl | Bl | Bl | Bl | Bl | Bl |

In this experiment, each well contained 1 µL of the compound to be tested (dissolved in DMSO), 100 µL of cells, and 50 µL of luciferase reagent.

The results of luciferase assay were as shown in the following table:

| Componds | RORgt EC50 (µM) |
|---|---|
| [structure] | 0.0236 |
| [structure] | 0.012 |
| [structure] | 0.858 |

-continued

| Componds | RORgt EC50 (μM) |
|---|---|
| (structure) | 1.61 |
| (structure) | 0.218 |
| (structure) | 0.025 |
| (structure) | 0.036 |
| (structure) | 0.101 |
| (structure) | 1.4 |

| Compounds | RORgt EC50 (μM) |
|---|---|
| 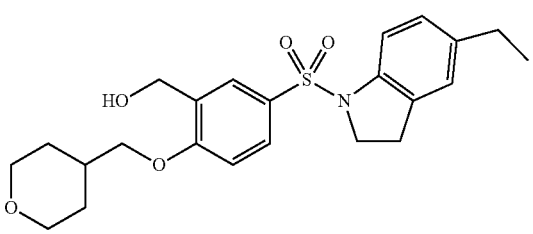 [SMILES: CCc1ccc2c(c1)C(C)CN2S(=O)(=O)c1ccc(OCC2CCOCC2)c(CO)c1] | 2.63 |
| 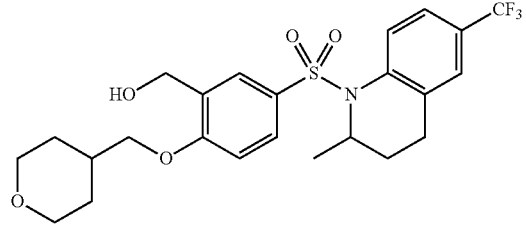 [SMILES: CC1CCc2cc(C(F)(F)F)ccc2N1S(=O)(=O)c1ccc(OCC2CCOCC2)c(CO)c1] | 0.015 |
| 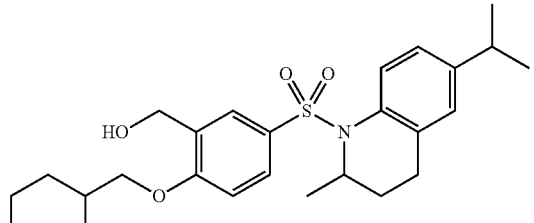 | 0.0149 |
| 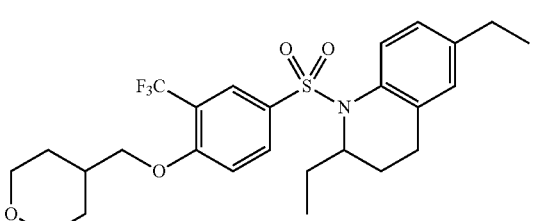 | 3.89 |
| 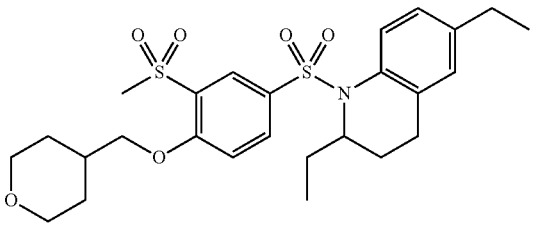 [SMILES: CCc1ccc2c(c1)CCC(CC)N2S(=O)(=O)c1ccc(OCC2CCOCC2)c(S(C)(=O)=O)c1] | 1.855 |
| 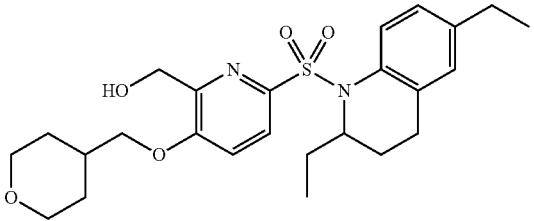 [SMILES: CCc1ccc2c(c1)CCC(CC)N2S(=O)(=O)c1ccc(OCC2CCOCC2)c(CO)n1] | 0.212 |

| Componds | RORgt EC50 (μM) |
|---|---|
| 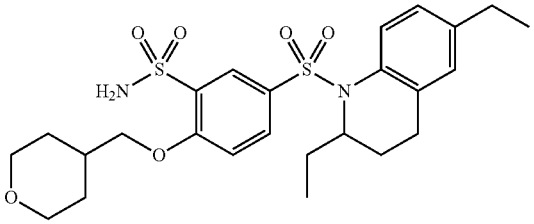 [SMILES: CCc1ccc2c(c1)CCC(CC)N2S(=O)(=O)c1ccc(OCC2CCOCC2)c(S(N)(=O)=O)c1] | 0.576 |
| 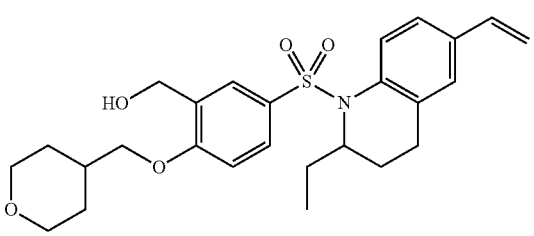 [SMILES: C=Cc1ccc2c(c1)CCC(CC)N2S(=O)(=O)c1ccc(OCC2CCOCC2)c(CO)c1] | 0.0355 |
| 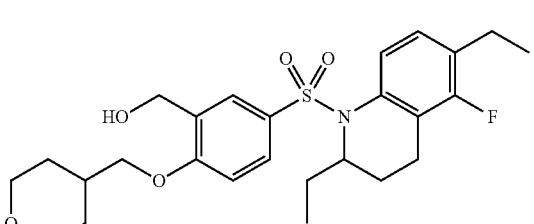 | 0.0136 |
| 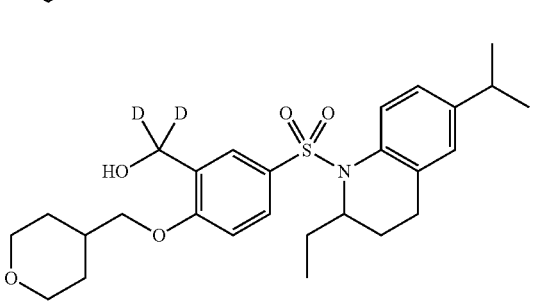 | 0.0115 |
| 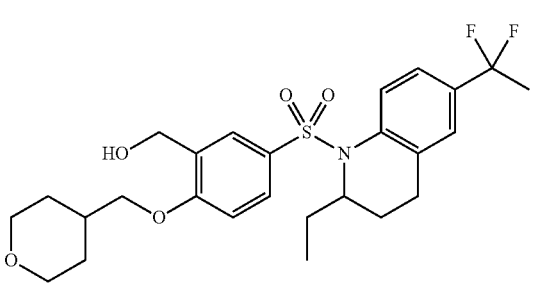 [SMILES: CCC1CCc2cc(C(C)(F)F)ccc2N1S(=O)(=O)c1ccc(OCC2CCOCC2)c(CO)c1] | 0.0156 |
| 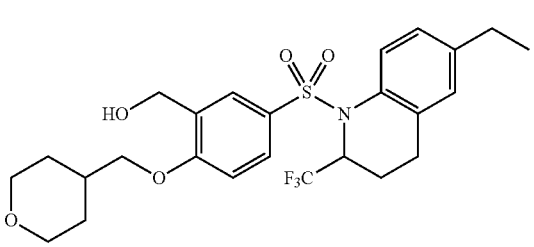 [SMILES: CCc1ccc2c(c1)CCC(C(F)(F)F)N2S(=O)(=O)c1ccc(OCC2CCOCC2)c(CO)c1] | 0.023 |

| Compounds | RORgt EC50 (μM) |
|---|---|
| (structure) | 0.655 |
| (structure) | 0.0179 |
| (structure) | 0.011 |
| (structure) | 0.689 |
| (structure) | 0.0142 |
| (structure) | 0.151 |

-continued
| Componds | RORgt EC50 (μM) |
|---|---|
| 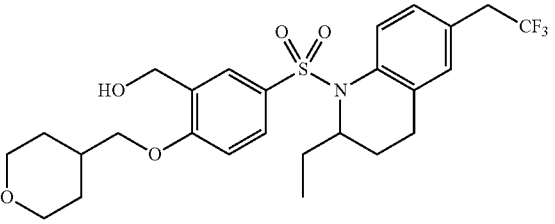 [SMILES: CCC1CCc2cc(CC(F)(F)F)ccc2N1S(=O)(=O)c1ccc(OCC2CCOCC2)c(CO)c1] | 0.023 |
| 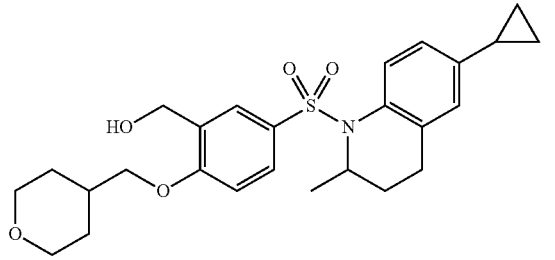 [SMILES: CC1CCc2cc(C3CC3)ccc2N1S(=O)(=O)c1ccc(OCC2CCOCC2)c(CO)c1] | 0.0207 |
| 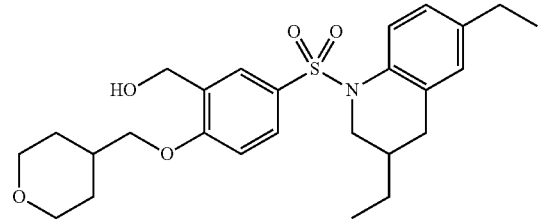 [SMILES: CCc1ccc2c(c1)CC(CC)CN2S(=O)(=O)c1ccc(OCC2CCOCC2)c(CO)c1] | 0.0316 |
| 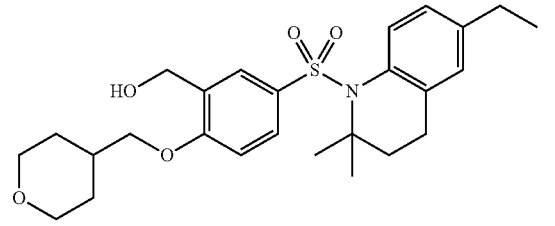 [SMILES: CCc1ccc2c(c1)CCC(C)(C)N2S(=O)(=O)c1ccc(OCC2CCOCC2)c(CO)c1] | 0.31 |
| 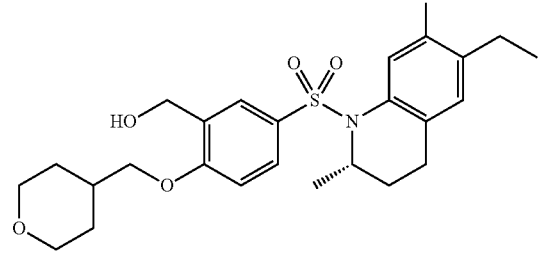 | 0.0965 |
| 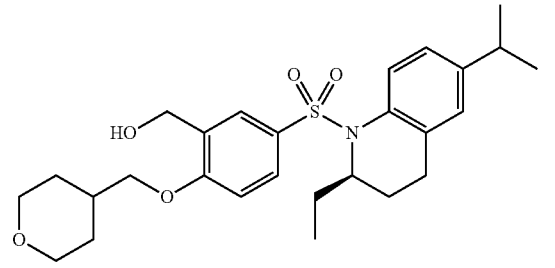 [SMILES: CC[C@@H]1CCc2cc(C(C)C)ccc2N1S(=O)(=O)c1ccc(OCC2CCOCC2)c(CO)c1] | 0.048 |

-continued

| Componds | RORgt EC50 (μM) |
|---|---|
| [structure] | 0.0042 |
| [structure] | 0.201 |
| [structure] | 0.0124 |
| [structure] | 0.480 |
| [structure] | 0.021 |
| [structure] | 0.0129 |

-continued
| Compounds | RORgt EC50 (μM) |
|---|---|
| 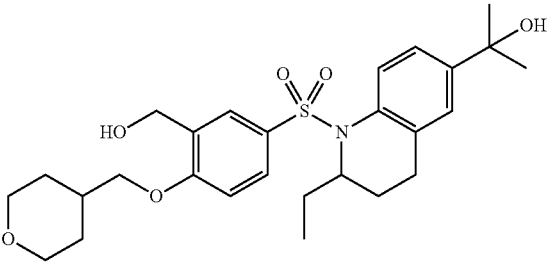 [SMILES: CCC1CCc2cc(C(C)(C)O)ccc2N1S(=O)(=O)c1ccc(OCC2CCOCC2)c(CO)c1] | 1.402 |
| 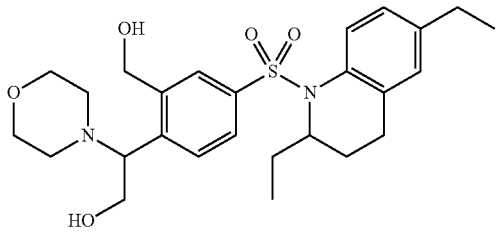 [SMILES: CCc1ccc2c(c1)CCC(CC)N2S(=O)(=O)c1ccc(C(CO)N2CCOCC2)c(CO)c1] | 3.122 |
| 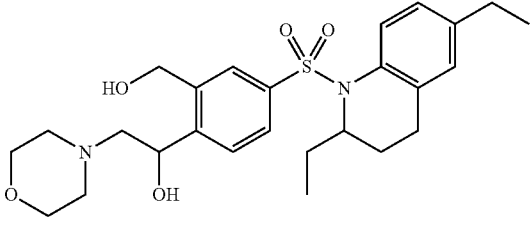 [SMILES: CCc1ccc2c(c1)CCC(CC)N2S(=O)(=O)c1ccc(C(O)CN2CCOCC2)c(CO)c1] | 0.595 |
| 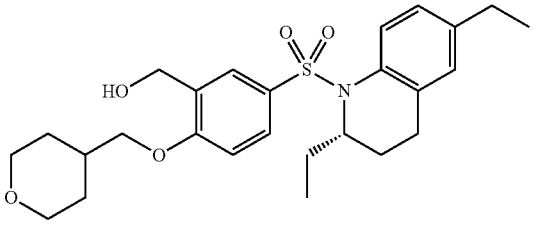 | 0.0349 |
| 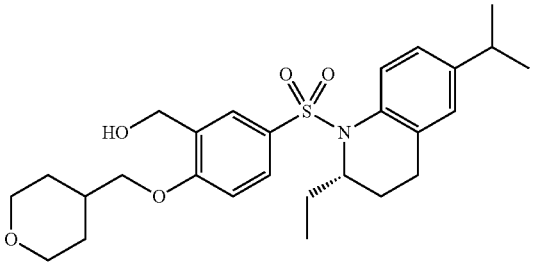 | 0.0068 |
| 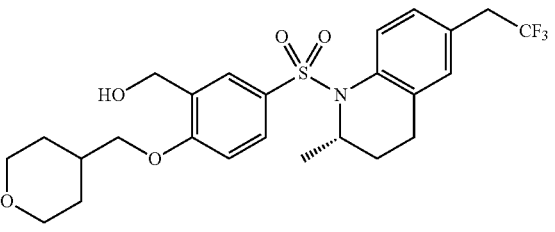 [SMILES: C[C@H]1CCc2cc(CC(F)(F)F)ccc2N1S(=O)(=O)c1ccc(OCC2CCOCC2)c(CO)c1] | 0.316 |

-continued
| Componds | RORgt EC50 (μM) |
|---|---|
| 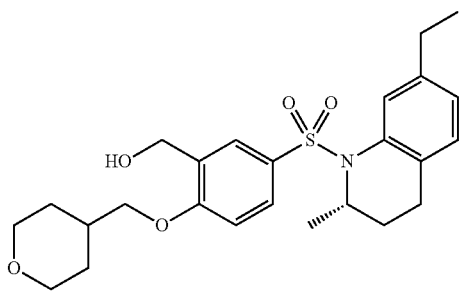 [SMILES: CCc1ccc2c(c1)N(S(=O)(=O)c1ccc(OCC3CCOCC3)c(CO)c1)[C@@H](C)CC2] | 0.223 |
| 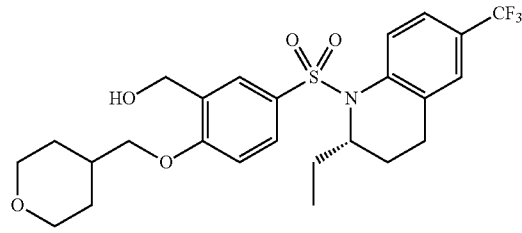 | 0.071 |
| 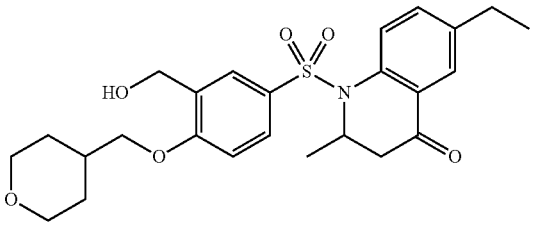 [SMILES: CCc1ccc2c(c1)C(=O)CC(C)N2S(=O)(=O)c1ccc(OCC2CCOCC2)c(CO)c1] | 0.076 |
| 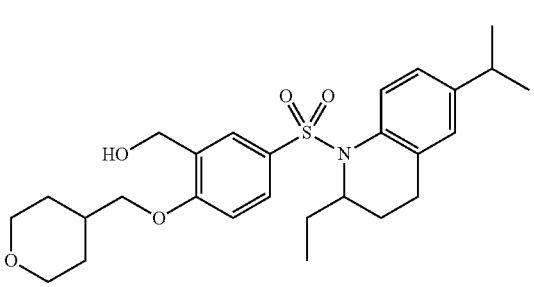 [SMILES: CCC1CCc2cc(C(C)C)ccc2N1S(=O)(=O)c1ccc(OCC2CCOCC2)c(CO)c1] | 0.0035 |
| 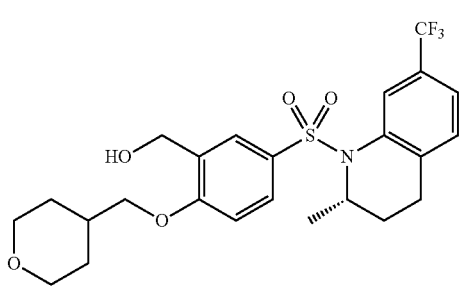 [SMILES: C[C@H]1CCc2ccc(C(F)(F)F)cc2N1S(=O)(=O)c1ccc(OCC2CCOCC2)c(CO)c1] | 0.33 |
| 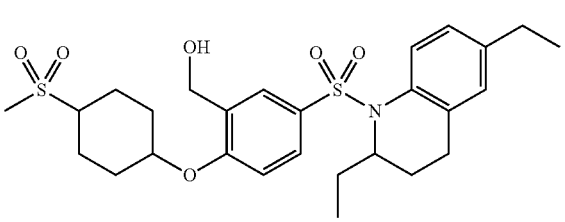 [SMILES: CCc1ccc2c(c1)CCC(CC)N2S(=O)(=O)c1ccc(OC2CCC(S(C)(=O)=O)CC2)c(CO)c1] | 2.152 |

-continued
| Componds | RORgt EC50 (μM) |
|---|---|
| 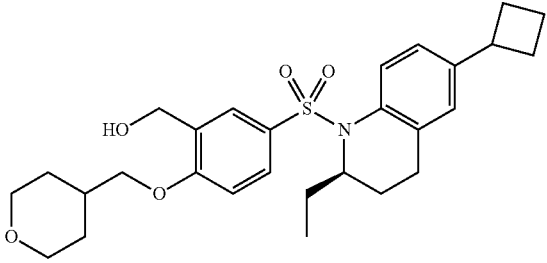 [SMILES: CC[C@@H]1CCc2cc(C3CCC3)ccc2N1S(=O)(=O)c1ccc(OCC2CCOCC2)c(CO)c1] | 0.0052 |
| 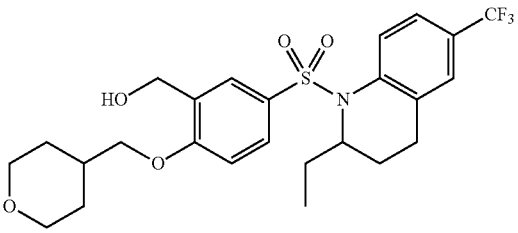 | 0.0211 |
| 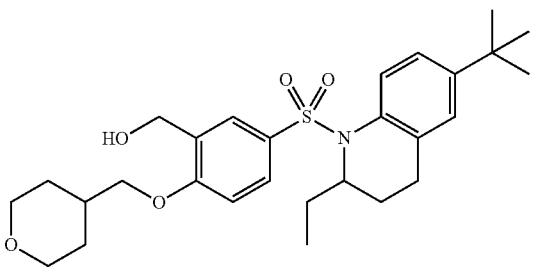 [SMILES: CCC1CCc2cc(C(C)(C)C)ccc2N1S(=O)(=O)c1ccc(OCC2CCOCC2)c(CO)c1] | 0.0702 |
| 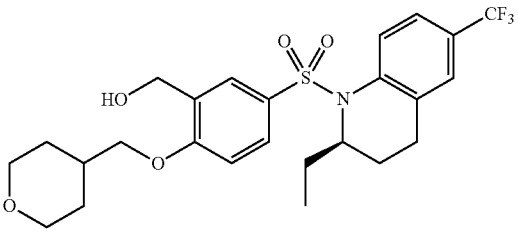 [SMILES: CC[C@@H]1CCc2cc(C(F)(F)F)ccc2N1S(=O)(=O)c1ccc(OCC2CCOCC2)c(CO)c1] | 0.0054 |
| 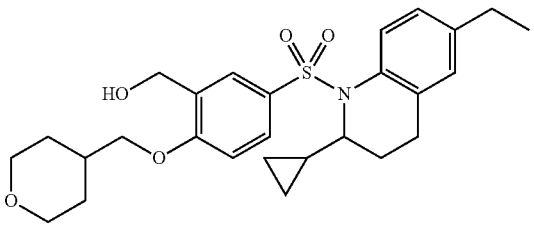 [SMILES: CCc1ccc2c(c1)CCC(C1CC1)N2S(=O)(=O)c1ccc(OCC2CCOCC2)c(CO)c1] | 0.007 |
| 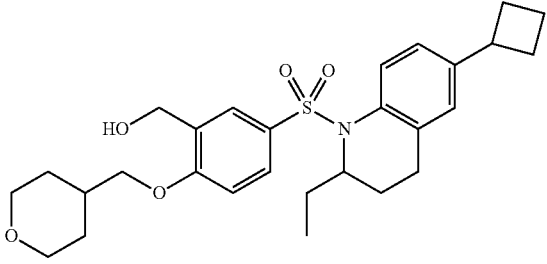 [SMILES: CCC1CCc2cc(C3CCC3)ccc2N1S(=O)(=O)c1ccc(OCC2CCOCC2)c(CO)c1] | 0.0055 |

-continued

| Componds | RORgt EC50 (μM) |
|---|---|
| (structure) | 0.01 |
| (structure) | 0.021 |
| (structure) | 0.146 |
| (structure) | 0.181 |
| (structure) | 0.803 |
| (structure) | 0.0032 |

| Componds | RORgt EC50 (μM) |
|---|---|
| 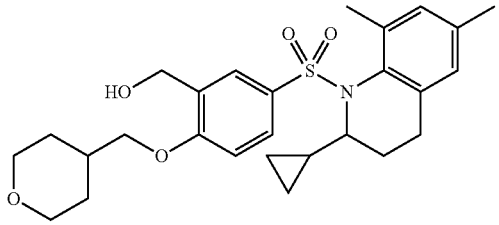 [SMILES: Cc1cc(C)c2c(c1)CCC(C1CC1)N2S(=O)(=O)c1ccc(OCC2CCOCC2)c(CO)c1] | 0.018 |
| 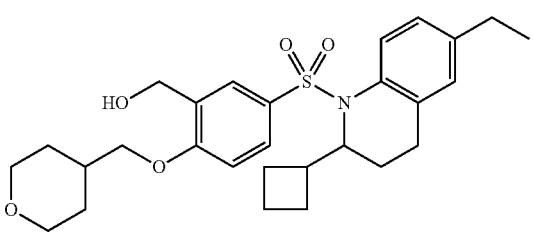 [SMILES: CCc1ccc2c(c1)CCC(C1CCC1)N2S(=O)(=O)c1ccc(OCC2CCOCC2)c(CO)c1] | 0.0081 |
| 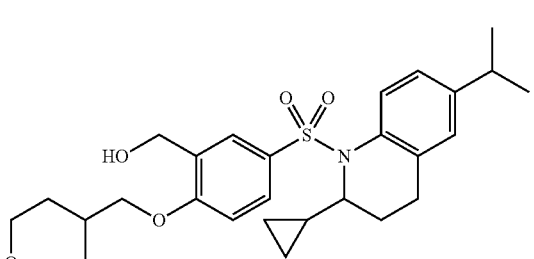 | 0.0066 |
What is claimed is:
1. A compound of formula (A) or a pharmaceutically acceptable salt thereof,
Formula (A)
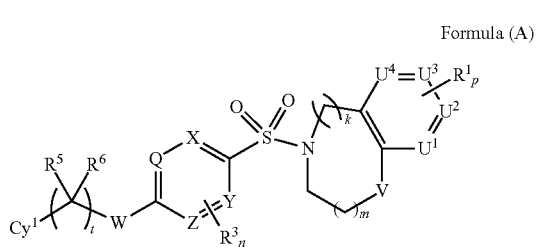
wherein $U^1$, $U^2$, $U^3$, and $U^4$ are each independently selected from C, CH or N;
X, Y, Z, and Q are each independently selected from C, CH or N;
V is selected from $CH_2$ or O;
W is selected from $CIR^7R^8$, O, S,
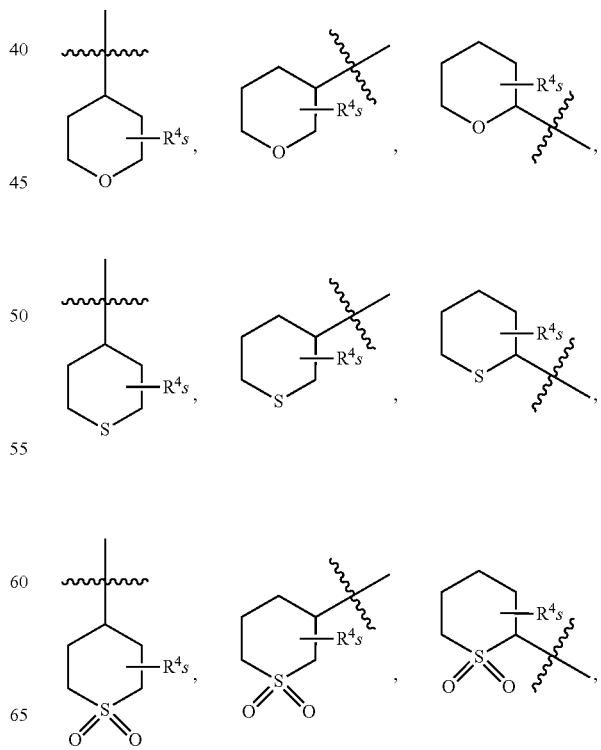
$Cy^1$ is selected from -continued

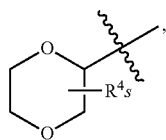 , 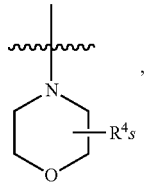 , 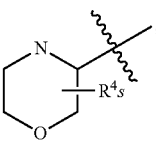 ,

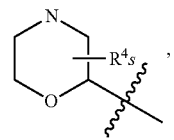 , 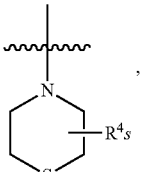 , 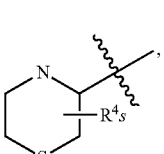 ,

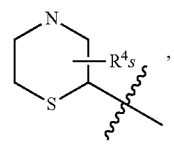 , 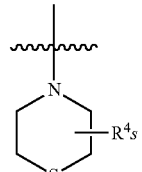 , 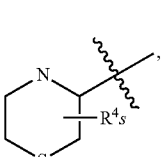 ,

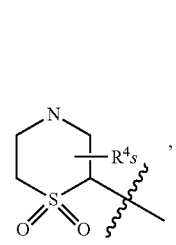 , 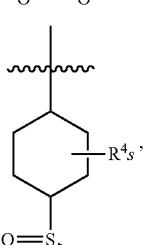 , 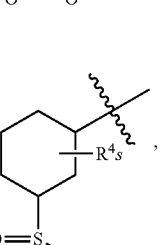 ,

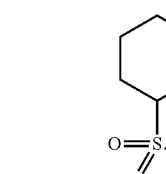 , 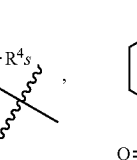 , 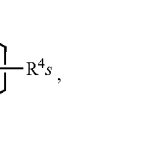 ,

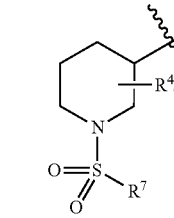 , or 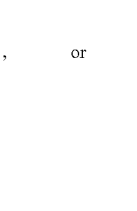 ;

$R^1$ is independently selected from $C_1$-$C_6$ alkyl, $C_2$-$C_6$ alkenyl, $C_2$-$C_6$ alkynyl, $C_1$-$C_6$ alkoxy, 3- to 6-membered cycloalkyl, halogen, hydroxy, cyano, amino, or nitro, wherein said $C_1$-$C_6$ alkyl, $C_2$-$C_6$ alkenyl, $C_2$-$C_6$ alkynyl, $C_1$-$C_6$ alkoxy or 3- to 6-membered cycloalkyl is optionally substituted with one, two or three substituents selected from halogen, hydroxy, cyano, amino or nitro;

$R^2$ is independently selected from $C_1$-$C_6$ alkyl, $C_1$-$C_6$ alkoxy, 3- to 8-membered cycloalkyl, 3- to 8-membered heterocycloalkyl,

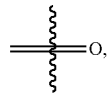

halogen, hydroxy, cyano, amino, or nitro, wherein said $C_1$-$C_6$ alkyl, $C_1$-$C_6$ alkoxy, 3- to 8-membered cycloalkyl, or 3- to 8-membered heterocycloalkyl is optionally substituted with one, two or three substituents selected from halogen, hydroxy, cyano, amino or nitro;

$R^3$ is independently selected from carboxy, halogen, hydroxy, cyano, amino, nitro, aminosulfonyl, $C_1$-$C_6$ alkyl, $C_1$-$C_6$ alkoxy, $C_1$-$C_6$ alkylsulfonyl, or 3- to 6-membered cycloalkyl, said $C_1$-$C_6$ alkyl, $C_1$-$C_6$ alkoxy, $C_1$-$C_6$ alkylsulfonyl or 3- to 6-membered cycloalkyl is optionally substituted with one, two or three substituents selected from deuterium, halogen, hydroxy, cyano, amino or nitro;

$R^4$ is independently selected from $C_1$-$C_6$ alkyl, $C_1$-$C_6$ alkoxy,

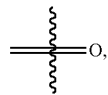

halogen, hydroxy, cyano, amino, or nitro, wherein said $C_1$-$C_6$ alkyl or $C_1$-$C_6$ alkoxy is optionally substituted with one, two or three substituents selected from halogen, hydroxy, cyano, amino or nitro;

$R^5$ and $R^6$ are independently selected from hydrogen, $C_1$-$C_6$ alkyl, $C_1$-$C_6$ alkoxy, halogen, hydroxy, cyano, amino, or nitro, wherein said $C_1$-$C_6$ alkyl or $C_1$-$C_6$ alkoxy is optionally substituted with one, two or three substituents selected from halogen, hydroxy, cyano, amino or nitro;

$R^7$ and $R^8$ are independently selected from hydrogen, $C_1$-$C_6$ alkyl, $C_1$-$C_6$ alkoxy, halogen, hydroxy, cyano, amino, or nitro, wherein said $C_1$-$C_6$ alkyl or $C_1$-$C_6$ alkoxy is optionally substituted with one, two or three substituents selected from halogen, hydroxy, cyano, amino or nitro; or $R^7$ and $R^8$ together constitute

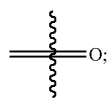

m is selected from 0 or 1; k is selected from 0 or 1; and m+k is 0 or 1;
n is selected from 0, 1, 2, 3, or 4;
p is selected from 0, 1, 2, 3, or 4;
q is selected from 0, 1, 2, 3, 4, 5 or 6;
s is selected from 0, 1, 2, 3, 4, 5, 6, 7, 8 or 9;
t is selected from 0, 1 or 2; and
when t=0 and X, Y, Z and Q are each represent CH, then n=1 and $R^3$ is hydroxymethyl.

2. The compound according to claim 1 or a pharmaceutically acceptable salt thereof, wherein at least one of $U^1$, $U^2$, $U^3$ and $U^4$ is CH, or at most one of $U^1$, $U^2$, $U^3$ and $U^4$ is N.

3. The compound according to claim 1 or a pharmaceutically acceptable salt thereof, wherein at least one of X, Y, Z and Q is CH, or at most one of X, Y, Z and Q is N.

4. The compound according to claim 1 or a pharmaceutically acceptable salt thereof, wherein W is selected from $CR^7R^8$ or O; $R^7$ and $R^8$ are independently selected from hydrogen, $C_1$-$C_3$ alkyl, $C_1$-$C_3$ alkoxy, fluorine, chlorine, bromine, iodine, hydroxyl, cyano, amino, or nitro, wherein said $C_1$-$C_3$ alkyl or $C_1$-$C_3$ alkoxy is optionally substituted with one, two or three substituents selected from fluorine, chlorine, bromine, iodine, hydroxyl, cyano, amino or nitro.

5. The compound according to claim 1 or a pharmaceutically acceptable salt thereof, wherein $Cy^1$ is selected from

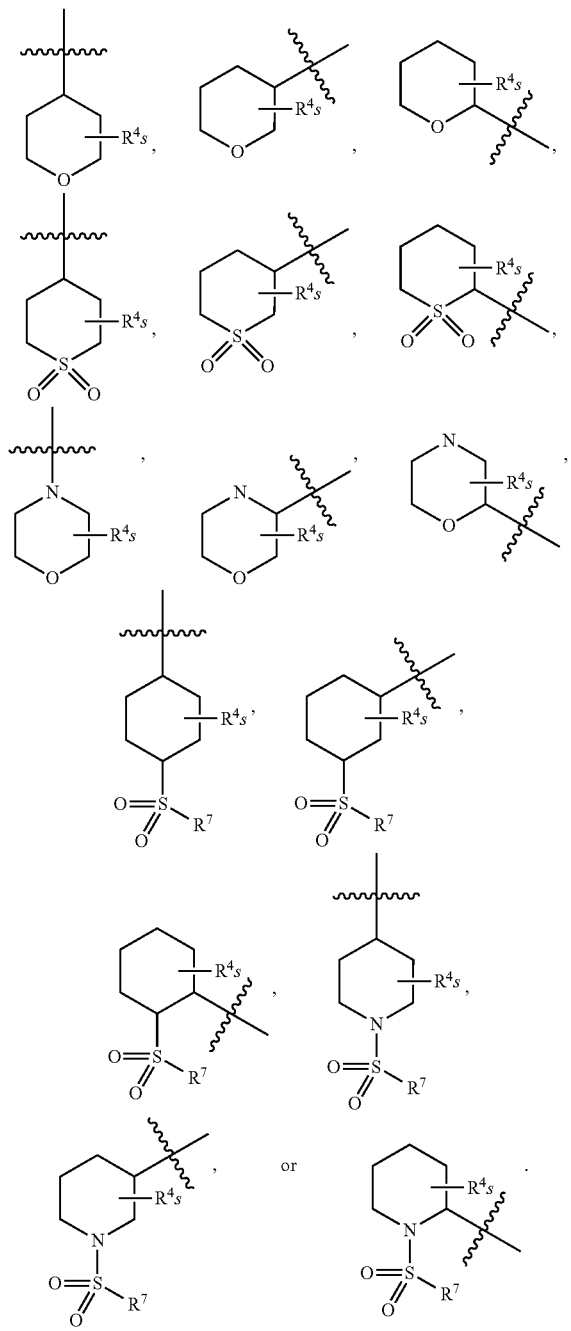

or

6. The compound according to claim 1 or a pharmaceutically acceptable salt thereof, wherein $R^1$ is independently selected from $C_1$-$C_4$ alkyl, $C_2$-$C_4$ alkenyl, $C_2$-$C_4$ alkynyl, $C_1$-$C_4$ alkoxy, 3- to 6-membered cycloalkyl, fluorine, chlorine, bromine, iodine, hydroxyl, cyano, amino, or nitro, wherein said $C_1$-$C_4$ alkyl, $C_2$-$C_4$ alkenyl, $C_2$-$C_4$ alkynyl, $C_1$-$C_4$ alkoxy, or 3- to 6-membered cycloalkyl is optionally substituted with one, two or three substituents selected from fluorine, chlorine, bromine, iodine, hydroxyl, cyano, amino or nitro.

7. The compound according to claim 1 or a pharmaceutically acceptable salt thereof, wherein $R^2$ is independently selected from $C_1$-$C_4$ alkyl, $C_1$-$C_4$ alkoxy, 3- to 6-membered cycloalkyl, 3- to 6-membered heterocycloalkyl,

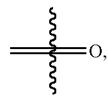

fluorine, chlorine, bromine, iodine, hydroxy, cyano, amino, or nitro, wherein said $C_1$-$C_4$ alkyl, $C_1$-$C_4$ alkoxy, 3- to 6-membered cycloalkyl, or 3- to 6-membered heterocycloalkyl is optionally substituted with one, two or three substituents selected from fluorine, chlorine, bromine, iodine, hydroxyl, cyano, amino or nitro.

8. The compound according to claim 1 or a pharmaceutically acceptable salt thereof, wherein $R^3$ is independently selected from carboxy, fluorine, chlorine, bromine, iodine, hydroxyl, cyano, amino, nitro, aminosulfonyl, $C_1$-$C_4$ alkyl, $C_1$-$C_4$ alkoxy, $C_1$-$C_4$ alkylsulfonyl, or 3- to 6-membered cycloalkyl; said $C_1$-$C_4$ alkyl, $C_1$-$C_4$ alkoxy, $C_1$-$C_4$ alkylsulfonyl or 3- to 6-membered cycloalkyl is optionally substituted with one, two or three substituents selected from deuterium, fluorine, chlorine, bromine, iodine, hydroxyl, cyano, amino or nitro.

9. The compound according to claim 1 or a pharmaceutically acceptable salt thereof, wherein $R^5$ and $R^6$ are independently selected from hydrogen, $C_1$-$C_3$ alkyl, $C_1$-$C_3$ alkoxy, fluorine, chlorine, bromine, iodine, hydroxyl, cyano, amino, or nitro, wherein said $C_1$-$C_3$ alkyl or $C_1$-$C_3$ alkoxy is optionally substituted with one, two or three substituents selected from fluorine, chlorine, bromine, iodine, hydroxyl, cyano, amino or nitro.

10. The compound according to claim 1 or a pharmaceutically acceptable salt thereof, wherein the compound of formula (A) has a structure represented by formula (a),

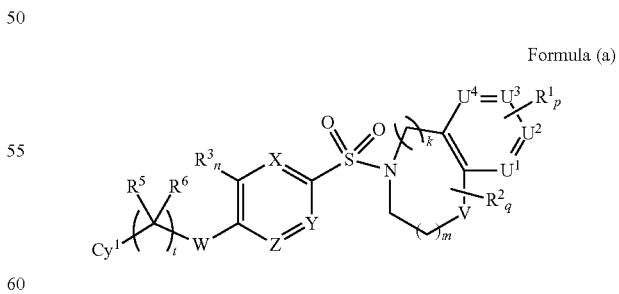

Formula (a)

wherein $U^1$, $U^2$, $U^3$, $U^4$, V, X, Y, Z, W, $Cy^1$, $R^1$, $R^2$, $R^3$, $R^4$, $R^5$, $R^6$, m, k, n, p, q, s, and t are defined as those in claim 1.

11. A compound or a pharmaceutically acceptable salt thereof, which is selected from the following compounds or a pharmaceutically acceptable salt thereof:

241
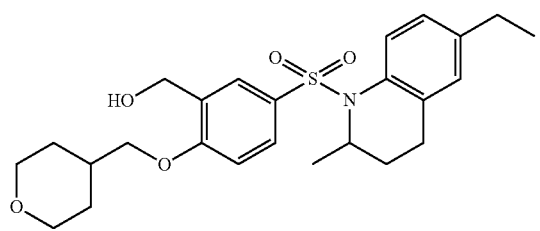
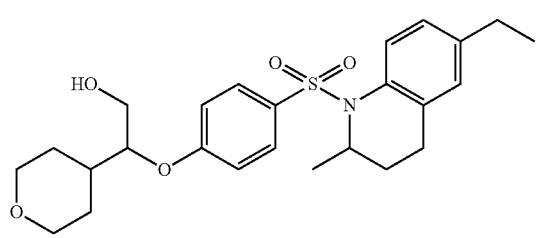
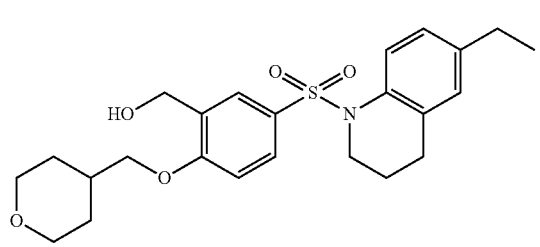
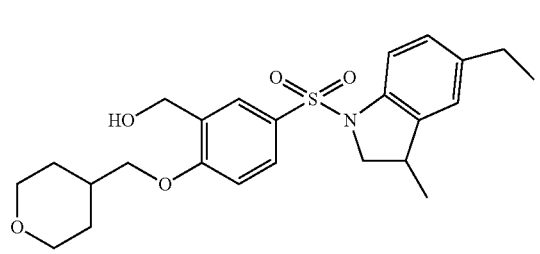
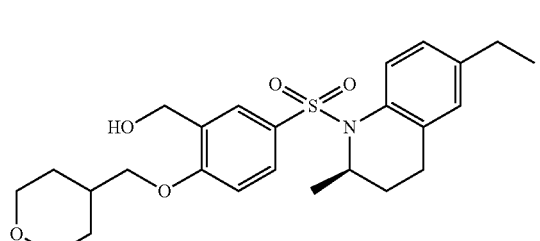
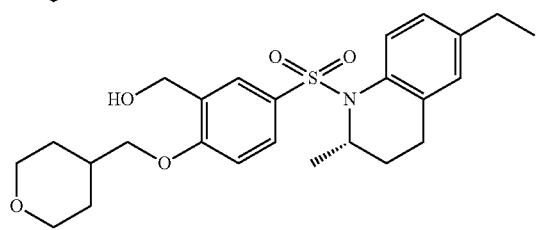
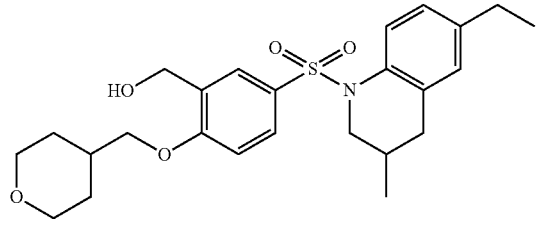
242
-continued
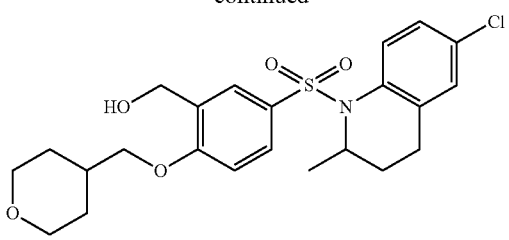
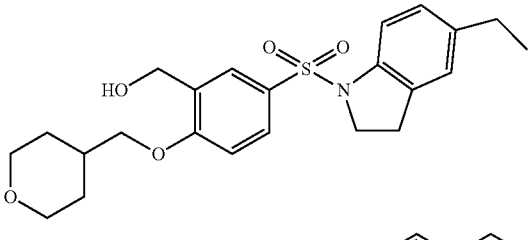
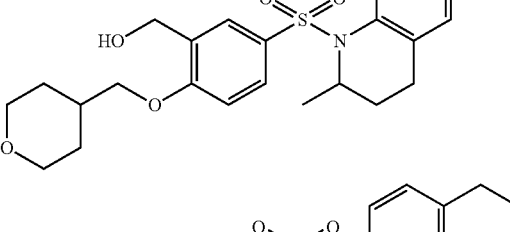
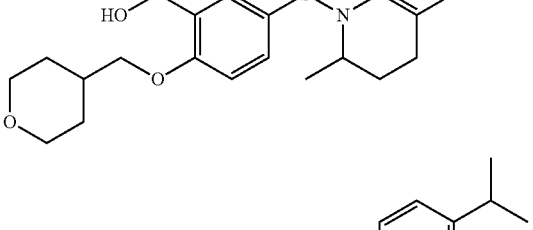
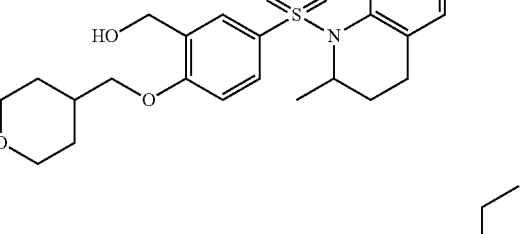
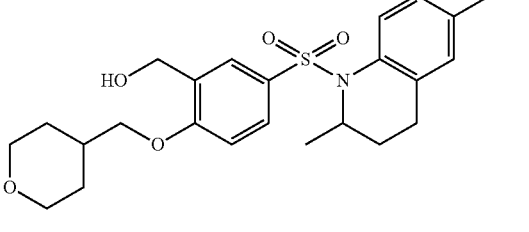

243
-continued
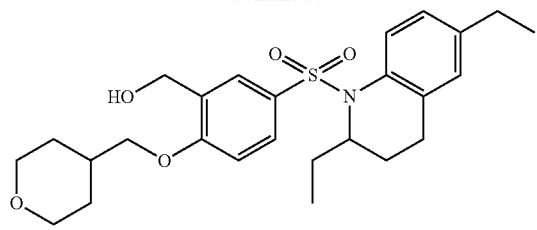
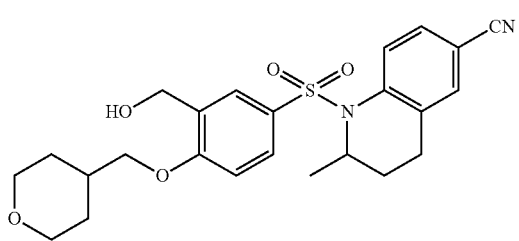
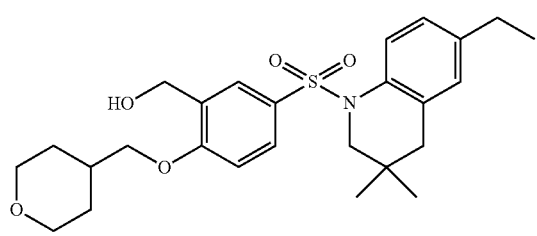
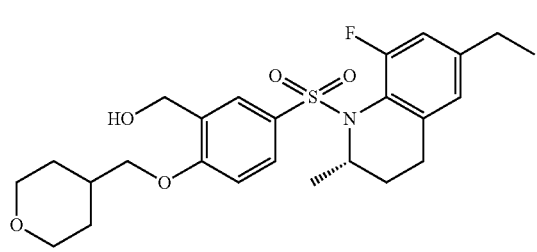
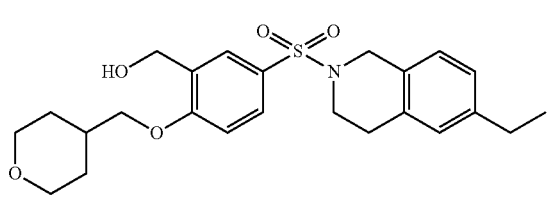
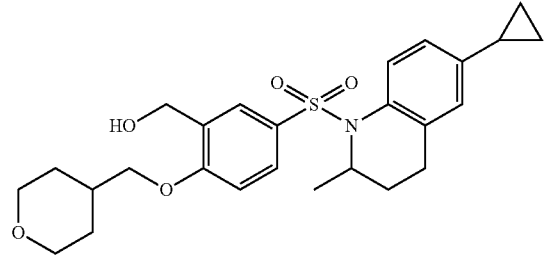
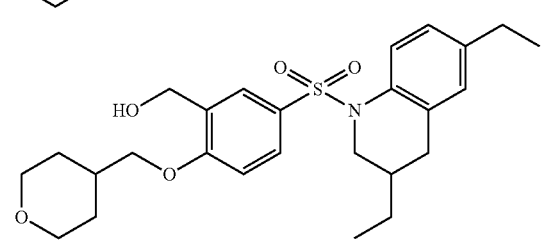
244
-continued
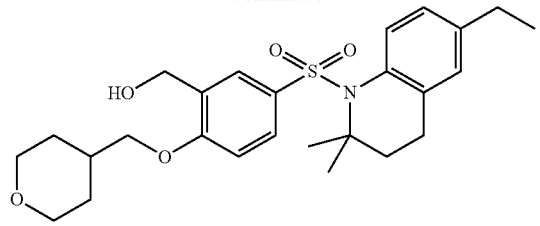
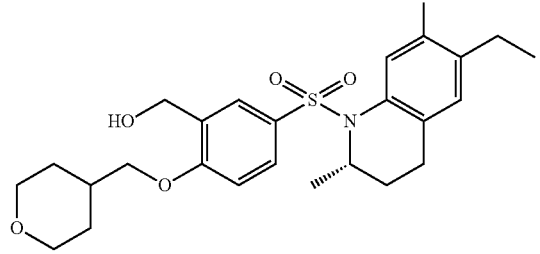
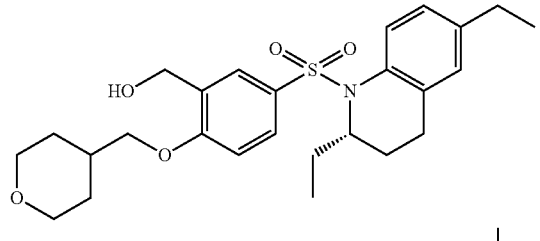
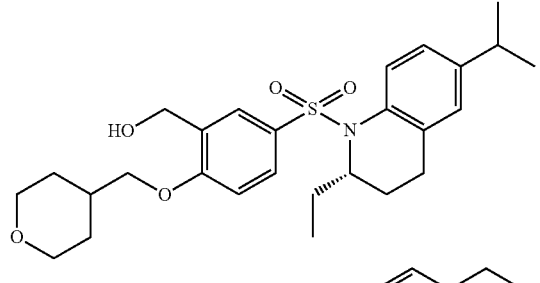
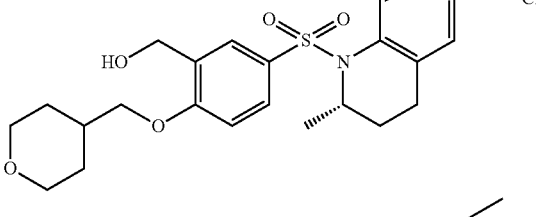
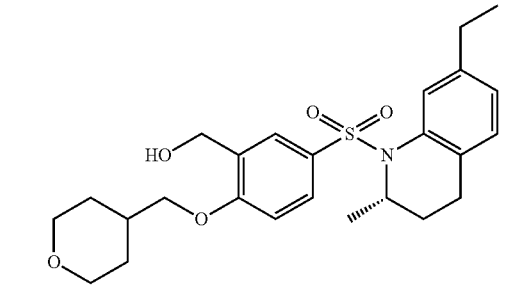
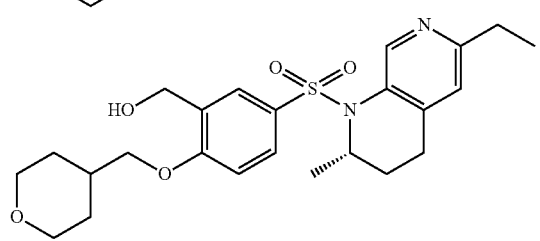

245
-continued
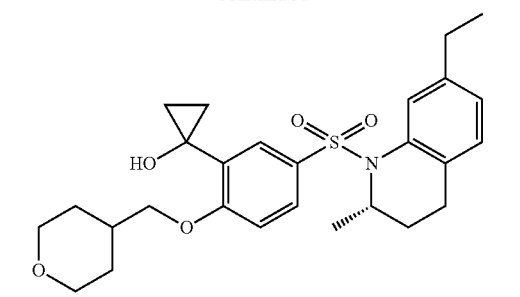
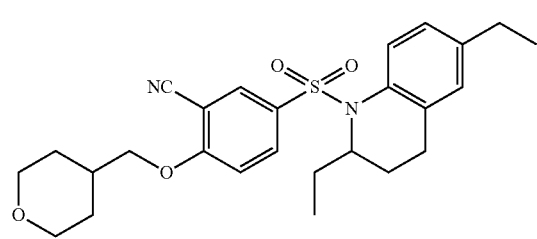
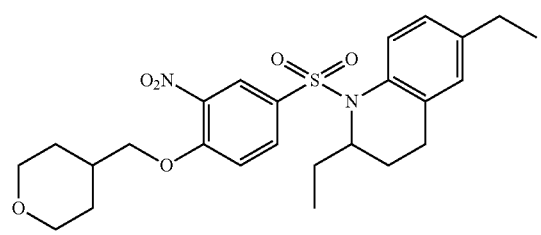
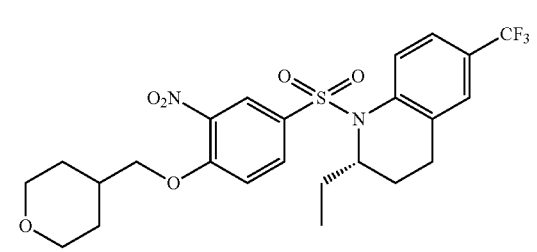
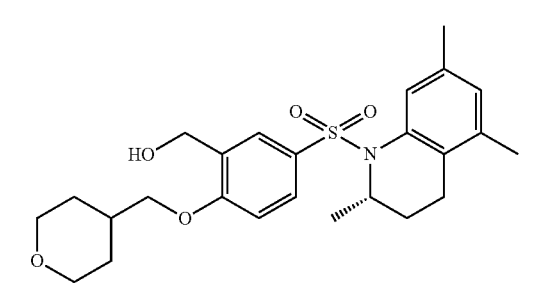
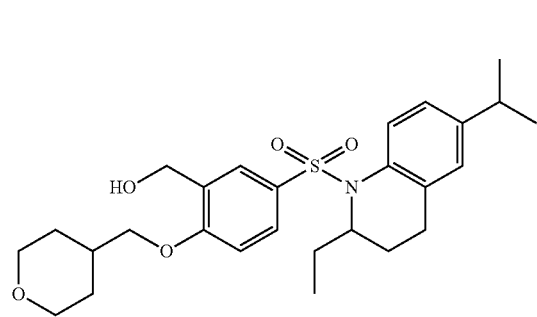
246
-continued
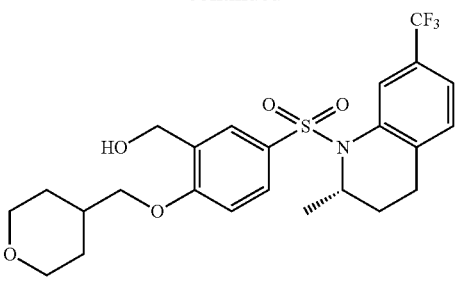
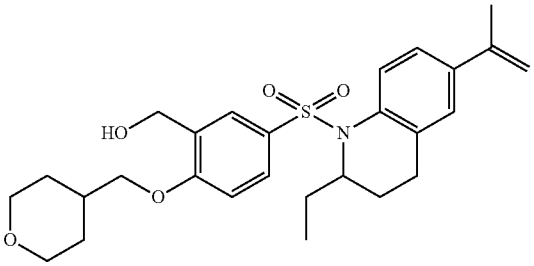
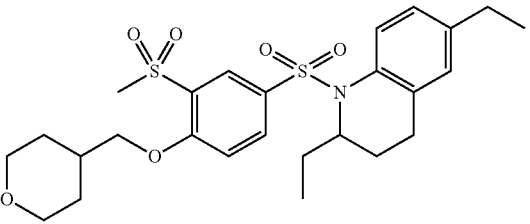
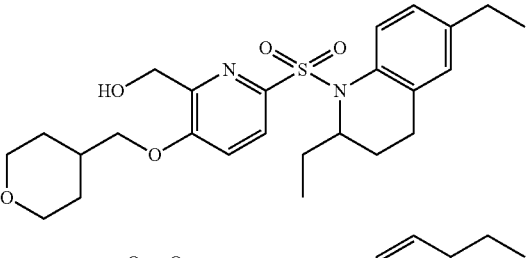
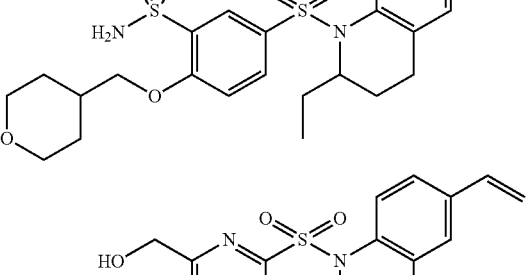
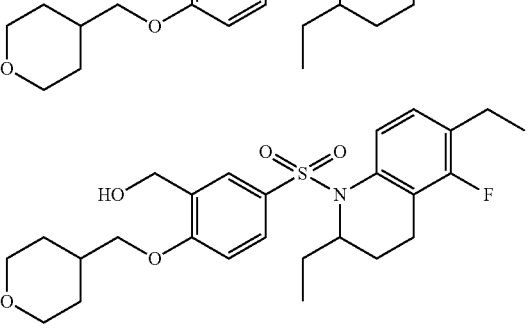

247
-continued
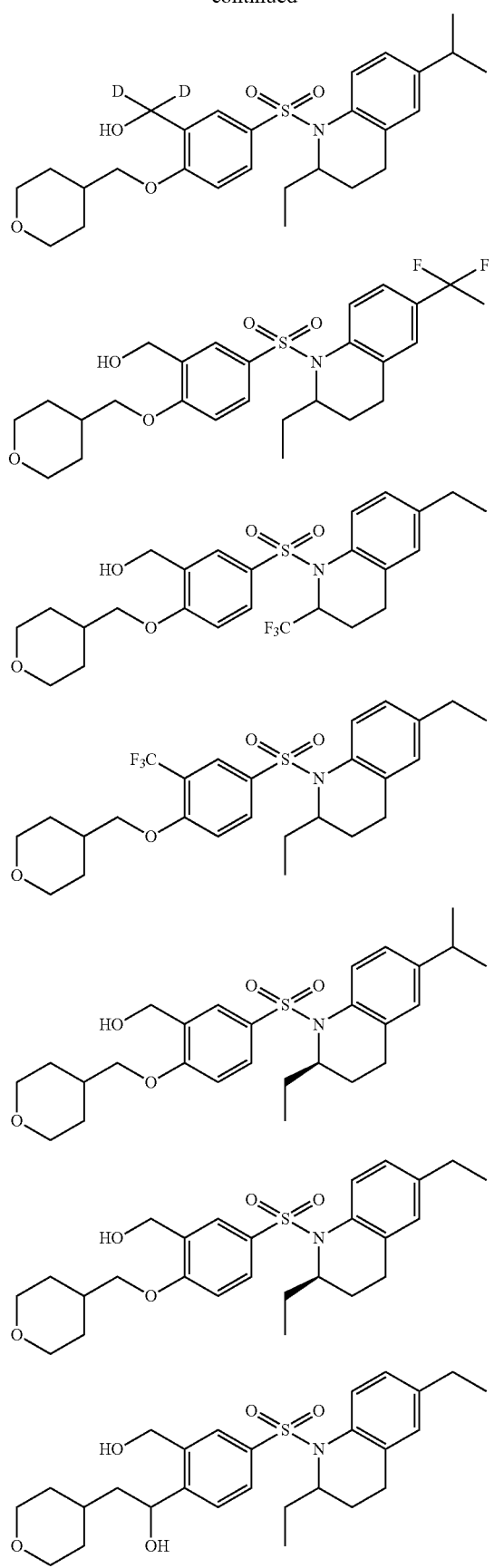
248
-continued
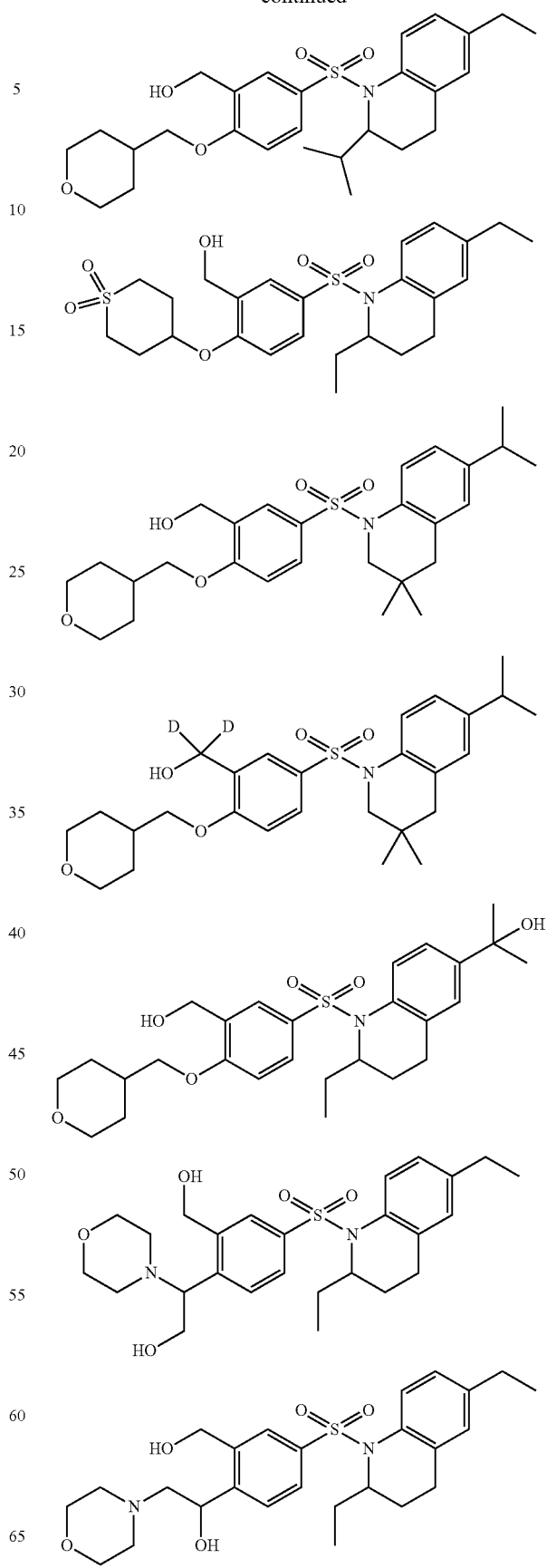

249
-continued
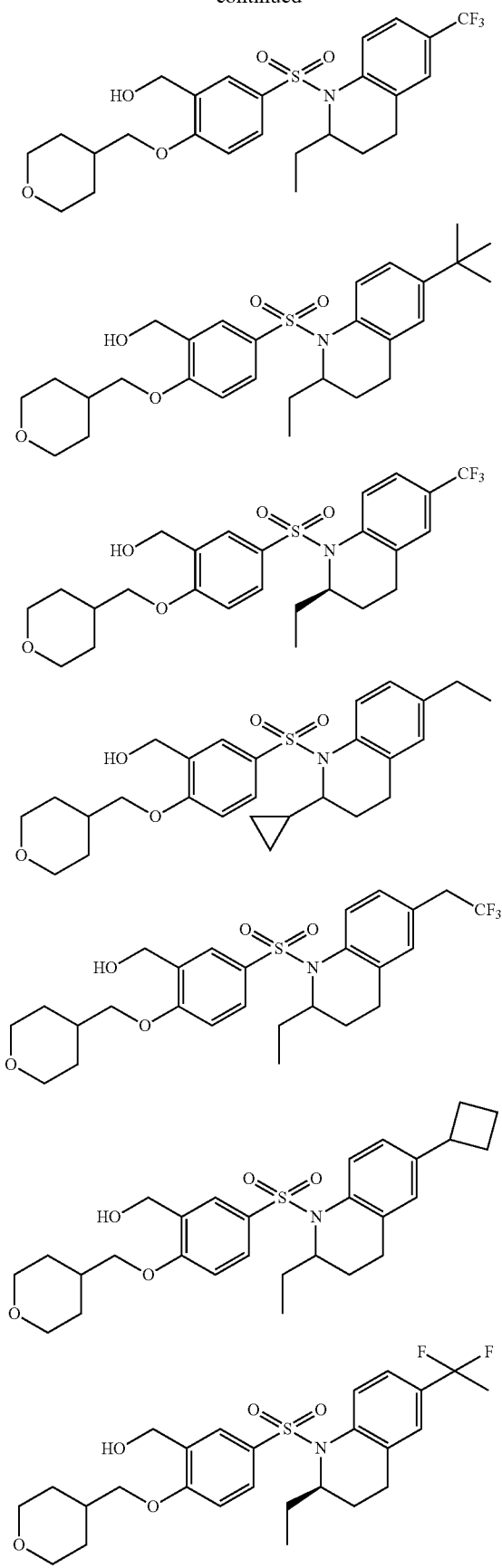
250
-continued
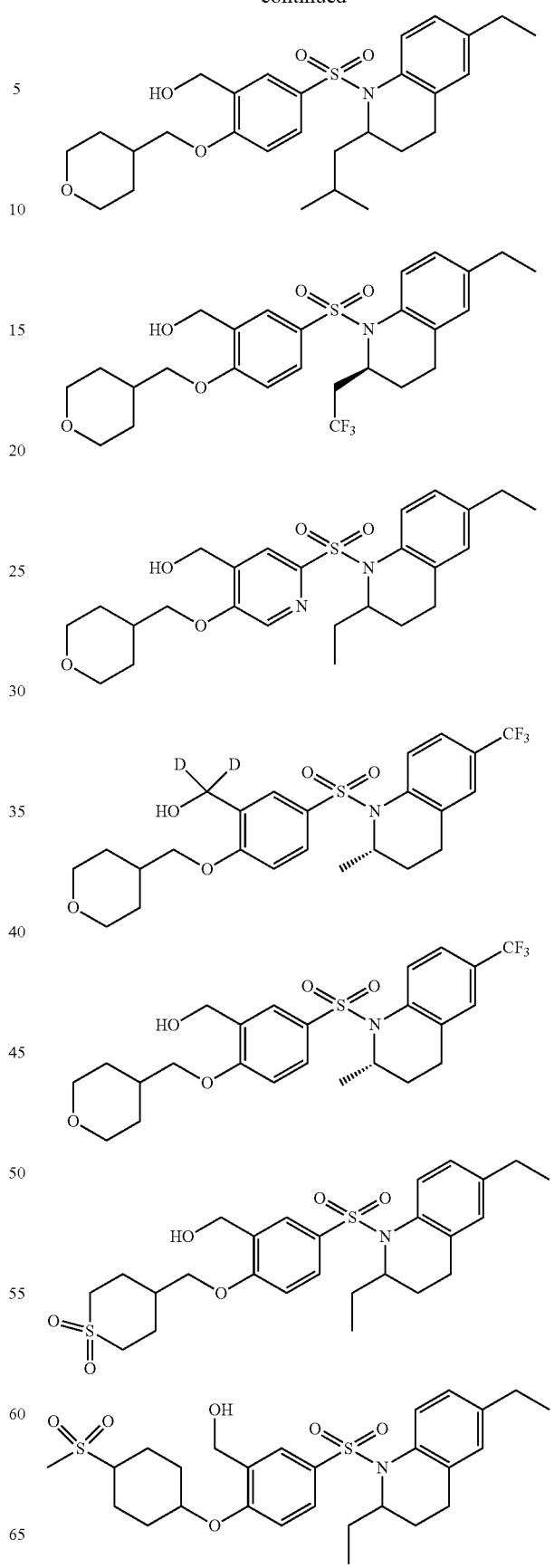

-continued

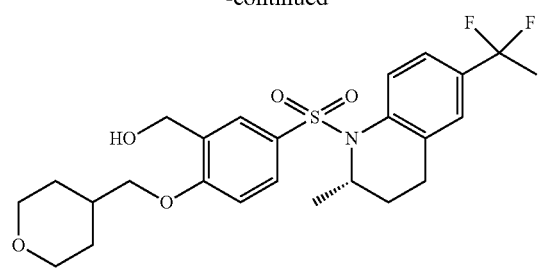

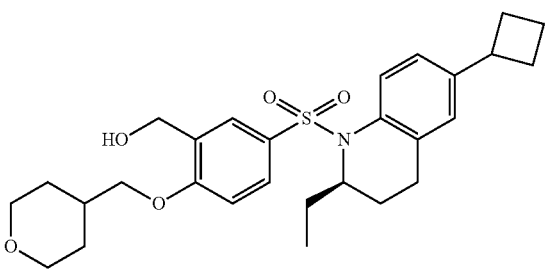

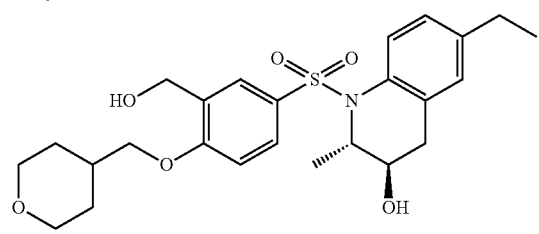

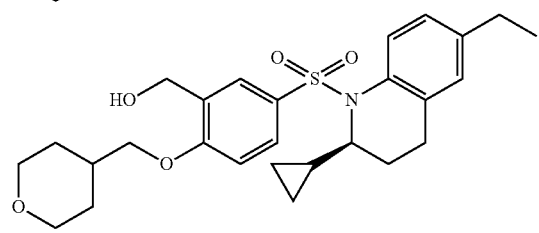

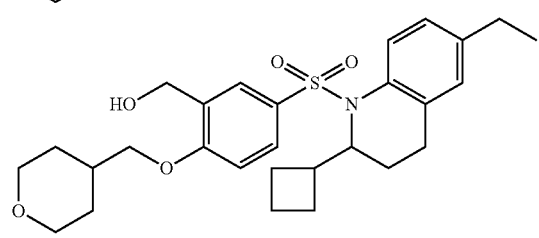

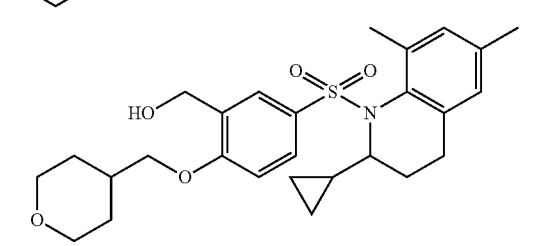

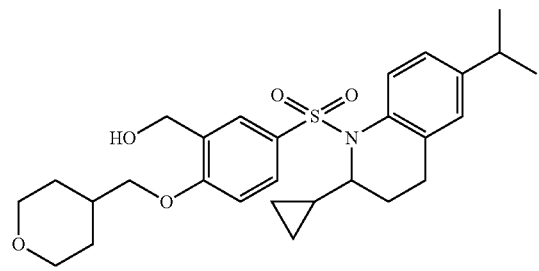

-continued

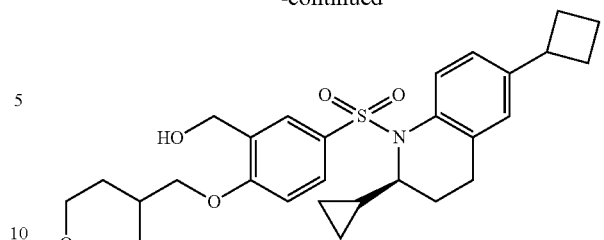

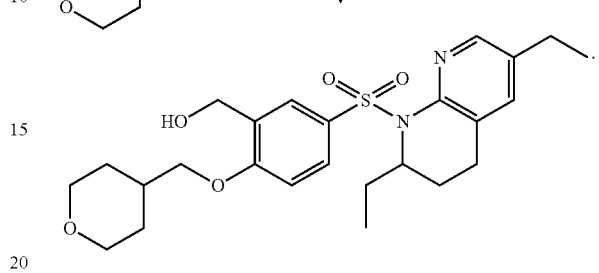

12. A compound of formula (I) or a pharmaceutically acceptable salt thereof,

Formula (I)

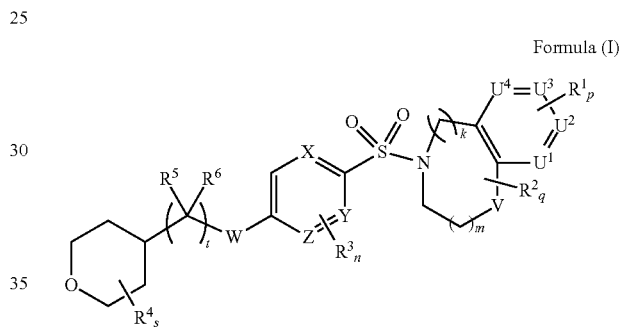

wherein $U^1$, $U^2$, $U^3$, $U^4$, X, Y, and Z are independently selected from C, CH or N;

V is selected from $CH_2$, NH, O, or S;

W is selected from $CR^7R^8$, $NR^7$, O, S,

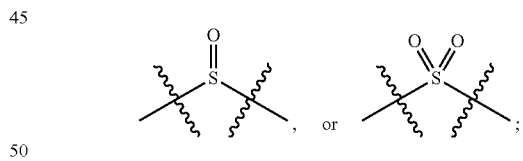

$R^1$ is selected from $C_1$-$C_6$ alkyl, $C_1$-$C_6$ alkoxy, 3- to 6-membered cycloalkyl, halogen, hydroxy, cyano, amino, or nitro, wherein said $C_1$-$C_6$ alkyl, $C_1$-$C_6$ alkoxy or 3- to 6-membered cycloalkyl is optionally substituted with one or more halogen, hydroxy, cyano, amino, or nitro;

$R^2$ and $R^4$ are independently selected from $C_1$-$C_6$ alkyl, $C_1$-$C_6$ alkoxy,

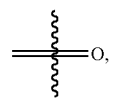 [SMILES: *=O]

halogen, hydroxy, cyano, amino, or nitro, wherein said $C_1$-$C_6$ alkyl or $C_1$-$C_6$ alkoxy is optionally substituted with one or more halogen, hydroxy, cyano, amino, or nitro;

$R^3$ is selected from carboxy, halogen, hydroxy, cyano, amino, nitro, $C_1$-$C_6$ alkyl, $C_1$-$C_6$ alkoxy, or $C_1$-$C_6$ alkylsulfonyl, wherein said $C_1$-$C_6$ alkyl, $C_1$-$C_6$ alkoxy or $C_1$-$C_6$ alkylsulfonyl is optionally substituted with one or more halogen, hydroxy, cyano, amino or nitro;

$R^5$ and $R^6$ are independently selected from hydrogen, $C_1$-$C_6$ alkyl, $C_1$-$C_6$ alkoxy, halogen, hydroxy, cyano, amino, or nitro, wherein said $C_1$-$C_6$ alkyl or $C_1$-$C_6$ alkoxy is optionally substituted with one or more halogen, hydroxy, cyano, amino or nitro;

$R^7$ and $R^8$ are independently selected from hydrogen, $C_1$-$C_6$ alkyl, $C_1$-$C_6$ alkoxy, halogen, hydroxy, cyano, amino, or nitro, wherein said $C_1$-$C_6$ alkyl or $C_1$-$C_6$ alkoxy is optionally substituted with one or more halogen, hydroxy, cyano, amino, or nitro; or $R^7$ and $R^8$ together constitute

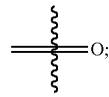

m is selected from 0 or 1; k is selected from 0 or 1; and m+k≤1;
n is selected from 0, 1, 2, 3, or 4;
p is selected from 0, 1, 2, 3, or 4;
q is selected from 0, 1, 2, 3, 4, 5, or 6;
s is selected from 0, 1, 2, 3, 4, 5, 6, 7, or 8; and
t is selected from 1 or 2.

13. A pharmaceutical composition, wherein the pharmaceutical composition comprises a therapeutically effective amount of the compound according to claim 1 or a pharmaceutically acceptable salt thereof, the pharmaceutical composition further comprises a pharmaceutically acceptable excipient.

14. A method for treating a RORγ receptor-mediated disease, the method comprising administering an effective amount of the compound according to claim 1 or a pharmaceutically acceptable salt thereof to a subject in need thereof, wherein the RORγ receptor is a RORγt receptor.

15. The compound according to claim 1 or a pharmaceutically acceptable salt thereof, wherein X, Y, Z and Q are all CH, or X is N, and Y, Z and Q are all CH, or Y is N, and X, Z and Q are all CH.

16. The compound according to claim 1 or a pharmaceutically acceptable salt thereof, wherein $Cy^1$ is selected from

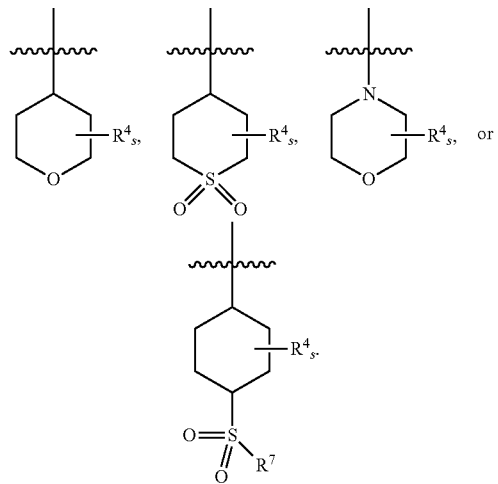

17. The compound according to claim 1 or a pharmaceutically acceptable salt thereof, wherein $R^5$ and $R^6$ are independently selected from hydrogen or hydroxylmethyl.

18. A method for treating a RORγ receptor-mediated disease, the method comprising administering an effective amount of the pharmaceutical composition of claim 13 to a subject in need thereof, wherein the RORγ receptor is a RORγt receptor.

* * * * *